(12) United States Patent
Weinhausel et al.

(10) Patent No.: US 10,718,026 B2
(45) Date of Patent: Jul. 21, 2020

(54) METHYLATION ASSAY

(75) Inventors: Andreas Weinhausel, Neckenmarkt (AT); Rudolf Pichler, Wampersdorf (AT); Christa Nohammer, Vienna (AT)

(73) Assignee: AIT Austrian Institute of Technology GMBH, Vienna (AT)

(*) Notice: Subject to any disclaimer, the term of this patent is extended or adjusted under 35 U.S.C. 154(b) by 0 days.

(21) Appl. No.: 13/146,903

(22) PCT Filed: Jan. 28, 2010

(86) PCT No.: PCT/EP2010/051033
§ 371 (c)(1),
(2), (4) Date: Jul. 28, 2011

(87) PCT Pub. No.: WO2010/086389
PCT Pub. Date: Aug. 5, 2010

(65) Prior Publication Data
US 2011/0287968 A1   Nov. 24, 2011

(30) Foreign Application Priority Data
Jan. 28, 2009   (EP) ................................ 09450020

(51) Int. Cl.
*C12Q 1/6886* (2018.01)

(52) U.S. Cl.
CPC ..... *C12Q 1/6886* (2013.01); *C12Q 2523/125* (2013.01); *C12Q 2600/112* (2013.01); *C12Q 2600/118* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| 8,911,937 | B2* | 12/2014 | Wojdacz | .......................... 435/6.1 |
| 2007/0020646 | A1* | 1/2007 | Hoon | .................... C12Q 1/6886 435/6.11 |
| 2007/0092498 | A1* | 4/2007 | Giordano | ............. C12Q 1/6886 424/93.21 |
| 2008/0299551 | A1* | 12/2008 | Hoon | ................................ 435/6 |
| 2009/0215709 | A1* | 8/2009 | Van Criekinge et al. | ...... 514/34 |
| 2010/0003189 | A1* | 1/2010 | Tlsty | ................ G01N 33/57492 424/1.49 |
| 2011/0287967 | A1 | 11/2011 | Weinhausel et al. | ............. 506/9 |

FOREIGN PATENT DOCUMENTS

| WO | WO 2003/052135 | 6/2003 |
| WO | WO 2007/008693 | 1/2007 |
| WO | WO 2010/086388 | 8/2010 |

OTHER PUBLICATIONS

Rauch et al. PNAS. Jan. 2008. 105: 252-257).*
Chen et al. American J Pathology. 2003. 163: 37-45.*
Nishiyama et al. Cancer Biology and Therapy. 2005. 4: 440-448.*
Battagli et al. Cancer Research. Dec. 2003. 63: 8695-8699.*
Fujii et al. Oncogene. 1998. 16: 2159-2164.*
Rathi et al. Clinical Cancer Research. 2003. 9: 3674-3578.*
Ehrlich et al. Oncogene 2002. 21: 5400-5413.*
Rauch et al. PNAS. 2007. 104:5527-5532.*
Agilent Gene List for the Human CpG island microarray, available via url: . <chem.agilent.com/cag/bsp/gene_lists.asp>, printed on Mar. 26, 2013.*
Buhmeida et al. AntiCancer Research. 2011. 31: 2975-2982.*
Smiraglia et al. Human Molecular Genetics. 2001. 10: 1413-1419.*
Okada et al Genes, Chromosomes & Cancer. Published online Feb. 5, 2010. 49: 452-462.*
Ushijima et al. Nature Reviews. 2005.5: 223-231.*
Muller-Tidow et al. FEBS Letters. 2001. 490: 75-78.*
D'Andrilli et a;/ Clinical Cancer Research. 2004. 10: 3098-3103.*
Breastcancer.org, "Meditation" and "Types of Complementary Techniques" available via url: <breastcancer.org>, printed on Jun. 14, 2017.*
Greenlee et al 2014. J Natl Cancer Inst Monogr. 50: 346-358.*
"[HG-U133A] Affymetrix human genome U133A array," retrieved from NCBI Database accession No. GLP96, 2002.
Bibikova et al., "High-throughput DNA methylation profiling using universal bead arrays," *Genome Research*, 16:383-393, 2006.
Cheng et al., "Mulitplexed profiling of candidate genes for CpG island methylation status using a flexible PCR/LDR/Universal Array assay," *Genome Research*, 16(2): 282-289, 2006.
International Search Report and Written Opinion issued in PCT/EP2010/051032, dated Jun. 22, 2010.
International Search Report and Written Opinion issued in PCT/EP2010/051033, dated Jun. 9, 2010.
Ishkanian et al., "A tiling resolution DNA microarray with complete coverage of the human genome," *Nat. Gen.*, 36(3): 299-303, 2004.
Ongenaert et al, "PubMeth: a cancer methylation database combining text-mining and expert annotation," *Nuc. Acids. Res.*, 36: D842-D846, 2008.
Rauch et al., "Homeobox gene methylation in lung cancer studied by genome-wide analysis with microarray-based methylated CpG island recovery assay," *Proc. Natl. Acad. Sci.*, 104(13): 5527-5532, 2007.
Sato et al., "Discovery of novel targets for aberrant methylation in pancreatic carcinoma using high throughput microarrays," *Cancer Res.*, 63(13): 3735-372, 2003.
Shames et al., "A genome-wide screen for promoter methylation in lung cancer identifies novel methylation in lung cancer identifies novel methylation markers for multiple malignancies," *PLOS Medicine*, 3(12): E486, 2006.
Tsou et al., "DNA methylation analysis: a powerful new tool for lung cancer diagnosis," *Oncogene*, 21(35): 5450-5461, 2002.

(Continued)

*Primary Examiner* — Carla J Myers
(74) *Attorney, Agent, or Firm* — Norton Rose Fulbright US LLP

(57) ABSTRACT

The present invention discloses a method of generating subsets of methylation specific markers from a set, having diagnostic power for various diseases, e.g. cancer of thyroid, breast, colon, or leukemia, in diverse samples; identified subsets of that set, as well as methods for the prognosis and diagnosis of diseases.

5 Claims, 7 Drawing Sheets

Figure 1:
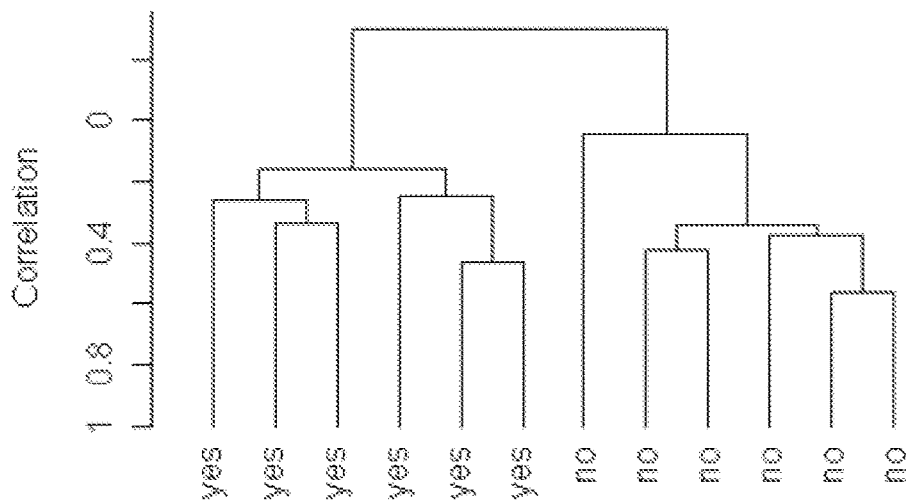

Specification includes a Sequence Listing.

(56) References Cited

OTHER PUBLICATIONS

Yan et al., "CpG island arrays: an application toward deciphering epigenetic signatures of breast cancer," *Clin. Cancer Res.*, 6(4): 1432-1438, 2000.

Shen, Lanlan et al: "Genome-wide profiling of ONA methylation reveals a class of normally methylated CpG island promoters", *PLoS Genetics*, vol. 3, No. 10, e181, Oct. 2007, pp. 2023-2036.

Anglim, Paul P. et al: "Identification of a panel of sensitive and specific DNA methylation markers for squamous cell lung cancer", *Molecular Cancer*, vol. 7, No. 62, Jan. 1, 2008, pp. 1-13.

Office Action dated Nov. 27, 2014 for European Patent Application No. 10701378.1, filed Jan. 28, 2010.

Parrella et al., "Nonrandom Distribution of Aberrant Promoter Methylation of Cancer-Related Genes in Sporadic Breast Tumors", Clinical Cacer Research, vol. 10, (2004), pp. 5349-5354.

\* cited by examiner

METHYLATION ASSAY

This application is a national phase application under 35 U.S.C. § 371 of International Application No. PCT/EP2010/051033 filed 28 Jan. 2010, which claims priority to European Application No. 09450020.4 filed 28 Jan. 2009. The entire text of each of the above-referenced disclosures is specifically incorporated herein by reference without disclaimer.

The present invention relates to cancer diagnostic methods and means therefore.

Neoplasms and cancer are abnormal growths of cells. Cancer cells rapidly reproduce despite restriction of space, nutrients shared by other cells, or signals sent from the body to stop reproduction. Cancer cells are often shaped differently from healthy cells, do not function properly, and can spread into many areas of the body. Abnormal growths of tissue, called tumors, are clusters of cells that are capable of growing and dividing uncontrollably. Tumors can be benign (noncancerous) or malignant (cancerous). Benign tumors tend to grow slowly and do not spread. Malignant tumors can grow rapidly, invade and destroy nearby normal tissues, and spread throughout the body. Malignant cancers can be both locally invasive and metastatic. Locally invasive cancers can invade the tissues surrounding it by sending out "fingers" of cancerous cells into the normal tissue. Metastatic cancers can send cells into other tissues in the body, which may be distant from the original tumor. Cancers are classified according to the kind of fluid or tissue from which they originate, or according to the location in the body where they first developed. All of these parameters can effectively have an influence on the cancer characteristics, development and progression and subsequently also cancer treatment. Therefore, reliable methods to classify a cancer state or cancer type, taking diverse parameters into consideration is desired. Since cancer is predominantly a genetic disease, trying to classify cancers by genetic parameters is one extensively studied route.

Extensive efforts have been undertaken to discover genes relevant for diagnosis, prognosis and management of (cancerous) disease. Mainly RNA-expression studies have been used for screening to identify genetic biomarkers. Over recent years it has been shown that changes in the DNA-methylation pattern of genes could be used as biomarkers for cancer diagnostics. In concordance with the general strategy identifying RNA-expression based biomarkers, the most convenient and prospering approach would start to identify marker candidates by genome-wide screening of methylation changes.

The most versatile genome-wide approaches up to now are using microarray hybridization based techniques. Although studies have been undertaken at the genomic level (and also the single-gene level) for elucidating methylation changes in diseased versus normal tissue, a comprehensive test obtaining a good success rate for identifying biomarkers is yet not available.

Developing biomarkers for disease (especially cancer)-screening, -diagnosis, and -treatment was improved over the last decade by major advances of different technologies which have made it easier to discover potential biomarkers through high-throughput screens. Comparing the so called "OMICs"-approaches like Genomics, Proteomics, Metabolomics, and derivates from those, Genomics is best developed and most widely used for biomarker identification. Because of the dynamic nature of RNA expression and the ease of nucleic acid extraction and the detailed knowledge of the human genome, many studies have used RNA expression profiling for elucidation of class differences for distinguishing the "good" from the "bad" situation like diseased vs. healthy, or clinical differences between groups of diseased patients. Over the years especially microarray-based expression profiling has become a standard tool for research and some approaches are currently under clinical validation for diagnostics. The plasticity over a broad dynamic range of RNA expression levels is an advantage using RNA and also a prerequisite of successful discrimination of classes, the low stability of RNA itself is often seen as a drawback. Because stability of DNA is tremendously higher than stability of RNA, DNA based markers are more promising markers and expected to give robust assays for diagnostics. Many of clinical markers in oncology are more or less DNA based and are well established, e.g. cytogenetic analyses for diagnosis and classification of different tumor-species. However, most of these markers are not accessible using the cheap and efficient molecular-genetic PCR routine tests. This might be due to 1) the structural complexity of changes, 2) the inter-individual differences of these changes at the DNA-sequence level, and 3) the relatively low "quantitative" fold-changes of those "chromosomal" DNA changes. In comparison, RNA-expression changes range over some orders of magnitudes and these changes can be easily measured using genome-wide expression microarrays. These expression arrays are covering the entire translated transcriptome by 20000-45000 probes. Elucidation of DNA changes via microarray techniques requires in general more probes depending on the requested resolution. Even order(s) of magnitude more probes are required than for standard expression profiling to cover the entire $3 \times 10^9$ bp human genome. For obtaining best resolution when screening biomarkers at the structural genomic DNA level, today genomic tiling arrays and SNP-arrays are available. Although costs of these techniques analysing DNA have decreased over recent years, for biomarker screening many samples have to be tested, and thus these tests are cost intensive.

Another option for obtaining stable DNA-based biomarkers relies on elucidation of the changes in the DNA methylation pattern of (malignant; neoplastic) disease. In the vertebrate genome methylation affects exclusively the cytosine residues of CpG dinucleotides, which are clustered in CpG islands. CpG islands are often found associated with gene-promoter sequences, present in the 5'-untranslated gene regions and are per default unmethylated. In a very simplified view, an unmethylated CpG island in the associated gene-promoter enables active transcription, but if methylated gene transcription is blocked. The DNA methylation pattern is tissue- and clone-specific and almost as stable as the DNA itself. It is also known that DNA-methylation is an early event in tumorigenesis which would be of interest for early and initial diagnosis of disease.

Shames D et al. (PLOS Medicine 3(12) (2006): 2244-2262) identified multiple genes that are methylated with high penetrance in primary lung, breast, colon and prostate cancers.

Sato N et al. (Cancer Res 63(13) (2003): 3735-3742) identified potential targets with aberrant methylation in pancreatic cancer. These genes were tested using a treatment with a demethylating agent (5-aza-2'-deoxycytidine and/or the histone deacetylase inhibitor trichostatin A) after which certain genes were increased transcribed.

Bibikova M et al. (Genome Res 16(3) (2006): 383-393) analysed lung cancer biopsy samples to identify methylated cpu sites to distinguish lung adenocarcinomas from normal lung tissues.

Yan P S et al. (Clin Cancer Res 6(4) (2000): 1432-1438) analysed CpG island hypermethylation in primary breast tumor.

Cheng Y et al. (Genome Res 16(2) (2006): 282-289) discussed DNA methylation in CpG islands associated with transcriptional silencing of tumor suppressor genes.

Ongenaert M et al. (Nucleic Acids Res 36 (2008) Database issue D842-D846) provided an overview over the methylation database "PubMeth".

Microarray for human genome-wide hybridization testings are known, e.g. the Affymetrix Human Genome U133A Array (NCB1 Database, Acc. No. GLP96).

In principle screening for biomarkers suitable to answering clinical questions including DNA-methylation based approaches would be most successful when starting with a genome-wide approach. A substantial number of differentially methylated genes has been discovered over years rather by chance than by rationality. Albeit some of these methylation changes have the potential being useful markers for differentiation of specifically defined diagnostic questions, these would lack the power for successful delineation of various diagnostic constellations. Thus, the rational approach would start at the genomic-screen for distinguishing the "subtypes" and diagnostically, prognostically and even therapeutically challenging constellations. These rational expectations are the base of starting genomic (and also other -omics) screenings but do not warrant to obtain the maker panel for all clinical relevant constellations which should be distinguished. This is neither unreliable when thinking about a universal approach (e.g. transcriptomics) suitable to distinguish for instance all subtypes in all different malignancies by focusing on a single class of target-molecules (e.g. RNA). Rather all omics-approaches together would be necessary and could help to improve diagnostics and finally patient management.

A goal of the present invention is to provide an alternative and more cost-efficient route to identify suitable markers for cancer diagnostics.

Therefore, in a first aspect, the present invention provides a method of determining a subset of diagnostic markers for potentially methylated genes from the genes of gene IDs 1-359 in table 1, suitable for the diagnosis or prognosis of a disease or tumor type in a sample, comprising
  a) obtaining data of the methylation status of at least 50 random genes selected from the 359 genes of gene ID 1-359 in at least 1 sample, preferably 2, 3, 4 or at least 5 samples, of a confirmed disease or tumor type positive state and at least one sample of a disease or tumor type negative state,
  b) correlating the results of the obtained methylation status with the disease or tumor type states,
  c) optionally repeating the obtaining a) and correlating b) steps for at least partially different at least 50 random genes selected from the 359 genes of gene IDs 1-359, and
  d) selecting as many marker genes which in a classification analysis together yield at least a 65%, preferably at least 70%, correct classification of the disease or tumor type or have a p-value of less than 0.1, preferably less than 0.05, even more preferred less than 0.01, in a random-variance t-test,
wherein the selected markers form the subset of the diagnostic markers.

The present invention provides a master set of 359 genetic markers which has been surprisingly found to be highly relevant for aberrant methylation in the diagnosis or prognosis of diseases. It is possible to determine a multitude of marker subsets from this master set which can be used to differentiate between various disease or tumor type.

The inventive 359 marker genes of table 1 (given in example 1 below) are: NHLH2, MTHFR, PRDM2, MLLT11, S100A9 (control), S100A9, S100A8 (control), S100A8, S100A2, LMNA, DUSP23, LAMC2, PTGS2, MARK1, DUSP10, PARP1, PSEN2, CLIC4, RUNX3, AIM1L, SFN, RPA2, TP73, TP73 (p73), POU3F1, MUTYH, UQCRH, FAF1, TACSTD2, TNFRSF25, DIRAS3, MSH4, GBP2, GBP2, LRRC8C, F3, NANOS1, MGMT, EBF3, DCLRE1C, KIF5B, ZNF22, PGBD3, SRGN, GATA3, PTEN, MMS19, SFRP5, PGR, ATM, DRD2, CADM1, TEAD1, OPCML, CALCA, CTSD, MYOD1, IGF2, BDNF, CDKN1C, WT1, HRAS, DDB1, GSTP1, CCND1, EPS8L2, PIWIL4, CHST11, UNG, CCDC62, CDK2AP1, CHFR, GRIN2B, CCND2, VDR, B4GALNT3, NTF3, CYP27B1, GPR92, ERCC5, GJB2, BRCA2, KL, CCNA1, SMAD9, C13orf15, DGKH, DNAJC15, RB1, RCBTB2, PARP2, APEX1, JUB, JUB (control_NM_198086), EFS, BAZ1A, NKX2-1, ESR2, HSPA2, PSEN1, PGF, MLH3, TSHR, THBS1, MYO5C, SMAD6, SMAD3, NOX5, DNAJA4, CRABP1, BCL2A1 (ID NO: 111), BCL2A1 (ID NO: 112), BNC1, ARRDC4, SOCS1, ERCC4, NTHL1, PYCARD, AXIN1, CYLD, MT3, MT1A, MT1G, CDH1, CDH13, DPH1, HIC1, NEUROD2 (control), NEUROD2, ERBB2, KRT19, KRT14, KRT17, JUP, BRCA1, COL1A1, CACNA1G, PRKAR1A, SPHK1, SOX15, TP53 (TP53_CGI23_1kb), TP53 (TP53 both CGIs 1 kb), TP53 (TP53_CGI36_1kb), TP53, NPTX1, SMAD2, DCC, MBD2, ONECUT2, BCL2, SERPINB5, SERPINB2 (control), SERPINB2, TYMS, LAMA1, SALL3, LDLR, STK11, PRDX2, RAD23A, GNA15, ZNF573, SPINT2, XRCC1, ERCC2, ERCC1, C5AR1 (NM_001736), C5AR1, POLD1, ZNF350, ZNF256, C3, XAB2, ZNF559, FHL2, IL1B, 1L1B (control), PAX8, DDX18, GAD1, DLX2, ITGA4, NEUROD1, STAT1, TMEFF2, HECW2, BOLL, CASP8, SERPINE2, NCL, CYP1B1, TACSTD1, MSH2, MSH6, MXD1, JAG1, FOXA2, THBD, CTCFL, CTSZ, GATA5, CXADR, APP, TTC3, KCNJ15, RIPK4, TFF1, SEZ6L, TIMP3, BIK, VHL, IRAK2, PPARG, MBD4, RBP1, XPC, ATR, LXN, RARRES1, SERPINI1, CLDN1, FAM43A, IQCG, THRB, RARB, TGFBR2, MLH1, DLEC1, CTNNB1, ZNF502, SLC6A20, GPX1, RASSF1, FHIT, OGG1, PITX2, SLC25A31, FBXW7, SFRP2, CHRNA9, GABRA2, MSX1, IGFBP7, EREG, AREG, ANXA3, BMP2K, APC, HSD17B4 (ID No 249), HSD17B4 (ID No 250), LOX, TERT, NEUROG1, NR3C1, ADRB2, CDX1, SPARC, C5orf4, PTTG1, DUSP1, CPEB4, SCGB3A1, GDNF, ERCC8, F2R, F2RL1, VCAN, ZDHHC11, RHOBTB3, PLAGL1, SASH1, ULBP2, ESR1, RNASET2, DLL1, HIST1H2AG, HLA-G, MSH5, CDKN1A, TDRD6, COL21A1, DSP, SERPINE1 (ID No 283), SERPINE1 (ID No 284), FBXL13, NRCAM, TWIST1, HOXA1, HOXA10, SFRP4, IGFBP3, RPA3, ABCB1, TFPI2, COL1A2, ARPC1B, PILRB, GATA4, MAL2, DLC1, EPPK1, LZTS1, INFRSF10B, INFRSF10C, INFRSF10D, INFRSF10A, WRN, SFRP1, SNAI2, RDHE2, PENK, RDH10, TGFBR1, ZNF462, KLF4, CDKN2A, CDKN2B, AQP3, TPM2, TJP2 (ID NO 320), TJP2 (ID No 321), PSAT1, DAPK1, SYK, XPA, ARMCX2, RHOXF1, FHL1, MAGEB2, TIMP1, AR, ZNF711, CD24, ABL1, ACTB, APC, CDH1 (Ecad 1), CDH1 (Ecad2), FMR1, GNAS, H19, HIC1, IGF2, KCNQ1, GNAS, CDKN2A (P14), CDKN2B (P15), CDKN2A (P16 VL), PITXA, PITXB, PITXC, PITXD, RB1, SFRP2, SNRPN, XIST, IRF4, UNC13B, GSTP1. Table 1 lists some marker genes in the double such as for different loci and control sequences.

It should be understood that any methylation specific region which is readily known to the skilled man in the art from prior publications or available databases (e.g. PubMeth at www.pubmeth.org) can be used according to the present invention. Of course, double listed genes only need to be represented once in an inventive marker set (or set of probes or primers therefor) but preferably a second marker, such as a control region is included (IDs given in the list above relate to the gene ID (or gene loci ID) given in table 1 of the example section).

One advantage making DNA methylation an attractive target for biomarker development, is the fact that cell free methylated DNA can be detected in body-fluids like serum, sputum, and urine from patients with cancerous neoplastic conditions and disease. For the purpose of biomarker screening, clinical samples have to be available. For obtaining a sufficient number of samples with clinical and "outcome" or survival data, the first step would be using archived (tissue) samples. Preferably these materials should fulfill the requirements to obtain intact RNA and DNA, but most archives of clinical samples are storing formalin fixed paraffin embedded (FFPE) tissue blocks. This has been the clinic-pathological routine done over decades, but that fixed samples are if at all only suitable for extraction of low quality of RNA. It has now been found that according to the present invention any such samples can be used for the method of generating an inventive subset, including fixed samples. The samples can be of lung, gastric, colorectal, brain, liver, bone, breast, prostate, ovarian, bladder, cervical, pancreas, kidney, thyroid, oesophaegeal, head and neck, neuroblastoma, skin, nasopharyngeal, endometrial, bile duct, oral, multiple myeloma, leukemia, soft tissue sarcoma, anal, gall bladder, endocrine, mesothelioma, wilms tumor, testis, bone, duodenum, neuroendocrine, salivary gland, larynx, choriocarcinoma, cardial, small bowel, eye, germ cell cancer. These cancers can then be subsequently diagnosed by the inventive set (or subsets).

The present invention provides a multiplexed methylation testing method which 1) outperforms the "classification" success when compared to genomewide screenings via RNA-expression profiling, 2) enables identification of biomarkers for a wide variety of diseases, without the need to prescreen candidate markers on a genomewide scale, and 3) is suitable for minimal invasive testing and 4) is easily scalable.

In contrast to the rational strategy for elucidation of biomarkers for differentiation of disease, the invention presents a targeted multiplexed DNA-methylation test which outperforms genome-scaled approaches (including RNA expression profiling) for disease diagnosis, classification, and prognosis.

The inventive set of 359 markers enables selection of a subset of markers from this 359 set which is highly characteristic of a given disease or tumor type. Preferably the disease is a neoplastic condition. However, not only cancer can be diagnosed with the inventive set or given selective subsets thereof, but a wide range of other diseases detected via the DNA methylation changes of the patient. Diseases can be genetic diseases of few, many or all cells in a subject patient (including cancer), or infectious diseases, which lead to altered gene regulation via DNA methylation, e.g. viral, in particular retroviral, infections. Preferably the disease is a trisomy, such as trisomy 21. Diseases, in particular neoplastic conditions, or tumor types include, without being limited thereto, cancer of different origin such as lung, gastric, colorectal, brain, liver, bone, breast, prostate, ovarian, bladder, cervical, pancreas, kidney, thyroid, oesophaegeal, head and neck, neuroblastoma, skin, nasopharyngeal, endometrial, bile duct, oral, multiple myeloma, leukemia, soft tissue sarcoma, anal, gall bladder, endocrine, mesothelioma, wilms tumor, testis, bone, duodenum, neuroendocrine, salivary gland, larynx, choriocarcinoma, cardial, small bowel, eye, germ cell cancer. Further indicators differentiating between diseases, neoplastic conditions or tumor types are e.g. benign (non (or limited) proliferative) or malignant, metastatic or non-metastatic tumors or nodules. It is sometimes possible to differentiate the sample type from which the methylated DNA is isolated, e.g. urine, blood, tissue samples.

The present invention is suitable to differentiate diseases, in particular neoplastic conditions, or tumor types. Diseases and neoplastic conditions should be understood in general including benign and malignant conditions. According to the present invention benign nodules (being at least the potential onset of malignancy) are included in the definition of a disease. After the development of a malignancy the condition is a preferred disease to be diagnosed by the markers screened for or used according to the present invention. The present invention is suitable to distinguish benign and malignant tumors (both being considered a disease according to the present invention). In particular the invention can provide markers (and their diagnostic or prognostic use) distinguishing between a normal healthy state together with a benign state on one hand and malignant states on the other hand. The invention is also suitable to differentiate between non-solid cancers including leukemia and healthy states. A diagnosis of a disease may include identifying the difference to a normal healthy state, e.g. the absence of any neoplastic nodules or cancerous cells. The present invention can also be used for prognosis of such conditions, in particular a prediction of the progression of a disease, such as a neoplastic condition, or tumor type. A particularly preferred use of the invention is to perform a diagnosis or prognosis of a metastasising neoplastic disease (distinguished from non-metastasising conditions).

In the context of the present invention "prognosis", "prediction" or "predicting" should not be understood in an absolute sense, as in a certainty that an individual will develop cancer or a disease or tumor type (including cancer progression), but as an increased risk to develop cancer or the disease or tumor type or of cancer progression. "Prognosis" is also used in the context of predicting disease progression, in particular to predict therapeutic results of a certain therapy of the disease, in particular neoplastic conditions, or tumor types. The prognosis of a therapy can e.g. be used to predict a chance of success (i.e. curing a disease) or chance of reducing the severity of the disease to a certain level. As a general inventive concept, markers screened for this purpose are preferably derived from sample data of patients treated according to the therapy to be predicted. The inventive marker sets may also be used to monitor a patient for the emergence of therapeutic results or positive disease progressions.

Some of the inventive, rationally selected markers have been found methylated in some instances. DNA methylation analyses in principle rely either on bisulfite deamination-based methylation detection or on using methylation sensitive restriction enzymes. Preferably the restriction enzyme-based strategy is used for elucidation of DNA-methylation changes. Further methods to determine methylated DNA are e.g. given in EP 1 369 493 A1 or U.S. Pat. No. 6,605,432. Combining restriction digestion and multiplex PCR amplification with a targeted microarray-hybridization is a particular advantageous strategy to perform the inventive methylation test using the inventive marker sets (or subsets). A microarray-hybridization step can be used for reading out the PCR results. For the analysis of the hybridization data statistical approaches for class comparisons and class prediction can be used. Such statistical methods are known from analysis of RNA-expression derived microarray data.

If only limiting amounts of DNA were available for analyses an amplification protocol can be used enabling selective amplification of the methylated DNA fraction prior methylation testing. Subjecting these amplicons to the methylation test, it was possible to successfully distinguish DNA from sensitive cases, e.g. distinguishing leukemia (CML) from normal healthy controls. In addition it was possible to distinguish breast-cancer patients from healthy normal controls using DNA from serum by the inventive methylation test upon preamplification. Both examples clearly illustrate that the inventive multiplexed methylation testing can be successfully applied when only limiting amounts of DNA are available. Thus, this principle might be the preferred method for minimal invasive diagnostic testing.

In most situations several genes are necessary for classification. Although the 359 marker set test is not a genome-wide test and might be used as it is for diagnostic testing, running a subset of markers—comprising the classifier which enables best classification—would be easier for routine applications. The test is easily scalable. Thus, to test only the subset of markers, comprising the classifier, the selected subset of primers/probes could be applied directly to set up of the lower multiplexed test (or single PCR-test). This was confirmed when serum DNA using a classifier for distinguishing healthy females from individuals with breast-tumors (or other specific tumors) was tested. Only the specific primers comprising the gene-classifier obtained from the methylation test were set up together in multiplexed PCR reactions. Data derived upon hybridization of PCR amplicons were in line with initial classification. Thus, correct classification with the down-scaled test using only a subset was possible.

In summary the inventive methylation test is a suitable tool for differentiation and classification of neoplastic disease. This assay can be used for diagnostic purposes and for defining biomarkers for clinical relevant issues to improve diagnosis of disease, and to classify patients at risk for disease progression, thereby improving disease treatment and patient management.

The first step of the inventive method of generating a subset, step a) of obtaining data of the methylation status, preferably comprises determining data of the methylation status, preferably by methylation specific PCR analysis, methylation specific digestion analysis. Methylation specific digestion analysis can include either or both of hybridization of suitable probes for detection to non-digested fragments or PCR amplification and detection of non-digested fragments.

The inventive selection can be made by any (known) classification method to obtain a set of markers with the given diagnostic (or also prognostic) value to categorize a certain disease or tumor type. Such methods include class comparisons wherein a specific p-value is selected, e.g. a p-value below 0.1, preferably below 0.08, more preferred below 0.06, in particular preferred below 0.05, below 0.04, below 0.02, most preferred below 0.01.

Preferably the correlated results for each gene b) are rated by their correct correlation to the disease or tumor type positive state, preferably by p-value test or t-value test or F-test. Rated (best first, i.e. low p- or t-value) markers are the subsequently selected and added to the subset until a certain diagnostic value is reached, e.g. the herein mentioned at least 70% (or more) correct classification of the disease or tumor type.

Class Comparison procedures include identification of genes that were differentially methylated among the two classes using a random-variance t-test. The random-variance t-test is an improvement over the standard separate t-test as it permits sharing information among genes about within-class variation without assuming that all genes have the same variance (Wright G. W. and Simon R, Bioinformatics 19:2448-2455, 2003). Genes were considered statistically significant if their p value was less than a certain value, e.g. 0.1 or 0.01. A stringent significance threshold can be used to limit the number of false positive findings. A global test can also be performed to determine whether the expression profiles differed between the classes by permuting the labels of which arrays corresponded to which classes. For each permutation, the p-values can be re-computed and the number of genes significant at the e.g. 0.01 level can be noted. The proportion of the permutations that give at least as many significant genes as with the actual data is then the significance level of the global test. If there are more than 2 classes, then the "F-test" instead of the "t-test" should be used.

Class Prediction includes the step of specifying a significance level to be used for determining the genes that will be included in the subset. Genes that are differentially methylated between the classes at a univariate parametric significance level less than the specified threshold are included in the set. It doesn't matter whether the specified significance level is small enough to exclude enough false discoveries. In some problems better prediction can be achieved by being more liberal about the gene sets used as features. The sets may be more biologically interpretable and clinically applicable, however, if fewer genes are included. Similar to cross-validation, gene selection is repeated for each training set created in the cross-validation process. That is for the purpose of providing an unbiased estimate of prediction error. The final model and gene set for use with future data is the one resulting from application of the gene selection and classifier fitting to the full dataset.

Models for utilizing gene methylation profile to predict the class of future samples can also be used. These models may be based on the Compound Covariate Predictor (Radmacher et al. Journal of Computational Biology 9:505-511, 2002), Diagonal Linear Discriminant Analysis (Dudoit et al. Journal of the American Statistical Association 97:77-87, 2002), Nearest Neighbor Classification (also Dudoit et al.), and Support Vector Machines with linear kernel (Ramaswamy et al. PNAS USA 98:15149-54, 2001). The models incorporated genes that were differentially methylated among genes at a given significance level (e.g. 0.01, 0.05 or 0.1) as assessed by the random variance t-test (Wright G. W. and Simon R. Bioinformatics 19:2448-2455, 2003). The prediction error of each model using cross validation, preferably leave-one-out cross-validation (Simon et al. Journal of the National Cancer Institute 95:14-18, 2003), is preferably estimated. For each leave-one-out cross-validation training set, the entire model building process was repeated, including the gene selection process. It may also be evaluated whether the cross-validated error rate estimate for a model was significantly less than one would expect from random prediction. The class labels can be randomly permuted and the entire leave-one-out cross-validation process is then repeated. The significance level is the proportion of the random permutations that gave a cross-validated error rate no greater than the cross-validated error rate obtained with the real methylation data. About 1000 random permutations may be usually used.

Another classification method is the greedy-pairs method described by Bo and Jonassen (Genome Biology 3(4): research0017.1-0017.11, 2002). The greedy-pairs approach starts with ranking all genes based on their individual t-scores on the training set. The procedure selects the best ranked gene $g_i$ and finds the one other gene $g_j$ that together with $g_i$ provides the best discrimination using as a measure the distance between centroids of the two classes with regard to the two genes when projected to the diagonal linear discriminant axis. These two selected genes are then removed from the gene set and the procedure is repeated on the remaining set until the specified number of genes have been selected. This method attempts to select pairs of genes that work well together to discriminate the classes.

Furthermore, a binary tree classifier for utilizing gene methylation profile can be used to predict the class of future samples. The first node of the tree incorporated a binary classifier that distinguished two subsets of the total set of classes. The individual binary classifiers were based on the "Support Vector Machines" incorporating genes that were differentially expressed among genes at the significance level (e.g. 0.01, 0.05 or 0.1) as assessed by the random variance t-test (Wright G. W. and Simon R. Bioinformatics 19:2448-2455, 2003). Classifiers for all possible binary partitions are evaluated and the partition selected was that for which the cross-validated prediction error was minimum. The process is then repeated successively for the two subsets of classes determined by the previous binary split. The prediction error of the binary tree classifier can be estimated by cross-validating the entire tree building process. This overall cross-validation included re-selection of the optimal partitions at each node and re-selection of the genes used for each cross-validated training set as described by Simon et al. (Simon et al. Journal of the National Cancer Institute 95:14-18, 2003). 10-fold cross validation in which one-tenth of the samples is withheld can be utilized, a binary tree developed on the remaining 9/10 of the samples, and then class membership is predicted for the 10% of the samples withheld. This is repeated 10 times, each time withholding a different 10% of the samples. The samples are randomly partitioned into 10 test sets (Simon R and Lam A. BRB-ArrayTools User Guide, version 3.2. Biometric Research Branch, National Cancer Institute).

Preferably the correlated results for each gene b) are rated by their correct correlation to the disease or tumor type positive state, preferably by p-value test. It is also possible to include a step in that the genes are selected d) in order of their rating.

Independent from the method that is finally used to produce a subset with certain diagnostic or predictive value, the subset selection preferably results in a subset with at least 60%, preferably at least 65%, at least 70%, at least 75%, at least 80% or even at least 85%, at least 90%, at least 92%, at least 95%, in particular preferred 100% correct classification of test samples of the disease or tumor type. Such levels can be reached by repeating c) steps a) and b) of the inventive method, if necessary.

To prevent increase of the number of the members of the subset, only marker genes with at least a significance value of at most 0.1, preferably at most 0.8, even more preferred at most 0.6, at most 0.5, at most 0.4, at most 0.2, or more preferred at most 0.01 are selected.

In particular preferred embodiments the at least 50 genes of step a) are at least 70, preferably at least 90, at least 100, at least 120, at least 140, at least 160, at least 180, at least 190, at least 200, at least 220, at least 240, at least 260, at least 280, at least 300, at least 320, at least 340, at least 350 or all, genes.

Since the subset should be small it is preferred that not more than 60, or not more than 40, preferably not more than 30, in particular preferred not more than 20, marker genes are selected in step d) for the subset.

In a further aspect the present invention provides a method of identifying a disease or tumor type in a sample comprising DNA from a patient, comprising providing a diagnostic subset of markers identified according to the method depicted above, determining the methylation status of the genes of the subset in the sample and comparing the methylation status with the status of a confirmed disease or tumor type positive and/or negative state, thereby identifying the disease or tumor type in the sample.

The methylation status can be determined by any method known in the art including methylation dependent bisulfite deamination (and consequently the identification of mC—methylated C—changes by any known methods, including PCR and hybridization techniques). Preferably, the methylation status is determined by methylation specific PCR analysis, methylation specific digestion analysis and either or both of hybridisation analysis to non-digested or digested fragments or PCR amplification analysis of non-digested fragments. The methylation status can also be determined by any probes suitable for determining the methylation status including DNA, RNA, PNA, LNA probes which optionally may further include methylation specific moieties.

As further explained below the methylation status can be particularly determined by using hybridisation probes or amplification primer (preferably PCR primers) specific for methylated regions of the inventive marker genes. Discrimination between methylated and non-methylated genes, including the determination of the methylation amount or ratio, can be performed by using e.g. either one of these tools.

The determination using only specific primers aims at specifically amplifying methylated (or in the alternative non-methylated) DNA. This can be facilitated by using (methylation dependent) bisulfite deamination, methylation specific enzymes or by using methylation specific nucleases to digest methylated (or alternatively non-methylated) regions—and consequently only the non-methylated (or alternatively methylated) DNA is obtained. By using a genome chip (or simply a gene chip including hybridization probes for all genes of interest such as all 359 marker genes), all amplification or non-digested products are detected. I.e. discrimination between methylated and non-methylated states as well as gene selection (the inventive set or subset) is before the step of detection on a chip.

Alternatively it is possible to use universal primers and amplify a multitude of potentially methylated genetic regions (including the genetic markers of the invention) which are, as described either methylation specific amplified or digested, and then use a set of hybridisation probes for the characteristic markers on e.g. a chip for detection. I.e. gene selection is performed on the chip.

Either set, a set of probes or a set of primers, can be used to obtain the relevant methylation data of the genes of the present invention. Of course, both sets can be used.

The method according to the present invention may be performed by any method suitable for the detection of methylation of the marker genes. In order to provide a robust and optionally re-useable test format, the determination of the gene methylation is preferably performed with a DNA-chip, real-time PCR, or a combination thereof. The DNA chip can be a commercially available general gene chip (also comprising a number of spots for the detection of genes not related to the present method) or a chip specifically designed for the method according to the present invention (which predominantly comprises marker gene detection spots).

Preferably the methylated DNA of the sample is detected by a multiplexed hybridization reaction. In further embodiments a methylated DNA is preamplified prior to hybridization, preferably also prior to methylation specific amplification, or digestion. Preferably, also the amplification reaction is multiplexed (e.g. multiplex PCR).

The inventive methods (for the screening of subsets or for diagnosis or prognosis of a disease or tumor type) are particularly suitable to detect low amounts of methylated DNA of the inventive marker genes. Preferably the DNA amount in the sample is below 500 ng, below 400 ng, below 300 ng, below 200 ng, below 100 ng, below 50 ng or even below 25 ng. The inventive method is particularly suitable to detect low concentrations of methylated DNA of the inventive marker genes. Preferably the DNA amount in the sample is below 500 ng, below 400 ng, below 300 ng, below 200 ng, below 100 ng, below 50 ng or even below 25 ng, per ml sample.

In another aspect the present invention provides a subset comprising or consisting of nucleic acid primers or hybridization probes being specific for a potentially methylated region of at least marker genes selected from one of the following groups a) CHRNA9, RPA2, CPEB4, CASP8, MSH2, ACTB, CTCFL, TPM2, SERPINB5, PIWIL4, NTF3, CDK2AP1
b) IGF2, KCNQ1, SCGB3A1, EFS, BRCA1, ITGA4, H19, PTTG1
c) KRT17, IGFBP7, RHOXF1, CLIC4, TP53, DLX2, ITGA4, AIM1L, SERPIN1, SERPIN2, TP53, XIST, TEAD1, CDKN2A, CTSD, OPCML, RPA2, BRCA2, CDH1, S100A9, SERPINB2, BCL2A1, UNC13B, ABL1, TIMP1, ATM, FBXW7, SFRP5, ACTB, MSX1, LOX, SOX15, DGKH, CYLD, XPA, XPC
d) NEUROD2, CTCFL, GBP2, SFN, MAGEB2, DIRAS3, ARMCX2, HRAS
e) SFN, DIRAS3, HRAS, ARMCX2, MAGEB2, GBP2, CTCFL, NEUROD2
f) PITX2, TJP2, CD24, ESR1, INFRSF10D, PRA3, RASSF1
g) GATA5, RASSF1, HIST1H2AG, NPTX1, UNC13B
h) SMAD3, NANOS1, TERT, BCL2, SPARC, SFRP2, MGMT, MYOD1, LAMA1
i) TJP2, CALCA, PITX2, TFPI2, CDKN2B
j) PITX2, INFRSF10D, PAX8, RAD23A, GJB2, F2R, TP53, NTHL1, TP53
k) ARRDC4, DUSP1, SMAD9, HOXA10, C3, ADRB2, BRCA2, SYK
l) PITX2, MT3, RPA3, INFRSF10D, PTEN, TP53, PAX8, TGFBR2, HIC1, CALCA, PSAT1, MBD2, NTF3, PLAGL1, F2R, GJB2, ARRDC4, NTHL1
m) MT3, RPA3, INFRSF10D, HOXA1, C13orf15, TGFBR2, HIC1, CALCA, PSAT1, NTF3, PLAGL1, F2R, GJB2, ARRDC4, NTHL1
n) PITX2, PAX8, CD24, TP53, ESR1, INFRSF10D, RAD23A, SCGB3A1. RARB, TP53, LZTS1
o) DUSP1, TFPI2, TJP2, S100A9, BAZ1A, CPEB4, AIM1L, CDKN2A, PITX2, ARPC1B, RPA3, SPARC, SFRP4, LZTS1, MSH4, PLAGL1, ABCB1, C13orf15, XIST, TDRD6, CCDC62, HOXA1, IRF4, HSD12B4, S100A9, MT3, KCNJ15, BCL2A1, S100A8, PITX2, THBD, NANOS1, SYK, SMAD2, GNAS, HRAS, RARRES1, APEX1, or
p) TJP2, CALCA, PITX2, PITX2, ESR1, EFSSMAD3, ARRDC4, CD24, FHL2, PITX2, RDHE2, KIF5B, C3, KRT17, RASSF1
q) CHRNA9, RPA2, CPEB4, CASP8, MSH2, ACTB, CTCFL, TPM2, SERPINB5, PIWIL4, NTF3, CDK2AP1
r) IGF2, KCNQ1, SCGB3A1, EFS, BRCA1, ITGA4, H19, PTTG1
s) KRT17, AQP3, TP53, ZNF462, NEUROG1, GATA3, MT1A, JUP, RGC32, SPINT2, DUSP1
t) NCL, XPA, MYOD1, Pitx2
u) SPARC, PIWIL4, SERPINB5, TEAD1, EREG, ZDHHC11, C5orf4
v) HSD17B4, DSP, SPARC, KRT17, SRGN, C5orf4, PIWIL4, SERPINB5, ZDHHC11, EREG
w) TIMP1, COL21A1, COL1A2, KL, CDKN2A
x) TIMP1, C0L21A1, COL1A2
y) BCL2A1, SERPINB2, SERPINE1, CLIC4, BCL2A1, ZNF256, ZNF573, GNAS, SERPINB2
z) TDRD6, XIST, LZTS1, IRF4
aa) TIMP1, COL21A1, COL1A2, KL, CDKN2A, Lamda,
bb) DSP, AR, IGF2, MSX1, SERPINE1
cc) FHL1, LMNA, GDNF
dd) FBXW7, GNAS, KRT14
ee) CHFR, AR, RBP1, MSX1, COL21A1, FHL1, RARB
ff) DCLRE1C, MLH1, RARB, OGG1, SNRPN, ITGA4
gg) FHL1, LMNA, GDNF
hh) FBXW7, GNAS, KRT14
ii) CHFR, AR, RBP1, MSX1, COL21A1, FHL1, RARB
jj) DCLRE1C, MLH1, RARB, OGG1, SNRPN, ITGA4
kk) SFN, DIRAS3, HRAS, ARMCX2, MAGEB2, GBP2, CTCFL, NEUROD2
ll) SFN, BAZ1A, DIRAS3, CTCFL, ARMCX2, GBP2, MAGEB2, NEUROD2
mm) DIRAS3, C5AR1, BAZ1A, SFN, ERCC1, SNRPN, PILRB, KRT17, CDKN2A, H19, EFS, TJP2, HRAS, NEUROD2, GBP2, CTCFL
nn) DIRAS3, C5AR1, SFN, BAZ1A, HIST1H2AG, XAB2, HOXA1, HIC1, GRIN2B, BRCA1, C13orf15, SLC25A31, CDKN2A, H19, EFS, TJP2, HRAS, NEUROD2, GBP2, CTCFL
oo) TFPI2, NEUROD2, DLX2, TTC3, TWIST1
pp) MAGEB2, MSH2, ARPC1B, NEUROD2, DDX18, PIWIL4, MSX1, COL1A2, ERCC4, GAD1, RDH10, TP53, APC, RHOXF1, ATM
qq) ACTB, EFS, CXADR, LAMC2, DNAJA4, CRABP1, PARP2, HIC1, MTHFR, S100A9, PTX2
rr) ACTB, EFS, CXADR, LAMC2, DNAJA4, PARP2, CRABP1, HIC1, SERPINI1, MTHFR, PITX2
ss) ACTB, EFS, PARP2, TP73, HIC1, BCL2A1, CRABP1, CXADR, BDNF, COL1A1
tt) EFS, ACTB, BCL2A1, TP73, HIC1, SERPINI1, CXADR
uu) ACTB, TP73, SERPINI1, CXADR, HIC1, BCL2A1, EFS
vv) FBXL13, PITX2, NKX2-1, IGF2, C5AR1, SPARC, RUNX3, CHST11, CHRNA9, ZNF462, HSD17B4, UNG, TJP2, ERBB2, SOX15, ERCC8, CDX1, ANXA3, CDH1, CHFR, TACSTD1, MT1A
ww) TP53, PTTG1, VHL, TP53, S100A2, ZNF573, RDH10, TSHR, MYO5C, MBD2, CPEB4, BRCA1, CD24, COL1A1, VDR, TP53, KLF4, ADRB2, ERCC2, SPINT2, XAB2, RB1, APEX1, RPA3, TP53, BRCA2, MSH2, BAZ1A, SPHK1, ERCC8, SER- PINI1, RPA2, SCGB3A1, MLH3, CDK2AP1, MT1G, PITX2, SFRP5, ZNF711, TGFBR2, C5AR1, DPH1, CDX1, GRIN2B, C5orf4, BOLL, HOXA1, NEUROD2, BCL2A1, ZNF502, FOXA2, MYOD1, HOXA10, TMEFF2, IQCG, LXN, SRGN, PTGS2, ONECUT2, PENK, PITX2, DLX2, SALL3, APC, APC, HIST1H2AG, ACTB, RASSF1, S100A9, TERT, TNFRSF25, HIC1, LAMC2, SPARC, WT1, PITX2, GNA15, ESR1, KL, HIC1 xx) HIC1, LAMC2, SPARC, WT1, PITX2, GNA15, KL, HIC1 yy) HIC1, KL, ESR1 or a set of at least 50%, preferably at least 60%, at least 70%, at least 80%, at least 90%, 100% of the markers of anyone of the above (a) to (yy). The present inventive set also includes sets with at least 50% of the above markers for each set since it is also possible to substitute parts of these subsets being specific for—in the case of binary conditions/differentiations—e.g. good or bad prognosis or distinguish between diseases or tumor types, wherein one part of the subset points into one direction for a certain tumor type or disease/differentiation. It is possible to further complement the 50% part of the set by additional markers specific for determining the other part of the good or bad differentiation or differentiation between two diseases or tumor types. Methods to determine such complementing markers follow the general methods as outlined herein.

Each of these marker subsets is particularly suitable to diagnose a certain disease or tumor type or distinguish between a certain disease or tumor type in a methylation specific assay of these genes.

Also provided is a set of nucleic acid primers or hybridization probes being specific for a potentially methylated region of marker genes selected from at least 180, preferably at least 200, more preferred at least 220, in particular preferred at least 240, even more preferred at least 260, most preferred at least 280, or even at least 300, preferably at least 320 or at least 340, or at least 360, marker genes of table 1. Of course the set may comprise even more primers or hybridization probes not given in table 1.

The inventive primers or probes may be of any nucleic acid, including RNA, DNA, PNA (peptide nucleic acids), LNA (locked nucleic acids). The probes might further comprise methylation specific moieties.

The present invention provides a (master) set of 360 marker genes, further also specific gene locations by the PCR products of these genes wherein significant methylation can be detected, as well as subsets therefrom with a certain diagnostic value to distinguish specific disease or tumor type. Preferably the set is optimized for a certain disease or tumor type. Cancer types include, without being limited thereto, cancer of different origin such as leukemia, a soft tissue cancer, for example breast cancer, colorectal cancer, head or neck cancer, cervical, prostate, thyroid, brain, eye or pancreatic cancer. Further indicators differentiating between disease or tumor type are e.g. benign (non (or limited) proliferative) or malignant, metastatic or non-metastatic. The set can also be optimized for a specific sample type in which the methylated DNA is tested. Such samples include blood, urine, saliva, hair, skin, tissues, in particular tissues of the cancer origin mentioned above, in particular breast or thyroid tissue. The sample my be obtained from a patient to be diagnosed. In preferred embodiments the test sample to be used in the method of identifying a subset is from the same type as a sample to be used in the diagnosis.

In practice, probes specific for potentially aberrant methylated regions are provided, which can then be used for the diagnostic method.

It is also possible to provide primers suitable for a specific amplification, like PCR, of these regions in order to perform a diagnostic test on the methylation state.

Such probes or primers are provided in the context of a set corresponding to the inventive marker genes or marker gene loci as given in table 1.

Such a set of primers or probes may have all 359 inventive markers present and can then be used for a multitude of different cancer detection methods. Of course, not all markers would have to be used to diagnose a certain disease or tumor type. It is also possible to use certain subsets (or combinations thereof) with a limited number of marker probes or primers for diagnosis of certain categories of cancer.

Therefore, the present invention provides sets of primers or probes comprising primers or probes for any single marker subset or any combination of marker subsets disclosed herein. In the following sets of marker genes should be understood to include sets of primer pairs and probes therefor, which can e.g. be provided in a kit.

Set a, CHRNA9, RPA2, CPEB4, CASP8, MSH2, ACTB, CTCFL, TPM2, SERPINB5, PIWIL4, NTF3, CDK2AP1 and sets with at least 50%, preferably at least 60%, at least 70%, at least 80% or at least 90% of these markers are in particular suitable to detect breast cancer and to distinguish between normal breast tissue, ductal and lobular breast carcinomas.

Set b, IGF2, KCNQ1, SCGB3A1, EFS, BRCA1, ITGA4, H19, PTTG1 and sets with at least 50%, preferably at least 60%, at least 70%, at least 80% or at least 90% of these markers are also suitable to detect breast cancer and to distinguish between normal breast tissue, ductal and lobular breast carcinomas.

Set c, KRT17, IGFBP7, RHOXF1, CLIC4, TP53, DLX2, ITGA4, AIM1L, SERPIN1, SERPIN2, TP53, XIST, TEAD1, CDKN2A, CTSD, OPCML, RPA2, BRCA2, CDH1, S100A9, SERPINB2, BCL2A1, UNC13B, ABL1, TIMP1, ATM, FBXW7, SFRP5, ACTB, MSX1, LOX, SOX15, DGKH, CYLD, XPA, XPC and sets with at least 50%, preferably at least 60%, at least 70%, at least 80% or at least 90% of these markers are suitable to diagnose neoplastic disease (chronic myeloid leukemia).

Set d, NEUROD2, CTCFL, GBP2, SFN, MAGEB2, DIRAS3, ARMCX2, HRAS and sets with at least 50%, preferably at least 60%, at least 70%, at least 80% or at least 90% of these markers are in particular suitable to detect minimal invasive cancer, in particular breast cancer.

Set e, SFN, DIRAS3, HRAS, ARMCX2, MAGEB2, GBP2, CTCFL, NEUROD2 and sets with at least 50%, preferably at least 60%, at least 70%, at least 80% or at least 90% of these markers are also suitable to detect cancer in limiting amounts of DNA, e.g. using minimal invasive testing using DNA from serum, in particular breast cancer.

Set f, PITX2, TJP2, CD24, ESR1, INFRSF10D, PRA3, RASSF1 and sets with at least 50%, preferably at least 60%, at least 70%, at least 80% or at least 90% of these markers can be used to diagnose thyroid carcinoma and distinguish between normal or benign states (including struma nodosa and follicular adenoma) and malign states (in particular follicular thyroid carcinoma, papillary thyroid carcinoma).

Set g, GATA5, RASSF1, HIST1H2AG, NPTX1, UNC13B and sets with at least 50%, preferably at least 60%, at least 70%, at least 80% or at least 90% of these markers can be used to diagnose thyroid carcinoma and distinguish between normal tissue against the sum of benign states (including struma nodosa and follicular adenoma) and malign states (in particular follicular thyroid carcinoma, papillary thyroid carcinoma and medullary thyroid carcinoma).

Set h, SMAD3, NANOS1, TERT, BCL2, SPARC, SFRP2, MGMT, MYOD1, LAMA1 and sets with at least 50%, preferably at least 60%, at least 70%, at least 80% or at least 90% of these markers can be used to diagnose thyroid carcinoma and distinguish between normal or benign states (including struma nodosa and follicular adenoma) together with malign states (in particular follicular thyroid carcinoma and papillary thyroid carcinoma) against medullary thyroid carcinoma.

Set i, TJP2, CALCA, PITX2, TFPI2, CDKN2B and sets with at least 50%, preferably at least 60%, at least 70%, at least 80% or at least 90% of these markers can be used to diagnose thyroid carcinoma and distinguish between malign states (in particular follicular thyroid carcinoma and papillary thyroid carcinoma) together with follicular adenoma against struma nodosa.

Set j, PITX2, INFRSF10D, PAX8, RAD23A, GJB2, F2R, TP53, NTHL1, TP53 and sets with at least 50%, preferably at least 60%, at least 70%, at least 80% or at least 90% of these markers can be used to diagnose thyroid carcinoma and distinguish between follicular adenoma (benign) and malign states selected from follicular thyroid carcinoma and papillary thyroid carcinoma.

Set k, ARRDC4, DUSP1, SMAD9, HOXA10, C3, ADRB2, BRCA2, SYK and sets with at least 50%, preferably at least 60%, at least 70%, at least 80% or at least 90% of these markers can be used to diagnose thyroid carcinoma and distinguish between follicular thyroid carcinoma and papillary thyroid carcinoma.

Set 1, PITX2, MT3, RPA3, INFRSF10D, PTEN, TP53, PAX8, TGFBR2, HIC1, CALCA, PSAT1, MBD2, NTF3, PLAGL1, F2R, GJB2, ARRDC4, NTHL1 and sets with at least 50%, preferably at least 60%, at least 70%, at least 80% or at least 90% of these markers can be used to diagnose thyroid carcinoma and distinguish between follicular adenoma (benign) and follicular thyroid carcinoma (malign).

Set m, MT3, RPA3, INFRSF10D, HOXA1, C13orf15, TGFBR2, HIC1, CALCA, PSAT1, NTF3, PLAGL1, F2R, GJB2, ARRDC4, NTHL1 and sets with at least 50%, preferably at least 60%, at least 70%, at least 80% or at least 90% of these markers can be used to diagnose thyroid carcinoma and distinguish between follicular adenoma (benign) and follicular thyroid carcinoma (malign).

Set n, PITX2, PAX8, CD24, TP53, ESR1, INFRSF10D, RAD23A, SCGB3A1, RARB, TP53, LZTS1 and sets with at least 50%, preferably at least 60%, at least 70%, at least 80% or at least 90% of these markers can be used to diagnose thyroid carcinoma and distinguish between follicular adenoma (benign) and papillary thyroid carcinoma (malign).

Set o, DUSP1, TFPI2, TJP2, S100A9, BAZ1A, CPEB4, AIM1L, CDKN2A, PITX2, ARPC1B, RPA3, SPARC, SFRP4, LZTS1, MSH4, PLAGL1, ABCB1, C13orf15, XIST, TDRD6, CCDC62, HOXA1, IRF4, HSD12B4, S100A9, MT3, KCNJ15, BCL2A1, S100A8, PITX2, THBD, NANOS1, SYK, SMAD2, GNAS, HRAS, RARRES1, APEX1 and sets with at least 50%, preferably at least 60%, at least 70%, at least 80% or at least 90% of these markers can be used to diagnose thyroid carcinoma and distinguish between struma nodosa (benign) and follicular thyroid carcinoma (malign).

Set p, TJP2, CALCA, PITX2, PITX2, ESR1, EFS, SSMAD3, ARRDC4, CD24, FHL2, PITX2, RDHE2, KIF5B, C3, KRT17, RASSF1 and sets with at least 50%, preferably at least 60%, at least 70%, at least 80% or at least 90% of these markers can be used to diagnose thyroid carcinoma and distinguish between struma nodosa (benign) and papillary thyroid carcinoma (malign).

Set q, CHRNA9, RPA2, CPEB4, CASP8, MSH2, ACTB, CTCFL, TPM2, SERPINB5, PIWIL4, NTF3, CDK2AP1 and sets with at least 50%, preferably at least 60%, at least 70%, at least 80% or at least 90% of these markers can be used to diagnose breast cancer, distinguish between breast cancer and healthy breast tissue and additionally to distinguish non malignant breast tissue from lobular breast carcinoma and ductal breast carcinoma.

Set r, IGF2, KCNQ1, SCGB3A1, EFS, BRCA1, ITGA4, H19, PTTG1 and sets with at least 50%, preferably at least 60%, at least 70%, at least 80% or at least 90% of these markers can be used to diagnose breast cancer, distinguish between breast cancer and healthy breast tissue and additionally to distinguish lobular breast carcinoma from ductal breast carcinoma.

Set s, KRT17, AQP3, TP53, ZNF462, NEUROG1, GATA3, MT1A, JUP, RGC32, SPINT2, DUSP1 and sets with at least 50%, preferably at least 60%, at least 70%, at least 80% or at least 90% of these markers can be used to diagnose breast cancer, distinguish between breast cancer and healthy breast tissue and additionally to distinguish non malignant breast tissue from lobular breast carcinoma and ductal breast carcinoma.

Set t, NCL, XPA, MYOD1, Pitx2 and sets with at least 50%, preferably at least 60%, at least 70%, at least 80% or at least 90% of these markers can be used to diagnose breast cancer, distinguish between breast cancer and healthy breast tissue and additionally to distinguish lobular breast carcinoma from ductal breast carcinoma.

Set u, SPARC, PIWIL4, SERPINB5, TEAD1, EREG, ZDHHC11, C5orf4 and sets with at least 50%, preferably at least 60%, at least 70%, at least 80% or at least 90% of these markers can be used to diagnose breast cancer and is additionally particularly suitable to distinguish between metastasising and non-metastasising cancer.

Set v, HSD17B4, DSP, SPARC, KRT17, SRGN, C5orf4, PIWIL4, SERPINB5, ZDHHC11, EREG and sets with at least 50%, preferably at least 60%, at least 70%, at least 80% or at least 90% of these markers can be used to diagnose breast cancer and is additionally particularly suitable to distinguish between metastasising and non-metastasising cancer.

Set w, TIMP1, COL21A1, COL1A2, KL, CDKN2A and sets with at least 50%, preferably at least 60%, at least 70%, at least 80% or at least 90% of these markers can be used to diagnose breast cancer and is additionally particularly suitable to distinguish between metastasising and non-metastasising cancer.

Set x, TIMP1, COL21A1, COL1A2 and sets with at least 50%, preferably at least 60%, at least 70%, at least 80% or at least 90% of these markers can be used to diagnose breast cancer and is additionally particularly suitable to distinguish between metastasising and non-metastasising cancer.

Set y, BCL2A1, SERPINB2, SERPINE1, CLIC4, BCL2A1, ZNF256, ZNF573, GNAS, SERPINB2 and sets with at least 50%, preferably at least 60%, at least 70%, at least 80% or at least 90% of these markers can be used to diagnose breast cancer and is additionally particularly suitable to distinguish between metastasising and non-metastasising cancer.

Set z, TDRD6, XIST, LZTS1, IRF4 and sets with at least 50%, preferably at least 60%, at least 70%, at least 80% or at least 90% of these markers can be used to diagnose breast cancer and is additionally particularly suitable to distinguish between metastasising and non-metastasising cancer.

Set aa, TIMP1, COL21A1, COL1A2, KL, CDKN2A and sets with at least 50%, preferably at least 60%, at least 70%, at least 80% or at least 90% of these markers can be used to diagnose cancerous metastases in bone, liver and lung and is additionally particularly suitable to distinguish between metastasising and non-metastasising cancer, in particular from primary breast cancer.

Set bb, DSP, AR, IGF2, MSX1, SERPINE1, and sets with at least 50%, preferably at least 60%, at least 70%, at least 80% or at least 90% of these markers can be used to diagnose cancerous metastases in bone, liver and lung and is additionally particularly suitable to distinguish between metastasising cancer in liver from metastasising cancer in bone and lung, in particular from primary beast cancer.

Set cc, FHL1, LMNA, GDNF and sets with at least 50%, preferably at least 60%, at least 70%, at least 80% or at least 90% of these markers can be used to diagnose cancer in bone, liver and lung and to distinguish between metastasising and non-metastasising cancer, in particular to distinguish metastases in liver from metastases in bone, and lung.

Set dd, FBXW7, GNAS, KRT14 and sets with at least 50%, preferably at least 60%, at least 70%, at least 80% or at least 90% of these markers can be used to diagnose cancer in bone, liver and lung and to distinguish between metastasising and non-metastasising cancer, in particular to distinguish metastases in liver and bone from metastases in lung.

Set ee, CHFR, AR, RBP1, MSX1, COL21A1, FHL1, RARB and sets with at least 50%, preferably at least 60%, at least 70%, at least 80% or at least 90% of these markers can be used to diagnose cancer in bone and liver and to distinguish between metastasising and non-metastasising cancer, in particular to distinguish metastases in bone from metastases in liver.

Set ff, DCLRE1C, MLH1, RARB, OGG1, SNRPN, ITGA4 and sets with at least 50%, preferably at least 60%, at least 70%, at least 80% or at least 90% of these markers can be used to diagnose cancer in liver and to distinguish between metastasising and non-metastasising cancer, in particular to distinguish metastasising liver cancer and non-metastasising cancer.

Set gg, FHL1, LMNA, GDNF and sets with at least 50%, preferably at least 60%, at least 70%, at least 80% or at least 90% of these markers can be used to diagnose cancer in bone, liver and lung and to distinguish between metastasising and non-metastasising cancer, in particular to distinguish metastases in liver from metastases in bone, and lung.

Set hh, FBXW7, GNAS, KRT14 and sets with at least 50%, preferably at least 60%, at least 70%, at least 80% or at least 90% of these markers can be used to diagnose cancer in bone, liver and lung and to distinguish between metastasising and non-metastasising cancer, in particular to distinguish metastases in liver and bone from metastases in lung.

Set ii, CHFR, AR, RBP1, MSX1, COL21A1, FHL1, RARB and sets with at least 50%, preferably at least 60%, at least 70%, at least 80% or at least 90% of these markers can be used to diagnose cancer in bone and liver and to distinguish between metastasising and non-metastasising cancer, in particular to distinguish metastases in bone from metastases in liver.

Set jj, DCLRE1C, MLH1, RARB, OGG1, SNRPN, ITGA4 and sets with at least 50%, preferably at least 60%, at least 70%, at least 80% or at least 90% of these markers can be used to diagnose cancer in liver and to distinguish between metastasising and non-metastasising cancer, in particular to distinguish metastasising liver cancer and non-metastasising cancer.

Set kk, SFN, DIRAS3, HRAS, ARMCX2, MAGEB2, GBP2, CTCFL, NEUROD2 and sets with at least 50%, preferably at least 60%, at least 70%, at least 80% or at least 90% of these markers can be used to identify breast cancer in particular in serum samples.

Set ll, SFN, BAZ1A, DIRAS3, CTCFL, ARMCX2, GBP2, MAGEB2, NEUROD2 and sets with at least 50%, preferably at least 60%, at least 70%, at least 80% or at least 90% of these markers can be used to identify breast cancer in particular in serum samples.

Set mm, DIRAS3, C5AR1, BAZ1A, SFN, ERCC1, SNRPN, PILRB, KRT17, CDKN2A, H19, EFS, TJP2, HRAS, NEUROD2, GBP2, CTCFL and sets with at least 50%, preferably at least 60%, at least 70%, at least 80% or at least 90% of these markers can be used to identify breast cancer in particular in serum samples.

Set nn, DIRAS3, C5AR1, SFN, BAZ1A, HIST1H2AG, XAB2, HOXA1, HIC1, GRIN2B, BRCA1, C13orf15, SLC25A31, CDKN2A, H19, EFS, TJP2, HRAS, NEUROD2, GBP2, CTCFL and sets with at least 50%, preferably at least 60%, at least 70%, at least 80% or at least 90% of these markers can be used to distinguish between nodule positive conditions (malign and benign tumors) and normal controls, in particular in serum samples.

Set oo, TFPI2, NEUROD2, DLX2, TTC3, TWIST1 and sets with at least 50%, preferably at least 60%, at least 70%, at least 80% or at least 90% of these markers can be used to distinguish between no metastasis and present metastasis conditions in breast cancer.

Set pp, MAGEB2, MSH2, ARPC1B, NEUROD2, DDX18, PIWIL4, MSX1, COL1A2, ERCC4, GAD1, RDH10, TP53, APC, RHOXF1, ATM and sets with at least 50%, preferably at least 60%, at least 70%, at least 80% or at least 90% of these markers can be used to predict the emergence of metastasis in breast cancer patients, in particular in patients that are currently diagnosed not to have metastasis. The emergence of a different metastasis can be e.g. within four months, within six months, within eight months, within one year or within eighteen months.

Set qq, ACTB, EFS, CXADR, LAMC2, DNAJA4, CRABP1, PARP2, HIC1, MTHFR, S100A9, PTX2 and sets with at least 50%, preferably at least 60%, at least 70%, at least 80% or at least 90% of these markers can be used to diagnose trisomy 21, in particular in both male and female patients.

Set rr, ACTB, EFS, CXADR, LAMC2, DNAJA4, PARP2, CRABP1, HIC1, SERPINI1, MTHFR, PITX2 and sets with at least 50%, preferably at least 60%, at least 70%, at least 80% or at least 90% of these markers can be used to diagnose trisomy 21 and to distinguish between normal and trisomy samples.

Set ss, ACTB, EFS, PARP2, TP73, HIC1, BCL2A1, CRABP1, CXADR, BDNF, COL1A1 and sets with at least 50%, preferably at least 60%, at least 70%, at least 80% or at least 90% of these markers can be used to distinguish normal from trisomy patients, in particular trisomy 21 patients.

Set tt, EFS, ACTB, BCL2A1, TP73, HIC1, SERPINI1, CXADR and sets with at least 50%, preferably at least 60%, at least 70%, at least 80% or at least 90% of these markers can be used to distinguish normal from trisomy, in particular trisomy 21 patients.

Set uu, ACTB, TP73, SERPINI1, CXADR, HIC1, BCL2A1, EFS and sets with at least 50%, preferably at least 60%, at least 70%, at least 80% or at least 90% of these markers can be used to distinguish normal from trisomy, in particular trisomy 21 patients.

In preferred embodiments the genes common to sets qq), rr), ss), tt) and uu) are used to diagnose trisomy, in particular trisomy 21.

Set vv, FBXL13, PITX2, NKX2-1, IGF2, C5AR1, SPARC, RUNX3, CHST11, CHRNA9, ZNF462, HSD17B4, UNG, TJP2, ERBB2, SOX15, ERCC8, CDX1, ANXA3, CDH1, CHFR, TACSTD1, MT1A and sets with at least 50%, preferably at least 60%, at least 70%, at least 80% or at least 90% of these markers can be used to diagnose arthritis, in particular osteoarthritis, and to distinguish arthritic DNA from healthy (non-arthritic) DNA, in particular DNA from cartilage tissue, or bone samples, e.g. subchondral bone.

Set ww, TP53, PTTG1, VHL, TP53, S100A2, ZNF573, RDH10, TSHR, MYO5C, MBD2, CPEB4, BRCA1, CD24, COL1A1, VDR, TP53, KLF4, ADRB2, ERCC2, SPINT2, XAB2, RB1, APEX1, RPA3, TP53, BRCA2, MSH2, BAZ1A, SPHK1, ERCC8, SERPINI1, RPA2, SCGB3A1, MLH3, CDK2AP1, MT1G, PITX2, SFRP5, ZNF711, TGFBR2, C5AR1, DPH1, CDX1, GRIN2B, C5orf4, BOLL, HOXA1, NEUROD2, BCL2A1, ZNF502, FOXA2, MYOD1, HOXA10, TMEFF2, IQCG, LXN, SRGN, PTGS2, ONECUT2, PENK, PITX2, DLX2, SALL3, APC, APC, HIST1H2AG, ACTB, RASSF1, S100A9, TERT, TNFR5F25, HIC1, LAMC2, SPARC, WT1, PITX2, GNA15, ESR1, KL, HIC1 and sets with at least 50%, preferably at least 60%, at least 70%, at least 80% or at least 90% of these markers can be used to diagnose breast cancer, in particular by using blood samples or samples derived from blood, including serum. In particular, this set is suitable to distinguish between cancerous cells of breast cancer and normal blood samples. This set allows an easy blood test, which may comprise disseminated cancerous cells. The present invention furthermore provides additional subsets suitable to detect and diagnose breast cancer by using any at least 3, at least 4, at least 5, at least 6, at least 7, at least 8, at least 9, at least 10 or more markers of the above set ww. These sub-subsets have been preferably validated according to any methods disclosed therein, in particular any cross-validation methods providing a positive classification for the diagnosis of breast cancer (in comparison to non cancerous samples) as mentioned above for step d), in particular having a p-value of less than 0.1, preferably less than 0.05, even more preferred less than 0.01, in a random-variance t-test.

Set xx, HIC1, LAMC2, SPARC, WT1, PITX2, GNA15, KL, HIC1 and sets with at least 50%, preferably at least 60%, at least 70%, at least 80% or at least 90% of these markers can be used to diagnose breast cancer, in particular by using blood samples or samples derived from blood, including serum. In particular, this set is suitable to distinguish between cancerous cells of breast cancer and normal blood samples. This set allows an easy blood test, which may comprise disseminated cancerous cells. Preferably, the set is used in a test together with control markers such as MARK1, PARP1, NHLH2, PSEN2, MTHFR, POS Biotin Control RET, DUSP10.

Set yy, HIC1, KL, ESR1 and sets with at least 50%, preferably at least 60%, at least 70%, at least 80% or at least 90% of these markers can be used to diagnose breast cancer, in particular by using blood samples or samples derived from blood, including serum. In particular, this set is suitable to distinguish between cancerous cells of breast cancer and normal blood samples. This set allows an easy blood test, which may comprise disseminated cancerous cells.

Also provided are combinations of the above mentioned subsets a) to yy), in particular sets comprising markers of 2, 3, 4, 5, 6, 7, 8, 9, 10, 11, 12, 13, 14, 15 or more of these subsets, preferably for the same disease or tumor type like breast, lung, liver, bone or thyroid cancer or trisomy 21 or arthritis, preferably complete sets a) to yy).

According to a preferred embodiment of the present invention, the methylation of at least two genes, preferably of at least three genes, especially of at least four genes, is determined. Specifically if the present invention is provided as an array test system, at least ten, especially at least fifteen genes, are preferred. In preferred test set-ups (for example in microarrays ("gene-chips")) preferably at least 20, even more preferred at least 30, especially at least 40 genes, are provided as test markers. As mentioned above, these markers or the means to test the markers can be provided in a set of probes or a set of primers, preferably both.

In a further embodiment the set comprises up to 100000, up to 90000, up to 80000, up to 70000, up to 60000 or 50000 probes or primer pairs (set of two primers for one amplification product), preferably up to 40000, up to 35000, up to 30000, up to 25000, up to 20000, up to 15000, up to 10000, up to 7500, up to 5000, up to 3000, up to 2000, up to 1000, up to 750, up to 500, up to 400, up to 300, or even more preferred up to 200 probes or primers of any kind, particular in the case of immobilized probes on a solid surface such as a chip.

In certain embodiments the primer pairs and probes are specific for a methylated upstream region of the open reading frame of the marker genes.

Preferably the probes or primers are specific for a methylation in the genetic regions defined by SEQ ID NOs 1081 to 1440, including the adjacent up to 500 base pairs, preferably up to 300, up to 200, up to 100, up to 50 or up to 10 adjacent, corresponding to gene marker IDs 1 to 359 of table 1, respectively. I.e. probes or primers of the inventive set (including the full 359 set, as well as subsets and combinations thereof) are specific for the regions and gene loci identified in table 1, last column with reference to the sequence listing, SEQ ID NOs: 1081 to 1440. As can be seen these SEQ IDs correspond to a certain gene, the latter being a member of the inventive sets, in particular of the subsets a) to yy), e.g.

Examples of specific probes or primers are given in table 1 with reference to the sequence listing, SEQ ID NOs 1 to 1080, which form especially preferred embodiments of the invention.

Preferably the set of the present invention comprises probes or primers for at least one gene or gene product of the list according to table 1, wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, especially preferred at least 100%, of the total probes or primers are probes or primers for genes of the list according to table 1. Preferably the set, in particular in the case of a set of hybridization probes, is provided immobilized on a solid surface, preferably a chip or in form of a microarray. Since—according to current technology—detection means for genes on a chip allow easier and more robust array design, gene chips using DNA molecules (for detection of methylated DNA in the sample) is a preferred embodiment of the present invention. Such gene chips also allow detection of a large number of nucleic acids.

Preferably the set is provided on a solid surface, in particular a chip, whereon the primers or probes can be immobilized. Solid surfaces or chips may be of any material suitable for the immobilization of biomolecules such as the moieties, including glass, modified glass (aldehyde modified) or metal chips.

The primers or probes can also be provided as such, including lyophilized forms or being in solution, preferably with suitable buffers. The probes and primers can of course be provided in a suitable container, e.g. a tube or micro tube.

The present invention also relates to a method of identifying a disease or tumor type in a sample comprising DNA from a subject or patient, comprising obtaining a set of nucleic acid primers (or primer pairs) or hybridization probes as defined above (comprising each specific subset or combinations thereof), determining the methylation status of the genes in the sample for which the members of the set are specific for and comparing the methylation status of the genes with the status of a confirmed disease or tumor type positive and/or negative state, thereby identifying the disease or tumor type in the sample. In general the inventive method has been described above and all preferred embodiments of such methods also apply to the method using the set provided herein.

The inventive marker set, including certain disclosed subsets and subsets, which can be identified with the methods disclosed herein, are suitable to distinguish between lung, gastric, colorectal, brain, liver, bone, breast, prostate, ovarian, bladder, cervical, pancreas, kidney, thyroid, oesophaegeal, head and neck, neuroblastoma, skin, nasopharyngeal, endometrial, bile duct, oral, multiple myeloma, leukemia, soft tissue sarcoma, anal, gall bladder, endocrine, mesothelioma, wilms tumor, testis, bone, duodenum, neuroendocrine, salivary gland, larynx, choriocarcinoma, cardial, small bowel, eye, germ cell cancer, cancer from benign conditions, in particular for diagnostic or prognostic uses. Preferably the markers used (e.g. by utilizing primers or probes of the inventive set) for the inventive diagnostic or prognostic method may be used in smaller amounts than e.g. in the set (or kit) or chip as such, which may be designed for more than one fine tuned diagnosis or prognosis. The markers used for the diagnostic or prognostic method may be up to 100000, up to 90000, up to 80000, up to 70000, up to 60000 or 50000, preferably up to 40000, up to 35000, up to 30000, up to 25000, up to 20,000, up to 15000, up to 10000, up to 7500, up to 5000, up to 3000, up to 2000, up to 1000, up to 750, up to 500, up to 400, up to 300, up to 200, up to 100, up to 80, or even more preferred up to 60.

The inventive marker set, including certain disclosed subsets, which can be identified with the methods disclosed herein, are suitable to distinguish between thyroid cancer from benign thyroid tissue, in particular for diagnostic or prognostic uses.

The inventive marker set, including certain disclosed subsets, which can be identified with the methods disclosed herein, are suitable to distinguish between breast cancer from normal tissue and benign breast tumors, in particular for diagnostic or prognostic uses.

The inventive marker set, including certain disclosed subsets, which can be identified with the methods disclosed herein, are suitable to distinguish between hereditary from sporadic breast cancer, in particular for diagnostic or prognostic uses.

The inventive marker set, including certain disclosed subsets, which can be identified with the methods disclosed herein, are suitable to distinguish between breast cancer responsive to herceptin treatment from likely non-responders, in particular for diagnostic or prognostic uses.

The present invention is further illustrated by the following figures and examples, without being restricted thereto.

FIGURES

FIG. 1: A 961 gene classifier derived from genome-wide expression profiling enables differentiation of a group of patients with (yes) and without (no) metastases during follow up of patients suffering from breast cancer upon analyses of primary tumor tissues. Dendrogramm obtained from clustering experiments using centered correlation (values shown on the vertical axis).

Figure 2:
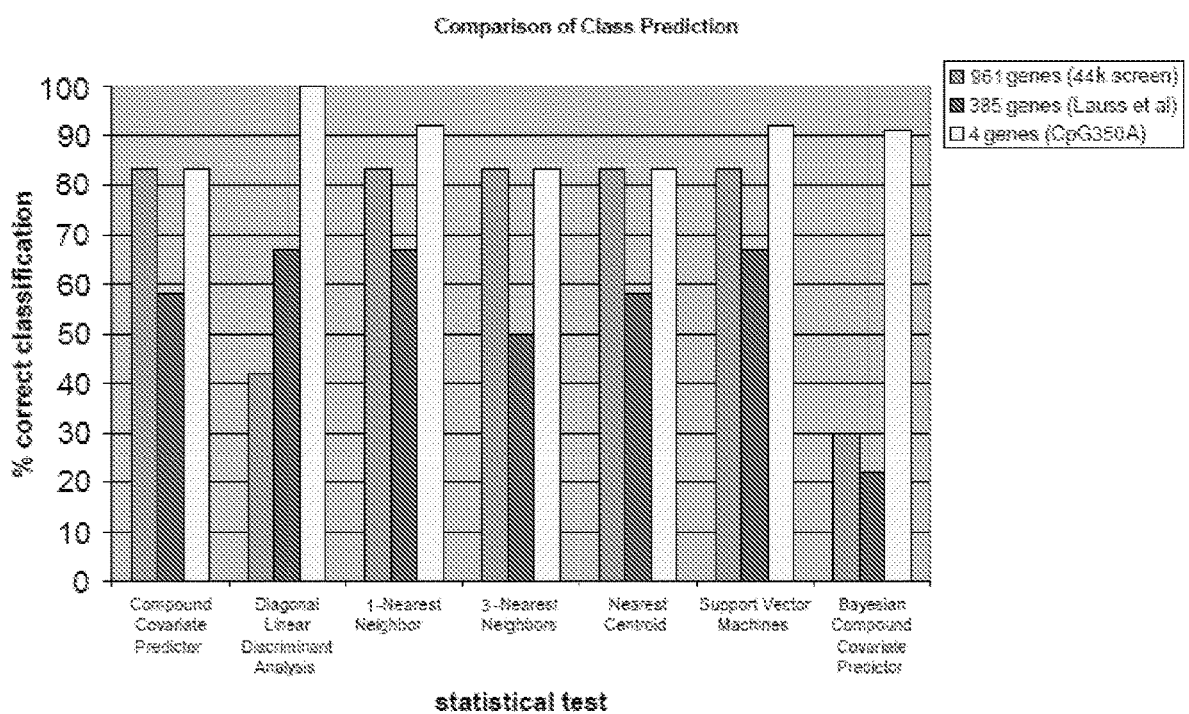

FIG. 2: Performance of expression profiling versus CpG360 methylation. Correct classification (%) using 7 different classification tests is depicted from a 961 gene-classifier, a targeted set of 385 genes (Lauss 2007), and a 4 gene DNA-methylation classifier derived from the methylation test (Cp-G360A). Although consisting of only 4 genes, the methylation based classifier performs best.

Figure 3:
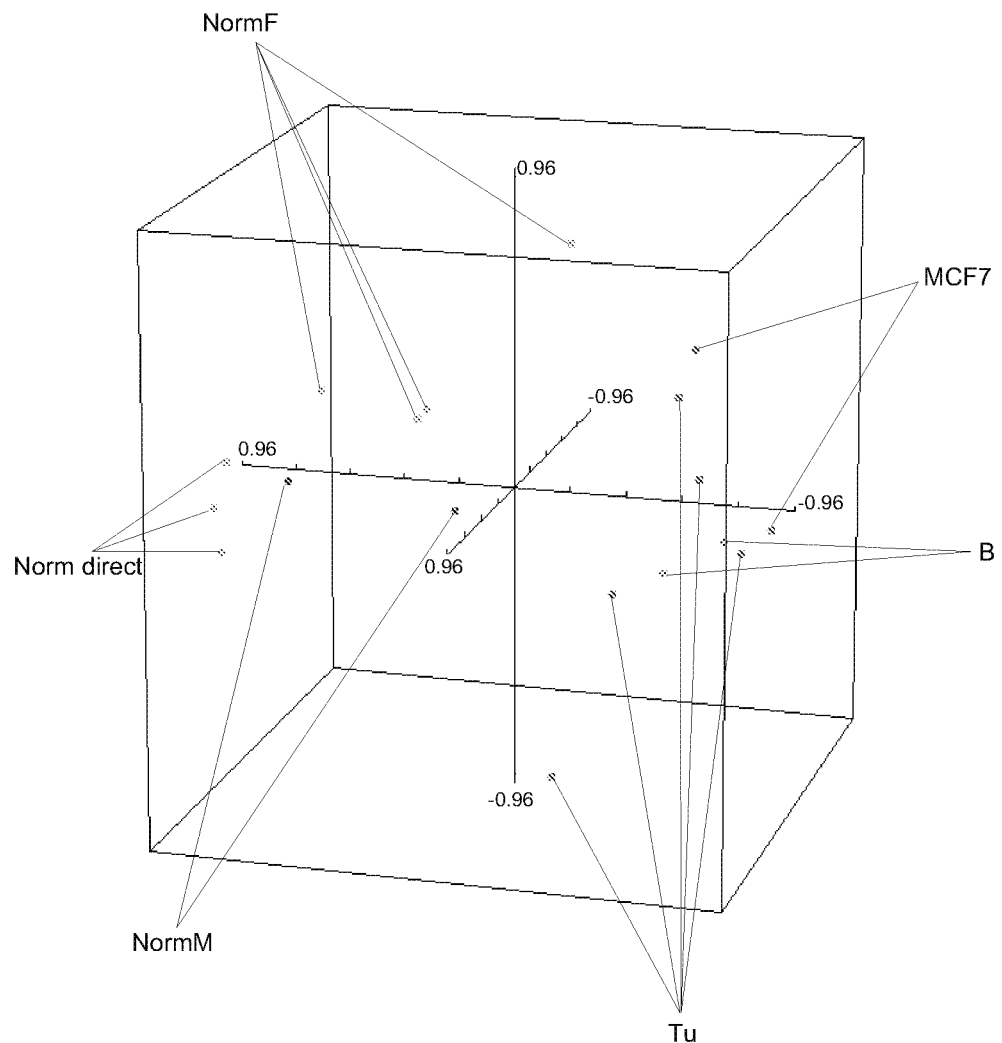

FIG. 3: Multidimensional scaling using the 19 gene classifier for serum testing of breast tumors illustrates good classification of tumor versus healthy controls. Methylation data from DNA-samples of benign tumors (B), the breast cancer cell line MCF7, normal females (NormF) and males (NormM) and several breast cancer patients (Tu) were derived from DNA upon preamplification of the methylated DNA; several normal controls (Norm_direct) were tested without preamplification.

Figure 4A:
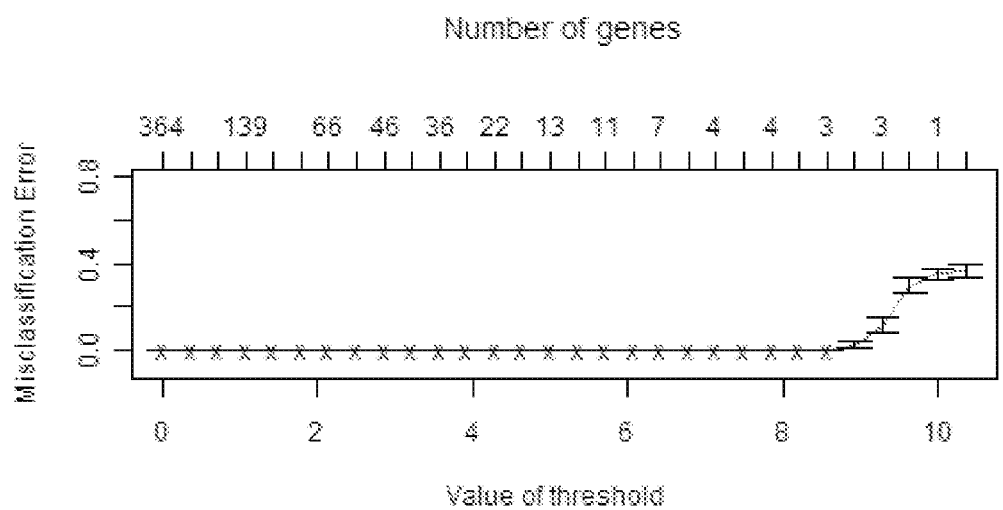
Figure 4B:
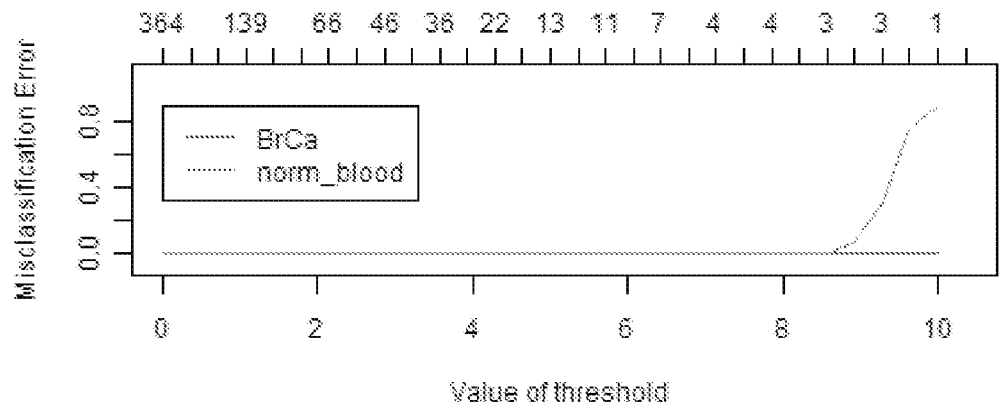

FIG. 4: Shows class prediction using PAMR (predicting analysis of microarrays) to determine the minimum subset of using the 359 marker genes of table 1. The minimal set contains only 3 markers (set yy). Further combinations resulted in the same misclassification error of 0%.

Figure 5:
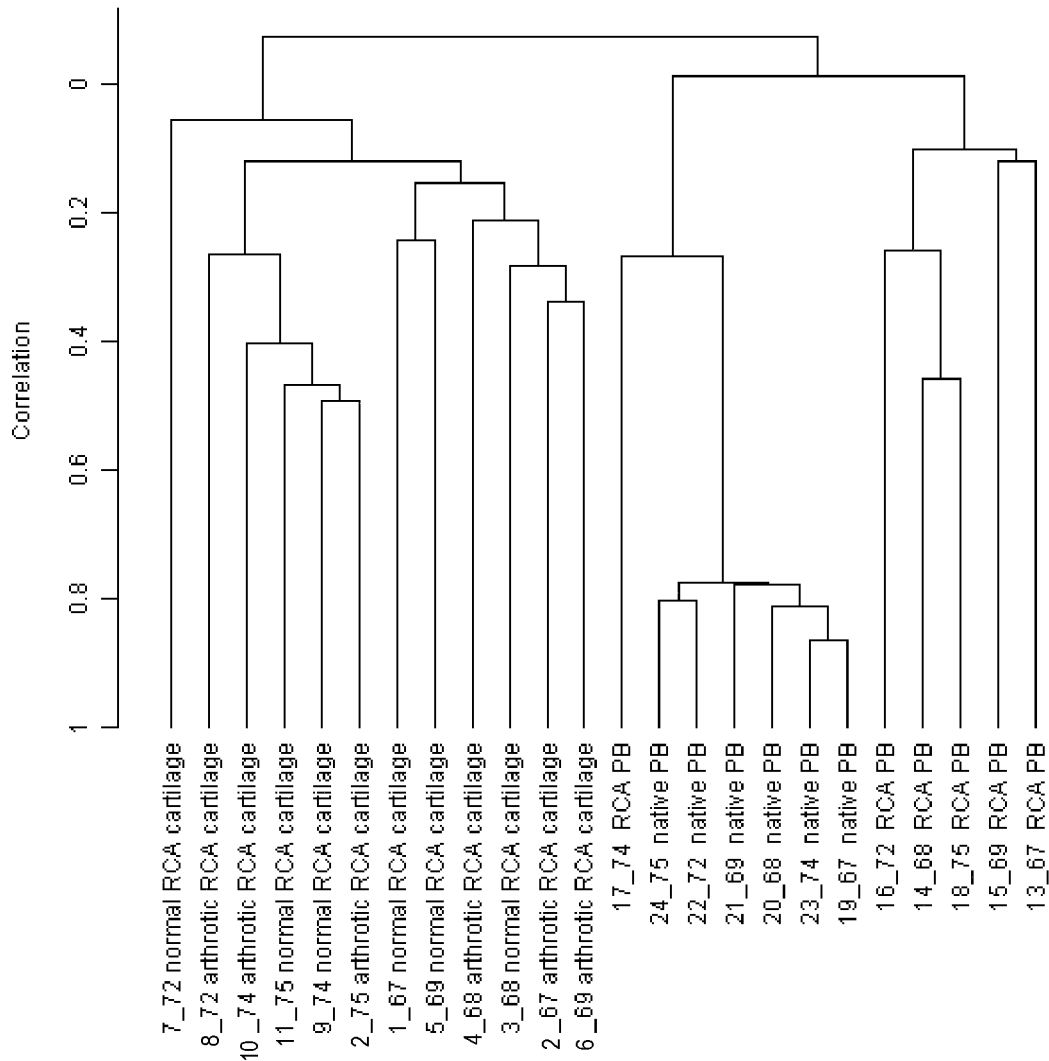

FIG. 5: Dendrogram for clustering experiments, using centered correlation and average linkage.

Figure 6:
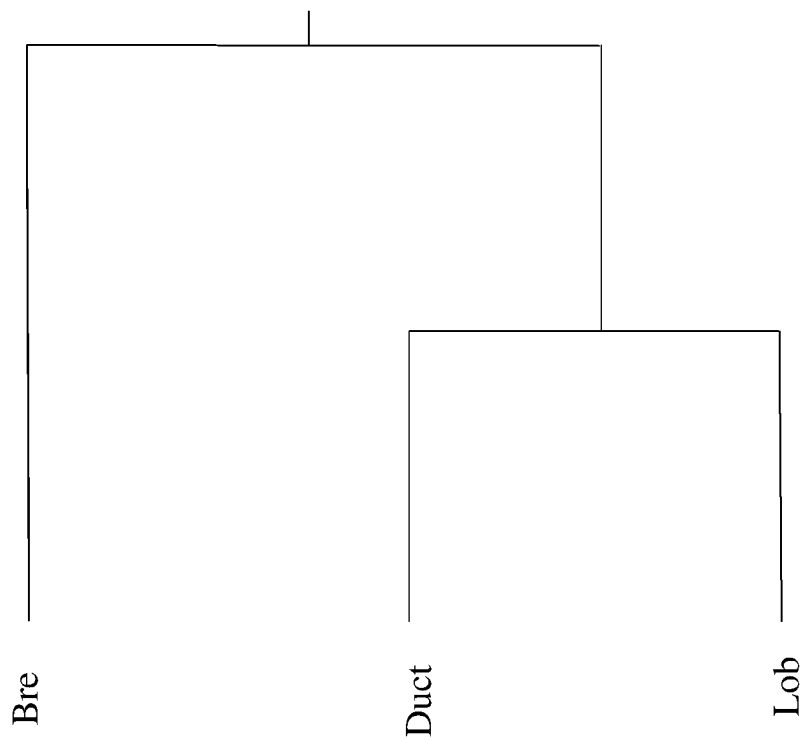

FIG. 6: Optimal Binary Tree prediction for classification of normal (Bre) breast tissue, and ductal (Duct) and lobular (Lob) breast carcinomas.

Figure 7:
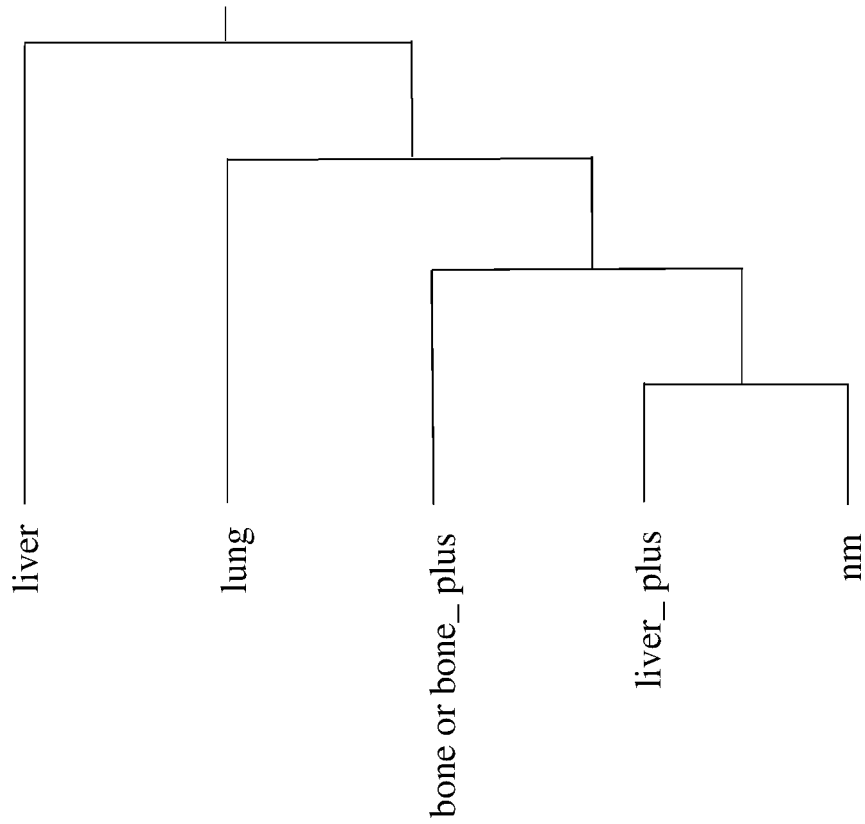

FIG. 7: Optimal Binary Tree for prediction of Organ of Metastases plus additional metastasised organ.

Figure 8:
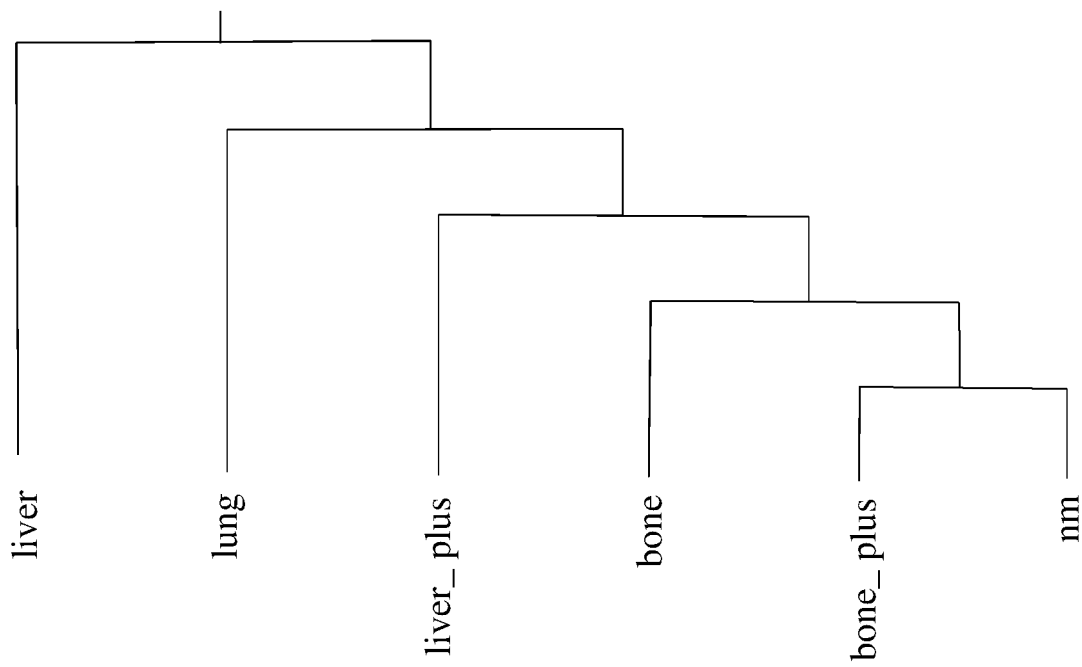

FIG. 8: Optimal Binary Binary Tree for prediction of Organ of Metastases plus additional metastasised organ with genefilters on.

EXAMPLES

Example 1: Gene List

TABLE 1

360 master set (with the 359 marker genes and one control) and sequence annotation

| gene ID | Gene Symbol | alt. Gene Symbol | hybridisation probe (SEQ ID NO:) | primer 1 (lp) (SEQ ID NO:) | primer 2 (rp) (SEQ ID NO:) | PCR product (SEQ ID NO:) |
|---|---|---|---|---|---|---|
| 1 | NHLH2 | NHLH2 | 1 | 361 | 721 | 1081 |
| 2 | MTHFR | MTHFR | 2 | 362 | 722 | 1082 |

TABLE 1-continued 360 master set (with the 359 marker genes and one control) and sequence annotation

| gene ID | Gene Symbol | alt. Gene Symbol | hybridisation probe (SEQ ID NO:) | primer 1 (lp) (SEQ ID NO:) | primer 2 (rp) (SEQ ID NO:) | PCR product (SEQ ID NO:) |
|---|---|---|---|---|---|---|
| 3 | PRDM2 | RIZ1 (PRDM2) | 3 | 363 | 723 | 1083 |
| 4 | MLLT11 | MLLT11 | 4 | 364 | 724 | 1084 |
| 5 | S100A9 | control_S100A9 | 5 | 365 | 725 | 1085 |
| 6 | S100A9 | S100A9 | 6 | 366 | 726 | 1086 |
| 7 | S100A8 | S100A8 | 7 | 367 | 727 | 1087 |
| 8 | S100A8 | control_S100A8 | 8 | 368 | 728 | 1088 |
| 9 | S100A2 | S100A2 | 9 | 369 | 729 | 1089 |
| 10 | LMNA | LMNA | 10 | 370 | 730 | 1090 |
| 11 | DUSP23 | DUSP23 | 11 | 371 | 731 | 1091 |
| 12 | LAMC2 | LAMC2 | 12 | 372 | 732 | 1092 |
| 13 | PTGS2 | PTGS2 | 13 | 373 | 733 | 1093 |
| 14 | MARK1 | MARK1 | 14 | 374 | 734 | 1094 |
| 15 | DUSP10 | DUSP10 | 15 | 375 | 735 | 1095 |
| 16 | PARP1 | PARP1 | 16 | 376 | 736 | 1096 |
| 17 | PSEN2 | PSEN2 | 17 | 377 | 737 | 1097 |
| 18 | CLIC4 | CLIC4 | 18 | 378 | 738 | 1098 |
| 19 | RUNX3 | RUNX3 | 19 | 379 | 739 | 1099 |
| 20 | AIM1L | NM_017977 | 20 | 380 | 740 | 1100 |
| 21 | SFN | SFN | 21 | 381 | 741 | 1101 |
| 22 | RPA2 | RPA2 | 22 | 382 | 742 | 1102 |
| 23 | TP73 | TP73 | 23 | 383 | 743 | 1103 |
| 24 | TP73 | p73 | 24 | 384 | 744 | 1104 |
| 25 | POU3F1 | 01.10.06 | 25 | 385 | 745 | 1105 |
| 26 | MUTYH | MUTYH | 26 | 386 | 746 | 1106 |
| 27 | UQCRH | UQCRH | 27 | 387 | 747 | 1107 |
| 28 | FAF1 | FAF1 | 28 | 388 | 748 | 1108 |
| 29 | TACSTD2 | TACSTD2 | 29 | 389 | 749 | 1109 |
| 30 | TNFRSF25 | TNFRSF25 | 30 | 390 | 750 | 1110 |
| 31 | DIRAS3 | DIRAS3 | 31 | 391 | 751 | 1111 |
| 32 | MSH4 | MSH4 | 32 | 392 | 752 | 1112 |
| 33 | GBP2 | Control | 33 | 393 | 753 | 1113 |
| 34 | GBP2 | GBP2 | 34 | 394 | 754 | 1114 |
| 35 | LRRC8C | LRRC8C | 35 | 395 | 755 | 1115 |
| 36 | F3 | F3 | 36 | 396 | 756 | 1116 |
| 37 | NANOS1 | NM_001009553 | 37 | 397 | 757 | 1117 |
| 38 | MGMT | MGMT | 38 | 398 | 758 | 1118 |
| 39 | EBF3 | EBF3 | 39 | 399 | 759 | 1119 |
| 40 | DCLRE1C | DCLRE1C | 40 | 400 | 760 | 1120 |
| 41 | KIF5B | KIF5B | 41 | 401 | 761 | 1121 |
| 42 | ZNF22 | ZNF22 | 42 | 402 | 762 | 1122 |
| 43 | PGBD3 | ERCC6 | 43 | 403 | 763 | 1123 |
| 44 | SRGN | Control | 44 | 404 | 764 | 1124 |
| 45 | GATA3 | GATA3 | 45 | 405 | 765 | 1125 |
| 46 | PTEN | PTEN | 46 | 406 | 766 | 1126 |
| 47 | MMS19 | MMS19L | 47 | 407 | 767 | 1127 |
| 48 | SFRP5 | SFRP5 | 48 | 408 | 768 | 1128 |
| 49 | PGR | PGR | 49 | 409 | 769 | 1129 |
| 50 | ATM | ATM | 50 | 410 | 770 | 1130 |
| 51 | DRD2 | DRD2 | 51 | 411 | 771 | 1131 |
| 52 | CADM1 | IGSF4 | 52 | 412 | 772 | 1132 |
| 53 | TEAD1 | Control | 53 | 413 | 773 | 1133 |
| 54 | OPCML | OPCML | 54 | 414 | 774 | 1134 |
| 55 | CALCA | CALCA | 55 | 415 | 775 | 1135 |
| 56 | CTSD | CTSD | 56 | 416 | 776 | 1136 |
| 57 | MYOD1 | MYOD1 | 57 | 417 | 777 | 1137 |
| 58 | IGF2 | IGF2 | 58 | 418 | 778 | 1138 |
| 59 | BDNF | BDNF | 59 | 419 | 779 | 1139 |
| 60 | CDKN1C | CDKN1C | 60 | 420 | 780 | 1140 |
| 61 | WT1 | WT1 | 61 | 421 | 781 | 1141 |
| 62 | HRAS | HRAS1 | 62 | 422 | 782 | 1142 |
| 63 | DDB1 | DDB1 | 63 | 423 | 783 | 1143 |
| 64 | GSTP1 | GSTP1 | 64 | 424 | 784 | 1144 |
| 65 | CCND1 | CCND1 | 65 | 425 | 785 | 1145 |
| 66 | EPS8L2 | EPS8L2 | 66 | 426 | 786 | 1146 |
| 67 | PIWIL4 | PIWIL4 | 67 | 427 | 787 | 1147 |
| 68 | CHST11 | CHST11 | 68 | 428 | 788 | 1148 |
| 69 | UNG | UNG | 69 | 429 | 789 | 1149 |
| 70 | CCDC62 | CCDC62 | 70 | 430 | 790 | 1150 |
| 71 | CDK2AP1 | CDK2AP1 | 71 | 431 | 791 | 1151 |
| 72 | CHFR | CHFR | 72 | 432 | 792 | 1152 |
| 73 | GRIN2B | GRIN2B | 73 | 433 | 793 | 1153 |
| 74 | CCND2 | CCND2 | 74 | 434 | 794 | 1154 |
| 75 | VDR | VDR | 75 | 435 | 795 | 1155 |

TABLE 1-continued 360 master set (with the 359 marker genes and one control) and sequence annotation

| gene ID | Gene Symbol | alt. Gene Symbol | hybridisation probe (SEQ ID NO:) | primer 1 (lp) (SEQ ID NO:) | primer 2 (rp) (SEQ ID NO:) | PCR product (SEQ ID NO:) |
|---|---|---|---|---|---|---|
| 76 | B4GALNT3 | control(wrong chr of HRAS1) | 76 | 436 | 796 | 1156 |
| 77 | NTF3 | NTF3 | 77 | 437 | 797 | 1157 |
| 78 | CYP27B1 | CYP27B1 | 78 | 438 | 798 | 1158 |
| 79 | GPR92 | GPR92 | 79 | 439 | 799 | 1159 |
| 80 | ERCC5 | ERCC5 | 80 | 440 | 800 | 1160 |
| 81 | GJB2 | GJB2 | 81 | 441 | 801 | 1161 |
| 82 | BRCA2 | BRCA2 | 82 | 442 | 802 | 1162 |
| 83 | KL | KL | 83 | 443 | 803 | 1163 |
| 84 | CCNA1 | CCNA1 | 84 | 444 | 804 | 1164 |
| 85 | SMAD9 | SMAD9 | 85 | 445 | 805 | 1165 |
| 86 | C13orf15 | RGC32 | 86 | 446 | 806 | 1166 |
| 87 | DGKH | DGKH | 87 | 447 | 807 | 1167 |
| 88 | DNAJC15 | DNAJC15 | 88 | 448 | 808 | 1168 |
| 89 | RB1 | RB1 | 89 | 449 | 809 | 1169 |
| 90 | RCBTB2 | RCBTB2 | 90 | 450 | 810 | 1170 |
| 91 | PARP2 | PARP2 | 91 | 451 | 811 | 1171 |
| 92 | APEX1 | APEX1 | 92 | 452 | 812 | 1172 |
| 93 | JUB | JUB | 93 | 453 | 813 | 1173 |
| 94 | JUB | control_NM_198086 | 94 | 454 | 814 | 1174 |
| 95 | EFS | EFS | 95 | 455 | 815 | 1175 |
| 96 | BAZ1A | BAZ1A | 96 | 456 | 816 | 1176 |
| 97 | NKX2-1 | TITF1 | 97 | 457 | 817 | 1177 |
| 98 | ESR2 | ESR2 | 98 | 458 | 818 | 1178 |
| 99 | HSPA2 | HSPA2 | 99 | 459 | 819 | 1179 |
| 100 | PSEN1 | PSEN1 | 100 | 460 | 820 | 1180 |
| 101 | PGF | PGF | 101 | 461 | 821 | 1181 |
| 102 | MLH3 | MLH3 | 102 | 462 | 822 | 1182 |
| 103 | TSHR | TSHR | 103 | 463 | 823 | 1183 |
| 104 | THBS1 | THBS1 | 104 | 464 | 824 | 1184 |
| 105 | MYO5C | MYO5C | 105 | 465 | 825 | 1185 |
| 106 | SMAD6 | SMAD6 | 106 | 466 | 826 | 1186 |
| 107 | SMAD3 | SMAD3 | 107 | 467 | 827 | 1187 |
| 108 | NOX5 | SPESP1 | 108 | 468 | 828 | 1188 |
| 109 | DNAJA4 | DNAJA4 | 109 | 469 | 829 | 1189 |
| 110 | CRABP1 | CRABP1 | 110 | 470 | 830 | 1190 |
| 111 | BCL2A1 | BCL2A1 | 111 | 471 | 831 | 1191 |
| 112 | BCL2A1 | BCL2A1 | 112 | 472 | 832 | 1192 |
| 113 | BNC1 | BNC1 | 113 | 473 | 833 | 1193 |
| 114 | ARRDC4 | ARRDC4 | 114 | 474 | 834 | 1194 |
| 115 | SOCS1 | SOCS1 | 115 | 475 | 835 | 1195 |
| 116 | ERCC4 | ERCC4 | 116 | 476 | 836 | 1196 |
| 117 | NTHL1 | NTHL1 | 117 | 477 | 837 | 1197 |
| 118 | PYCARD | PYCARD | 118 | 478 | 838 | 1198 |
| 119 | AXIN1 | AXIN1 | 119 | 479 | 839 | 1199 |
| 120 | CYLD | NM_015247 | 120 | 480 | 840 | 1200 |
| 121 | MT3 | MT3 | 121 | 481 | 841 | 1201 |
| 122 | MT1A | MT1A | 122 | 482 | 842 | 1202 |
| 123 | MT1G | MT1G | 123 | 483 | 843 | 1203 |
| 124 | CDH1 | CDH1 | 124 | 484 | 844 | 1204 |
| 125 | CDH13 | CDH13 | 125 | 485 | 845 | 1205 |
| 126 | DPH1 | DPH1 | 126 | 486 | 846 | 1206 |
| 127 | HIC1 | HIC1 | 127 | 487 | 847 | 1207 |
| 128 | NEUROD2 | control_NEUROD2 | 128 | 488 | 848 | 1208 |
| 129 | NEUROD2 | NEUROD2 | 129 | 489 | 849 | 1209 |
| 130 | ERBB2 | ERBB2 | 130 | 490 | 850 | 1210 |
| 131 | KRT19 | KRT19 | 131 | 491 | 851 | 1211 |
| 132 | KRT14 | KRT14 | 132 | 492 | 852 | 1212 |
| 133 | KRT17 | KRT17 | 133 | 493 | 853 | 1213 |
| 134 | JUP | JUP | 134 | 494 | 854 | 1214 |
| 135 | BRCA1 | BRCA1 | 135 | 495 | 855 | 1215 |
| 136 | COL1A1 | COL1A1 | 136 | 496 | 856 | 1216 |
| 137 | CACNA1G | CACNA1G | 137 | 497 | 857 | 1217 |
| 138 | PRKAR1A | PRKAR1A | 138 | 498 | 858 | 1218 |
| 139 | SPHK1 | SPHK1 | 139 | 499 | 859 | 1219 |
| 140 | SOX15 | SOX15 | 140 | 500 | 860 | 1220 |
| 141 | TP53 | TP53_CGI23_1kb | 141 | 501 | 861 | 1221 |
| 142 | TP53 | TP53_bothCGIs_1kb | 142 | 502 | 862 | 1222 |
| 143 | TP53 | TP53_CGI36_1kb | 143 | 503 | 863 | 1223 |
| 144 | TP53 | TP53 | 144 | 504 | 864 | 1224 |
| 145 | NPTX1 | NPTX1 | 145 | 505 | 865 | 1225 |
| 146 | SMAD2 | SMAD2 | 146 | 506 | 866 | 1226 |
| 147 | DCC | DCC | 147 | 507 | 867 | 1227 |
| 148 | MBD2 | MBD2 | 148 | 508 | 868 | 1228 |

TABLE 1-continued 360 master set (with the 359 marker genes and one control) and sequence annotation

| gene ID | Gene Symbol | alt. Gene Symbol | hybridisation probe (SEQ ID NO:) | primer 1 (lp) (SEQ ID NO:) | primer 2 (rp) (SEQ ID NO:) | PCR product (SEQ ID NO:) |
|---|---|---|---|---|---|---|
| 149 | ONECUT2 | ONECUT2 | 149 | 509 | 869 | 1229 |
| 150 | BCL2 | BCL2 | 150 | 510 | 870 | 1230 |
| 151 | SERPINB5 | SERPINB5 | 151 | 511 | 871 | 1231 |
| 152 | SERPINB2 | Control | 152 | 512 | 872 | 1232 |
| 153 | SERPINB2 | SERPINB2 | 153 | 513 | 873 | 1233 |
| 154 | TYMS | TYMS | 154 | 514 | 874 | 1234 |
| 155 | LAMA1 | LAMA1 | 155 | 515 | 875 | 1235 |
| 156 | SALL3 | SALL3 | 156 | 516 | 876 | 1236 |
| 157 | LDLR | LDLR | 157 | 517 | 877 | 1237 |
| 158 | STK11 | STK11 | 158 | 518 | 878 | 1238 |
| 159 | PRDX2 | PRDX2 | 159 | 519 | 879 | 1239 |
| 160 | RAD23A | RAD23A | 160 | 520 | 880 | 1240 |
| 161 | GNA15 | GNA15 | 161 | 521 | 881 | 1241 |
| 162 | ZNF573 | ZNF573 | 162 | 522 | 882 | 1242 |
| 163 | SPINT2 | SPINT2 | 163 | 523 | 883 | 1243 |
| 164 | XRCC1 | XRCC1 | 164 | 524 | 884 | 1244 |
| 165 | ERCC2 | ERCC2 | 165 | 525 | 885 | 1245 |
| 166 | ERCC1 | ERCC1 | 166 | 526 | 886 | 1246 |
| 167 | C5AR1 | NM_001736 | 167 | 527 | 887 | 1247 |
| 168 | C5AR1 | C5AR1 | 168 | 528 | 888 | 1248 |
| 169 | POLD1 | POLD1 | 169 | 529 | 889 | 1249 |
| 170 | ZNF350 | ZNF350 | 170 | 530 | 890 | 1250 |
| 171 | ZNF256 | ZNF256 | 171 | 531 | 891 | 1251 |
| 172 | C3 | C3 | 172 | 532 | 892 | 1252 |
| 173 | XAB2 | XAB2 | 173 | 533 | 893 | 1253 |
| 174 | ZNF559 | ZNF559 | 174 | 534 | 894 | 1254 |
| 175 | FHL2 | FHL2 | 175 | 535 | 895 | 1255 |
| 176 | IL1B | IL1B | 176 | 536 | 896 | 1256 |
| 177 | IL1B | control_IL1B | 177 | 537 | 897 | 1257 |
| 178 | PAX8 | PAX8 | 178 | 538 | 898 | 1258 |
| 179 | DDX18 | DDX18 | 179 | 539 | 899 | 1259 |
| 180 | GAD1 | GAD1 | 180 | 540 | 900 | 1260 |
| 181 | DLX2 | DLX2 | 181 | 541 | 901 | 1261 |
| 182 | ITGA4 | ITGA4 | 182 | 542 | 902 | 1262 |
| 183 | NEUROD1 | NEUROD1 | 183 | 543 | 903 | 1263 |
| 184 | STAT1 | STAT1 | 184 | 544 | 904 | 1264 |
| 185 | TMEFF2 | TMEFF2 | 185 | 545 | 905 | 1265 |
| 186 | HECW2 | HECW2 | 186 | 546 | 906 | 1266 |
| 187 | BOLL | BOLL | 187 | 547 | 907 | 1267 |
| 188 | CASP8 | CASP8 | 188 | 548 | 908 | 1268 |
| 189 | SERPINE2 | SERPINE2 | 189 | 549 | 909 | 1269 |
| 190 | NCL | NCL | 190 | 550 | 910 | 1270 |
| 191 | CYP1B1 | CYP1B1 | 191 | 551 | 911 | 1271 |
| 192 | TACSTD1 | TACSTD1 | 192 | 552 | 912 | 1272 |
| 193 | MSH2 | MSH2 | 193 | 553 | 913 | 1273 |
| 194 | MSH6 | MSH6 | 194 | 554 | 914 | 1274 |
| 195 | MXD1 | MXD1 | 195 | 555 | 915 | 1275 |
| 196 | JAG1 | JAG1 | 196 | 556 | 916 | 1276 |
| 197 | FOXA2 | FOXA2 | 197 | 557 | 917 | 1277 |
| 198 | THBD | THBD | 198 | 558 | 918 | 1278 |
| 199 | CTCFL | BORIS | 199 | 559 | 919 | 1279 |
| 200 | CTSZ | CTSZ | 200 | 560 | 920 | 1280 |
| 201 | GATA5 | GATA5 | 201 | 561 | 921 | 1281 |
| 202 | CXADR | CXADR | 202 | 562 | 922 | 1282 |
| 203 | APP | APP | 203 | 563 | 923 | 1283 |
| 204 | TTC3 | TTC3 | 204 | 564 | 924 | 1284 |
| 205 | KCNJ15 | Control | 205 | 565 | 925 | 1285 |
| 206 | RIPK4 | RIPK4 | 206 | 566 | 926 | 1286 |
| 207 | TFF1 | TFF1 | 207 | 567 | 927 | 1287 |
| 208 | SEZ6L | SEZ6L | 208 | 568 | 928 | 1288 |
| 209 | TIMP3 | TIMP3 | 209 | 569 | 929 | 1289 |
| 210 | BIK | BIK | 210 | 570 | 930 | 1290 |
| 211 | VHL | VHL | 211 | 571 | 931 | 1291 |
| 212 | IRAK2 | IRAK2 | 212 | 572 | 932 | 1292 |
| 213 | PPARG | PPARG | 213 | 573 | 933 | 1293 |
| 214 | MBD4 | MBD4 | 214 | 574 | 934 | 1294 |
| 215 | RBP1 | RBP1 | 215 | 575 | 935 | 1295 |
| 216 | XPC | XPC | 216 | 576 | 936 | 1296 |
| 217 | ATR | ATR | 217 | 577 | 937 | 1297 |
| 218 | LXN | LXN | 218 | 578 | 938 | 1298 |
| 219 | RARRES1 | RARRES1 | 219 | 579 | 939 | 1299 |
| 220 | SERPINI1 | SERPINI1 | 220 | 580 | 940 | 1300 |
| 221 | CLDN1 | CLDN1 | 221 | 581 | 941 | 1301 |
| 222 | FAM43A | FAM43A | 222 | 582 | 942 | 1302 |

TABLE 1-continued 360 master set (with the 359 marker genes and one control) and sequence annotation

| gene ID | Gene Symbol | alt. Gene Symbol | hybridisation probe (SEQ ID NO:) | primer 1 (lp) (SEQ ID NO:) | primer 2 (rp) (SEQ ID NO:) | PCR product (SEQ ID NO:) |
|---|---|---|---|---|---|---|
| 223 | IQCG | IQCG | 223 | 583 | 943 | 1303 |
| 224 | THRB | THRB | 224 | 584 | 944 | 1304 |
| 225 | RARB | RARB | 225 | 585 | 945 | 1305 |
| 226 | TGFBR2 | TGFBR2 | 226 | 586 | 946 | 1306 |
| 227 | MLH1 | MLH1 | 227 | 587 | 947 | 1307 |
| 228 | DLEC1 | DLEC1 | 228 | 588 | 948 | 1308 |
| 229 | CTNNB1 | CTNNB1 | 229 | 589 | 949 | 1309 |
| 230 | ZNF502 | ZNF502 | 230 | 590 | 950 | 1310 |
| 231 | SLC6A20 | SLC6A20 | 231 | 591 | 951 | 1311 |
| 232 | GPX1 | GPX1 | 232 | 592 | 952 | 1312 |
| 233 | RASSF1 | RASSF1A | 233 | 593 | 953 | 1313 |
| 234 | FHIT | FHIT | 234 | 594 | 954 | 1314 |
| 235 | OGG1 | OGG1 | 235 | 595 | 955 | 1315 |
| 236 | PITX2 | PITX2 | 236 | 596 | 956 | 1316 |
| 237 | SLC25A31 | SLC25A31 | 237 | 597 | 957 | 1317 |
| 238 | FBXW7 | FBXW7 | 238 | 598 | 958 | 1318 |
| 239 | SFRP2 | SFRP2 | 239 | 599 | 959 | 1319 |
| 240 | CHRNA9 | CHRNA9 | 240 | 600 | 960 | 1320 |
| 241 | GABRA2 | GABRA2 | 241 | 601 | 961 | 1321 |
| 242 | MSX1 | MSX1 | 242 | 602 | 962 | 1322 |
| 243 | IGFBP7 | IGFBP7 | 243 | 603 | 963 | 1323 |
| 244 | EREG | EREG | 244 | 604 | 964 | 1324 |
| 245 | AREG | AREG | 245 | 605 | 965 | 1325 |
| 246 | ANXA3 | ANXA3 | 246 | 606 | 966 | 1326 |
| 247 | BMP2K | BMP2K | 247 | 607 | 967 | 1327 |
| 248 | APC | APC | 248 | 608 | 968 | 1328 |
| 249 | HSD17B4 | HSD17B4 | 249 | 609 | 969 | 1329 |
| 250 | HSD17B4 | HSD17B4 | 250 | 610 | 970 | 1330 |
| 251 | LOX | LOX | 251 | 611 | 971 | 1331 |
| 252 | TERT | TERT | 252 | 612 | 972 | 1332 |
| 253 | NEUROG1 | NEUROG1 | 253 | 613 | 973 | 1333 |
| 254 | NR3C1 | NR3C1 | 254 | 614 | 974 | 1334 |
| 255 | ADRB2 | ADRB2 | 255 | 615 | 975 | 1335 |
| 256 | CDX1 | CDX1 | 256 | 616 | 976 | 1336 |
| 257 | SPARC | SPARC | 257 | 617 | 977 | 1337 |
| 258 | C5orf4 | Control | 258 | 618 | 978 | 1338 |
| 259 | PTTG1 | PTTG1 | 259 | 619 | 979 | 1339 |
| 260 | DUSP1 | DUSP1 | 260 | 620 | 980 | 1340 |
| 261 | CPEB4 | CPEB4 | 261 | 621 | 981 | 1341 |
| 262 | SCGB3A1 | SCGB3A1 | 262 | 622 | 982 | 1342 |
| 263 | GDNF | GDNF | 263 | 623 | 983 | 1343 |
| 264 | ERCC8 | ERCC8 | 264 | 624 | 984 | 1344 |
| 265 | F2R | F2R | 265 | 625 | 985 | 1345 |
| 266 | F2RL1 | F2RL1 | 266 | 626 | 986 | 1346 |
| 267 | VCAN | CSPG2 | 267 | 627 | 987 | 1347 |
| 268 | ZDHHC11 | ZDHHC11 | 268 | 628 | 988 | 1348 |
| 269 | RHOBTB3 | RHOBTB3 | 269 | 629 | 989 | 1349 |
| 270 | PLAGL1 | PLAGL1 | 270 | 630 | 990 | 1350 |
| 271 | SASH1 | SASH1 | 271 | 631 | 991 | 1351 |
| 272 | ULBP2 | ULBP2 | 272 | 632 | 992 | 1352 |
| 273 | ESR1 | ESR1 | 273 | 633 | 993 | 1353 |
| 274 | RNASET2 | RNASET2 | 274 | 634 | 994 | 1354 |
| 275 | DLL1 | DLL1 | 275 | 635 | 995 | 1355 |
| 276 | HIST1H2AG | HIST1H2AG | 276 | 636 | 996 | 1356 |
| 277 | HLA-G | HLA-G | 277 | 637 | 997 | 1357 |
| 278 | MSH5 | MSH5 | 278 | 638 | 998 | 1358 |
| 279 | CDKN1A | CDKN1A | 279 | 639 | 999 | 1359 |
| 280 | TDRD6 | TDRD6 | 280 | 640 | 1000 | 1360 |
| 281 | COL21A1 | COL21A1 | 281 | 641 | 1001 | 1361 |
| 282 | DSP | DSP | 282 | 642 | 1002 | 1362 |
| 283 | SERPINE1 | SERPINE1 | 283 | 643 | 1003 | 1363 |
| 284 | SERPINE1 | SERPINE1 | 284 | 644 | 1004 | 1364 |
| 285 | FBXL13 | FBXL13 | 285 | 645 | 1005 | 1365 |
| 286 | NRCAM | NRCAM | 286 | 646 | 1006 | 1366 |
| 287 | TWIST1 | TWIST1 | 287 | 647 | 1007 | 1367 |
| 288 | HOXA1 | HOXA1 | 288 | 648 | 1008 | 1368 |
| 289 | HOXA10 | HOXA10 | 289 | 649 | 1009 | 1369 |
| 290 | SFRP4 | SFRP4 | 290 | 650 | 1010 | 1370 |
| 291 | IGFBP3 | IGFBP3 | 291 | 651 | 1011 | 1371 |
| 292 | RPA3 | RPA3 | 292 | 652 | 1012 | 1372 |
| 293 | ABCB1 | ABCB1 | 293 | 653 | 1013 | 1373 |
| 294 | TFPI2 | TFPI2 | 294 | 654 | 1014 | 1374 |
| 295 | COL1A2 | COL1A2 | 295 | 655 | 1015 | 1375 |
| 296 | ARPC1B | ARPC1B | 296 | 656 | 1016 | 1376 |

TABLE 1-continued

360 master set (with the 359 marker genes and one control) and sequence annotation

| gene ID | Gene Symbol | alt. Gene Symbol | hybridisation probe (SEQ ID NO:) | primer 1 (lp) (SEQ ID NO:) | primer 2 (rp) (SEQ ID NO:) | PCR product (SEQ ID NO:) |
|---|---|---|---|---|---|---|
| 297 | PILRB | PILRB | 297 | 657 | 1017 | 1377 |
| 298 | GATA4 | GATA4 | 298 | 658 | 1018 | 1378 |
| 299 | MAL2 | NM_052886 | 299 | 659 | 1019 | 1379 |
| 300 | DLC1 | DLC1 | 300 | 660 | 1020 | 1380 |
| 301 | EPPK1 | NM_031308 | 301 | 661 | 1021 | 1381 |
| 302 | LZTS1 | LZTS1 | 302 | 662 | 1022 | 1382 |
| 303 | TNFRSF10B | TNFRSF10B | 303 | 663 | 1023 | 1383 |
| 304 | TNFRSF10C | TNFRSF10C | 304 | 664 | 1024 | 1384 |
| 305 | TNFRSF10D | TNFRSF10D | 305 | 665 | 1025 | 1385 |
| 306 | TNFRSF10A | TNFRSF10A | 306 | 666 | 1026 | 1386 |
| 307 | WRN | WRN | 307 | 667 | 1027 | 1387 |
| 308 | SFRP1 | SFRP1 | 308 | 668 | 1028 | 1388 |
| 309 | SNAI2 | SNAI2 | 309 | 669 | 1029 | 1389 |
| 310 | RDHE2 | RDHE2 | 310 | 670 | 1030 | 1390 |
| 311 | PENK | PENK | 311 | 671 | 1031 | 1391 |
| 312 | RDH10 | RDH10 | 312 | 672 | 1032 | 1392 |
| 313 | TGFBR1 | TGFBR1 | 313 | 673 | 1033 | 1393 |
| 314 | ZNF462 | ZNF462 | 314 | 674 | 1034 | 1394 |
| 315 | KLF4 | KLF4 | 315 | 675 | 1035 | 1395 |
| 316 | CDKN2A | p14_CDKN2A | 316 | 676 | 1036 | 1396 |
| 317 | CDKN2B | CDKN2B | 317 | 677 | 1037 | 1397 |
| 318 | AQP3 | AQP3 | 318 | 678 | 1038 | 1398 |
| 319 | TPM2 | TPM2 | 319 | 679 | 1039 | 1399 |
| 320 | TJP2 | TJP2 | 320 | 680 | 1040 | 1400 |
| 321 | TJP2 | TJP2 | 321 | 681 | 1041 | 1401 |
| 322 | PSAT1 | PSAT1 | 322 | 682 | 1042 | 1402 |
| 323 | DAPK1 | DAPK1 | 323 | 683 | 1043 | 1403 |
| 324 | SYK | SYK | 324 | 684 | 1044 | 1404 |
| 325 | XPA | XPA | 325 | 685 | 1045 | 1405 |
| 326 | ARMCX2 | ARMCX2 | 326 | 686 | 1046 | 1406 |
| 327 | RHOXF1 | OTEX | 327 | 687 | 1047 | 1407 |
| 328 | FHL1 | FHL1 | 328 | 688 | 1048 | 1408 |
| 329 | MAGEB2 | MAGEB2 | 329 | 689 | 1049 | 1409 |
| 330 | TIMP1 | TIMP1 | 330 | 690 | 1050 | 1410 |
| 331 | AR | AR_humara | 331 | 691 | 1051 | 1411 |
| 332 | ZNF711 | ZNF6 | 332 | 692 | 1052 | 1412 |
| 333 | CD24 | CD24 | 333 | 693 | 1053 | 1413 |
| 334 | ABL1 | ABL | 334 | 694 | 1054 | 1414 |
| 335 | ACTB | Aktin_VL | 335 | 695 | 1055 | 1415 |
| 336 | APC | APC | 336 | 696 | 1056 | 1416 |
| 337 | CDH1 | Ecad1 | 337 | 697 | 1057 | 1417 |
| 338 | CDH1 | Ecad2 | 338 | 698 | 1058 | 1418 |
| 339 | FMR1 | FX | 339 | 699 | 1059 | 1419 |
| 340 | GNAS | GNASexAB | 340 | 700 | 1060 | 1420 |
| 341 | H19 | H19 | 341 | 701 | 1061 | 1421 |
| 342 | HIC1 | Igf2 | 342 | 702 | 1062 | 1422 |
| 343 | IGF2 | Igf2 | 343 | 703 | 1063 | 1423 |
| 344 | KCNQ1 | LIT1 | 344 | 704 | 1064 | 1424 |
| 345 | GNAS | NESP55 | 345 | 705 | 1065 | 1425 |
| 346 | CDKN2A | P14 | 346 | 706 | 1066 | 1426 |
| 347 | CDKN2B | P15 | 347 | 707 | 1067 | 1427 |
| 348 | CDKN2A | P16_VL | 348 | 708 | 1068 | 1428 |
| 349 | PITX2 | PitxA | 349 | 709 | 1069 | 1429 |
| 350 | PITX2 | PitxB | 350 | 710 | 1070 | 1430 |
| 351 | PITX2 | PitxC | 351 | 711 | 1071 | 1431 |
| 352 | PITX2 | PitxD | 352 | 712 | 1072 | 1432 |
| 353 | RB1 | Rb | 353 | 713 | 1073 | 1433 |
| 354 | SFRP2 | SFRP2_VL | 354 | 714 | 1074 | 1434 |
| 355 | SNRPN | SNRPN | 355 | 715 | 1075 | 1435 |
| 356 | XIST | XIST | 356 | 716 | 1076 | 1436 |
| 357 | IRF4 | chr6_control | 357 | 717 | 1077 | 1437 |
| 358 | UNC13B | chr9_control | 358 | 718 | 1078 | 1438 |
| 359 | GSTP1 | GSTP1 | 360 | 720 | 1080 | 1440 |
| 360 | Lamda (control) | lambda_PCR | 359 | 719 | 1079 | 1439 |

Example 2: Samples

Samples from solid tumors were derived from initial surgical resection of primary tumors. Tumor tissue sections were derived from histopathology and histopathological data as well clinical data were monitored over the time of clinical management of the patients and/or collected from patient reports in the study center. Anonymised data were provided.

Example 3: DNA and RNA Isolation

Tissue samples were homogenized in a FASTPREP homogenizer (MP Biomedicals, Eschwege, Germany) in lysis buffer provided with the Qiagen "All Prep" nucleic acid preparation kit (Qiagen, Hilden, Germany). DNA and RNA concentrations were measured on a Nanodrop photometer. RNA quality was controlled using a BioAnalyser (Agilent, Waldbronn, Germany). All conditions were according to manufacturer's recommendations.

Example 4: Whole Genome Expression Profiling

RNA samples derived from breast cancer tissue were analyzed with 44 k human whole genome oligo microarrays (Agilent Technologies).
RNA expression levels from different samples were analyzed on a single microarray using the Single-Color Low RNA Input Linear Amplification Kit PLUS (Agilent Technologies, Waldbronn, Germany). For each amplification, 200 ng of total RNA were employed and amplified samples were prepared for hybridization using the Gene Expression Hybridization Kit (Agilent Technologies). Hybridization was performed over night at 65° C. in a rotating hybridization oven (Agilent Technologies). Stringency washes, image acquisition and feature extraction was performed according to the manufacturer's protocol (Agilent Technologies, Waldbronn, Germany).

Example 5: Principle of the Assay and Design

The invention assay is a multiplexed assay for DNA methylation testing of up to (or even more than) 360 methylation candidate markers, enabling convenient methylation analyses for tumor-marker definition. In its best mode the test is a combined multiplex-PCR and microarray hybridization technique for multiplexed methylation testing. The inventive marker genes, PCR primer sequences, hybridization probe sequences and expected PCR products are given in table 1, above.

Targeting hypermethylated DNA regions in the inventive marker genes in several neoplasias, methylation analysis is performed via methylation dependent restriction enzyme (MSRE) digestion of 500 ng of starting DNA. A combination of several MSREs warrants complete digestion of unmethylated DNA. All targeted DNA regions have been selected in that way that sequences containing multiple MSRE sites are flanked by methylation independent restriction enzyme sites. This strategy enables pre-amplification of the methylated DNA fraction before methylation analyses. Thus, the design and pre-amplification would enable methylation testing on serum, urine, stool etc. when DNA is limiting.

When testing DNA without pre-amplification upon digestion of 500 ng the methylated DNA fraction is amplified within 16 multiplex PCRs and detected via microarray hybridization. Within these 16 multiplex-PCR reactions 360 different human DNA products can be amplified. From these about 20 amplicons serve as digestion & amplification controls and are either derived from known differentially methylated human DNA regions, or from several regions without any sites of MSREs used in this system. The primer set (every reverse primer is biotinylated) used is targeting 347 different sites located in the 5'UTR of 323 gene regions.

After PCR amplicons are pooled and positives are detected using strepavidin-Cy3 via microarray hybridization. Although the melting temperature of CpG rich DNA is very high, primer and probe-design as well as hybridization conditions have been optimized, thus this assay enables unequivocal multiplexed methylation testing of human DNA samples. The assay has been designed such that 24 samples can be run in parallel using 384well PCR plates. Handling of many DNA samples in several plates in parallel can be easily performed enabling completion of analyses within 1-2 days.

The entire procedure provides the user to setup a specific PCR test and subsequent gel-based or hybridization-based testing of selected markers using single primer-pairs or primer-subsets as provided herein or identified by the inventive method from the 360 marker set.

Example 6: MSRE Digestion of DNA

MSRE digestion of DNA (about 500 ng) was performed at 37° C. over night in a volume of 30 μl in 1× Tango-restriction enzyme digestion buffer (MBI Fermentas) using 8 units of each MSREs AciI (New England Biolabs), Hin 6 I and Hpa II (both from MBI Fermentas). Digestions were stopped by heat inactivation (10 min, 75° C.) and subjected to PCR amplification.

Example 7: PCR Amplification

An aliquot of 20 μl MSRE digested DNA (or in case of preamplification of methylated DNA—see below—about 500 ng were added in a volume of 20 μl) was added to 280 μl of PCR-Premix (without primers). Premix consisted of all reagents obtaining a final concentration of 1× HotStarTaq Buffer (Qiagen); 160 μM dNT-Ps, 5% DMSO and 0.6 U Hot Firepol Taq (Solis Biodyne) per 20 μl reaction. Alternatively an equal amount of HotStarTaq (Qiagen) could be used. Eighteen (18) μl of the Pre-Mix including digested DNA were aliquoted in 16 0.2 ml PCR tubes and to each PCR tube 2 μl of each primer-premix 1-16 (containing 0.83 pmol/μl of each primer) were added. PCR reactions were amplified using a thermal cycling profile of 15 min/95° C. and 40 cycles of each 40 sec/95° C., 40 sec/65° C., 1 min 20 sec/72° C. and a final elongation of 7 min/72° C., then reactions were cooled. After amplification the 16 different multiplex-PCR amplicons from each DNA sample were pooled. Successful amplification was controlled using 10 μl of the pooled 16 different PCR reactions per sample. Positive amplification obtained a smear in the range of 100-300 bp on EtBr stained agarose gels; negative amplification controls must not show a smear in this range.

Example 8: Microarray Hybridization and Detection

Microarrays with the probes of the 360 marker set are blocked for 30 min in 3M Urea containing 0.1% SDS, at room temperature submerged in a stirred choplin char. After blocking slides are washed in 0.1×SSC/0.2% SDS for 5 min, dipped into water and dried by centrifugation.

The PCR-amplicon-pool of each sample is mixed with an equal amount of 2× hybridization buffer (7×SSC, 0.6% SDS, 50% formamide), desaturated for 5 min at 95° C. and held at 70° C. until loading an aliquot of 100 µl onto an array covered by a gasket slide (Agilent). Arrays are hybridized under maximum speed of rotation in an Agilent-hybridization oven for 16 h at 52° C. After removal of gasket-slides microarray-slides are washed at room temperature in wash-solution I (1×SSC, 0.2% SDS) for 5 min and wash solution II (0.1×SSC, 0.2% SDS) for 5 min, and a final wash by dipping the slides 3 times into wash solution III (0.1×SSC), the slides are dried by centrifugation.

For detection of hybridized biotinylated PCR amplicons, streptavidin-Cy3-conjugate (Caltag Laboratories) is diluted 1:400 in PBST-MP (1×PBS, 0.1% Tween 20; 1% skimmed dry milk powder [Sucofin; Germany]), pipetted onto microarrays covered with a coverslip and incubated 30 min at room temperature in the dark. Then coverslips are washed off from the slides using PBST (1×PBS, 0.1% Tween 20) and then slides are washed in fresh PBST for 5 min, rinsed with water and dried by centrifugation.

Example 9: DNA Preamplification for Methylation Profiling (Optional)

In many situations DNA amount is limited. Although the inventive methylation test is performing well with low amounts of DNA (see above), especially minimal invasive testing using cell free DNA from serum, stool, urine, and other body fluids is of diagnostic relevance.

In the present case only 10-100 ng were obtained from 1 ml of serum when testing cell free DNA from serum of breast cancer patients. From a set of patients with "chronic lymphatic leukemia" (CML) only limited amounts of about 100 ng were available; thus those samples were also pre-amplified prior methylation testing as follows: DNA was digested with restriction enzyme FspI (and/or Csp6I, and/or MseI, and/or Tsp509I; or their isoschizomeres) and after (heat) inactivation of the restriction enzyme the fragments were circularized using T4 DNA ligase. Ligation-products were digested using a mixture of methylation sensitive restriction enzymes. Upon enzyme-inactivation the entire mixture was amplified using rolling circle amplification (RCA) by phi29-phage polymerase. The RCA-amplicons were then directly subjected to the multiplex-PCRs of the inventive methylation test without further need of digestion of the DNA prior amplification.

Alternatively the preamplified DNA which is enriched for methylated DNA regions can be directly subjected to fluo-rescent-labelling and the labeled products can be hybridized onto the microarrays using the same conditions as described above for hybridization of PCR products. Then the strepta-vidin-Cy3 detection step has to be omitted and slides should be scanned directly upon stringency washes and drying the slides. Based on the experimental design for microarray analyses, either single labeled or dual-labeled hybridizations might be generated. From our experiences we successfully used the single label-design for class comparisons. Although the preamplification protocol enables analyses of spurious amounts of DNA, it is also suited for performing genomic methylation screens.

To elucidate methylation biomarkers for prediction of metastasis risk on a genomewide level we subjected 500 ng of DNA derived from primary tumor samples to amplification of the methylated DNA using the procedure outlined above. RCA-amplicons derived from metastasised and non-metastasised samples were labelled using the CGH Labeling Kit (Enzo, Farmingdale, N.Y.) and labelled products hybridized onto human 244 k CpG island arrays (Agilent, Wald-bronn, Germany). All manipulations were according the instructions of the manufacturers.

Example 10: Data Analysis

Hybridizations performed on a chip with probes for the inventive 360 marker genes were scanned using a GenePix 4000A scanner (Molecular Devices, Ismaning, Germany) with a PMT setting to 700V/cm (equal for both wavelengths). Raw image data were extracted using GenePix 6.0 software (Molecular Devices, Ismaning, Germany).

Hybridizations performed on whole genome arrays were scanned using an Agilent DNA microarray scanner and raw image data were extracted using the Agilent Feature Extraction Software (v9.5.3.1).

Microarray data analyses were performed using BRB-ArrayTools developed by Dr. Richard Simon and BRB-ArrayTools Development Team. The software package BRB Array Tools (version 3.6; in the www at linus.nci.nih.gov/BRB-ArrayTools.html) was used according recommendations of authors and settings used for analyses are delineated in the results if appropriate. For every hybridization, background intensities were subtracted from foreground intensities for each spot. Global normalization was used to median center the log-ratios on each array in order to adjust for differences in spot/label intensities.

P-values (p) used for feature selection for classification and prediction were based on the univariate significance levels (alpha). P-values (p) and mis-classification rate during cross validation (MCR) were given along the result data.

Example 11: Multiplexed Methylation Testing Outperforms the "Classification" Success when Compared to Genomewide and Targeted Screenings Via RNA Expression Profiling RNA and DNA breast cancer tissue samples of the primary tumor from patients were used for genomic expression profiling and DNA methylation analyses, respectively, for elucidation of biomarkers to predict metastasis during follow up of disease. From the 44 k expression analyses of patient samples with (n=6) and without (n=6) metastases class-prediction did elucidate 961 different RNA-expression markers suitable for classification of either group (FIG. 1). Cross validation obtained a 83% correct classification for prediction of development of metastases during follow up of breast cancer patients.

In addition expression data of a subset of 385 biomarkers elucidated by Lauss 2007 (Lauss M, Kriegner A, Vierlinger K, Visne I, Yildiz A, Dilayeroglu E, Noehammer C. Consensus genes of the literature to predict breast cancer recurrence 33. Breast Cancer Res Treat 2008; 110:235-44) from the 44 k Agilent expression arrays was used as second comparison for class prediction and obtained 67% correct classification of patients with and without metastasis.

Using the inventive DNA methylation data of the same primary tumor samples as used for class prediction via expression profiling, good classification of both primary tumor groups by only a few genes (n=4; p=0.01) was obtained. Class prediction using these classifiers gave a correct classification of more than 83% by using different statistical tests. Best classification of 100% was obtained using diagonal linear discriminant analysis. In FIG. 2 the performance of genome-scaled and "targeted" expression profiling is presented of a predefined marker set (Lauss 2007) versus the inventive methylation testing for the purpose of predicting the risk of metastasis in breast cancer patients when analysing primary tumor tissue.

Example 12: Multiplexed Methylation Testing Enables Identification of Biomarkers for a Wide Variety of (Neoplastic) Diseases 12.1 Classification of Tumor Vs Normal & histologically Different Tumor Subgroups Exemplified Using Breast Cancer Patient Tissue Although prediction of the risk of metastasis is a major challenge and would be of great interest for therapeutic intervention, it is also of interest to distinguish histological entities of primary breast tumors and also to distinguish normal tissue from tumor tissue. Therefore DNA derived from several ductal (n=8) and lobular (n=8) primary tumors were subjected to the methylation test. From several patients normal tissue (n=4) adjacent to the primary tumor was also available for analysis. Class prediction using binary tree algorithm within BRB-AT did elucidate good classification (MCR=12.5%) of histopathological distinct subgroups of lobular and ductal breast primary tumors by a 8-gene classifier (p<0.005). Although normal tissue adjacent to the neoplastic nodes was available only from 4 patients, 12 methylation-markers enable distinction from tumors (p<0.005; MCR=30%; table 3).

Binary tree prediction for classification of normal (Bre) breast tissue, and ductal (Duct) and lobular (Lob) breast carcinomas. Gene classifiers discriminating nodes 1) and 2) of the binary tree are listed in subtables 1) & 2), respectively. Optimal Binary Tree as shown in FIG. 6.

TABLE 2

Cross-validation error rates for a fixed tree structure shown below

| Node | Group 1 Classes | Group 2 Classes | Mis-classification rate (%) |
|---|---|---|---|
| 1 | Bre | Duct, Lob | 30 |
| 2 | Duct | Lob | 12, 5 |

Node 1

TABLE 3

Composition of classifier (12 genes) - Sorted by p-value:

| | Parametric p-value | t-value | % CV support | Geom mean of intensities in group 1 | Geom mean of intensities in group 2 | Gene symbol |
|---|---|---|---|---|---|---|
| 1 | 5.82e−05 | −5.217 | 35 | 1343.4132985 | 21174.1289278 | CHRNA9 |
| 2 | 0.0006143 | 4.141 | 95 | 1599.9071878 | 824.7000158 | RPA2 |
| 3 | 0.0007052 | 4.079 | 85 | 2063.3995618 | 350.2638104 | CPEB4 |
| 4 | 0.0018077 | −3.656 | 25 | 1072.6323837 | 2314.8492042 | CASP8 |
| 5 | 0.0023551 | 3.537 | 95 | 491.7930375 | 277.2894179 | MSH2 |
| 6 | 0.0024582 | 3.518 | 90 | 2139.495605 | 407.0543144 | ACTB |
| 7 | 0.0024956 | 3.511 | 90 | 513.7445949 | 283.0545393 | CTCFL |
| 8 | 0.0025706 | −3.498 | 25 | 211.6684594 | 272.432498 | TPM2 |
| 9 | 0.00346 | −3.364 | 85 | 726.4778494 | 19458.747759 | SERPINB5 |
| 10 | 0.0035762 | −3.349 | 100 | 464.1379972 | 3076.4135783 | PIWIL4 |
| 11 | 0.0036246 | −3.342 | 90 | 356.3151461 | 2092.5026725 | NTF3 |
| 12 | 0.0037267 | 3.33 | 20 | 1278.6604587 | 419.69101 | CDK2AP1 |

Node 2

TABLE 4

Composition of classifier (8 genes)- Sorted by p-value:

| | Parametric p-value | t-value | % CV support | Geom mean of intensities in group 1 | Geom mean of intensities in group 2 | Gene symbol |
|---|---|---|---|---|---|---|
| 1 | 0.0001136 | −5.293 | 30 | 4902.6591549 | 26841.3804373 | IGF2 |
| 2 | 0.0001792 | −5.044 | 35 | 2927.8176757 | 12908.2539897 | KCNQ1 |
| 3 | 0.0013497 | −3.987 | 80 | 651.8291224 | 3430.8937904 | SCGB3A1 |
| 4 | 0.0014207 | −3.961 | 15 | 3942.4418214 | 30572.6979298 | EFS |
| 5 | 0.0017484 | −3.856 | 80 | 562.2147524 | 10348.9103352 | BRCA1 |
| 6 | 0.0032727 | 3.539 | 80 | 981.9197084 | 533.1453151 | ITGA4 |
| 7 | 0.0033906 | −3.521 | 80 | 290.4681662 | 518.4060518 | H19 |
| 8 | 0.0039029 | −3.45 | 80 | 249.580905 | 595.0171743 | PTTG1 |

For testing the usability of the inventive methylation test on neoplasias other than breast cancer, several solid tumor entities of the thyroid, brain and also leukemia (ALL, CML) samples were tested. Different clinical relevant classes for each setting were analysed and all samples and most subgroups could be successfully classified.

Example 13: Classification of Diseased Versus Healthy on Minimal Amounts of Initial DNA Samples Upon Preamplification Confirms Suitability of the Test for Diagnosis of Neoplastic Disease 13.1 Classification Upon Preamplification Exemplified by Distinguishing Chronic Myeloid Leukemia (CML) and Normal DNA The methylation pattern of a set of 28 different DNA samples derived from a patient suffering from chronic myeloid leukemia versus 12 normal controls were analysed. DNA samples were derived from 8 CML patients at diagnosis, 13 patients within their chronic phase of disease, 3 patients were in the accelerated phase and 3 were blast crisis patients.

Because only limited amounts of DNA were available from patients, DNA (100 ng) from CML-patients and controls were subjected to preamplification outlined in example 6.

The amplicons derived from the preamplification procedure were directly subjected to the inventive methylation test.

Binary Tree Prediction of leukemias versus normal controls did perform well to distinguish leukemia at the different stages of disease from normals by a 36-gene classifier ($p<0.005$; MCR=12.5%). Although some more specific analyses were performed to distinguish different subtypes, this example does illustrate that the test is suitable for classification of neoplastic disease upon selective preamplification of methylated DNA. Thus even if only limiting amounts of sample-DNA are available, the inventive methylation test can successfully be applied upon preamplification.

TABLE 5

Composition of classifier (36 genes) - Sorted by p-value:

| | Parametric p-value | t-value | % CV support | Geom mean of intensities in group 1 | Geom mean of intensities in group 2 | Fold-change | Gene symbol |
|---|---|---|---|---|---|---|---|
| 1 | 1.1e−06 | −5.793 | 95 | 1263.9802574 | 4806.832556 | 0.2629549 | KRT17 |
| 2 | 5.1e−06 | −5.303 | 100 | 1463.3193409 | 1920.7523898 | 0.7618469 | IGFBP7 |
| 3 | 9.1e−06 | −5.121 | 100 | 1511.2662562 | 2955.7308068 | 0.5113004 | RHOXF1 |
| 4 | 1.72e−05 | −4.918 | 95 | 20637.941078 | 46618.878139 | 0.4426949 | CLIC4 |
| 5 | 2.71e−05 | 4.771 | 92 | 14820.0920262 | 1079.0081152 | 13.7349217 | TP53 |
| 6 | 4.23e−05 | −4.627 | 35 | 790.262932 | 1029.0132426 | 0.7679813 | DLX2 |
| 7 | 5.23e−05 | −4.558 | 100 | 1475.3864164 | 1927.1702779 | 0.7655714 | ITGA4 |
| 8 | 5.48e−05 | −4.543 | 95 | 7088.9368921 | 17609.331244 | 0.4025671 | AIM1L |
| 9 | 5.56e−05 | −4.538 | 100 | 14379.9182852 | 22804.2747276 | 0.6305799 | SERPINE1 |
| 10 | 0.0001345 | −4.248 | 100 | 9717.5611883 | 17598.3595625 | 0.5521856 | SERPINB2 |
| 11 | 0.0002954 | 3.985 | 88 | 11354.6816924 | 2022.493242 | 5.6142001 | TP53 |
| 12 | 0.0003989 | −3.883 | 100 | 11221.6384365 | 29143.990982 | 0.3850412 | XIST |
| 13 | 0.0004322 | 3.856 | 100 | 742.5848866 | 546.520133 | 1.3587512 | TEAD1 |
| 14 | 0.000434 | −3.854 | 30 | 862.109825 | 1386.5854709 | 0.6217502 | CDKN2A |
| 15 | 0.0006597 | 3.711 | 100 | 660.6032958 | 524.9889814 | 1.2583184 | CSD |
| 16 | 0.0007378 | 3.672 | 100 | 785.2529086 | 617.6193603 | 1.2714189 | OPCML |
| 17 | 0.0007806 | −3.652 | 100 | 1381.0481047 | 1965.8965177 | 0.702503 | RPA2 |
| 18 | 0.0010337 | −3.554 | 100 | 1183.5538583 | 1688.740182 | 0.7008502 | BRCA2 |
| 19 | 0.001152 | 3.516 | 35 | 1438.1953436 | 669.5215427 | 2.1480942 | CDH1 |
| 20 | 0.001172 | 3.51 | 100 | 11818.780587 | 2031.174303 | 5.8186934 | S100A9 |
| 21 | 0.0013513 | −3.459 | 100 | 6127.7927364 | 19156.6698358 | 0.3198778 | SERPINB2 |
| 22 | 0.0022834 | −3.271 | 100 | 11693.5413074 | 21146.1880984 | 0.5529858 | BCL2A1 |
| 23 | 0.0022851 | −3.271 | 100 | 10468.9977669 | 23016.6853434 | 0.4548399 | UNC13B |
| 24 | 0.0027352 | 3.205 | 85 | 1917.243492 | 745.0787808 | 2.5732091 | ABL1 |
| 25 | 0.0027712 | −3.2 | 100 | 667.4659158 | 800.35431 | 0.833963 | TIMP1 |
| 26 | 0.0027872 | 3.198 | 40 | 640.0521798 | 537.6900011 | 1.190374 | ATM |
| 27 | 0.0028429 | −3.191 | 100 | 2336.84516 | 3238.4943236 | 0.7215838 | FBXW7 |
| 28 | 0.0031125 | 3.158 | 100 | 725.8979125 | 597.4123838 | 1.2150701 | SFRP5 |
| 29 | 0.0035124 | 3.113 | 100 | 620.6367677 | 497.0320247 | 1.2486857 | ACTB |
| 30 | 0.0035612 | 3.108 | 35 | 567.9891823 | 489.9503223 | 1.1592791 | MSX1 |
| 31 | 0.00361535 | −3.102 | 100 | 627.0854408 | 711.048915 | 0.881916 | LOX |
| 32 | 0.0044333 | −3.026 | 92 | 778.7345672 | 1044.8511153 | 0.7453067 | SOX15 |
| 33 | 0.0047223 | −3.002 | 82 | 695.3700608 | 871.1853197 | 0.7981885 | DGKH |
| 34 | 0.0048254 | −2.994 | 100 | 672.1331334 | 786.3575687 | 0.8547424 | CYLD |
| 35 | 0.0049438 | −2.985 | 90 | 823.3337589 | 977.9374174 | 0.8419084 | XPA |
| 36 | 0.0049751 | −2.982 | 65 | 744.8636247 | 935.0874611 | 0.7965711 | XPC |

13.2 Classification of Diseased Versus Healthy Individuals Using DNA Samples Derived from Serum Confirms Suitability of the Test for Minimal Invasive Diagnostic Testing of Cancer (Breast Cancer)

DNA was isolated from serum of breast cancer patients (n=16) at initial diagnosis and female healthy controls (n=6) and two patients with benign tumors. The minute amounts of serum DNA (about 10-100 ng/ml) derived from patients and controls were subjected to preamplification of the methylated DNA fraction as outlined in the methods. Derived amplicons were subjected to methylation testing using the inventive methylation test. Using different statistical methods for class prediction did successfully elucidate classifiers for distinguishing patients with malign tumors (n=18) from benign and healthy controls (n=8). Binary Tree Prediction of serum from tumors versus controls did perform well to distinguish diseased from normal individuals by a 9-gene classifier (p<0.005; MCR=16.7%). This example does illustrate that the test is suitable for classification of neoplastic disease, in this case breast cancer, from serum of patients. In other words the test enables minimal invasive diagnosis of malignancies.

TABLE 6

Comparison of T (malign tumors)/N (benign node & normal), Composition of classifier (9 genes) - Sorted by p-value:

|   | Parametric p-value | t-value | % CV support | Geom mean of intensities in group 1 | Geom mean of intensities in group 2 | Fold-change | Gene symbol |
|---|---|---|---|---|---|---|---|
| 1 | 4.65e−05 | 5.052 | 100 | 471.4190504 | 111.5926927 | 4.2244616 | NEUROD2 |
| 2 | 0.0002572 | 4.349 | 100 | 210.9118362 | 103.7369196 | 2.0331415 | CTCFL |
| 3 | 0.0004392 | 4.13 | 33 | 539.5395846 | 182.6963182 | 2.953205 | GBP2 |
| 4 | 0.0009924 | −3.795 | 83 | 182.6828637 | 864.2332187 | 0.2113814 | SFN |
| 5 | 0.0011568 | 3.732 | 100 | 2533.774643 | 367.7414847 | 6.8900974 | MAGEB2 |
| 6 | 0.0017215 | −3.567 | 100 | 430.8628796 | 756.3748064 | 0.569642 | DIRAS3 |
| 7 | 0.0032818 | 3.297 | 67 | 2315.4228952 | 492.0946 | 4.7052394 | ARMCX2 |
| 8 | 0.0039912 | 3.215 | 100 | 9327.275399 | 1851.01709 | 5.0390002 | HRAS |

TABLE 7

Performance of classifiers during cross-validation

|  | Compound-Covariate Predictor Correct? | Diagonal Linear Discriminant Analysis Correct? | 1-Nearest Neighbor | 3-Nearest Neighbors Correct? | Nearest Centroid Correct? | Support Vector-Machines Correct? | Bayesian Compound Covariate Predictor Correct? |
|---|---|---|---|---|---|---|---|
| Mean percent of correct classification: | 83 | 79 | 75 | 83 | 79 | 71 | 85 |

Performance of the 3-Nearest Neighbours Classifier:

| Class | Sensitivity | Specificity | PPV | NPV |
|---|---|---|---|---|
| Norm | 0.625 | 0.938 | 0.833 | 0.833 |
| T | 0.938 | 0.625 | 0.833 | 0.833 |

TABLE 8

Composition of classifier - Sorted by t-value:

|   | Parametric p-value | t-value | % CV support | Geom mean of intensities in group 1 | Geom mean of intensities in group 2 | Fold-change | Gene symbol |
|---|---|---|---|---|---|---|---|
| 1 | 0.0009924 | −3.795 | 100 | 182.6826576 | 864.2335483 | 0.2113811 | SFN |
| 2 | 0.0017215 | −3.567 | 100 | 430.8637112 | 756.3752883 | 0.5696428 | DIRAS3 |
| 3 | 0.0039912 | 3.215 | 33 | 9327.2785112 | 1851.017692 | 5.0390002 | HRAS |
| 4 | 0.0032818 | 3.297 | 67 | 2315.42463 | 492.0942152 | 4.7052466 | ARMCX2 |
| 5 | 0.0011568 | 3.732 | 100 | 2533.773004 | 367.7411692 | 6.8900988 | MAGEB2 |
| 6 | 0.0004392 | 4.13 | 100 | 539.5397658 | 182.6961002 | 2.953209 | GBP2 |
| 7 | 0.0002572 | 4.349 | 100 | 210.9118779 | 103.7366691 | 2.0331468 | CTCFL |
| 8 | 4.65e−05 | 5.052 | 100 | 471.419219 | 111.5924047 | 4.2244741 | NEUROD2 |

Example 14: Thyroid-Cancer-Diagnostics: Diagnostic Methylation Markers for Elucidation of Nodular Thyroid Disease 6 Histological Classes were Used:
SD . . . normal thyroid tissue
SN . . . Struma nodosa (benign)
FTA=folicular adenoma (benign)
FTC . . . Follicular thyroid carcinoma (malign)
PTC . . . Papillary thyroid carcinoma (malign)
MTC . . . Medullary thyroid carcinoma (malign)
1. Of diagnostic importance would be to distinguish "benign" vs. "malign" entities.

MTC has been excluded within this class comparison due to its low frequency (about 5% of all thyroid malignancies) but is elucidated by the different genes in chapter 2.

2. Within the "binary tree prediction approach" MTC is distinguished from other entities (FTA, FTC, PTC, SN) as depicted in "node 2" classification list
3. Although in 2) all classes are distinguished (sometimes to a not very good correct classification rate), those contrasts which are of utmost clinical/diagnostic relevance were analysed in detail for distinguishing
   3.1. FTC vs FTA using "Class Prediction" for defining a 18 gene classifier (100% correct classification)
   3.2. FTC vs FTA using another feature selection strategy resulting in a 15 gene classifier (97% correct classification)
   3.3. PTC vs FTA
   3.4. FTC vs SN
   3.5. PTC vs SN
      14.1. Benign (SN, FTA) vs Malign (FTC, PTC)

TABLE 9

Sorted by p-value of the univariate test. Class 1: benign; Class 2: FTC or PTC.

| | Parametric p-value | FDR | Geom mean of intensities in class 1 | Geom mean of intensities in class 2 | Ratio of geom means | Gene symbol |
|---|---|---|---|---|---|---|
| 1 | 0.0004498 | 0.1632774 | 15390.3295197 | 33003.877353 | 0.4663188 | PITX2 |
| 2 | 0.0026894 | 0.3850159 | 12719.7083391 | 7482.6386146 | 1.6998961 | TJP2 |
| 3 | 0.0037242 | 0.3850159 | 93.6738594 | 412.2559349 | 0.2272226 | CD24 |
| 4 | 0.0043096 | 0.3850159 | 1279.8569969 | 3807.3051919 | 0.3361582 | ESR1 |
| 5 | 0.0059178 | 0.3850159 | 4082.770499 | 8974.2819351 | 0.4549412 | TNFRSF10D |
| 6 | 0.0063639 | 0.3850159 | 205.8665472 | 306.0085302 | 0.6727477 | RPA3 |
| 7 | 0.0082777 | 0.4292579 | 2312.8421749 | 942.9182575 | 2.4528554 | RASSF1 |

The first 7 genes are significant at the nominal 0.01 level of the univariate test The support vector machine classifier was used for class prediction. There were 5 nodes in the classification tree. Cross-validation error rates for a fixed optimal binary tree structure shown below

| Node | Group 1 Classes | Group 2 Classes | Misclassification rate (%) |
|---|---|---|---|
| 1 | FTA, FTC, MTC, PTC, SN | SD | 6.8 |
| 2 | FTA, FTC, PTC, SN | MTC | 7.2 |
| 3 | FTA, FTC, PTC | SN | 20.0 |
| 4 | FTA | FTC, PTC | 33.9 |
| 5 | FTC | PTC | 35.9 |

Results of classification, Node 1: Cross-validation results for a fixed tree structure:
patients correct classified
FTA 16/17
FTC 20/20
MTC 7/7
PTC 18/18
SD 0/5
SN 18/18
Percent correctly classified: 93%

| | Parametric p-value | t-value | % CV support | Geom mean of intensities in group 1 | Geom mean of intensities in group 2 | Gene symbol |
|---|---|---|---|---|---|---|
| 1 | 7.6e−06 | −4.766 | 94 | 7972.9295449 | 22387.9297622 | GATA5 |
| 2 | 0.0013152 | 3.322 | 98 | 51673.1951146 | 6884.5033099 | RASSF1 |
| 3 | 0.0065761 | 2.785 | 98 | 840.4207092 | 82.2749271 | HIST1H2AG |
| 4 | 0.0082313 | −2.705 | 99 | 42.4588683 | 64.5227571 | NPTX1 |
| 5 | 0.0085479 | 2.692 | 97 | 13341.9608122 | 8480.082485 | UNC13B |

Results of classification, Node 2: Cross-validation results for a fixed tree structure
Composition of classifier (9 genes):
patients correct classified
FTA 16/17
FTC 19/20
MTC 4/8
PTC 19/19
SN 19/19
Percent correctly classified: 93%

TABLE 11

Composition of classifier (9 genes)- Sorted by p-value:

|   | Parametric p-value | t-value | % CV support | Geom mean of intensities in group 1 | Geom mean of intensities in group 2 | Gene symbol |
|---|---|---|---|---|---|---|
| 1 | 1.13e−05 | −4.682 | 90 | 230.8307324 | 1924.0226549 | SMAD3 |
| 2 | 5.72e−05 | 4.248 | 94 | 67109.2566153 | 31234.9115127 | NANOS1 |
| 3 | 0.0004394 | −3.666 | 94 | 767.1296668 | 2348.478919 | TERT |
| 4 | 0.000625 | 3.559 | 94 | 332.5916816 | 195.6267289 | BCL2 |
| 5 | 0.0008654 | −3.46 | 94 | 686.8001735 | 2490.5408809 | SPARC |
| 6 | 0.0011196 | −3.379 | 91 | 115.0495548 | 188.2352474 | SFRP2 |
| 7 | 0.0043949 | 2.931 | 94 | 243.4255487 | 148.0133095 | MGMT |
| 8 | 0.0048542 | −2.896 | 92 | 274.3754341 | 810.9295588 | MYOD1 |
| 9 | 0.0057496 | −2.837 | 92 | 38.9398369 | 84.6344764 | LAMA1 |

Results of classification, Node 3:
Cross-validation results for a fixed tree structure:
patients correct classified
FTA 17/17
FTC 18/20
PTC 18/19
SN 7/18
Percent correctly classified: 80%

TABLE 12

Composition of classifier (5 genes) - Sorted by p-value:

|   | Parametric p-value | t-value | % CV support | Geom mean of intensities in group 1 | Geom mean of intensities in group 2 | Gene symbol |
|---|---|---|---|---|---|---|
| 1 | 0.0005992 | −3.588 | 85 | 7870.9503963 | 16201.151645 | TJP2 |
| 2 | 0.0015263 | 3.294 | 85 | 635.4086799 | 213.4944584 | CALCA |
| 3 | 0.0017838 | 3.243 | 85 | 485.262328 | 290.1960934 | PITX2 |
| 4 | 0.0027934 | 3.095 | 80 | 48.3355088 | 27.4294727 | TFPI2 |
| 5 | 0.0047821 | −2.91 | 85 | 1128.2868733 | 1710.0622275 | CDKN2B |

Results of classification, Node 4:
Cross-validation results for a fixed tree structure:
patients correct classified
FTA 5/17
FTC 15/20
PTC 16/18
Percent correctly classified: 66%

TABLE 13

Composition of classifier (9 genes) - Sorted by p-value:

|   | Parametric p-value | t-value | % CV support | Geom mean of intensities in group 1 | Geom mean of intensities in group 2 | Gene symbol |
|---|---|---|---|---|---|---|
| 1 | 1.04e−05 | −4.863 | 64 | 3920.5540125 | 11889.0217619 | PITX2 |
| 2 | 0.0013466 | −3.381 | 22 | 10441.5689576 | 26229.9132005 | TNFRSF10D |
| 3 | 0.0046454 | −2.954 | 38 | 46.3169574 | 96.5053948 | PAX8 |
| 4 | 0.0054482 | 2.896 | 64 | 33347.6108478 | 21919.0919927 | RAD23A |
| 5 | 0.0064941 | 2.832 | 60 | 12965.7235207 | 8197.6874068 | GJB2 |
| 6 | 0.0065537 | 2.828 | 55 | 139.8606592 | 62.8034203 | F2R |
| 7 | 0.0073249 | −2.787 | 57 | 72.5515718 | 127.581594 | TP53 |
| 8 | 0.0078556 | 2.761 | 56 | 84134.0800225 | 52673.1287104 | NTHL1 |
| 9 | 0.00959 | −2.686 | 62 | 136.247048 | 271.3403127 | TP53 |

Results of classification, Node 5:
Cross-validation results for a fixed tree structure:
patients correct classified
FTC 12/20
PTC 13/19
Percent correctly classified: 64%

TABLE 14

Composition of classifier (8 genes) - Sorted by p-value

| | Parametric p-value | t-value | % CV support | Geom mean of intensities in group 1 | Geom mean of intensities in group 2 | Gene symbol |
|---|---|---|---|---|---|---|
| 1 | 0.0016883 | −3.387 | 44 | 35.5300087 | 56.3898442 | ARRDC4 |
| 2 | 0.0017438 | 3.375 | 44 | 198.6487641 | 41.0217973 | DUSP1 |
| 3 | 0.0020618 | −3.315 | 44 | 108.3530993 | 160.6650355 | SMAD9 |
| 4 | 0.0040023 | 3.069 | 41 | 1193.6368555 | 666.0832986 | HOXA10 |
| 5 | 0.0056114 | −2.941 | 24 | 127.6207843 | 222.4011791 | C3 |
| 6 | 0.0059259 | 2.92 | 40 | 2394.3665853 | 1528.6234599 | ADRB2 |
| 7 | 0.0059449 | 2.919 | 44 | 122.6625475 | 64.1040342 | BRCA2 |
| 8 | 0.0074916 | 2.829 | 41 | 5198.3451454 | 2129.3367628 | SYK |

Example 15: Specific Diagnostically Challenging Contrasts 15.1 FTC/FTA Using a 18 Gene List Derived from the Test Obtained 100% Correct Classification

TABLE 15

Composition of classifier - Sorted by t-value (Sorted by gene pairs) Class 1: FTA; Class 2: FTC

| | Parametric p-value | t-value | % CV support | Geom mean of intensities in class 1 | Geom mean of intensities in class 2 | Ratio of geom means | Gene symbol |
|---|---|---|---|---|---|---|---|
| 1 | 0.0007423 | −3.67 | 100 | 10627.1525329 | 26519.7470807 | 0.400726 | PITX2 |
| 2 | 0.0034319 | −3.121 | 100 | 328.8689371 | 979.8430866 | 0.3356343 | MT3 |
| 3 | 0.0074763 | −2.826 | 100 | 207.6507576 | 338.9036062 | 0.6127133 | RPA3 |
| 4 | 0.0088903 | −2.758 | 100 | 3488.3504846 | 8791.8091348 | 0.3967728 | TNFRSF10D |
| 5 | 0.0332087 | −2.21 | 100 | 3258.5247053 | 5669.669334 | 0.5747292 | PTEN |
| 6 | 0.0567379 | −1.965 | 100 | 29707.6166671 | 47300.7954894 | 0.6280574 | TP53 |
| 7 | 0.0828438 | −1.781 | 100 | 4579.1636841 | 7646.1012782 | 0.5988887 | PAX8 |
| 8 | 0.1254796 | −1.567 | 100 | 42.1725109 | 86.8790615 | 0.4854163 | TGFBR2 |
| 9 | 0.1302653 | −1.547 | 100 | 449.1377587 | 856.0744763 | 0.524648 | HIC1 |
| 10 | 0.2417368 | 1.189 | 100 | 706.5562394 | 454.4492607 | 1.5547528 | CALCA |
| 11 | 0.1943858 | 1.321 | 100 | 239.4600021 | 123.344525 | 1.9413914 | PSAT1 |
| 12 | 0.0550058 | 1.98 | 100 | 235.3149757 | 165.6298484 | 1.4207281 | MBD2 |
| 13 | 0.0520253 | 2.006 | 100 | 98.2107223 | 50.7706867 | 1.9343981 | NTF3 |
| 14 | 0.0310386 | 2.24 | 100 | 1193.7407767 | 704.5901877 | 1.6942342 | PLAGL1 |
| 15 | 0.0249361 | 2.335 | 100 | 105.8274714 | 38.2692353 | 2.7653406 | F2R |
| 16 | 0.0177839 | 2.478 | 100 | 189.6068895 | 118.9530389 | 1.5939642 | GJB2 |
| 17 | 0.0056226 | 2.936 | 100 | 77.328539 | 44.8368212 | 1.724666 | ARRDC4 |
| 18 | 0.0016393 | 3.391 | 100 | 139.2179613 | 66.1471574 | 2.1046704 | NTHL1 |

15.2 FTC/FTA 15 Gene List/97% Correct Classification Performance of the Support Vector Machine Classifier

TABLE 16

Composition of classifier - Sorted by t-value: Class 1: FTA; Class 2: FTC

| | Parametric p-value | t-value | % CV support | Geom mean of intensities in class 1 | Geom mean of intensities in class 2 | Ratio of geom means | Gene symbol |
|---|---|---|---|---|---|---|---|
| 1 | 0.0034319 | −3.121 | 100 | 328.8689371 | 979.8430866 | 0.3356343 | MT3 |
| 2 | 0.0074763 | −2.826 | 100 | 207.6507576 | 338.9036062 | 0.6127133 | RPA3 |
| 3 | 0.0088903 | −2.758 | 100 | 3488.3504846 | 8791.8091348 | 0.3967728 | TNFRSF10D |

TABLE 16-continued

Composition of classifier - Sorted by t-value: Class 1: FTA; Class 2: FTC

|   | Parametric p-value | t-value | % CV support | Geom mean of intensities in class 1 | Geom mean of intensities in class 2 | Ratio of geom means | Gene symbol |
|---|---|---|---|---|---|---|---|
| 4 | 0.0183961 | −2.464 | 100 | 500.9652123 | 3828.0253981 | 0.1308678 | HOXA1 |
| 5 | 0.0461873 | −2.061 | 100 | 382.1794446 | 1120.8851782 | 0.3409622 | C13orf15 |
| 6 | 0.1254796 | −1.567 | 100 | 42.1725109 | 86.8790615 | 0.4854163 | TGFBR2 |
| 7 | 0.1302653 | −1.547 | 100 | 449.1377587 | 856.0744763 | 0.524648 | HIC1 |
| 8 | 0.2417368 | 1.189 | 100 | 706.5562394 | 454.4492607 | 1.5547528 | CALCA |
| 9 | 0.1943858 | 1.321 | 100 | 239.4600021 | 123.344525 | 1.9413914 | PSAT1 |
| 10 | 0.0520253 | 2.006 | 100 | 98.2107223 | 50.7706867 | 1.9343981 | NTF3 |
| 11 | 0.0310386 | 2.24 | 100 | 1193.7407767 | 704.5901877 | 1.6942342 | PLAGL1 |
| 12 | 0.0249361 | 2.335 | 100 | 105.8274714 | 38.2692353 | 2.7653406 | F2R |
| 13 | 0.0177839 | 2.478 | 100 | 189.6068895 | 118.9530389 | 1.5939642 | GJB2 |
| 14 | 0.0056226 | 2.936 | 100 | 77.328539 | 44.8368212 | 1.724666 | ARRDC4 |
| 15 | 0.0016393 | 3.391 | 100 | 139.2179613 | 66.1471574 | 2.1046704 | NTHL1 |

15.3 PTC Vs FTA

|   | Parametric p-value | FDR | Permutation P-value | Geom mean of intensities in class 1 | Geom mean of intensities in class 2 | Ratio of geom means | Gene symbol |
|---|---|---|---|---|---|---|---|
| 1 | 9e−06 | 0.003267 | <1e−07 | 10627.1525329 | 41548.9754391 | 0.2557741 | PITX2 |
| 2 | 0.0011266 | 0.2044779 | 0.004 | 4579.1636841 | 12649.089991 | 0.3620153 | PAX8 |
| 3 | 0.0030935 | 0.3304224 | 0.005 | 72.7004543 | 605.7807776 | 0.1200112 | CD24 |
| 4 | 0.0040729 | 0.3304224 | 0.004 | 14001.0650248 | 35757.8144724 | 0.3915526 | TP53 |
| 5 | 0.0047034 | 0.3304224 | 0.004 | 1301.897851 | 5982.0029003 | 0.2176358 | ESR1 |
| 6 | 0.0067281 | 0.3304224 | 0.011 | 3488.3504846 | 9170.4514823 | 0.3803903 | TNFRSF10D |
| 7 | 0.0080894 | 0.3304224 | 0.004 | 351.0381929 | 224.3668614 | 1.5645724 | RAD23A |
| 8 | 0.0082387 | 0.3304224 | 0.005 | 493.173919 | 328.2626049 | 1.5023762 | SCGB3A1 |
| 9 | 0.0090574 | 0.3304224 | 0.014 | 70.3369564 | 179.1866865 | 0.3925345 | RARB |
| 10 | 0.0098888 | 0.3304224 | 0.01 | 29707.6166671 | 60906.5322265 | 0.4877575 | TP53 |
| 11 | 0.0100128 | 0.3304224 | 0.006 | 40730.0866495 | 65963.7621444 | 0.6174615 | LZTS1 |

15.4 FTC Vs. SN

TABLE 17

Sorted by p-value of the univariate test. Class 1: FTC; Class 2: SN.

|   | Parametric p-value | FDR | Permutation p-value | Geom mean of intensities in class 1 | Geom mean of intensities in class 2 | Ratio of geom means | Gene symbol |
|---|---|---|---|---|---|---|---|
| 1 | 0.0001902 | 0.0690426 | 0.001 | 617.2317683 | 77.9996257 | 7.9132658 | DUSP1 |
| 2 | 0.0009414 | 0.1708641 | 0.001 | 1598.7129792 | 725.1613837 | 2.2046306 | TFPI2 |
| 3 | 0.002919 | 0.353199 | 0.001 | 7596.7179137 | 17030.8826818 | 0.4460554 | TJP2 |
| 4 | 0.0062938 | 0.3685067 | <1e−07 | 30706.7471674 | 46583.449712 | 0.6591772 | S100A9 |
| 5 | 0.0074514 | 0.3685067 | 0.011 | 1978.8381175 | 951.6412902 | 2.079395 | BAZ1A |
| 6 | 0.0076248 | 0.3685067 | 0.014 | 1068.6927823 | 324.8969332 | 3.2893286 | CPEB4 |
| 7 | 0.0087305 | 0.3685067 | 0.008 | 2327.8433497 | 4631.7277355 | 0.5025864 | AIM1L |
| 8 | 0.0094108 | 0.3685067 | 0.015 | 306.9167833 | 477.1071652 | 0.6432869 | CDKN2A |
| 9 | 0.0101347 | 0.3685067 | 0.011 | 506.0097267 | 305.058238 | 1.6587316 | PITX2 |
| 10 | 0.0101517 | 0.3685067 | 0.009 | 629.5647187 | 308.7009013 | 2.0394003 | ARPC1B |
| 11 | 0.0145524 | 0.4327851 | 0.012 | 338.9036062 | 204.2831471 | 1.6589869 | RPA3 |
| 12 | 0.0163339 | 0.4327851 | 0.015 | 1096.5902687 | 526.3310126 | 2.0834612 | SPARC |
| 13 | 0.0175799 | 0.4327851 | 0.022 | 207.2717258 | 85.0712211 | 2.4364494 | SFRP4 |
| 14 | 0.0217937 | 0.4327851 | 0.016 | 48008.7943522 | 69129.0285292 | 0.694481 | LZTS1 |
| 15 | 0.0222054 | 0.4327851 | 0.018 | 3056.7199356 | 4651.428799 | 0.6571572 | MSH4 |
| 16 | 0.0251521 | 0.4327851 | 0.021 | 704.5901877 | 1149.2082587 | 0.6131092 | PLAGL1 |
| 17 | 0.0259637 | 0.4327851 | 0.022 | 691.9006502 | 404.5251677 | 1.710402 | ABCB1 |
| 18 | 0.0266262 | 0.4327851 | 0.038 | 1120.8851782 | 314.8255261 | 3.5603377 | C13orf15 |
| 19 | 0.0273075 | 0.4327851 | 0.018 | 7468.3489385 | 10584.1070705 | 0.7056192 | XIST |
| 20 | 0.0278106 | 0.4327851 | 0.02 | 45641.108997 | 65531.535737 | 0.6964755 | TDRD6 |
| 21 | 0.0289685 | 0.4327851 | 0.025 | 2691.4611924 | 672.8581417 | 4.0000425 | CCDC62 |
| 22 | 0.0304257 | 0.4327851 | 0.041 | 3828.0253981 | 624.614573 | 6.1286201 | HOXA1 |
| 23 | 0.0312402 | 0.4327851 | 0.023 | 19976.272345 | 37682.6754197 | 0.5301182 | IRF4 |
| 24 | 0.0325566 | 0.4327851 | 0.028 | 120.2738711 | 77.7875134 | 1.5461848 | HS-D17B4 |

TABLE 17-continued

Sorted by p-value of the univariate test. Class 1: FTC; Class 2: SN.

|    | Parametric p-value | FDR | Permutation p-value | Geom mean of intensities in class 1 | Geom mean of intensities in class 2 | Ratio of geom means | Gene symbol |
|----|---|---|---|---|---|---|---|
| 25 | 0.0328057 | 0.4327851 | 0.013 | 60485.6819034 | 78581.8893126 | 0.7697153 | S100A9 |
| 26 | 0.0346826 | 0.4327851 | 0.03  | 979.8430866 | 401.5309564 | 2.4402679 | MT3 |
| 27 | 0.0348862 | 0.4327851 | 0.036 | 1570.0860171 | 3111.2674317 | 0.5046451 | KCNJ15 |
| 28 | 0.0363938 | 0.4327851 | 0.039 | 3344.498928 | 7281.6808209 | 0.4593031 | BCL2A1 |
| 29 | 0.0367524 | 0.4327851 | 0.018 | 63981.1014967 | 83037.9187618 | 0.7705046 | S100A8 |
| 30 | 0.0368974 | 0.4327851 | 0.018 | 9.8079183 | 12.7233411 | 0.7708603 | PITX2 |
| 31 | 0.0371835 | 0.4327851 | 0.053 | 333.6158957 | 117.368527 | 2.8424647 | THBD |
| 32 | 0.0388934 | 0.4327851 | 0.018 | 63985.495979 | 82680.140137 | 0.773892 | NANOS1 |
| 33 | 0.0393441 | 0.4327851 | 0.037 | 265.1037031 | 115.7135044 | 2.2910351 | SYK |
| 34 | 0.0405833 | 0.4332864 | 0.049 | 68.4151156 | 26.5907226 | 2.5728942 | SMAD2 |
| 35 | 0.0425023 | 0.4408096 | 0.026 | 63258.4006083 | 81300.2101398 | 0.7780841 | GNAS |
| 36 | 0.0442148 | 0.4458326 | 0.039 | 28643.7793504 | 39779.2329068 | 0.7200687 | HRAS |
| 37 | 0.045838  | 0.4497079 | 0.038 | 166.7951409 | 107.7412818 | 1.548108 | RAR-RES1 |
| 38 | 0.0493413 | 0.4549756 | 0.058 | 3627.4139501 | 1382.0601968 | 2.6246425 | APEX1 |

The first 38 genes which discriminate among classes and are significant at the nominal 0.05 level of the univariate test

15.5 PTC/SN

TABLE 18

Genes which discriminate among classes - Sorted by p-value of the univariate test. Class 1: PTC; Class 2: SN.

|    | Parametric p-value | FDR | Permutation p-value | Geom mean of intensities in class 1 | Geom mean of intensities in class 2 | Ratio of geom means | Gene symbol |
|----|---|---|---|---|---|---|---|
| 1  | 0.0004834 | 0.1754742 | 0.001 | 7364.4053912 | 17030.8826818 | 0.4324148 | TJP2 |
| 2  | 0.0029185 | 0.5297078 | 0.001 | 850.5244086 | 196.5548657 | 4.3271603 | CALCA |
| 3  | 0.0082748 | 0.7365111 | 0.002 | 527.4006737 | 305.058238 | 1.7288524 | PITX2 |
| 4  | 0.0088548 | 0.7365111 | 0.011 | 392.9370376 | 107.8943318 | 3.6418691 | PITX2 |
| 5  | 0.0110205 | 0.7365111 | 0.007 | 5982.0029003 | 1260.4527178 | 4.7459161 | ESR1 |
| 6  | 0.0218315 | 0.7365111 | 0.019 | 22020.0815781 | 8631.2877113 | 2.5511931 | EFS |
| 7  | 0.0218385 | 0.7365111 | 0.028 | 1180.0797724 | 450.0621262 | 2.6220375 | SMAD3 |
| 8  | 0.0220838 | 0.7365111 | 0.018 | 81.0202419 | 47.8687482 | 1.6925498 | ARRDC4 |
| 9  | 0.022633  | 0.7365111 | 0.029 | 605.7807776 | 117.5201124 | 5.1546988 | CD24 |
| 10 | 0.0268848 | 0.7365111 | 0.03  | 344.6965278 | 135.8880329 | 2.5366217 | FHL2 |
| 11 | 0.0278054 | 0.7365111 | 0.029 | 41548.9754391 | 21436.2761698 | 1.9382553 | PITX2 |
| 12 | 0.0280178 | 0.7365111 | 0.037 | 31.359712 | 18.3735789 | 1.706783 | RDHE2 |
| 13 | 0.0304272 | 0.7365111 | 0.035 | 405.5645143 | 674.0128306 | 0.6017163 | KIF5B |
| 14 | 0.0320551 | 0.7365111 | 0.03  | 3376.2127479 | 2270.1502473 | 1.48722 | C3 |
| 15 | 0.0323087 | 0.7365111 | 0.041 | 1354.0969048 | 2261.8338945 | 0.5986721 | KRT17 |
| 16 | 0.0324633 | 0.7365111 | 0.033 | 715.141549 | 2466.2116679 | 0.2899757 | RASSF1 |

The first 16 genes are significant at the nominal 0.05 level of the univariate test Example 16: DNA Methylation Biomarkers for Breast Cancer Diagnostics 1. distinguishing Breast Cancer (BrCa) from healthy breast tissue
2. Metastasis Markers: elucidation and prediction of patients at risk to develop metastases using tissue specimens from the primary tumor at the time of initial surgery
    2.1. ARC-CpG 360 test on original tumor DNA
    2.2. ARC-CpG 360 test on original tumor DNA (using housekeeping genes normalisation)
    2.3. ARC-CpG 360 test on original tumor DNA (using multiplex-normalisation)
    2.4. distinguishing Metastasis/non-Metastasis applying the ARC-CpG 360 test on APA (adapter-primed amplification) products of original tumor DNA
    2.5. applying the original DNA (APA-template) into the test
3. genelists for prediction of organ of metastases
    3.1. Organ of Metastases
    3.2. Organ of Metastases plus additional secondary affected metas. organ ("liver plus", "lung plus", "bone plus")
4. Breast Cancer (BrCa) diagnosis using DNA derived from serum of patients
    methylated DNA from serum of breast cancer patients was RCA-preamplified and subjected to ARC-CpG360 testing
    4.1. Identification of BrCa patients—compound covariate predictor: patient (T) vs controls (N)
    4.2. Identification of BrCa patients—support vector machines predictor: patient (T) vs controls (N)
    4.3. Identification of BrCa patients—greedy pairs & Compound Covariate Predictor=96% correct
    4.4. Identification of BrCa patients—final combined list—greedy pairs=100% correct

Abbreviations lob . . . lobular breast carcinoma
duct . . . ductal breast carcinoma
bre or healthy . . . non malignant breast tissue
ben . . . breast tissue derived from benign nodular disease (fibro adenoma)
m . . . patient-samples (initial diagnosis) developing metastases during follow up
nm . . . patient-samples (initial diagnosis) with NO metastases during follow up
T . . . tumor patient
N . . . normal control individuum—in this settings the group N contains 4 healthy females and 2 females with a confirmed benign tumor (fibroadenoma).

16.1. Distinguishing Breast Cancer (BrCa) from Healthy Breast Tissue

16.1.1. Lob/Duct/Healthy

Binary Tree Prediction
Cross-validation error rate for a fixed binary tree shown below:

| Node | Group 1 Classes | Group 2 Classes | Mis-classification rate (%) |
|---|---|---|---|
| 1 | Bre | Duct, Lob | 30 |
| 2 | Duct | Lob | 12.5 |

Node 1

TABLE 19

Composition of classifier - Sorted by p-value

| | Parametric p-value | t-value | % CV support | Geom mean of intensities in group 1 | Geom mean of intensities in group 2 | Gene symbol |
|---|---|---|---|---|---|---|
| 1 | 5.82E−05 | −5.217 | 35 | 1343.413299 | 21174.12893 | CHRNA9 |
| 2 | 0.0006143 | 4.141 | 95 | 1599.907188 | 824.7000158 | RPA2 |
| 3 | 0.0007052 | 4.079 | 85 | 2063.399562 | 350.2638104 | CPEB4 |
| 4 | 0.0018077 | −3.656 | 25 | 1072.632384 | 2314.849204 | CASP8 |
| 5 | 0.0023551 | 3.537 | 95 | 491.7930375 | 277.2894179 | MSH2 |
| 6 | 0.0024582 | 3.518 | 90 | 2139.495605 | 407.0543144 | ACTB |
| 7 | 0.0024956 | 3.511 | 90 | 513.7445949 | 283.0545393 | CTCFL |
| 8 | 0.0025706 | −3.498 | 25 | 211.6684594 | 272.432498 | TPM2 |
| 9 | 0.00346 | −3.364 | 85 | 726.4778494 | 19458.74776 | SERPINB5 |
| 10 | 0.0035762 | −3.349 | 100 | 464.1379972 | 3076.413578 | PIWIL4 |
| 11 | 0.0036246 | −3.342 | 90 | 356.3151461 | 2092.502673 | NTF3 |
| 12 | 0.0037267 | 3.33 | 20 | 1278.660459 | 419.69101 | CDK2AP1 |

Node 2

TABLE 20

Composition of classifier - Sorted by p-value

| | Parametric p-value | t-value | % CV support | Geom mean of intensities in group 1 | Geom mean of intensities in group 2 | Gene symbol |
|---|---|---|---|---|---|---|
| 1 | 0.0001136 | −5.293 | 30 | 4902.659155 | 26841.38044 | IGF2 |
| 2 | 0.0001792 | −5.044 | 35 | 2927.817676 | 12908.25399 | KCNQ1 |
| 3 | 0.0013497 | −3.987 | 80 | 651.8291224 | 3430.89379 | SCGB3A1 |
| 4 | 0.0014207 | −3.961 | 15 | 3942.441821 | 30572.69793 | EFS |
| 5 | 0.0017484 | −3.856 | 80 | 562.2147524 | 10348.91034 | BRCA1 |
| 6 | 0.0032727 | 3.539 | 80 | 981.9197084 | 533.1453151 | ITGA4 |
| 7 | 0.0033906 | −3.521 | 80 | 290.4681662 | 518.4060518 | H19 |
| 8 | 0.0039029 | −3.45 | 80 | 249.580905 | 595.0171743 | PTTG1 |

16.1.2. Lob/Duct/Healthy [Derived from Analyses Using Non-Mixed Hybridization Conditions]

Binary Tree Prediction

| Node | Group 1 Classes | Group 2 Classes | Misclassification rate (%) |
|---|---|---|---|
| 1 | ductal, lobular | healty breast tissue | 20 |
| 2 | ductal | lobular | 25 |

Node 1

TABLE 21

Composition of classifier - Sorted by p-value

| | Parametric p-value | t-value | % CV support | Geom mean of intensities in group 1 | Geom mean of intensities in group 2 | Gene symbol |
|---|---|---|---|---|---|---|
| 1 | 0.0001584 | −4.906 | 95 | 1225.466145 | 2352.054843 | KRT17 |
| 2 | 0.0010777 | −3.931 | 80 | 7629.719066 | 25785.92874 | AQP3 |
| 3 | 0.0011404 | −3.863 | 65 | 3075.245649 | 7924.300179 | TP53__CGI123__1kb |
| 4 | 0.001804 | −3.657 | 85 | 12069.49535 | 23941.78937 | ZNF462 |
| 5 | 0.0020403 | −3.602 | 90 | 16292.52677 | 37090.74165 | NEUROG1 |
| 6 | 0.002325 | −3.543 | 35 | 1207.584347 | 3266.184892 | GATA3 |
| 7 | 0.0026734 | −3.48 | 100 | 1094.800331 | 2308.87233 | MT1A |
| 8 | 0.0036363 | −3.341 | 95 | 8217.05373 | 20320.07329 | JUP |
| 9 | 0.0036861 | −3.364 | 85 | 14702.60309 | 36953.21634 | RGC32 |
| 10 | 0.0038635 | −3.314 | 50 | 31489.03904 | 49462.09959 | SPINT2 |
| 11 | 0.0044948 | −3.338 | 45 | 1039.178568 | 2203.389201 | DUSP1 |

Node 2

TABLE 22

Composition of classifier - Sorted by t-value

| | Parametric p-value | t-value | % CV support | Geom meanof intensities in group 1 | Geom mean of intensities in group 2 | Gene symbol |
|---|---|---|---|---|---|---|
| 1 | 0.0005054 | −7.957 | 75 | 535.29315 | 1030.403284 | NCL |
| 2 | 0.0007899 | −4.262 | 80 | 2247.443537 | 4043.09435 | XPA |
| 3 | 0.0013895 | 3.972 | 80 | 14070.47463 | 4143.73097 | MYOD1 |
| 4 | 0.0030063 | 3.582 | 45 | 14993.90774 | 7184.50258 | hy__41-Pitx2 |

16.2. Distinguishing Breast Cancer (BrCa) from Benign Breast Tissue

16.2.1. Metastasis Markers

16.2.1.1. NM Vs M Via Class Prediction (88% Correct Classif; SVM)

TABLE 23

Composition of classifier - Sorted by t-value: Class 1: m; Class 2: nm.

| | Parametric p-value | t-value | % CV support | Geom mean of intensities in class 1 | Geom mean of intensities in class 2 | Ratio of geom means | Gene symbol |
|---|---|---|---|---|---|---|---|
| 1 | 0.0046263 | −3.152 | 92 | 4618.6739493 | 122964.4785573 | 10.2011225 | SPARC |
| 2 | 0.0053288 | 3.394 | 88 | 1444.9276316 | 1646.777971 | 12.2340396 | PIWIL4 |
| 3 | 0.0004492 | 4.555 | 100 | 27438.2922955 | 13506.1416447 | 2.0315419 | SERPINB5 |
| 4 | 0.0001677 | 4.728 | 100 | 783.1275118 | 498.3793173 | 1.5713483 | TEAD1 |
| 5 | 0.0005684 | 4.962 | 100 | 9591.5219686 | 1035.8974395 | 9.2591425 | EREG |
| 6 | 8e−07 | 8.333 | 100 | 7422.5296339 | 2919.4183827 | 2.5424686 | ZDHHC11 |
| 7 | 1.3e−06 | 12.86 | 100 | 4921.0334002 | 682.5406118 | 7.2098763 | C5orf4 |

16.2.1.2. NM Vs M Via Class Prediction
(Alternatively Normalised Upon "Housekeeping
Genes" 79% Correct Classif; SVM)

TABLE 24

Composition of classifier: - Sorted by t-value: Class 1: m; Class 2: nm.

| | Parametric p-value | t-value | % CV support | Geom mean of intensities in class 1 | Geom mean of intensities in class 2 | Fold-change | Gene symbol |
|---|---|---|---|---|---|---|---|
| 1 | 0.0001415 | −14.234 | 96 | 816.9876694 | 22923.064881 | 0.0356404 | HSD17B4 |
| 2 | 0.0083213 | −4.853 | 79 | 666.243811 | 1526.6299468 | 0.4364147 | DSP |
| 3 | 0.007109 | −2.968 | 29 | 9716.9365382 | 49855.3171528 | 0.1949027 | SPARC |
| 4 | 0.0064307 | 3.132 | 67 | 1836.3963711 | 722.3717675 | 2.5421763 | KRT17 |
| 5 | 0.002913 | 3.348 | 92 | 59846.4011636 | 52021.1516203 | 1.1504244 | SRGN |
| 6 | 0.0032404 | 3.599 | 92 | 5491.6264846 | 757.0224107 | 7.2542456 | C5orf4 |
| 7 | 0.000719 | 4.31 | 100 | 2679.7639487 | 996.300545 | 2.6897144 | PIWIL4 |
| 8 | 0.0003903 | 4.629 | 100 | 50887.0698062 | 27462.471286 | 1.8529676 | SERPINB5 |
| 9 | 0.0001157 | 5.283 | 100 | 13765.8286072 | 5936.1478811 | 2.3189834 | ZDHHC11 |
| 10 | 3.19e−05 | 6.444 | 100 | 23438.6348936 | 1484.7197091 | 15.7865722 | EREG |

16.2.1.3. NM Vs M_Upon Multiplex Normalisation
Class Prediction (Binary Tree Prediction 83%
Correct Classified)

TABLE 25

Composition of classifier - Sorted by p-value: Class 1: m (n = 18) Class 2: nm (n = 5)

| | Parametric p-value | t-value | % CV support | Geom mean of intensities in group 1 | Geom mean of intensities in group 2 | Ratio of geom means | Gene symbol |
|---|---|---|---|---|---|---|---|
| 1 | <1e−07 | −1e+07 | 87 | 885.547163 | 1982.5964469 | 0.4466603 | TIMP1 |
| 2 | <1e−07 | 1e+07 | 100 | 1453.0368811 | 685.1212898 | 2.1208462 | COL21A1 |
| 3 | <1e−07 | 1e+07 | 91 | 658.5014611 | 551.9419886 | 1.1930628 | COL1A2 |
| 4 | 0.0014608 | −5.539 | 87 | 471.8007783 | 761.7592596 | 0.6193568 | KL |
| 5 | 0.0031096 | 3.87 | 100 | 1080.7271447 | 802.5161476 | 1.3466734 | CDKN2A |

TABLE 26

Composition of classifier - Sorted by p-value

| | Parametric p-value | t-value | % CV support | Geom mean of intensities in group 1 | Geom mean of intensities in group 2 | Ratio of geom means | Gene symbol |
|---|---|---|---|---|---|---|---|
| 1 | <1e−07 | −1e+07 | 87 | 885.547163 | 1982.5964469 | 0.4466603 | TIMP1 |
| 2 | <1e−07 | 1e+07 | 100 | 1453.0368811 | 685.1212898 | 2.1208462 | COL21A1 |
| 3 | <1e−07 | 1e+07 | 91 | 658.5014611 | 551.9419886 | 1.1930628 | COL1A2 |

16.2.1.4. NM Vs M_Upon APA Class Prediction
(Diagonal Linear Discriminant=100% Correct
Classif; SVM=92%)

TABLE 27

Composition of classifier - Sorted by t-value: Class 1: m; Class 2: nm. [n = 6 per each group]

| | Parametric p-value | t-value | % CV support | Geom mean of intensities in class 1 | Geom mean of intensities in class 2 | Fold-change | Gene symbol |
|---|---|---|---|---|---|---|---|
| 1 | 6.8e−06 | −8.508 | 100 | 699.2454811 | 3384.966489 | 0.2065738 | BCL2A1 |
| 2 | 1.24e−05 | −7.956 | 100 | 1144.4907092 | 6068.1628967 | 0.1886058 | SERPINB2 |
| 3 | 4.68e−05 | −6.81 | 100 | 1612.7663831 | 6041.3773778 | 0.2669534 | SERPINE1 |
| 4 | 5.75e−05 | −6.644 | 100 | 2910.0453562 | 9519.5437319 | 0.3056917 | CLIC4 |

TABLE 27-continued

Composition of classifier - Sorted by t-value: Class 1: m; Class 2: nm. [n = 6 per each group]

| | Parametric p-value | t-value | % CV support | Geom mean of intensities in class 1 | Geom mean of intensities in class 2 | Fold-change | Gene symbol |
|---|---|---|---|---|---|---|---|
| 5 | 0.0002064 | −5.671 | 100 | 599.5692432 | 5858.0250012 | 0.1023501 | BCL2A1 |
| 6 | 0.0009722 | 4.605 | 17 | 196.0758645 | 122.9028821 | 1.5953724 | ZNF256 |
| 7 | 0.0003679 | 5.26 | 75 | 329.0570275 | 139.2977392 | 2.3622568 | ZNF573 |
| 8 | 5.61e−05 | 6.664 | 100 | 1752.8553582 | 626.6081244 | 2.7973709 | GNAS |
| 9 | 5.32e−05 | 6.706 | 100 | 360.9191684 | 110.8183685 | 3.2568533 | SERPINB2 |

16.2.1.5. NM Vs M Using the APA-Template for Class Prediction (SVM=92%)

TABLE 28

Composition of classifier-Sorted by t-value: Class 1: m; Class 2: nm.

| | Parametric p-value | t-value | % CV support | Geom mean of intensities in class 1 | Geom mean of intensities in class 2 | Fold-change | Gene symbol |
|---|---|---|---|---|---|---|---|
| 1 | 2.9e−05 | −7.206 | 100 | 4505.2826317 | 10969.8418903 | 0.4106971 | TDRD6 |
| 2 | 0.0001947 | −5.713 | 100 | 966.693001 | 4664.3939694 | 0.2072494 | XIST |
| 3 | 0.0006817 | −4.84 | 17 | 1735.0546548 | 10070.7577787 | 0.1722864 | LZTS1 |
| 4 | 0.0009291 | −4.635 | 8 | 1817.5569529 | 4443.2023065 | 0.4090646 | IRF4 |

Example 17: Genelists for Prediction of Organ of Metastases

17.1. Organ of Metastases (Binary Tree Classification)

Optimal Binary Tree: Cross-validation error rates for a fixed tree structure shown below

| Node | Group 1 Classes | Group 2 Classes | Mis-classification rate (%) |
|---|---|---|---|
| 1 | bone, liver, lung | nm | 17.4 |
| 2 | bone, lung | liver | 38.9 |

Node 1

TABLE 29

Composition of classifier (6 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | <1e−07 | −1e+07 | 87 | 885.547163 | 1982.5964469 | TIMP1 |
| 2 | <1e−07 | 1e+07 | 100 | 1453.0368811 | 685.1212898 | COL21A1 |
| 3 | <1e−07 | 1e+07 | 91 | 658.5014611 | 551.9419886 | COL1A2 |
| 4 | 0.0014608 | −5.539 | 87 | 471.8007783 | 761.7592596 | KL |
| 5 | 0.0031096 | 3.87 | 100 | 1080.7271447 | 802.5161476 | CDKN2A |

TABLE 30

Composition of classifier (5 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | <1e−07 | −1e+07 | 74 | 994.3330391 | 2108.8274433 | DSP |
| 2 | <1e−07 | −1e+07 | 74 | 687.6303563 | 866.946662 | AR |
| 3 | <1e−07 | −1e+07 | 65 | 691.236265 | 940.8722888 | IGF2 |
| 4 | <1e−07 | 1e+07 | 39 | 5211.29731 | 3933.2245813 | MSX1 |
| 5 | 0.0072751 | 3.073 | 74 | 1005.7377143 | 322.8701475 | SERPINE1 |

17.2. Organ of Metastases Plus Additional Metastasised Organ (Binary Tree Classification)

Optimal Binary Tree as shown in FIG. 7.
Cross-Validation Error Rates for a Fixed Tree Structure Shown Below

| Node | Group 1 Classes | Group 2 Classes | Misclassification rate (%) |
|---|---|---|---|
| 1 | bone, bone_plus, liver_plus, lung, nm | liver | 6.0 |
| 2 | bone, bone_plus, liver_plus, nm | lung | 14.3 |
| 3 | bone, bone_plus | liver_plus, nm | 34.5 |
| 4 | liver_plus | nm | 30.8 |

17.2.1. Results of Classification, Node 1

TABLE 31

Composition of classifier (3 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | 0.0044929 | −2.995 | 97 | 1134.7396026 | 4430.9188978 | FHL1 |
| 2 | 0.0061218 | −2.835 | 97 | 1110.6532166 | 4041.6310709 | LMNA |
| 3 | 0.0093569 | −10.265 | 96 | 569.1243774 | 1809.4934445 | GDNF |

17.2.2. Results of Classification, Node 2

TABLE 32

Composition of classifier (3 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | 0.0042145 | −3.015 | 91 | 1086.2923057 | 4114.6963495 | FBXW7 |
| 2 | 0.0051555 | 2.902 | 91 | 1004.7376123 | 747.4623897 | GNAS |
| 3 | 0.0070253 | −2.807 | 91 | 17268.610511 | 36023.2972547 | KRT14 |

17.2.3. Results of Classification, Node 3

TABLE 33

Composition of classifier (7 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | <1e−07 | 1e+07 | 82 | 607.7955262 | 569.3935126 | CHFR |
| 2 | <1e−07 | −1e+07 | 85 | 1309.6825512 | 1651.2140652 | AR |

TABLE 33-continued

Composition of classifier (7 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 3 | <1e−07 | 1e+07 | 85 | 1398.6556505 | 806.4521355 | RBP1 |
| 4 | <1e−07 | 1e+07 | 87 | 960.7559369 | 725.130163 | MSX1 |
| 5 | 7.52e−05 | 5.181 | 87 | 1664.6672496 | 972.9860114 | COL21A1 |
| 6 | 0.0010054 | 3.572 | 82 | 830.8587676 | 413.1576982 | FHL1 |
| 7 | 0.0021561 | −4.721 | 87 | 756.3671177 | 1687.904231 | RARB |

17.2.4 Results of Classification, Node 4

TABLE 34

Composition of classifier (6 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | <1e−07 | −1e+07 | 34 | 443.8813201 | 503.5217148 | DCLRE1C |
| 2 | <1e−07 | −1e+07 | 37 | 725.130163 | 1044.2751516 | MLH1 |
| 3 | <1e−07 | 1e+07 | 22 | 1229.1322892 | 634.3496625 | RARB |
| 4 | 0.000336 | 5.966 | 37 | 1360.7555882 | 586.6980829 | OGG1 |
| 5 | 0.0014183 | −3.605 | 39 | 15781.5120063 | 28485.4843024 | SNRPN |
| 6 | 0.0077342 | 3.073 | 37 | 730.2708489 | 578.3124727 | ITGA4 |

17.3. Organ of Metastases Plus Additional Metastasised Organ (Binary Tree Classification)—Genefilters on GENEFILTERS ON=Exclude a gene under any of the following conditions:
Less than 20% of methylation data have at least a 1.5-fold change in either direction from gene's median value
Optimal Binary Tree as shown in FIG. 8.
Cross-Validation Error Rates for a Fixed Tree Structure Shown Below

| Node | Group 1 Classes | Group 2 Classes | Misclassification rate (%) |
|---|---|---|---|
| 1 | bone, bone_plus, liver_plus, lung, nm | liver | 6.0 |
| 2 | bone, bone_plus, liver_plus, nm | lung | 14.3 |
| 3 | bone, bone_plus | liver_plus, nm | 34.5 |
| 5 | liver_plus | nm | 30.8 |

17.3.1. Results of Classification, Node 1

TABLE 35

Composition of classifier (3 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | 0.0044929 | −2.995 | 97 | 1134.7396026 | 4430.9188978 | FHL1 |
| 2 | 0.0061218 | −2.835 | 97 | 1110.6532166 | 4041.6310709 | LMNA |
| 3 | 0.0093569 | −10.265 | 96 | 569.1243774 | 1809.4934445 | GDNF |

17.3.2. Results of Classification, Node 2

TABLE 36

Composition of classifier (3 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | 0.0042145 | −3.015 | 91 | 1086.2923057 | 4114.6963495 | FBXW7 |
| 2 | 0.0051555 | 2.902 | 91 | 1004.7376123 | 747.4623897 | GNAS |
| 3 | 0.0070253 | −2.807 | 91 | 17268.610511 | 36023.2972547 | KRT14 |

17.3.3. Results of Classification, Node 3

TABLE 37

Composition of classifier (7 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | <1e−07 | 1e+07 | 82 | 607.7955262 | 569.3935126 | CHFR |
| 2 | <1e−07 | −1e+07 | 85 | 1309.6825512 | 1651.2140652 | AR |
| 3 | <1e−07 | 1e+07 | 85 | 1398.6556505 | 806.4521355 | RBP1 |
| 4 | <1e−07 | 1e+07 | 87 | 960.7559369 | 725.130163 | MSX1 |
| 5 | 7.52e−05 | 5.181 | 87 | 1664.6672496 | 972.9860114 | COL21A1 |
| 6 | 0.0010054 | 3.572 | 82 | 830.8587676 | 413.1576982 | FHL1 |
| 7 | 0.0021561 | −4.721 | 87 | 756.3671177 | 1687.904231 | RARB |

17.3.4. Results of Classification, Node 4

TABLE 38

Composition of classifier (6 genes)-Sorted by p-value:

| | Parametric p-value | t-value | % CV support | Geom mean of intensities in group 1 | Geom mean of intensities in group 2 | Gene symbol |
|---|---|---|---|---|---|---|
| 1 | <1e−07 | −1e+07 | 34 | 443.8813201 | 503.5217148 | DCLRE1C |
| 2 | <1e−07 | −1e+07 | 37 | 725.130163 | 1044.2751516 | MLH1 |
| 3 | <1e−07 | 1e+07 | 22 | 1229.1322892 | 634.3496625 | RARB |
| 4 | 0.000336 | 5.966 | 37 | 1360.7555882 | 586.6980829 | OGG1 |
| 5 | 0.0014183 | −3.605 | 39 | 15781.5120063 | 28485.4843024 | SNRPN |
| 6 | 0.0077342 | 3.073 | 37 | 730.2708489 | 578.3124727 | ITGA4 |

Example 17.4: Breast Cancer (BrCa) Diagnosis Using DNA Derived from Serum of Patients

Example 17.4.1: Classifier Defined Using the Inventive Methylation Test can be Used for Correct Diagnosis and Confirms Scalability of the Test For designing a practical test including only diagnostically relevant classifiers performance of different feature extraction strategies using cross-validation from candidate markers derived from the methylation test of all 360 markers was evaluated.

The different feature extraction strategies were based on settings of using either p-values (p<0.005), a "Greedy Pairs" approach (n=10 greedy pairs), and recursive feature elimination method. From these approaches a final marker panel for serum-testing was chosen obtaining 100% of correct classification during cross validation by statistical tests like Compound Covariate Predictor, Diagonal Linear Discriminant Analysis, 1-Nearest Neighbour Centroid, and Bayesian Compound Covariate Predictor; other approaches like 3-Nearest Neighbours and Support Vector Machines resulted in 95% correct classification during cross validation.

Only 19 selected biomarkers derived from feature extraction of all 360 marker-candidates were used in a separate assay and serum-DNA samples from patients and controls were analyzed. Using the 19 methylation markers 100% correct classification of tumor-samples (n=9) versus controls (n=9; FIG. 3) was obtained.

17.4.2. T Vs N (Compound Covariate Predictor=83% Correct)

TABLE 39

Composition of classifier-Sorted by t-value: Class 1: Norm; Class 2: T.

|   | Parametric p-value | t-value | % CV support | Geom mean of intensities in class 1 | Geom mean of intensities in class 2 | Ratio of geom means | Gene symbol |
|---|---|---|---|---|---|---|---|
| 1 | 0.0009924 | −3.795 | 100 | 182.6826576 | 864.2335483 | 0.2113811 | SFN |
| 2 | 0.0017215 | −3.567 | 100 | 430.8637112 | 756.3752883 | 0.5696428 | DIRAS3 |
| 3 | 0.0039912 | 3.215 | 33 | 9327.2785112 | 1851.017692 | 5.0390002 | HRAS |
| 4 | 0.0032818 | 3.297 | 67 | 2315.42463 | 492.0942152 | 4.7052466 | ARMCX2 |
| 5 | 0.0011568 | 3.732 | 100 | 2533.773004 | 367.7411692 | 6.8900988 | MAGEB2 |
| 6 | 0.0004392 | 4.13 | 100 | 539.5397658 | 182.6961002 | 2.953209 | GBP2 |
| 7 | 0.0002572 | 4.349 | 100 | 210.9118779 | 103.7366691 | 2.0331468 | CTCFL |
| 8 | 4.65e−05 | 5.052 | 100 | 471.419219 | 111.5924047 | 4.2244741 | NEUROD2 |

17.4.3. T Vs N (SVM=82% Correct; p<0.005)

Genes significantly different between the classes at 0.005 significance level were used for class prediction.

TABLE 40

Composition of classifier-Sorted by t-value: Class 1: N; Class 2: T.

|   | Parametric p-value | t-value | % CV support | Geom mean of intensities in class 1 | Geom mean of intensities in class 2 | Ratio of geom means | Gene symbol |
|---|---|---|---|---|---|---|---|
| 1 | 0.0028166 | −3.404 | 82 | 182.0198994 | 864.2335483 | 0.2106142 | SFN |
| 2 | 0.0039431 | −3.257 | 18 | 542.4776162 | 3257.6193811 | 0.1665258 | BAZ1A |
| 3 | 0.004628 | −3.187 | 36 | 424.1334102 | 756.3752883 | 0.5607447 | DIRAS3 |
| 4 | 0.0040079 | 3.25 | 23 | 173.3967213 | 103.7366691 | 1.6715085 | CTCFL |
| 5 | 0.0025889 | 3.44 | 86 | 2890.0918027 | 492.0942152 | 5.8730457 | ARMCX2 |
| 6 | 0.0025277 | 3.451 | 82 | 514.9868762 | 182.6961002 | 2.818817 | GBP2 |
| 7 | 0.001122 | 3.8 | 100 | 3333.4640957 | 367.7411692 | 9.064702 | MAGEB2 |
| 8 | 0.0007163 | 3.992 | 100 | 371.1393872 | 111.5924047 | 3.3258481 | NEUROD2 |

17.4.4. T Vs N—(Compound Covariate Predictor=96% Correct; Greedy Pairs)

TABLE 41

Composition of classifier-Sorted by t-value: (Sorted by gene pairs): Class 1: control; Class 2: nodule.

|   | Parametric p-value | t-value | % CV support | Geom mean of intensities in class 1 | Geom mean of intensities in class 2 | Ratio of geom means | Gene symbol |
|---|---|---|---|---|---|---|---|
| 1 | 0.0040902 | −3.204 | 100 | 408.6274761 | 723.1907249 | 0.5650342 | DIRAS3 |
| 2 | 0.0102828 | −2.806 | 88 | 146.3029435 | 291.7333957 | 0.5014954 | C5AR1 |
| 3 | 0.0187014 | −2.539 | 29 | 674.9273185 | 2949.7082217 | 0.2288116 | BAZ1A |
| 4 | 0.0310794 | −2.303 | 75 | 211.5738315 | 692.4423152 | 0.3055472 | SFN |
| 5 | 0.0153636 | 2.628 | 67 | 909.4898258 | 414.8518794 | 2.1923242 | ERCC1 |
| 6 | 0.0117751 | 2.747 | 58 | 58722.6132538 | 23154.0614983 | 2.536169 | SNRPN |
| 7 | 0.0046581 | 3.149 | 96 | 1042.5891538 | 616.8970018 | 1.6900539 | PILRB |
| 8 | 0.0029542 | 3.342 | 58 | 433.4268347 | 122.3498971 | 3.542519 | KRT17 |
| 9 | 0.002417 | 3.426 | 88 | 406.0865778 | 179.1092016 | 2.2672569 | CDKN2A |
| 10 | 0.0013165 | 3.679 | 100 | 280.1112178 | 130.2537509 | 2.150504 | H19 |
| 11 | 0.0003286 | 4.249 | 100 | 4797.264763 | 388.9828036 | 12.3328454 | EFS |
| 12 | 4.74e−05 | 5.043 | 100 | 3137.4870686 | 206.916935 | 15.163027 | TJP2 |
| 13 | 4.7e−05 | 5.047 | 100 | 17562.5781485 | 1794.0631479 | 9.7892753 | HRAS |
| 14 | 8.6e−06 | 5.757 | 100 | 626.2244064 | 119.1399358 | 5.256209 | NEUROD2 |
| 15 | 4e−06 | 6.084 | 100 | 756.2912007 | 184.117749 | 4.1076496 | GBP2 |
| 16 | 2e−07 | 7.476 | 100 | 270.479735 | 103.314681 | 2.6180184 | CTCFL |

17.4.5. Nodule Pos Vs Control—(Final Combined List=100% Correct; Greedy Pairs)

TABLE 42

Composition of classifier-Sorted by t-value: (Sorted by gene pairs): Class 1: control; Class 2: nodule.

| | Parametric p-value | t-value | % CV support | Geom mean of intensities in class 1 | Geom mean of intensities in class 2 | Ratio of geom means | Gene symbol |
|---|---|---|---|---|---|---|---|
| 1 | 0.002777 | −3.41 | 100 | 408.6274761 | 756.3752883 | 0.5402444 | DIRAS3 |
| 2 | 0.0046055 | −3.189 | 100 | 146.3029435 | 307.9355304 | 0.475109 | C5AR1 |
| 3 | 0.0069521 | −3.008 | 100 | 211.5738315 | 864.2335483 | 0.2448109 | SFN |
| 4 | 0.0119639 | −2.764 | 100 | 674.9273185 | 3257.6193811 | 0.2071842 | BAZ1A |
| 5 | 0.0145723 | −2.674 | 100 | 95.6598704 | 1248.1664664 | 0.0766403 | HIST1H2AG |
| 6 | 0.034443 | −2.27 | 100 | 228.3104891 | 740.1844071 | 0.3084508 | XAB2 |
| 7 | 0.0652645 | −1.951 | 100 | 194.6905166 | 1615.4690261 | 0.1205164 | HOXA1 |
| 8 | 0.1230854 | −1.61 | 100 | 95.6598704 | 338.6602819 | 0.2824656 | HIC1 |
| 9 | 0.1947696 | −1.342 | 86 | 156.5831319 | 461.8227948 | 0.3390546 | GRIN2B |
| 10 | 0.2069144 | −1.304 | 95 | 450.7980877 | 2854.7340614 | 0.1579125 | BRCA1 |
| 11 | 0.2618903 | −1.155 | 73 | 324.1771597 | 942.5932597 | 0.3439205 | C13 or-f15 |
| 12 | 0.0113646 | 2.788 | 100 | 11527.7038774 | 2200.8436107 | 5.2378569 | SLC25A31 |
| 13 | 0.0040259 | 3.248 | 100 | 406.0865778 | 183.0652326 | 2.2182616 | CDKN2A |
| 14 | 0.0030653 | 3.367 | 100 | 280.1112178 | 134.6291251 | 2.0806138 | H19 |
| 15 | 0.0008291 | 3.93 | 100 | 4797.264763 | 419.1038337 | 11.4464827 | EFS |
| 16 | 0.0001457 | 4.675 | 100 | 3137.4870686 | 226.6055522 | 13.8455878 | TJP2 |
| 17 | 0.0001405 | 4.691 | 100 | 17562.5781485 | 1851.017692 | 9.4880661 | HRAS |
| 18 | 4.1e−06 | 6.256 | 100 | 626.2244064 | 111.5924049 | 5.6117117 | NEUROD2 |
| 19 | 3.7e−06 | 6.309 | 100 | 756.2912007 | 182.6961002 | 4.1396133 | GBP2 |
| 20 | 9e−07 | 6.994 | 100 | 270.479735 | 103.7366691 | 2.6073686 | CTCFL |

Example 18: Breast Cancer Methylation Markers 18.1. Diagnosis of Existing Metastases Tumor-DNA from patients should be tested by the following markers for elucidating metastases already present, which might be not detectable by routine clinical examination or imaging.

patient groups:
   0 . . . no metastasis at diagnosis and durign follow up
   1 . . . metastasis during follow up
   2 . . . metastasis at diagnosis Binary Tree Classification algorithm was used. Feature selection was based on the univariate significance level (alpha=0.01) The support vector machine classifier was used for class prediction There were 2 nodes in the classification tree.

Optimal Binary Tree:

| Node | Group 1 Classes | Group 2 Classes | Mis-classification rate (%) |
|---|---|---|---|
| 1 | 0, 1 | 2 | 14.6 |
| 2 | 0 | 1 | 45.2 |

Node 1

TABLE 43

Composition of classifier (5 genes) sorted by p-value:

| | Parametric p-value | t-value | % CV support | Geom mean of intensities in group 1 | Geom mean of intensities in group 2 | Gene symbol |
|---|---|---|---|---|---|---|
| 1 | 0.0002927 | −3.92 | 98 | 149.7469303 | 1031.3845804 | TFPI2 |
| 2 | 0.0049604 | 2.952 | 98 | 221.1562041 | 133.2523039 | NEUROD2 |
| 3 | 0.0057474 | −2.897 | 94 | 639.3980244 | 6450.0516594 | DLX2 |
| 4 | 0.006399 | −2.857 | 92 | 99.6970101 | 112.7940118 | TTC3 |
| 5 | 0.0066379 | −2.843 | 98 | 99.6970101 | 109.6402212 | TWIST1 |

18.2. Prediction of Metastases in Lymphnode-Negative Patients at Initial-Diagnosis Survival Risk Prediction Using BRB-ArrayTools

TABLE 44

Genes used in classifier of risk groups:

| | p-value | % CV Support | Unique id | Gene symbol |
|---|---|---|---|---|
| 1 | 0.0037508 | 100 | Ahy_329_chrX: 30143481-30143982 +_299-362 | MAGEB2 |
| 2 | 0.0062305 | 100 | Ahy_193_chr2: 47483597-47484030 +_217-278 | MSH2 |
| 3 | 0.0078116 | 100 | Ahy_296_chr7: 98809925-98810139 +_127-191 | ARPC1B |
| 4 | 0.0096053 | 100 | Ahy_128_chr17: 35016970-35017711 +_250-313 | NEUROD2 |
| 5 | 0.0156618 | 100 | Ahy_179_chr2: 118288805-118289169 +_64-128 | DDX18 |
| 6 | 0.0182671 | 94.44 | Ahy_67_chr11: 93939956-93940471 +_256-312 | PIWIL4 |
| 7 | 0.0196289 | 94.44 | Ahy_242_chr4: 4911767-4913093 +_771-835 | MSX1 |
| 8 | 0.0220021 | 88.89 | Ahy_295_chr7: 93861567-93861950 +_62-118 | COL1A2 |
| 9 | 0.0362384 | 55.56 | Ahy_116_chr16: 13921618-13921939 +_51-102 | ERCC4 |
| 10 | 0.0370792 | 55.56 | Ahy_180_chr2: 171383096-171383604 +_124-178 | GAD1 |
| 11 | 0.0415033 | 44.44 | Ahy_312_chr8: 74368624-74368884 +_181-233 | RDH10 |
| 12 | 0.0460605 | 38.89 | Ahy_144_chr17: 7532353-7532949 +_96-151 | TP53 |
| 13 | 0.0465973 | 38.89 | 336_hy_5-APC_chr5: 112101294 + 112101593 | APC |
| 14 | 0.0468988 | 38.89 | Ahy_327_chrX: 119133199-119133871 +_406-456 | RHOXF1 |
| 15 | 0.0492264 | 27.78 | Ahy_50_chr11: 107598519-107599317 +_128-192 | ATM |

15 genes selected by fitting Cox proportional hazards models (alpha equals to 0.05)
The coefficients of the fitted Cox proportional hazards model using the principal components from the training dataset is (25.622, −19.237)
The percent of variability explained by the first 2 principal components is 75.797
The p-value in the table is testing the hypothesis if expression data is predictive of survival.

TABLE 45

Loading matrix of the significant genes and the correlations between the principal components and the signficant genes:

| # | Gene Id | Loading matrix Components 1 | 2 | Correlation Components 1 | 2 | Weights (wi) |
|---|---|---|---|---|---|---|
| 1 | Ahy_329_chrX:30143481-30143982 + _299-362 | 0.0029 | −0.028866 | 0.203377 | −0.914529 | 0.629601 |
| 2 | Ahy_193_chr2:47483597-47484030 + _217-278 | 0.003603 | −0.038489 | 0.159604 | −0.770223 | 0.832737 |
| 3 | Ahy_296_chr7:98809925-98810139 + _127-191 | 0.003666 | −0.031576 | 0.210928 | −0.820656 | 0.701377 |
| 4 | Ahy_128_chr17:35016970-35017711 + _250-313 | 0.002716 | −0.038498 | 0.125766 | −0.805352 | 0.810188 |
| 5 | Ahy_179_chr2:118288805-118289169 + _64-128 | −0.087461 | −0.012034 | −0.995391 | −0.06187 | −2.009412 |
| 6 | Ahy_67_chr11:93939956-93940471 + _256-312 | 0.002163 | −0.034139 | 0.111459 | −0.794654 | 0.712153 |
| 7 | Ahy_242_chr4:4911767-4913093 + _771-835 | 0.001206 | −0.0369 | 0.065085 | −0.899444 | 0.740761 |
| 8 | Ahy_295_chr7:93861567-93861950 + _62-118 | 0.002463 | −0.046455 | 0.104953 | −0.894288 | 0.956776 |
| 9 | Ahy_116_chr16:13921618-13921939 + _51-102 | 0.004042 | −0.066151 | 0.098532 | −0.728487 | 1.376125 |
| 10 | Ahy_180_chr2:171383096-171383604 + _124-178 | −0.001504 | −0.026585 | −0.108194 | −0.86396 | 0.472896 |
| 11 | Ahy_312_chr8:74368624-74368884 + _181-233 | 0.007667 | −0.011363 | 0.395218 | −0.264602 | 0.415028 |
| 12 | Ahy_144_chr17:7532353-7532949 + _96-151 | 0.005862 | −0.024068 | 0.357628 | −0.663303 | 0.613198 |
| 13 | 336_hy_5-APC_chr5:112101294 + 112101593 | −0.000651 | −0.03758 | −0.035225 | −0.918987 | 0.70626 |
| 14 | Ahy_327_chrX:119133199-119133871 + _406-456 | 0.004291 | −0.026025 | 0.212693 | −0.582789 | 0.61058 |
| 15 | Ahy_50_chr11:107598519-107599317 + _128-192 | −0.012402 | −0.013367 | −0.314198 | −0.152973 | −0.060634 |

A new sample is predicted as high (low) risk if its prognostic index is larger than (smaller than or equal to) 1.532975.
The prognostic index can be computed by the simple formula $\Sigma w_i x_i - 149.6498$ where $w_i$ and $x_i$ are the weight and logged gene expression for the i-th gene.

Genes used in classifier of risk groups:
26 genes selected by fitting Cox proportional hazards models (alpha equals to 0.05)

The Cox proportional hazards model is fitted using the principal components and clinical covariates from the training dataset. The estimated coefficients are (−3.184, −20.948) for the principal components and (−0.709, 0.148) for the clinical covariates The percent of variability explained by the first 2 principal components is 64.388

The p-value in the table is testing the hypothesis if the expression data is predictive of survival over and above the covariates.

Example 19: Methylation Markers in Non-Tumor/Non-Neoplastic Disease: Trisomy Diagnosis DNA derived from Cytogen fixed cells of Healthy Controls (5 females . . . 46XX; 5 males . . . 46XY) and Trisomy-Patients (5 females . . . 47XX+21; 6 . . . males 47XY+21; and single samples with trisomy of chr13 . . . 47XX+13, and trisomy of chr 9 . . . 47XX+9 and one blinded sample with trisomy) were used for DNA Methylation testing. The following data-analysis exemplifies successful class-distinction of normal (class label . . . "46") and Down Syndrome patients (trisomy of chr21, class label . . . "47"). The entire set of DNAs was amplified within the 359 marker set by Multiplex PCRs on 2 different PCR machines and data derived from both runs were used either together for analysis or separately. When a set of data was used from only the "Biorad"-PCR-machine, which was used for standard-analysis, this is indicated as "biorad+21".

Surprisingly, it was found that not only genes of the triplicated chromosome were affected but also genes which are not located on the additional chromosome are aberrantly methylated and serve as markers for detection of syndromal disease.

This is of relevance for diagnostic testing of patients suspected suffering from disease and also for prenatal testing (DNA derived from aminocentesis, chorionic villi, and DNA derived from fetal-cells or free DNA in serum of peripheral blood of pregnant women).

Optimal Binary Tree: BinTree pred. (p<0.01)

| Node | Group1 Classes | Group2 Classes | Misclassification rate (%) |
|---|---|---|---|
| 1 | 46, XX, 46, XY | 47, XX, +21, 47, XY, +21 | 9.5 |
| 2 | 46, XX | 46, XY | 0.0 |
| 3 | 47, XX, +21 | 47, XY, +21 | 18.2 |

Results of Classification, NODE 1:
Cross-validation results for a fixed tree structure:
Percent correctly classified: 90, n=42

TABLE 46

Composition of classifier (11 genes) - Sorted by p-value:

|  | Parametric p-value | t-value | % CV support | Geom mean of intensities in group 1 | Geom mean of intensities in group 2 | Gene symbol |
|---|---|---|---|---|---|---|
| 1 | <1e−07 | −8.939 | 100 | 26.2297563 | 299.1552258 | ACTB |
| 2 | <1e−07 | 6.614 | 100 | 43831.04637 | 16409.8564721 | EFS |
| 3 | 1.86e−05 | −4.859 | 45 | 446.5210876 | 1138.2292585 | CXADR |
| 4 | 0.0004148 | 3.852 | 100 | 3404.2623323 | 682.6474171 | LAMC2 |
| 5 | 0.0007597 | 3.646 | 100 | 704.8390278 | 374.8116065 | DNAJA4 |
| 6 | 0.0009826 | 3.557 | 57 | 296.2648173 | 199.6190304 | CRABP1 |
| 7 | 0.0010948 | 3.519 | 100 | 91.4371797 | 43.0799191 | PARP2 |
| 8 | 0.0034859 | 3.105 | 100 | 714.6509687 | 75.5611248 | HIC1 |
| 9 | 0.0082896 | −2.778 | 100 | 61.5445201 | 120.8377761 | MTHFR |
| 10 | 0.009118 | 2.741 | 100 | 12450.4822201 | 9277.9418641 | S100A9 |
| 11 | 0.0099499 | 2.706 | 29 | 609.1583527 | 298.7768473 | PITX2 |

Results of classification, NODE 2:
Cross-validation results for a fixed tree structure: Percent correctly classified: 100, n=20

TABLE 47

Composition of classifier (19 genes) - Sorted by p-value:

|  | Parametric p-value | t-value | % CV support | Geom mean of intensities in group 1 | Geom mean of intensities in group 2 | Gene symbol |
|---|---|---|---|---|---|---|
| 1 | <1e−07 | −13.941 | 14 | 15.8798348 | 2957.3432764 | CD24 |
| 2 | <1e−07 | 13.671 | 19 | 2668.7251209 | 17.7527793 | ZNF711 |
| 3 | <1e−07 | 11.335 | 48 | 1615.9344933 | 30.188622 | TIMP1 |
| 4 | 1.4e−06 | 7.072 | 14 | 1420.7155328 | 830.8084043 | POS_CY5-eco2-rev |
| 5 | 1.7e−06 | 6.94 | 48 | 11496.8897368 | 2410.9349326 | ARMCX2 |
| 6 | 6.6e−06 | 6.266 | 48 | 93.7282473 | 47.6707692 | COL1A1 |
| 7 | 4.51e−05 | 5.336 | 48 | 129.006147 | 81.0186421 | ERCC5 |
| 8 | 0.0006501 | −4.115 | 36 | 9.9445011 | 11.4645991 | AR |
| 9 | 0.0016144 | −3.707 | 17 | 11631.003866 | 52089.9344084 | GNAS |

TABLE 47-continued

Composition of classifier (19 genes) - Sorted by p-value:

|    | Parametric p-value | t-value | % CV support | Geom mean of intensities in group 1 | Geom mean of intensities in group 2 | Gene symbol |
|----|---|---|---|---|---|---|
| 10 | 0.0017296 | 3.676 | 48 | 170.4636123 | 122.580017 | MGMT |
| 11 | 0.0028615 | −3.449 | 48 | 56.36552 | 93.40326 | CHFR |
| 12 | 0.0034384 | 3.366 | 48 | 361.5641932 | 242.7586681 | CRABP1 |
| 13 | 0.0034864 | −3.36 | 43 | 9.3628581 | 22.3617625 | AQP3 |
| 14 | 0.004945 | 3.202 | 48 | 46538.2390013 | 37786.9380902 | POS Biotin Control RET |
| 15 | 0.0059798 | −3.115 | 48 | 9.3405726 | 10.7177413 | PITX2 |
| 16 | 0.0080556 | 2.978 | 48 | 53003.5731701 | 36245.8700609 | EFS |
| 17 | 0.0086325 | 2.946 | 48 | 95.2926476 | 54.091425 | VHL |
| 18 | 0.0087052 | 2.943 | 48 | 637.5015326 | 328.8235918 | ERCC2 |
| 19 | 0.0099932 | −2.879 | 48 | 9.3628581 | 12.9281326 | NCL |

Results of classification, NODE 3:
Cross-validation results for a fixed tree structure:
Percent correctly classified: 82, n=22

TABLE 48

Composition of classifier (11 genes) - Sorted by p-value:

|    | Parametric p-value | t-value | % CV support | Geom mean of intensities in group 1 | Geom mean of intensities in group 2 | Gene symbol |
|----|---|---|---|---|---|---|
| 1 | 0.0012615 | 3.75 | 52 | 173.2673485 | 117.5876988 | BCL2 |
| 2 | 0.0016726 | −3.629 | 19 | 59.0751712 | 1395.1448164 | CD24 |
| 3 | 0.002108 | −3.529 | 52 | 56552.8064611 | 67733.3704627 | NANOS1 |
| 4 | 0.0028926 | −3.392 | 52 | 18716.8236267 | 26773.3646074 | SLC25A31 |
| 5 | 0.0033836 | 3.324 | 26 | 843.9887744 | 35.1710947 | ZNF711 |
| 6 | 0.0043579 | −3.214 | 52 | 95.5863694 | 141.5416174 | POLD1 |
| 7 | 0.004588 | 3.191 | 43 | 232.7772087 | 87.3233153 | PENK |
| 8 | 0.0054855 | 3.113 | 17 | 7904.0316031 | 1250.5200729 | ARMCX2 |
| 9 | 0.0063042 | 3.051 | 50 | 616.5029552 | 52.8096314 | TIMP1 |
| 10 | 0.0079761 | −2.947 | 45 | 53.8713383 | 160.551704 | TFPI2 |
| 11 | 0.0085383 | 2.916 | 52 | 110.7146251 | 46.2232459 | MLH1 |

Example 19.1: ClassComparison "46 Vs 47+21".
(p<0.01)

Genes which discriminate among classes:

TABLE 49

Sorted by p-value of the univariate test. Class 1: 46; Class 2: 47.

|    | Parametric p-value | FDR | Permutation p-value | Geom mean of intensities in class 1 | Geom mean of intensities in class 2 | Fold-change | Gene symbol |
|----|---|---|---|---|---|---|---|
| 1 | <1e−07 | <1e−07 | <1e−07 | 26.2297507 | 299.1554009 | 0.0876793 | ACTB |
| 2 | <1e−07 | <1e−07 | <1e−07 | 43831.0370599 | 16409.8711513 | 2.6710165 | EFS |
| 3 | 2.14e−05 | 0.0025965 | <1e−07 | 446.5208014 | 1138.2287757 | 0.3922944 | CXADR |
| 4 | 0.0004799 | 0.0436709 | 6e−04 | 3404.2610882 | 682.6476534 | 4.9868495 | LAMC2 |
| 5 | 0.0009099 | 0.060918 | 0.0011 | 704.8391804 | 374.8118214 | 1.8805148 | DNAJA4 |
| 6 | 0.0010416 | 0.060918 | 0.0017 | 91.4371688 | 43.0798954 | 2.1225021 | PARP2 |
| 7 | 0.0011715 | 0.060918 | 0.0015 | 296.2646359 | 199.6190547 | 1.4841501 | CRABP1 |
| 8 | 0.0038155 | 0.1736052 | 0.0055 | 714.6504806 | 75.5611006 | 9.4579152 | HIC1 |
| 9 | 0.0047377 | 0.1916136 | 0.0042 | 322.4549643 | 832.851493 | 0.3871698 | SERPINI1 |
| 10 | 0.0070581 | 0.2569148 | 0.0062 | 61.544479 | 120.8378342 | 0.5093146 | MTHFR |
| 11 | 0.0099878 | 0.3127852 | 0.0109 | 609.1584168 | 298.7770249 | 2.0388396 | PITX2 |

The first 11 genes are significant at the nominal 0.01 level of the univariate test Example 19.2: ClassComparison "46 Vs 47+21: Biorad+21 Only". (p<0.01)

Genes which discriminate among classes:

TABLE 50

Sorted by p-value of the univariate test: Class 1: 46; Class 2: 47.

| | Parametric p-value | FDR | Permutation p-value | Geom mean of intensities in class 1 | Geom mean of intensities in class 2 | Fold-change | Gene symbol |
|---|---|---|---|---|---|---|---|
| 1 | 2.7e−06 | 0.0009828 | 1e−04 | 18.0666655 | 228.9046182 | 0.0789266 | ACTB |
| 2 | 1.59e−05 | 0.0028938 | <1e−07 | 41656.7741883 | 16422.5582909 | 2.5365582 | EFS |
| 3 | 6.42e−05 | 0.0077896 | 2e−04 | 69.2968567 | 22.2049528 | 3.1207838 | PARP2 |
| 4 | 0.0020864 | 0.1703593 | 0.0021 | 104.6171977 | 181.6457027 | 0.5759409 | TP73 |
| 5 | 0.0023401 | 0.1703593 | 0.0033 | 1953.6772836 | 47.6937676 | 40.9629472 | HIC1 |
| 6 | 0.003829 | 0.2322927 | 0.0047 | 125.2431033 | 98.1869116 | 1.275558 | BCL2A1 |
| 7 | 0.0062407 | 0.2805858 | 0.0083 | 269.5782085 | 189.825032 | 1.4201405 | CRABP1 |
| 8 | 0.0071887 | 0.2805858 | 0.0081 | 379.9209916 | 826.9335478 | 0.4594335 | CXADR |
| 9 | 0.0075367 | 0.2805858 | 0.008 | 39.7360154 | 24.2201702 | 1.6406167 | BDNF |
| 10 | 0.0077084 | 0.2805858 | 0.0135 | 60.1600015 | 29.6481479 | 2.0291319 | COL1A1 |

The first 10 genes are significant at the nominal 0.01 level of the univariate test Example 19.3: ClassComparison "46 Vs 47+21: Biorad+21 Only". (p<0.01)

Genes which discriminate among classes:

TABLE 51

Sorted by p-value of the univariate test: Class 1: 46; Class 2: 47.

| | Parametric p-value | FDR | Permutation p-value | Geom mean of intensities in class 1 | Geom mean of intensities in class 2 | Fold-change | Gene symbol |
|---|---|---|---|---|---|---|---|
| 1 | 2.69e−05 | 0.0097916 | 1e−04 | 42029.2186248 | 16444.7647514 | 2.5557811 | EFS |
| 2 | 0.0003623 | 0.0659386 | 2e−04 | 64 | 242.1740917 | 0.2642727 | ACTB |
| 3 | 0.0024993 | 0.232414 | 0.003 | 126.3628755 | 98.3196704 | 1.2852248 | BCL2A1 |
| 4 | 0.0027336 | 0.232414 | 0.0035 | 105.5875206 | 181.8913172 | 0.5804979 | TP73 |
| 5 | 0.0031925 | 0.232414 | 0.0039 | 2349.2769746 | 165.0059246 | 14.237531 | HIC1 |
| 6 | 0.004255 | 0.2581367 | 0.0022 | 289.2552131 | 788.814123 | 0.3666963 | SERPINI1 |
| 7 | 0.0051369 | 0.2671188 | 0.0055 | 383.3177597 | 828.0516714 | 0.4629153 | CXADR |

The first 7 genes are significant at the nominal 0.01 level of the univariate test Example 19.4: ClassPrediction "46 Vs 47+21: Biorad+21 Only". (p<0.05 & 0.005)

Correct Classif: 90%
p<0.05 many genes. • set p<0.005
• CorrClass=90% (most methods OK)

TABLE 53

Composition of classifier - Sorted by t-value: Class 1: 46; Class 2: 47.

| | Parametric p-value | t-value | % CV support | Geom mean of intensities in class 1 | Geom mean of intensities in class 2 | Fold-change | Gene symbol |
|---|---|---|---|---|---|---|---|
| 1 | 0.0002749 | −4.45 | 100 | 64 | 242.1740917 | 0.2642727 | ACTB |
| 2 | 0.0030869 | −3.388 | 52 | 105.5875206 | 181.8913172 | 0.5804979 | TP73 |
| 3 | 0.0042385 | −3.247 | 43 | 289.2552131 | 788.814123 | 0.3666963 | SERPINI1 |
| 4 | 0.0049355 | −3.18 | 29 | 383.3177597 | 828.0516714 | 0.4629153 | CXADR |
| 5 | 0.0023831 | 3.502 | 86 | 2349.2769746 | 165.0059246 | 14.237531 | HIC1 |
| 6 | 0.0018513 | 3.613 | 100 | 126.3628755 | 98.3196704 | 1.2852248 | BCL2A1 |
| 7 | 2.97e−05 | 5.446 | 100 | 42029.2186248 | 16444.7647514 | 2.5557811 | EFS |

Example 19.5: ClassPred "46 Vs47 Prediction".
(p<0.005)

Feature selection criteria:
Genes significantly different between the classes at 0.005 significance level were used for class prediction.
Cross-validation method:
Leave-one-out cross-validation method was used to compute misclassification rate.
T-values used for the (Bayesian) compound covariate predictor were truncated at abs(t)=10 level.
Equal class prevalences is used in the Bayesian compound covariate predictor.
Threshold of predicted probability for a sample being predicted to a class from the Bayesian compound covariate predictor 0.8.
Performance of Classifiers During Cross-Validation

| | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|
| Mean percent of correct classification: | 86 | 90 | 86 | 86 | 81 | 81 | 89 |

Performance of Classifiers During Cross-Validation:
Let, for some class A,
    n11=number of class A samples predicted as A
    n12=number of class A samples predicted as non-A
    n21=number of non-A samples predicted as A
    n22=number of non-A samples predicted as non-A
Then the following parameters can characterize performance of classifiers:

$$\text{Sensitivity} = n11/(n11+n12)$$

$$\text{Specificity} = n22/(n21+n22)$$

$$\text{Positive Predictive Value (PPV)} = n11/(n11+n21)$$

$$\text{Negative Predictive Value (NPV)} = n22/(n12+n22)$$

Sensitivity is the probability for a class A sample to be correctly predicted as class A,
Specificity is the probability for a non class A sample to be correctly predicted as non-A,
PPV is the probability that a sample predicted as class A actually belongs to class A,
NPV is the probability that a sample predicted as non class A actually does not belong to class A.
For each classification method and each class, these parameters are listed in the tables below.

Performance of the Compound Covariate Predictor Classifier:

| Class | Sensitivity | Specificity | PPV | NPV |
|---|---|---|---|---|
| 46 | 0.9 | 0.818 | 0.818 | 0.9 |
| 47 | 0.818 | 0.9 | 0.9 | 0.818 |

Performance of the Diagonal Linear Discriminant Analysis Classifier:

| Class | Sensitivity | Specificity | PPV | NPV |
|---|---|---|---|---|
| 46 | 0.9 | 0.909 | 0.9 | 0.909 |
| 47 | 0.909 | 0.9 | 0.909 | 0.9 |

Performance of the 1-Nearest Neighbor Classifier:

| Class | Sensitivity | Specificity | PPV | NPV |
|---|---|---|---|---|
| 46 | 0.9 | 0.818 | 0.818 | 0.9 |
| 47 | 0.818 | 0.9 | 0.9 | 818 |

Performance of the 3-Nearest Neighbors Classifier:

| Class | Sensitivity | Specificity | PPV | NPV |
|---|---|---|---|---|
| 46 | 0.9 | 0.818 | 0.818 | 0.9 |
| 47 | 0.818 | 0.9 | 0.9 | 0.818 |

Performance of the Nearest Centroid Classifier:

| Class | Sensitivity | Specificity | PPV | NPV |
|---|---|---|---|---|
| 46 | 0.8 | 0.818 | 0.8 | 0.818 |
| 47 | 0.818 | 0.8 | 0.818 | 0.8 |

Performance of the Support Vector Machine Classifier:

| Class | Sensitivity | Specificity | PPV | NPV |
|---|---|---|---|---|
| 46 | 0.8 | 0.818 | 0.8 | 0.818 |
| 47 | 0.818 | 0.8 | 0.818 | 0.8 |

Performance of the Bayesian Compound Covariate Classifier:

| Class | Sensitivity | Specificity | PPV | NPV |
|---|---|---|---|---|
| 46 | 0.8 | 0.818 | 0.8 | 0.818 |
| 47 | 0.818 | 0.8 | 0.818 | 0.8 |

Predictions of Classifiers for New Samples:

TABLE 54

Composition of classifier - Sorted by t-value: Class 1: 46; Class 2: 47.

| | Parametric p-value | t-value | % CV support | Geom mean of intensities in class 1 | Geom mean of intensities in class 2 | Fold-change | Gene symbol |
|---|---|---|---|---|---|---|---|
| 1 | 0.0002749 | −4.45 | 100 | 64 | 242.1740917 | 0.2642727 | ACTB |
| 2 | 0.0030869 | −3.388 | 52 | 105.5875206 | 181.8913172 | 0.5804979 | TP73 |
| 3 | 0.0042385 | −3.247 | 43 | 289.2552131 | 788.814123 | 0.3666963 | SERPINI1 |
| 4 | 0.0049355 | −3.18 | 29 | 383.3177597 | 828.0516714 | 0.4629153 | CXADR |
| 5 | 0.0023831 | 3.502 | 86 | 2349.2769746 | 165.0059246 | 14.237531 | HIC1 |
| 6 | 0.0018513 | 3.613 | 100 | 126.3628755 | 98.3196704 | 1.2852248 | BCL2A1 |
| 7 | 2.97e-05 | 5.446 | 100 | 42029.2186248 | 16444.7647514 | 2.5557811 | EFS |

Cross-Validation ROC curve from the Bayesian Compound Covariate Predictor
The area under the curve is 0.882.
Note: the classification rule used above is different from the class prediction. Here, if a sample's posterior probability is greater than the threshold, it is predicted as Class 1. Otherwise, it is predicted as Class 2.

Example 20: Osteoarthritis

Osteoarthritis (OA, also known as degenerative arthritis, degenerative joint disease) is a group of diseases and mechanical abnormalities involving degradation of joints, [1] including articular cartilage and the subchondral bone next to it.
6 arthritic and healthy paired cartilage DNA patient samples of (N=12) & corresponding PB (N=6) were used for enrichment of the Methylated DNA fraction using Restriction enzymes and Rolling-Circle Amplification (RCA). RCA-amplicons (n=18) and unamplified DNA from PB (n=6, methylationsensitive digested) were subjected to the ARC-CpG360 assay (FIG. 5).
Class Prediction: A) Paired-Cartilage
Performance of classifiers during cross-validation, n=6

| | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? |
|---|---|---|---|---|---|---|
| Mean percent of correct classification: | 67 | 83 | 33 | 50 | 33 | 50 |

Performance of classifiers during cross-validation delineated a classifier via Diagonal Linear Discriminant Analysis which enables correct classification of DNA from healthy versus diseased cartilage tissue in 83% of samples.

TABLE 55

Composition of classifier-Sorted by t-value

| | Parametric p-value | t-value | % CV support | Geometric mean of intensities (class arthrotic/class normal) | Gene symbol |
|---|---|---|---|---|---|
| 1 | 0.0185586 | −2.985 | 83 | 0.5493273 | FBXL13 |
| 2 | 0.027527 | −2.722 | 67 | 0.2052959 | PITX2 |
| 3 | 0.0423156 | −2.438 | 17 | 0.7049576 | NKX2-1 |
| 4 | 0.0449374 | −2.398 | 33 | 0.5942176 | IGF2 |
| 5 | 0.0477784 | 2.358 | 50 | 2.4204466 | C5AR1 |
| 6 | 0.047474 | 2.362 | 17 | 1.670202 | SPARC |
| 7 | 0.046836 | 2.371 | 17 | 1.5802621 | RUNX3 |
| 8 | 0.0434389 | 2.421 | 17 | 1.4389923 | CHST11 |
| 9 | 0.0380021 | 2.509 | 50 | 3.4404592 | CHRNA9 |
| 10 | 0.0359301 | 2.545 | 17 | 1.6254011 | ZNF462 |
| 11 | 0.0276139 | 2.72 | 33 | 1.6783556 | HSD17B4 |
| 12 | 0.0241659 | 2.808 | 50 | 1.551163 | UNG |
| 13 | 0.0227629 | 2.848 | 67 | 2.7837216 | TJP2 |
| 14 | 0.016604 | 3.061 | 83 | 1.5403679 | ERBB2 |
| 15 | 0.015781 | 3.095 | 100 | 2.0464503 | SOX15 |
| 16 | 0.0149683 | 3.131 | 100 | 1.6185261 | ERCC8 |
| 17 | 0.0138961 | 3.182 | 100 | 2.1115571 | CDX1 |
| 18 | 0.0119595 | 3.286 | 100 | 1.9932115 | ANXA3 |
| 19 | 0.0115563 | 3.309 | 100 | 2.0830817 | CDH1 |
| 20 | 0.0107385 | 3.36 | 100 | 2.4788401 | CHFR |
| 21 | 0.0055854 | 3.826 | 100 | 1.8857188 | TACSTD1 |
| 22 | 0.0044074 | 4 | 100 | 1.8445127 | MT1A |

Example 21: Breast Cancer Vs. Blood DNA

Example 21.1: Class Prediction Using "Grid of Alpha Levels": Resulted in 100% Correct Classification 47 breast cancer ("BrCa") samples and 30 samples of normal blood ("norm blood") were compared.
Feature selection criteria:
Genes significantly different between the classes at the 0.01, 0.005, 0.001 and 0.0005 significance levels were used to build four predictors. The predictor with the lowest cross-validation mis-classification rate was selected. The best predictor consisted of genes significantly different between the classes at the 5e-04 significance level.
Cross-validation method:
Leave-one-out cross-validation method was used to compute mis-classification rate.
T-values used for the (Bayesian) compound covariate predictor were truncated at abs(t)=10 level.
Equal class prevalences is used in the Bayesian compound covariate predictor.
Threshold of predicted probability for a sample being predicted to a class from the Bayesian compound covariate predictor 0.8.
Performance of classifiers during cross-validation.

TABLE 56

Composition of classifier: Sorted by t-value Class 1: BrCa; Class 2: norm_blood.

|  | Parametric p-value | t-value | % CV support | Geom mean of intensities in class 1 | Geom mean of intensities in class 2 | Fold-change | Gene symbol |
|---|---|---|---|---|---|---|---|
| 1 | <1e-07 | -10.192 | 100 | 581.9607527 | 2066.8543933 | 0.2815683 | TP53 |
| 2 | <1e-07 | -10.007 | 100 | 30.3630111 | 390.9291534 | 0.0776688 | PTTG1 |
| 3 | <1e-07 | -7.138 | 100 | 10.2807227 | 24.2271482 | 0.4243472 | VHL |
| 4 | <1e-07 | -6.863 | 100 | 2433.1393149 | 11571.0250817 | 0.2102786 | TP53 |
| 5 | <1e-07 | -6.745 | 100 | 113.8926251 | 213.2313311 | 0.5341271 | S100A2 |
| 6 | <1e-07 | -6.3 | 100 | 78.7543028 | 241.6231137 | 0.3259386 | ZNF573 |
| 7 | <1e-07 | -6.151 | 100 | 13.0942808 | 70.9312653 | 0.1846052 | RDH10 |
| 8 | <1e-07 | -6.027 | 100 | 27.8148612 | 101.37664 | 0.2743715 | TSHR |
| 9 | <1e-07 | -5.975 | 100 | 102.1907296 | 202.934491 | 0.5035651 | MYO5C |
| 10 | 1e-07 | -5.822 | 100 | 25.9644556 | 47.8594791 | 0.5425144 | MBD2 |
| 11 | 2e-07 | -5.719 | 100 | 29.9780381 | 163.8095123 | 0.1830055 | CPEB4 |
| 12 | 5e-07 | -5.473 | 100 | 1242.4890989 | 13706.2371809 | 0.0906514 | BRCA1 |
| 13 | 7e-07 | -5.421 | 100 | 14.3528907 | 88.9052761 | 0.1614403 | CD24 |
| 14 | 8e-07 | -5.36 | 100 | 19.8988206 | 45.7988124 | 0.4344833 | COL1A1 |
| 15 | 1.5e-06 | -5.215 | 100 | 63.2128488 | 117.7699291 | 0.5367486 | VDR |
| 16 | 3.4e-06 | -5.007 | 100 | 7063.8038144 | 21541.1220722 | 0.3279218 | TP53 |
| 17 | 9.7e-06 | -4.736 | 100 | 10.3922114 | 15.4418189 | 0.6729914 | KLF4 |
| 18 | 2.05e-05 | -4.538 | 100 | 194.0106476 | 295.136251 | 0.6573596 | ADRB2 |
| 19 | 2.16e-05 | -4.524 | 100 | 33.8347806 | 59.1097765 | 0.5724058 | ERCC2 |
| 20 | 2.32e-05 | -4.504 | 100 | 316.2948312 | 476.1390035 | 0.664291 | SPINT2 |
| 21 | 2.56e-05 | -4.478 | 100 | 27.1553404 | 61.1937894 | 0.4437597 | XAB2 |
| 22 | 3.04e-05 | -4.432 | 100 | 9.7251889 | 29.7932448 | 0.3264226 | RB1 |
| 23 | 3.5e-05 | -4.393 | 100 | 110.1984227 | 366.9788491 | 0.3002855 | APEX1 |
| 24 | 7.07e-05 | -4.2 | 100 | 21.7743077 | 36.9890032 | 0.5886698 | RPA3 |
| 25 | 7.24e-05 | -4.194 | 100 | 49.4353161 | 162.4154057 | 0.3043758 | TP53 |
| 26 | 7.89e-05 | -4.169 | 100 | 70.2357258 | 95.2611175 | 0.7372969 | BRCA2 |
| 27 | 0.0001138 | -4.067 | 100 | 13.1493016 | 24.7622599 | 0.5310219 | MSH2 |
| 28 | 0.0001867 | -3.925 | 100 | 200.1169773 | 302.9095968 | 0.6606492 | BAZ1A |
| 29 | 0.000196 | -3.911 | 100 | 44.5680521 | 67.7167396 | 0.6581541 | SPHK1 |
| 30 | 0.0002554 | -3.834 | 94 | 9.5632348 | 11.7355308 | 0.8148958 | ERCC8 |
| 31 | 0.0003086 | -3.778 | 92 | 34.6349298 | 111.9317778 | 0.3094289 | SERPINI1 |
| 32 | 0.0004311 | -3.679 | 65 | 76.5476171 | 119.9722941 | 0.6380441 | RPA2 |
| 33 | 0.0004492 | 3.666 | 44 | 168.2611214 | 62.8807961 | 2.6758745 | SCGB3A1 |
| 34 | 0.0004454 | 3.669 | 48 | 36.905444 | 21.1329044 | 1.7463498 | MLH3 |
| 35 | 0.0003335 | 3.755 | 75 | 132.3215201 | 69.3169998 | 1.9089332 | CDK2AP1 |
| 36 | 0.0002437 | 3.847 | 100 | 191.0556435 | 45.1565979 | 4.2309574 | MT1G |
| 37 | 0.0002289 | 3.866 | 100 | 93.3071908 | 28.5533588 | 3.2678184 | PITX2 |
| 38 | 0.00021 | 3.891 | 99 | 76.2715173 | 41.100932 | 1.8557126 | SFRP5 |
| 39 | 0.0001806 | 3.935 | 100 | 715.1506468 | 251.9240299 | 2.8387552 | ZNF711 |
| 40 | 0.0001618 | 3.966 | 100 | 23.4848688 | 13.06566 | 1.7974499 | TGFBR2 |
| 41 | 0.0001434 | 4.001 | 100 | 67.7035483 | 42.5803248 | 1.5900195 | C5AR1 |
| 42 | 5.07e-05 | 4.292 | 100 | 6138.5702191 | 2908.6652747 | 2.1104423 | DPH1 |
| 43 | 4.81e-05 | 4.306 | 100 | 726.1545624 | 289.4745739 | 2.5085262 | CDX1 |
| 44 | 4.1e-05 | 4.35 | 100 | 415.6613951 | 61.1458309 | 6.7978698 | GRIN2B |
| 45 | 1.3e-05 | 4.659 | 100 | 2580.4330049 | 1416.7684153 | 1.8213513 | C5orf4 |
| 46 | 1.21e-05 | 4.677 | 100 | 1762.9771933 | 228.8977899 | 7.702028 | BOLL |
| 47 | 1.09e-05 | 4.705 | 100 | 1470.4249627 | 57.6374636 | 25.5116182 | HOXA1 |
| 48 | 1e-05 | 4.727 | 100 | 37.0764001 | 23.4491451 | 1.5811408 | NEUROD2 |
| 49 | 9.5e-06 | 4.74 | 100 | 1002.9875797 | 558.3939525 | 1.7962006 | BCL2A1 |
| 50 | 6.2e-06 | 4.853 | 100 | 4712.4542557 | 852.0366138 | 5.5308119 | ZNF502 |
| 51 | 5.8e-06 | 4.867 | 100 | 91.6412336 | 15.2503602 | 6.0091193 | FOXA2 |
| 52 | 8e-07 | 5.378 | 100 | 354.1785276 | 58.7331318 | 6.0303021 | MYOD1 |
| 53 | 3e-07 | 5.592 | 100 | 59.1621472 | 12.9632046 | 4.563852 | HOXA10 |
| 54 | 3e-07 | 5.618 | 100 | 81.915233 | 23.9168463 | 3.4250014 | TMEFF2 |
| 55 | 3e-07 | 5.623 | 100 | 61.6877515 | 25.0045823 | 2.4670579 | IQCG |
| 56 | 2e-07 | 5.703 | 100 | 15711.1916492 | 3845.3741759 | 4.0857381 | LXN |
| 57 | 1e-07 | 5.868 | 100 | 25235.2889441 | 2245.5822795 | 11.2377485 | SRGN |

TABLE 56-continued

Composition of classifier: Sorted by t-value Class 1: BrCa; Class 2: norm_blood.

|    | Parametric p-value | t-value | % CV support | Geom mean of intensities in class 1 | Geom mean of intensities in class 2 | Fold-change | Gene symbol |
|----|--------------------|---------|--------------|-------------------------------------|-------------------------------------|-------------|-------------|
| 58 | <1e−07 | 5.891  | 100 | 1622.6683399  | 292.168739   | 5.5538739  | PTGS2 |
| 59 | <1e−07 | 5.937  | 100 | 537.1429664   | 78.7019778   | 6.825025   | ONECUT2 |
| 60 | <1e−07 | 5.942  | 100 | 954.6123795   | 234.95102    | 4.0630272  | PENK |
| 61 | <1e−07 | 6.045  | 100 | 808.638251    | 217.5513421  | 3.7169996  | PITX2 |
| 62 | <1e−07 | 6.216  | 100 | 228.9531126   | 17.2253564   | 13.2916328 | DLX2 |
| 63 | <1e−07 | 6.37   | 100 | 661.7259764   | 39.2863454   | 16.8436633 | SALL3 |
| 64 | <1e−07 | 6.628  | 100 | 313.1300204   | 25.0349085   | 12.5077358 | APC |
| 65 | <1e−07 | 6.636  | 100 | 655.1243028   | 19.0405908   | 34.4067213 | APC |
| 66 | <1e−07 | 8.047  | 100 | 3277.6244939  | 159.1958845  | 20.5886258 | HIST1H2AG |
| 67 | <1e−07 | 8.498  | 100 | 218.902004    | 44.7493459   | 4.8917364  | ACTB |
| 68 | <1e−07 | 9.002  | 100 | 101.6498894   | 20.326238    | 5.00092    | RASSF1 |
| 69 | <1e−07 | 9.048  | 100 | 6949.0703311  | 1969.9487149 | 3.5275387  | S100A9 |
| 70 | <1e−07 | 9.123  | 100 | 107.9389071   | 31.2555688   | 3.4534296  | TERT |
| 71 | <1e−07 | 9.128  | 100 | 103.4939268   | 27.6736892   | 3.7397951  | TNFRSF25 |
| 72 | <1e−07 | 11.265 | 100 | 228.3911666   | 29.7177708   | 7.6853398  | HIC1 |
| 73 | <1e−07 | 11.344 | 100 | 6290.5863578  | 663.9267849  | 9.4748194  | LAMC2 |
| 74 | <1e−07 | 12.189 | 100 | 1400.1258136  | 122.8672147  | 11.3954387 | SPARC |
| 75 | <1e−07 | 12.205 | 100 | 4609.2719639  | 104.5974377  | 44.066777  | WT1 |
| 76 | <1e−07 | 12.74  | 100 | 21262.8209077 | 4561.748182  | 4.6611124  | PITX2 |
| 77 | <1e−07 | 14.974 | 100 | 149.3852585   | 23.7225098   | 6.2971945  | GNA15 |
| 78 | <1e−07 | 15.745 | 100 | 2646.4240937  | 79.6479263   | 33.2265285 | ESR1 |
| 79 | <1e−07 | 16.193 | 100 | 8358.7943596  | 230.2362876  | 36.3052864 | KL |
| 80 | <1e−07 | 17.733 | 100 | 22781.9857745 | 663.1165477  | 34.3559301 | HIC1 |

Example 21.2: Class Prediction:→8 Gene-Pairs 100% Correct

TABLE 57

Composition of classifiers from Class Prediction Analysis - Sorted by gene pairs

|    | Pair | Parametric p-value | t-value | % CV support | Geom mean of intensities in class 1 | Geom mean of intensities in class 2 | Fold-change | Gene symbol |
|----|------|--------------------|---------|--------------|-------------------------------------|-------------------------------------|-------------|-------------|
| 1  | 1 | <1e−07    | 12.205 | 100 | 4609.2719639  | 104.5974377  | 44.066777  | WT1 |
| 2  | 1 | 0.065477  | 1.868  | 100 | 17937.6116667 | 15996.4869627 | 1.1213469 | POS Biotin Control RET |
| 3  | 2 | <1e−07    | 16.193 | 100 | 8358.7943596  | 230.2362876  | 36.3052864 | KL |
| 4  | 2 | 0.0233866 | 2.313  | 100 | 18.6345896    | 14.6005275   | 1.2762956  | blank |
| 5  | 3 | <1e−07    | 17.733 | 100 | 22781.9857745 | 663.1165477  | 34.3559301 | HIC1 |
| 6  | 3 | 0.9280704 | 0.091  | 100 | 107.9277389   | 106.2344604  | 1.0159391  | NHLH2 |
| 7  | 4 | <1e−07    | 14.974 | 100 | 149.3852585   | 23.7225098   | 6.2971945  | GNA15 |
| 8  | 4 | 0.1759659 | 1.366  | 100 | 56.6108267    | 45.0988576   | 1.2552608  | MTHFR |
| 9  | 5 | <1e−07    | 12.74  | 100 | 21262.8209077 | 4561.748182  | 4.6611124  | PITX2 |
| 10 | 5 | 0.6239663 | −0.492 | 100 | 61.244381     | 64.0038056   | 0.9568866  | MARK1 |
| 11 | 6 | <1e−07    | 11.265 | 100 | 228.3911666   | 29.7177708   | 7.6853398  | HIC1 |
| 12 | 6 | 0.0565577 | 1.936  | 100 | 30.4016365    | 25.1157341   | 1.2104618  | DUSP10 |
| 13 | 7 | <1e−07    | 11.344 | 99  | 6290.5863578  | 663.9267849  | 9.4748194  | LAMC2 |
| 14 | 7 | 0.709874  | −0.373 | 100 | 112.0102998   | 115.0285582  | 0.9737608  | PARP1 |
| 15 | 8 | <1e−07    | 12.189 | 96  | 1400.1258136  | 122.8672147  | 11.3954387 | SPARC |
| 16 | 8 | 0.8672748 | 0.168  | 100 | 59.8259107    | 59.022835    | 1.0136062  | PSEN2 |

TABLE 58

Composition of classifier - Sorted by t-value
Rows 1-8 in the table contain control genes, 9-16 diagnostic genes suitable for class-prediction (=elucidation of Breast Cancer) Class 1: BrCa; Class 2: norm_blood.

|   | Parametric p-value | t-value | % CV support | Geom mean of intensities in class 1 | Geom mean of intensities in class 2 | Fold-change | Gene symbol |
|---|--------------------|---------|--------------|-------------------------------------|-------------------------------------|-------------|-------------|
| 1 | 0.6239663 | −0.492 | 100 | 61.244381   | 64.0038056  | 0.9568866 | MARK1 |
| 2 | 0.709874  | −0.373 | 100 | 112.0102998 | 115.0285582 | 0.9737608 | PARP1 |
| 3 | 0.9280704 | 0.091  | 100 | 107.9277389 | 106.2344604 | 1.0159391 | NHLH2 |

TABLE 58-continued

Composition of classifier - Sorted by t-value
Rows 1-8 in the table contain control genes, 9-16 diagnostic genes suitable for class-prediction (=elucidation of Breast Cancer) Class 1: BrCa; Class 2: norm_blood.

|  | Parametric p-value | t-value | % CV support | Geom mean of intensities in class 1 | Geom mean of intensities in class 2 | Fold-change | Gene symbol |
|---|---|---|---|---|---|---|---|
| 4 | 0.8672748 | 0.168 | 100 | 59.8259107 | 59.022835 | 1.0136062 | PSEN2 |
| 5 | 0.1759659 | 1.366 | 100 | 56.6108267 | 45.0988576 | 1.2552608 | MTHFR |
| 6 | 0.065477 | 1.868 | 100 | 17937.6116667 | 15996.4869627 | 1.1213469 | POS Biotin Control RET |
| 7 | 0.0565577 | 1.936 | 100 | 30.4016365 | 25.1157341 | 1.2104618 | DUSP10 |
| 8 | 0.0233866 | 2.313 | 100 | 18.6345896 | 14.6005275 | 1.2762956 | blank |
| 9 | <1e-07 | 11.265 | 100 | 228.3911666 | 29.7177708 | 7.6853398 | HIC1 |
| 10 | <1e-07 | 11.344 | 99 | 6290.5863578 | 663.9267849 | 9.4748194 | LAMC2 |
| 11 | <1e-07 | 12.189 | 96 | 1400.1258136 | 122.8672147 | 11.3954387 | SPARC |
| 12 | <1e-07 | 12.205 | 100 | 4609.2719639 | 104.5974377 | 44.066777 | WT1 |
| 13 | <1e-07 | 12.74 | 100 | 21262.8209077 | 4561.748182 | 4.6611124 | PITX2 |
| 14 | <1e-07 | 14.974 | 100 | 149.3852585 | 23.7225098 | 6.2971945 | GNA15 |
| 15 | <1e-07 | 16.193 | 100 | 8358.7943596 | 230.2362876 | 36.3052864 | KL |
| 16 | <1e-07 | 17.733 | 100 | 22781.9857745 | 663.1165477 | 34.3559301 | HIC1 |

Example 21.3: Class Prediction Using PAMR→100% Correct Concept: Define Minimal Set of Genes Using PAM (Prediction Analysis of Microarrays) Elucidates 3 Genes Sufficient for 100% Correct Diagnostic Testing Cross-validation mis-classification rate as a function of the threshold parameter. Threshold 8.57 was selected.

Prediction Table: a cross-tabulation of true (rows) versus predicted (columns) classes for the PAM fit (Fig. 4a and b)

|  | BrCa | norm_blood |
|---|---|---|
| BrCa | 47 | 0 |
| norm_blood | 0 | 30 |

Cross-validation mis-classification rate: 0 percent.

These Parameters are Listed in the Table Below

| Class | Sensitivity | Specificity | PPV | NPV |
|---|---|---|---|---|
| BrCa | 1 | 1 | 1 | 1 |
| norm_blood | 1 | 1 | 1 | 1 |

TABLE 59

Composition of PAM classifier-3 genes selected by PAM (threshold equal to 8.57)

|  | Geom mean of intensities in class 1 | Geom mean of intensities in class 2 | Fold-change | Gene symbol |
|---|---|---|---|---|
| 1 | 22781.9857745 | 663.1165477 | 34.3559301 | HIC1 |
| 2 | 8358.7943596 | 230.2362876 | 36.3052864 | KL |
| 3 | 2646.4240937 | 79.6479263 | 33.2265285 | ESR1 |

Class 1: BrCa;
Class 2: norm_blood.

The invention claimed is:

1. A method of detecting increased amounts of methyl moieties bound to HIC1, KL, and ESR1 genes in a sample from a patient and treating breast cancer in the patient comprising:
   obtaining a blood, serum, or breast tissue sample comprising DNA from a patient suspected of having or identified as being at risk for breast cancer;
   subjecting the DNA in the sample to bisulfite deamination or methylation-sensitive restriction digestion;
   obtaining a set of nucleic acid primers or hybridization probes specific for HIC1, KL, and ESR1;
   detecting increased numbers of methyl moieties bound to HIC1, KL, and ESR1 genes in the sample in which the DNA has been subjected to bisulfite deamination or methylation-sensitive restriction digestion relative to the amounts of methyl moieties bound to the HIC1, KL, and ESR1 genes in a blood, serum, or breast tissue sample from normal, control human subjects using the set of nucleic acid primers or hybridization probes specific for HIC1, KL, and ESR1, wherein detecting increased numbers of methyl moieties bound to ESR1 comprises detecting increased numbers of methyl moieties bound in a region of ESR1 consisting of SEQ ID NO:1353 and 300 adjacent base pairs and administering a breast cancer therapy to the patient after detecting the increased numbers of methyl moieties bound to the HIC1, KL and ESR1 genes in the sample relative to the samples from normal, control human subjects.

2. The method of claim 1, wherein detecting increased numbers of methyl moieties is performed by methylation specific PCR analysis, methylation specific digestion analysis and either or both of hybridization analysis to non-digested or digested fragments or PCR amplification analysis of non-digested or digested fragments.

3. The method of claim 1, wherein detecting increased numbers of methyl moieties bound to the HIC1 and KL genes comprises detecting increased numbers of methyl moieties bound in a region of the HIC1 gene consisting of SEQ ID NO:1207 and 500 adjacent base pairs and a region of the KL gene consisting of SEQ ID NO:1163 and 500 adjacent base pairs.

4. The method of claim 1, wherein detecting increased numbers of methyl moieties bound to the HIC1, KL, and ESR1 genes comprises detecting increased numbers of methyl moieties bound in a region of the HIC1 gene consisting of SEQ ID NO:1207 and 200 adjacent base pairs, a region of the KL gene consisting of SEQ ID NO:1163 and 200 adjacent base pairs, and a region of the ESR1 gene consisting of SEQ ID NO:1353 and 200 adjacent base pairs.

5. A method of treating breast cancer comprising administering a breast cancer therapy to a human patient for breast cancer after the human patient has been identified as having an increased likelihood of having or developing breast cancer based on an increase in methylation of the ESR1, KL, and HIC1 genes in a blood, serum, or breast tissue sample from the patient as compared to methylation of the ESR1, KL, and HIC1 genes a sample from a normal, control human subject, wherein the methylation status of the ESR1, KL, and HIC1 genes in the sample from the patient and in the sample from the control human subject have been determined using a set of polynucleotides that hybridize specifically to genomic regions associated with HIC1, KL, and ESR1 genes, wherein the genomic regions have been subjected to bisulfite deamination or methylation-sensitive restriction digestion, and wherein the methylation status of the ESR1 gene has been determined by determining the methylation status of a region of the ESR1 gene consisting of SEQ ID NO:1353 and 500 adjacent base pairs.

* * * * *

```
                        SEQUENCE LISTING

<160> NUMBER OF SEQ ID NOS: 1440

<210> SEQ ID NO 1
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 1
cggccggtca ggaatcccca tcctggagcg caggcggaga gccagtggct              50

<210> SEQ ID NO 2
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 2
ccaaaaaagg tgacactgcc ccctcccagt ggctccatgc tcctcagcta tggctgtccg   60
``` ggcc 64

<210> SEQ ID NO 3
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 3
cgccccgccc ccgccaacaa ccgccgctct gattggcccg gcgcttgtct ctt    53

<210> SEQ ID NO 4
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 4
agcggcctca gcctgcgcac cccaggagcg tggatgacta cggccacccc    50

<210> SEQ ID NO 5
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 5
gcagccgaga gggtcaggcc cccataggtc ctcagcctgc ttcaacctca aaggggatgg    60
ggg    63

<210> SEQ ID NO 6
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 6
tcctggcagc attaccacac tgctcacctg tgaagcaatc ttccggagac agggccaaag    60
ggcca    65

<210> SEQ ID NO 7
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 7
ctgacaagag acatgcaggg ctgagaggca gctccttttt atagcggtta ggcttggcca    60
gctgc    65

<210> SEQ ID NO 8
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 8

-continued

```
tggcatccac ttgcttgatc cagccagatt cccactccca tgccctctcc actattgcga    60
ttgc                                                                  64

<210> SEQ ID NO 9
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 9
ctgcttcgtg ccctctggtg gctaaggcgt gtcattgcag tgccggcctc ctgtcatcct    60
cc                                                                    62

<210> SEQ ID NO 10
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 10
ccggcgcact ccgactccga gcagtctctg tccttcgacc cgagccccgc                50

<210> SEQ ID NO 11
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 11
taggtggtga gttacttggc tcggagcggg cgaggggacg cgtgggcgga gcg            53

<210> SEQ ID NO 12
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 12
aaccacctga tcaaggaaaa ggaaggcaca gcggagcgca gagtgagaac caccaaccga    60
ggcgc                                                                 65

<210> SEQ ID NO 13
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 13
cgggggtagg ctttgctgtc tgagggcgtc tggctgtgga gctgaaggag gcgctgctga    60
g                                                                     61

<210> SEQ ID NO 14
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 14
```
gccccgcatc cctaatgagg gaatgaatgg agaggccccc tcggctggcg ccc            53

<210> SEQ ID NO 15
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 15
cggggccacg cgctaagggc ccgaacttgg cagctgaccg tcccggacag                50

<210> SEQ ID NO 16
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 16
ccaccgaaca cgccgcaccg gccaccgccg ttccctgata gattgctgat gc             52

<210> SEQ ID NO 17
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 17
gaactgggtc gtggaaggat cgcggggagc ggccctcagg ccttcggcct cact           54

<210> SEQ ID NO 18
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 18
ccagcacttt gggaggccga ggcgggcgga tcacgaggtc aggagatcga gaccatcct      59

<210> SEQ ID NO 19
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 19
ggcggctggt gcttgggtct acgggaatac gcataacagc ggccgtcagg gcgcc          55

<210> SEQ ID NO 20
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 20
tcagattcct cagggccgca gaggtgtgga gctggttggg ccggttcttc accctcctcc     60
c                                                                    61

<210> SEQ ID NO 21

```
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 21
ctggccgagg tggccaccgg tgacgacaag aagcgcatca ttgactcagc ccgg          54

<210> SEQ ID NO 22
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 22
ctaaccttcc tcgccgcctt cctgcgggtg accccaaac gcccagctc cgc             53

<210> SEQ ID NO 23
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 23
ccgacttgga cgcggccagc tggagaggcg gagcgccggg aggagacctt                50

<210> SEQ ID NO 24
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 24
acagagtcgg caccggcgtc cccagctctg ccgaagatcg cggtcgggtc                50

<210> SEQ ID NO 25
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 25
ggggatggag aactctcctc gcttcgtcct ctctcccggg gaatccctaa ccccgcactg     60
cg                                                                   62

<210> SEQ ID NO 26
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 26
gtggctcggg tccacccggg ctgcgagccg gcagcacagg ccaataggca attag          55

<210> SEQ ID NO 27
<211> LENGTH: 58
<212> TYPE: DNA
<213> ORGANISM: Artificial Sequence
<220> FEATURE:
<223> OTHER INFORMATION: probe/primer/pcr
```

<400> SEQUENCE: 27
ctcaccccgc gacttacccc acacccgct ctccagaacc cccatatggg cgctcacc    58

<210> SEQ ID NO 28
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 28
acacaccact gcagcgttca aacgctggga agaagactcc cttgtggcac cggaaaccca    60
cgagg    65

<210> SEQ ID NO 29
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 29
ccgccacgaa cttggggtgc agccgatagc gctcgcggaa gagccgcctc    50

<210> SEQ ID NO 30
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 30
ctccatagcc ctccgacggg cgcccagggg cttcccggct ccgtgctctc t    51

<210> SEQ ID NO 31
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 31
tggacacccc aagagctcac tcctccgcgg ttttatattc cgacttgcgc acaggagcgg    60
ggtgc    65

<210> SEQ ID NO 32
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 32
ccgcccgttt cagcggcgca gcttctgtag ttgggctact ggaggggtcg ctcagaaacc    60
tca    63

<210> SEQ ID NO 33
<211> LENGTH: 69
<212> TYPE: DNA
<213> ORGANISM: Artificial Sequence
<220> FEATURE:
<223> OTHER INFORMATION: probe/primer/pcr

<400> SEQUENCE: 33
aacccaggct tgtcagccta agaacacggg atctcttcac tgtggttcat gtgtagagtg    60
gagtttcca    69

<210> SEQ ID NO 34
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 34
cagtcccctg ccgtgcgctc gcattcctca gcccttgggt ggtccatggg a    51

<210> SEQ ID NO 35
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 35
caggtgggcg tctcaggggt gggagtggcc gcgtcgtgaa gcggagagag ga    52

<210> SEQ ID NO 36
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 36
ctgcaaggga tgactcaccc cagtgattca accgcgccac cgagcgcgga gctg    54

<210> SEQ ID NO 37
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 37
ttgtatggat ttcgcccagg ggaaagcgct ccaacgcgcg gtgcaaacgg aagccactg    59

<210> SEQ ID NO 38
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 38
gaggaccagg gccggcgtgc cggcgtccag cgaggatgcg cagactgcct    50

<210> SEQ ID NO 39
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 39
acgcaccgcg gctcctcgcg tccagccgcg gccaaggaag ttactactcg cccaaat    57

```
<210> SEQ ID NO 40
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 40
cgctgcctcg ccattgggcg gccgaacgca gccacgtcca atcagaggag t          51

<210> SEQ ID NO 41
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 41
gaggttctgg ggaccgggag agtggccacc ttcttcctcc tcgcgaagag caggccggg     59

<210> SEQ ID NO 42
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 42
agtgggattg gggcacttgg ggcgctcggg gcctgcgtcg gatactcggg tc         52

<210> SEQ ID NO 43
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 43
tcaagccgcc tcaggtgagc gctccttggc gctacttccg gtctcaggtg aggccgc      57

<210> SEQ ID NO 44
<211> LENGTH: 70
<212> TYPE: DNA
<213> ORGANISM: Artificial Sequence
<220> FEATURE:
<223> OTHER INFORMATION: probe/primer/pcr

<400> SEQUENCE: 44
ttgtgacgtg tgttctgggc agggtttgag gttttggaac attttctaaa agggacagag    60
agcaccctgc                                                           70

<210> SEQ ID NO 45
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 45 cgggggga ga agtcctggag cgggtttggg ttgcagtttc cttgtgccgg ggatcctgtc   60
c                                                                    61

<210> SEQ ID NO 46
<211> LENGTH: 61
<212> TYPE: DNA
```

```
<213> ORGANISM: Artificial Sequence
<220> FEATURE:
<223> OTHER INFORMATION: probe/primer/pcr

<400> SEQUENCE: 46
gaggattatt cgtcttctcc ccattccgct gccgccgctg ccaggcctct ggctgctgag    60
g                                                                    61

<210> SEQ ID NO 47
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 47
ccctctctcc cctggcccgc aaagttttgg cggagccatc gctggggctg agc           53

<210> SEQ ID NO 48
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 48 ccaggggaa cttgtggcag tgcagcatct caggccaggg gaagccgtag gcctccatga     60

<210> SEQ ID NO 49
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 49
cgccacccag agcccgaggt ttgcccttca gaagcggacc cgcagactcc tcggact       57

<210> SEQ ID NO 50
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 50
cgccgaaatg aaacccgcct ccgttcgcct tcggaactgt cgtcacttcc gtcctcagac    60
ttgga                                                                65

<210> SEQ ID NO 51
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 51
tcccttgttt tgaggcggga acgcaaccct cgaccgccca ctgcgctccc a              51

<210> SEQ ID NO 52
<211> LENGTH: 50
<212> TYPE: DNA
<213> ORGANISM: Artificial Sequence
<220> FEATURE:
<223> OTHER INFORMATION: probe/primer/pcr
```

```
<400> SEQUENCE: 52
ggcagccggg aaatcccgtg tccccactcg tggcagagga cgctgtgggg          50

<210> SEQ ID NO 53
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 53
cccccacagt tttcatgtga tcaggaattc agcataggct ataagacgga gtgctccatg   60
tcaa                                                               64

<210> SEQ ID NO 54
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 54
ggggttgtca tggcagcagc tccatccctg accgccactt tctcccggtg ccg          53

<210> SEQ ID NO 55
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 55
aagttccgcc agtgcacagc aaccaatggg cggaggggtc ctttgcccct gggttgc      57

<210> SEQ ID NO 56
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 56
agttgggccg gatcagctga cccgcgtgtt tgcacccgga ccggtcacgt g            51

<210> SEQ ID NO 57
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 57
gggccgctgc ctactgtggg cctgcaaggc gtgcaagcgc aagaccacca              50

<210> SEQ ID NO 58
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 58
acctccctgc tgcgtgtcgc aaaccgaaca gcgggcgttg gccctcctgc              50
```

<210> SEQ ID NO 59
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 59
gggacccgga gctccaggct gcgccttgcg cccgggtcag acattattta gctcttcggt    60
tgagc    65

<210> SEQ ID NO 60
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 60
ggccgtgcgg ggctcaccgg agatcagagg cccggacagc ttcttgatcg cc    52

<210> SEQ ID NO 61
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 61
ccactgcctg cggtagaacc tggtcccgca tagcttggac tcggataagt caagttctct    60
tcca    64

<210> SEQ ID NO 62
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 62
gggccgcagg cccctgagga gcgatgacgg aatataagct ggtggtggtg ggc    53

<210> SEQ ID NO 63
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 63
gcaggacccg gatgagagcg cacgcttcgg ggtctccggg aagtcgcggc    50

<210> SEQ ID NO 64
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 64
aagagggaaa ggcttccccg gccagctgcg cggcgactcc ggggactcca g    51

<210> SEQ ID NO 65
<211> LENGTH: 50

```
<212> TYPE: DNA
<213> ORGANISM: Artificial Sequence
<220> FEATURE:
<223> OTHER INFORMATION: probe/primer/pcr

<400> SEQUENCE: 65
agggatggct tttgggctct gcccctcgct gctcccggcg tttggcgccc        50

<210> SEQ ID NO 66
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 66
gcccgctctc gggtgactcc gcaacctgtc gctcaggttc ctcctctccc ggcc    54

<210> SEQ ID NO 67
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 67
tgctggacat ccaccgcctc caggcagttt cgccgtcaca ccgtcgccat ctgtagc   57

<210> SEQ ID NO 68
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 68
ggccgcgaag cgactccgat cctccctctg agccttgctc agctctgccc cgc       53

<210> SEQ ID NO 69
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 69
cgcgcgttcg ctgcctcctc agctccagga tgatcggcca gaagacgctc tactccttt  60 tctcc                                                             65

<210> SEQ ID NO 70
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 70
cgggggcgga ggaaacacct atgaaccctc cggcagcctt ccttgccggg cg         52

<210> SEQ ID NO 71
<211> LENGTH: 50
<212> TYPE: DNA
<213> ORGANISM: Artificial Sequence
<220> FEATURE:
<223> OTHER INFORMATION: probe/primer/pcr
```

-continued

<400> SEQUENCE: 71
agggccagcc cttgggggct cccagatggg gcgtccacgt gacccactgc    50

<210> SEQ ID NO 72
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 72
gtgaaaggtc ggcgaaagag gagtaaagac ggcgagacgc gtccacgcag ggggagtctg    60
tgcg    64

<210> SEQ ID NO 73
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 73
gcgctgaggt gcagcgcacg gggcttcacc tgcaacgtgt cgattggacg    50

<210> SEQ ID NO 74
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 74
gaggcctcat gcctccgggg aaaggaaggg gtggtggtgt ttgcgcaggg ggagc    55

<210> SEQ ID NO 75
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 75
cgaagtggaa accggagttg cgtcattgct cccacccgat atcaccttgg cagcgaccgc    60
g    61

<210> SEQ ID NO 76
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 76
atggggtgct catcttcctg gagctgagga gctgggacgg gcatggggtg ctcatcctcc    60
tg    62

<210> SEQ ID NO 77
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 77
ttccagccgg tgattgcaat ggacaccgaa ctgctgcgac aacagagacg ctacaactca    60
ccgcg                                                               65

<210> SEQ ID NO 78
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 78
cagagaagac tcacgcagtg agcagtccgc aagcccgctg gcggcagcgg c            51

<210> SEQ ID NO 79
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 79
gacacaccca cctcagcaga tctcagccca tccctcccag ctcagtgcac tcacccaacc    60
ccac                                                                64

<210> SEQ ID NO 80
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 80
cggagtgctg caagcgcaga aaatatacgt catgtgcgga ggcggagctt ccgccctgcg    60

<210> SEQ ID NO 81
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 81
ggcccaagga cgtgtgttgg tccagccccc cggttccccg agacccacgc                50

<210> SEQ ID NO 82
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 82
acctctggag cgggttagtg gtggtggtag tgggttggga cgagcgcgtc ttccgcagtc    60
cca                                                                 63

<210> SEQ ID NO 83
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 83

```
cccttggaag gcgtggaatt aggagagaaa tcccttagtg ggcacacgag tgagtgcccc    60
ttgga                                                                65

<210> SEQ ID NO 84
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 84
ccggccgcct cccaggctgg aatccctcga cacttggtcc ttcccgcccc              50

<210> SEQ ID NO 85
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 85
tgcgtgggtc gcctcgcgtc tctctctccc accccacctc tgagatttct tgccagcacc    60

<210> SEQ ID NO 86
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 86
gacttcgcgt cgcccttcca cgagcgccac ttccactacg aggagcacct ggagcgcat     59

<210> SEQ ID NO 87
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 87
gaggctgcga gcctgggctc ccagggagtt cgactggcag aggcgggtgc ag            52

<210> SEQ ID NO 88
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 88
ccattctcct gcctcagcct cccaagtagc tgggactaca ggcgcctgcc accactcccg    60
gc                                                                   62

<210> SEQ ID NO 89
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 89
caggggacgt tgaaattatt tttgtaacgg gagtcgggag aggacggggc gtccccgac     60 gtgcg                                                                65
```

<210> SEQ ID NO 90
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 90
accctggaac gacgccaaac gcgacccta ccagaggact cgcgcatgcg cagc     54

<210> SEQ ID NO 91
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 91
gttcccaaag ggtttctgca gtttcacgga gcttttcaca ttccactcgg          50

<210> SEQ ID NO 92
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 92
gaaagacacc gcggaactcc cgcgagcgga gacccgccaa ggcccctcca g        51

<210> SEQ ID NO 93
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 93
ccctctccgc cccaaacagc tccccactcc cccagcctgc ccccaccctc          50

<210> SEQ ID NO 94
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 94
attggggcta cactcaccac aagagcagca aacaaagcac tgggtgtggt agaggctgtc     60
caggg                                                                65

<210> SEQ ID NO 95
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 95
cccagcgggg cccttagcag agcctctcca atcctcggcg cctcccctac acagggttcg     60

<210> SEQ ID NO 96
<211> LENGTH: 56
<212> TYPE: DNA

```
<213> ORGANISM: Artificial Sequence
<220> FEATURE:
<223> OTHER INFORMATION: probe/primer/pcr

<400> SEQUENCE: 96
gcgcccaagg ccctgcttct tccccttcc tcttcccctt gcccagccgc gacttc         56

<210> SEQ ID NO 97
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 97
cccagccgag caggggaag catccccagc tcccgcaccc aagtccctgg                50

<210> SEQ ID NO 98
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 98
gccgccacct gttgaggaaa gcgagcgcac ctcctgcagc tcaggctccg gg            52

<210> SEQ ID NO 99
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 99
cgggagcgga ttgggtctgg gagttcccag aggcggctat aagaaccggg aactgggcgc    60
g                                                                    61

<210> SEQ ID NO 100
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 100
ggcggggaag cgtatgtgcg tgatggggag tccgggcaag ccaggaaggc acc           53

<210> SEQ ID NO 101
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 101
ggagcccgca gtgcgtgcga ggggctctcg gcaggtccag acgcctcgcc               50

<210> SEQ ID NO 102
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 102
```
cgcatccggc tccgaaagct gcgcgcagcc atcatcaggg cccttctggt gtt        53

<210> SEQ ID NO 103
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 103
gccgctgcca gtcgactcaa ccaccggagt ggcccctgca gttggatagc aacgagaatc    60
ctcc                                                                 64

<210> SEQ ID NO 104
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 104
ggcaggaaag ggcccgaagg cagcgaaggc gaacgcggcg caccaacctg              50

<210> SEQ ID NO 105
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 105
acagggtctt cccacccaca gggcacccag gcgcagcgga gccaggaggg              50

<210> SEQ ID NO 106
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 106
accagccgca caactttga aggctcgccg gcccatgtgg ggtctttctg gcggc          55

<210> SEQ ID NO 107
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 107
cagccgggca gataacaaaa cacacccaa agtgggcctc gcatcggccc tcgcattcct     60
gt                                                                   62

<210> SEQ ID NO 108
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 108
ggcctcgacg ccgaggggtg tccctctcct ctcctggtca gggaacgcag caactga       57

<210> SEQ ID NO 109
<211> LENGTH: 56
<212> TYPE: DNA
<213> ORGANISM: Artificial Sequence
<220> FEATURE:
<223> OTHER INFORMATION: probe/primer/pcr

<400> SEQUENCE: 109
gggcggcagt cagagctgga gctccgggga atcagacggg cagccaaagg agcaga        56

<210> SEQ ID NO 110
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 110
cggaagtgcc ccggtcctgg aggggtgga agttggggag cccaggcagg a              51

<210> SEQ ID NO 111
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 111
ccgagaggga agaaaaaaat accctctttg ggccaggcac ggtggctcac ccctgtaatc    60
ccagc                                                                 65

<210> SEQ ID NO 112
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 112
tcccagcact ttgggaggct gaggcgagcg gatcacgaga tcagaagatc gagaccatcc    60
tggc                                                                  64

<210> SEQ ID NO 113
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 113
ccccgggacc ggataacgcc ctaaatcagc gcagctgagg cgaggccgtg gcc           53

<210> SEQ ID NO 114
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 114
ctcgcgaccc cggctccggg cctctgccga cctcaggggc aggaaagagt c             51

<210> SEQ ID NO 115
<211> LENGTH: 51

```
<212> TYPE: DNA
<213> ORGANISM: Artificial Sequence
<220> FEATURE:
<223> OTHER INFORMATION: probe/primer/pcr

<400> SEQUENCE: 115
cccgaggctc gcccgactcc tggctgccct ggactcccct ccctcctccc t        51

<210> SEQ ID NO 116
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 116
ctccagctgc actgccaccc agcctgcctg gtgctggtgc tcaacacgca gc        52

<210> SEQ ID NO 117
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 117
ccggcctttc cgccagaggg cggcacagaa ctacaactcc cagcaagctc ccaaggcg  58

<210> SEQ ID NO 118
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 118
gggaaggagc ctcagctccg ctccaggtcc tccaccaggt aggactggga ctcccttagg  60
gcctg                                                             65

<210> SEQ ID NO 119
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 119
gggagtgtcc tcctccggga cagccggact cccgccgact tctgggcggc        50

<210> SEQ ID NO 120
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 120
ggggagcgtg cggggtcgcc accatcggga cccccagagg agagaggact tg        52

<210> SEQ ID NO 121
<211> LENGTH: 52
<212> TYPE: DNA
<213> ORGANISM: Artificial Sequence
<220> FEATURE:
<223> OTHER INFORMATION: probe/primer/pcr
```

<400> SEQUENCE: 121
gacagatgca gtgcgtgcgc cggagcccaa gcgcacaaac ggaaagagcg gg    52

<210> SEQ ID NO 122
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 122
tcctttgcgt ccggccctct ttcccctgac cataaaagca gccgctggct gctgggcc    58

<210> SEQ ID NO 123
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 123
tgcggcttct ctcaccctgc caggccttcc cagcttccct gaggttgcct gctacacccg    60

<210> SEQ ID NO 124
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 124
gccccagccc tgcgcccctt cctctcccgt cgtcaccgct tcccttcttc ca    52

<210> SEQ ID NO 125
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 125
cccgcacccc tattgtccag ccagctggag ctccggccag atcccgggct g    51

<210> SEQ ID NO 126
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 126
gcagagttcg tgcagggagt tcgcacatag gagagcaccg gtccgggagt gccaggctcg    60

<210> SEQ ID NO 127
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 127
cggccggtgt gtgtccccgc aggagagtgt gctgggcaga cgatgctgga c    51

<210> SEQ ID NO 128
<211> LENGTH: 64

<212> TYPE: DNA
<213> ORGANISM: Artificial Sequence
<220> FEATURE:
<223> OTHER INFORMATION: probe/primer/pcr

<400> SEQUENCE: 128 ttttgggac aaccatggag gggtcctccg tctcggcctc ttcgcatatc cccctccgtg    60
atcc    64

<210> SEQ ID NO 129
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 129
cggcgggtca gatctcgctc cctttcggac aacttacctc ggagaggagt caagggaga    60 gggga    65

<210> SEQ ID NO 130
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 130
cccggacgag ctctcctatc ccgaagttgt ggacagtcga gacgctcagg gcagccgggc    60

<210> SEQ ID NO 131
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 131
cggccggtgg aggggggaag ggaggaatgg tgtcaggggc ggatatctga gccctgag    58

<210> SEQ ID NO 132
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 132
caccaaagcc accacccaag ccagcaccaa ggccaccacc atatcctccc ccaaagccac    60
tacca    65

<210> SEQ ID NO 133
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 133
ccgccaggcc cgctgggtgg aatgtggtca tgtttcagac tgccgatggc ttcca    55

<210> SEQ ID NO 134
<211> LENGTH: 56
<212> TYPE: DNA

```
<213> ORGANISM: Artificial Sequence
<220> FEATURE:
<223> OTHER INFORMATION: probe/primer/pcr

<400> SEQUENCE: 134
cctgtccgga tccctccccg ccttgctcag atctctggtt cgcggagctc cgaggc        56

<210> SEQ ID NO 135
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 135
gcgcaggggc ccagttatct gagaaacccc acagcctgtc ccccgtccag gaagtctcag    60
cgag                                                                 64

<210> SEQ ID NO 136
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 136
tcctgcccca gtaagcgttg gaccgggaga cgcagtgctc agcatcggtc agcaggg       57

<210> SEQ ID NO 137
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 137
gcgccgagga gtcgggacag ccccggagct tcatgcggct caacgacctg              50

<210> SEQ ID NO 138
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 138
ggccccagcg gagactcggc agggctcagg tttcctggac cggatgactg acctgagc     58

<210> SEQ ID NO 139
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 139
cgccggctgc gaagttgagc gaaaagtttg aggccggagg gagcgaggcc gg           52

<210> SEQ ID NO 140
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 140
```

```
ggagccgctt ggcctcctcc acgaagggcc gcttctcgtc ctcgtccagc agc            53
```

<210> SEQ ID NO 141
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 141

```
aaatgtggag ccaaacaata acagggctgc cgggcctctc agattgcgac ggtcctcctc    60
ggcc                                                                  64
```

<210> SEQ ID NO 142
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 142

```
cctctcagat tgcgacggtc ctcctcggcc tggcgggcaa accctggtt tagcacttct     60 ca                                                                    62
```

<210> SEQ ID NO 143
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 143

```
tctccccacg cttcccgat gaataaaaat gcggactctg aactgatgcc accgcctccc     60
ga                                                                    62
```

<210> SEQ ID NO 144
<211> LENGTH: 56
<212> TYPE: DNA
<213> ORGANISM: Artificial Sequence
<220> FEATURE:
<223> OTHER INFORMATION: probe/primer/pcr

<400> SEQUENCE: 144

```
gcccaatcgg aaggtggacc gaaatcccgc gacagcaaga ggcccgtagc gacccg        56
```

<210> SEQ ID NO 145
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 145

```
cgtgggggc tgtttcccgt ctgtccagcc gcgcccactt ctcaggccca aag             53
```

<210> SEQ ID NO 146
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 146

```
gggcccctcg tgttgctgaa cgagggcggg ttcgcgatgt aaataagccc agaggtgggg      60
tc                                                                     62
```

<210> SEQ ID NO 147
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 147

```
cctgggtccc ctcggctctc ggaagaaaaa ccaacagcat ctccagctct cgcgcggaat      60
tgtc                                                                   64
```

<210> SEQ ID NO 148
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 148

```
cataagatgc cctcctgcgg gccctcacct tttgacactg cctcccaccg cactggggtc      60
aa                                                                     62
```

<210> SEQ ID NO 149
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 149

```
atcccgctgc accacgccat gagcatgtcc tgcgactcgt ctccgcctgg c               51
```

<210> SEQ ID NO 150
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 150

```
gcgcggtgaa gggcgtcagg tgcagctggc tggacatctc ggcgaagtcg                 50
```

<210> SEQ ID NO 151
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 151

```
catttctttc aattgtggac aagctgccaa gaggcttgag taggagagga gtgccgccga      60
ggcgg                                                                  65
```

<210> SEQ ID NO 152
<211> LENGTH: 70
<212> TYPE: DNA
<213> ORGANISM: Artificial Sequence
<220> FEATURE:
<223> OTHER INFORMATION: probe/primer/pcr

<400> SEQUENCE: 152

```
aagttcactg agggttgtaa gagtcagaat ggactccatg gaagttatgg ggtgtgaatc    60
aaacctcaca                                                          70

<210> SEQ ID NO 153
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 153
cagcactttg ggaggccgag gtgggcggat tgcctgaggt caggagtttg agaccagcct    60
gg                                                                  62

<210> SEQ ID NO 154
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 154
gggcaacaca cacagcagcg acagccggga ggtaagccgc gtcccagcgg              50

<210> SEQ ID NO 155
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 155
ctgaggggag gagaaactgg gctgcggggg tccgggaggg tggattccga gaaactatgt    60
gccc                                                                64

<210> SEQ ID NO 156
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 156
gtgtcccagc gcgttgacgc agcctgtgat ccctcgcgag gcgaggagaa ggtc          54

<210> SEQ ID NO 157
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 157
aaccccgacc tcaggtgatc tgcccaaaag tgctgggatt acaggcgtca gccaccgcgc    60
c                                                                   61

<210> SEQ ID NO 158
<211> LENGTH: 62
<212> TYPE: DNA
<213> ORGANISM: Artificial Sequence
<220> FEATURE:
<223> OTHER INFORMATION: probe/primer/pcr
```

<400> SEQUENCE: 158
aggacgaagt tgaccctgac cgggccgtct cccagttctg aggcccgggt cccactggaa    60
ct                                                                  62

<210> SEQ ID NO 159
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 159
ggagacgcgt tgccttcggc cgggaccact gcacctgccc gcgtgggtaa t             51

<210> SEQ ID NO 160
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 160
cacaaaggcc aaggagggag tgcgcaggtc acgtgcgccg gtggtcagcg               50

<210> SEQ ID NO 161
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 161
ctgacctggc gctgctgccc ctggtgcctg acggaggatg agaaggccgc c             51

<210> SEQ ID NO 162
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 162
aaaagtggct cggaacccca atcccggtt agattgcagg caccgccgga cgctggctcc    60
c                                                                   61

<210> SEQ ID NO 163
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 163
gttctgttgg gggcgaggcc cgcgcaagcc ccgcctcttc cccggcacca g             51

<210> SEQ ID NO 164
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 164
gcgtcgacac tgcgcaagcc cagtcgcgcc tctccagagc gggaagagcg               50

<210> SEQ ID NO 165
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 165
tgtctgagta ttgatcgaac ccaggagttc gagatcagct tgagcaagat agcgagaacc    60
cccgc    65

<210> SEQ ID NO 166
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 166
gaaagactgc agagggatcg aggcggccca ctgccagcac ggccagcgtg g    51

<210> SEQ ID NO 167
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 167
ttagagtccc ctgggtgtgt gccccgcaga gggagctctg gcctcagtgc ccagtgtgc    59

<210> SEQ ID NO 168
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 168
ttagagtccc ctgggtgtgt gccccgcaga gggagctctg gcctcagtgc ccagtgtgc    59

<210> SEQ ID NO 169
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 169
ggggacgagc aggaaaaggc cggggtgggg gtggaattcc tcggcgggca g    51

<210> SEQ ID NO 170
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 170
gggagcctga ggcaggagaa tcgcttgaat ccgggaggcg gaggttgcag taagccgaga    60
tcgc    64

<210> SEQ ID NO 171

```
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 171
ctttcggagg cctcattggc tgaaggtcgc cgtcgcccaa cgcaggccat tctgggt      57

<210> SEQ ID NO 172
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 172
cctcctgggg tcaagtgatc atcctggctc aaccacccaa gtagccggga ctacgggtgg   60
ccgc                                                                64

<210> SEQ ID NO 173
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 173
ccaatgcccc aacgcaggcc accccggct cctctgtgga ctcacgaaga caaggtc       57

<210> SEQ ID NO 174
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 174
ctctgagagc cacagtcagg tctgtcctca ggggtcgagg cggctgcgct ggggcct      57

<210> SEQ ID NO 175
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 175
ggacagcccg ctcgggagtc gggcctggaa gcaggcggac agcgtcacct               50

<210> SEQ ID NO 176
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 176
gccaggatgg tctcgatctc ctgaccttgt gatctgcccg cctcggcctc ccaaagtgtt   60
ggg                                                                 63

<210> SEQ ID NO 177
<211> LENGTH: 65
<212> TYPE: DNA
<213> ORGANISM: Artificial Sequence
```

<220> FEATURE:
<223> OTHER INFORMATION: probe/primer/pcr

<400> SEQUENCE: 177
tgcccagggg agccctccat ttgtagaatg aatgagagtc caggttatga acagtgcctg    60
gagtg    65

<210> SEQ ID NO 178
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 178
gaccggtttt atcccgctga ggccctggga gatgggtctg gcgaggctcg taggccgc    58

<210> SEQ ID NO 179
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 179
gcggaacctc aaattgcggc agcggaacct aaagtttcag ggtgagatgc gttgactcgc    60
ggtgg    65

<210> SEQ ID NO 180
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 180
gctcagtccc tccggtgtgc aggaccccgg aagtcctccc cgcacagctc tcgct    55

<210> SEQ ID NO 181
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 181
cgggcaggcg ggaccgggag gtcaataact gcagcgtccg agctgagccc a    51

<210> SEQ ID NO 182
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 182
cgcggtgggc cgacttcccc tcctcttccc tctctccttc ctttagcccg ctggcgcc    58

<210> SEQ ID NO 183
<211> LENGTH: 54
<212> TYPE: DNA
<213> ORGANISM: Artificial Sequence
<220> FEATURE:
<223> OTHER INFORMATION: probe/primer/pcr

```
<400> SEQUENCE: 183
tccccggcat gcgccatatg gtcttcccgg tccagccaag agcctggaac cacg        54

<210> SEQ ID NO 184
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 184
ctccgcgctc agccaattag acgcggctgt tccgtgggcg ccaccgcctc             50

<210> SEQ ID NO 185
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 185
gcgagagggt cgtccgctga aagctgcgc cggagacgcg ggaagctgct g            51

<210> SEQ ID NO 186
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 186
gacccgcctg cgtcgccacc ctctcgccgc tccctgccgc caccttcctc             50

<210> SEQ ID NO 187
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 187
gaggggtccg ggacgaagcc acccgcgcgg taggggcga cttagcggtt tca          53

<210> SEQ ID NO 188
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 188
ccccgaacaa aaaattcaaa tgggaaagag aggcagatgg cagagaacag gggaggggct  60
gggca                                                             65

<210> SEQ ID NO 189
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 189
gcggcgagga gggtcacagc cggaaagagg cagcggtggc gcctgcagac             50
```

```
<210> SEQ ID NO 190
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 190
ggcggtctcc ggttcgccaa tgtggctggg tccgtaggct tgggcagcct              50

<210> SEQ ID NO 191
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 191
cctccccttt gcgtgcggag ctgggctttg cgtgcgccgc ttctggaaag tcg          53

<210> SEQ ID NO 192
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 192
agcctactca ctcccccaac tcccgggcgg tgactcatca acgagcacca gcggccaga    59

<210> SEQ ID NO 193
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 193
caggaggtga ggaggtttcg acatggcggt gcagccgaag gagacgctgc agttggagag   60
cg                                                                 62

<210> SEQ ID NO 194
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 194
agatttcccg ccagcaggag ccgcgcggta gatgcggtgc ttttaggagc tccgtccgac   60
a                                                                  61

<210> SEQ ID NO 195
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 195
cgggcgtggt ggtgggcacc tgtaatccca gctactcaga aggttgaggc aggagaatcg   60
cttga                                                              65

<210> SEQ ID NO 196
```

```
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 196
tcccaaatcc gagtctgcgg agcctgggag ggctcccagc ttcctatcca aaccgcgcc      59

<210> SEQ ID NO 197
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 197
ccctggtcga gcccctttc ctcccgggtc cacagcgagt ccctgagga aggaggg         57

<210> SEQ ID NO 198
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 198
cagggacccg cgagtccctg gacacgcact ggccaacgcc agaccccatc               50

<210> SEQ ID NO 199
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 199
caagcagccc tcggccagac caagcacact ccctcggagg cctggcaggg               50

<210> SEQ ID NO 200
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 200
gagaaggagc gacccccaaa acgaagcggc tggatctgac cttccaaggc ctgttggcga    60
cgc                                                                 63

<210> SEQ ID NO 201
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 201
ttcttccccg cagggtcagc gctggggctc cggccgtaga gccacgtgac c             51

<210> SEQ ID NO 202
<211> LENGTH: 64
<212> TYPE: DNA
<213> ORGANISM: Artificial Sequence
<220> FEATURE:
<223> OTHER INFORMATION: probe/primer/pcr
```

<400> SEQUENCE: 202
attcatttct gttatggaac tgtcgcggca ctacaaagtc tctatgtagt tataaataaa    60
cgtt                                                                64

<210> SEQ ID NO 203
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 203
accgagtgcg ctgctgtgcg agtgggatcc gccgcgtcct tgctctgccc              50

<210> SEQ ID NO 204
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 204
gtgtggtgag tgtgggtgtg tgcgcgtctc ctcgcgtccc tcgctgaggt gcct          54

<210> SEQ ID NO 205
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 205
gcctgggctg ccagacgtcg ccatcattgt tccatgcaga tcatgcccat cctgtgcaga    60
ag                                                                  62

<210> SEQ ID NO 206
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 206
gcgggtccga ggcgcaaggc gagctggaga ccccgaaaac cagggccact c             51

<210> SEQ ID NO 207
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 207
tctccatggt ggccattgcc tcctctctgc tccaaaggcg accccgagtc agggatgaga    60
ggc                                                                 63

<210> SEQ ID NO 208
<211> LENGTH: 50
<212> TYPE: DNA
<213> ORGANISM: Artificial Sequence
<220> FEATURE:
<223> OTHER INFORMATION: probe/primer/pcr

```
<400> SEQUENCE: 208
cgcgggactc cgcgggatct cgctgttcct cgctctgctc ctggggagcc                50

<210> SEQ ID NO 209
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 209
cgcccctttt ttggagggcc gatgaggtaa tgcggctctg ccattggtct gaggggc        58

<210> SEQ ID NO 210
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 210
gttctgttgc caatgccatt cagacccag tccgggattc cgcgctcggg gtgcg           55

<210> SEQ ID NO 211
<211> LENGTH: 56
<212> TYPE: DNA
<213> ORGANISM: Artificial Sequence
<220> FEATURE:
<223> OTHER INFORMATION: probe/primer/pcr

<400> SEQUENCE: 211
tttccgcgag cgcgttccat cctctaccga gcgcgcgcga agactacgga ggtcga         56

<210> SEQ ID NO 212
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 212
acccgggttc agcgggtccc gatccgaggg cgtgcgagct gagcctcctg                50

<210> SEQ ID NO 213
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 213
gagagtggac gcgggaaagc cggtggctcc cgccgtgggc cctactgtgc                50

<210> SEQ ID NO 214
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 214
ggctacagcc gccatttcca cgctccacca atcaaatcca ttctcgagga agacgcaccg    60
cccc                                                                  64
```

```
<210> SEQ ID NO 215
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 215
agcgcgcaca aagcctgcgg gaggatccat tgtagcggtc gctcctcccc gcttagcg      58

<210> SEQ ID NO 216
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 216
atcgggcgaa gctcgcggga aaccgctctg ggtgcgcagg acaaagacgc g             51

<210> SEQ ID NO 217
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 217
cgacggagcc gtgtggaggc caaaactcct cccggaagcc gctactggcc ccg           53

<210> SEQ ID NO 218
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 218
cgccccacta ctgcctgcag cgggcttcct tactccgcct gctggttcct actggaggag    60
aggcc                                                                65

<210> SEQ ID NO 219
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 219
gcactcgtag cgcgctgggc gagccggacc ggaagttgaa gaagtgaagc gccg          54

<210> SEQ ID NO 220
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 220
tgaagggagg gcttggtgtg gggacttgca ctgggcagag gggcagcttc cctgagagca    60
gcta                                                                 64

<210> SEQ ID NO 221
<211> LENGTH: 50
<212> TYPE: DNA
```

```
<213> ORGANISM: Artificial Sequence
<220> FEATURE:
<223> OTHER INFORMATION: probe/primer/pcr

<400> SEQUENCE: 221
cgggagcgcc cggttgggga acgcgcggct ggcggcgtgg ggaccacccg         50

<210> SEQ ID NO 222
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 222
cagcaccgga gagggcgcac tgcaaaggcg ggcagcagac cgtggagagc         50

<210> SEQ ID NO 223
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 223
ggcgcagagg cgtcacgcac tccatggtaa cgacgctcgg cccgaagatg gc      52

<210> SEQ ID NO 224
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 224
gccgcgtctg cgaaccggtg acctggtttc ccctccagcc ctcacggctg         50

<210> SEQ ID NO 225
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 225
cgagctgttt gaggactggg atgccgagaa cgcgagcgat ccgagcaggg tttgtctggg    60
c                                                             61

<210> SEQ ID NO 226
<211> LENGTH: 56
<212> TYPE: DNA
<213> ORGANISM: Artificial Sequence
<220> FEATURE:
<223> OTHER INFORMATION: probe/primer/pcr

<400> SEQUENCE: 226
gcagcgctga gttgaagttg agtgagtcac tcgcgcgcac ggagcgacga caccccc      56

<210> SEQ ID NO 227
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 227
```

```
cgcgcgctcg ccgtccgcca cataccgctc gtagtattcg tgctcagcct cgtagtggc    59
```

<210> SEQ ID NO 228
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 228

```
cggaagggt gaggccggaa gccgaagtgc cgcagggagt tagcggcgtc tcg    53
```

<210> SEQ ID NO 229
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 229

```
ggggcgtcg ggcttgggac aggggaggat accagggcca ccttccccaa ccc    53
```

<210> SEQ ID NO 230
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 230

```
cgggctggag ggttatctgg gaagtcagcc ccggcctcgg tcctctccac gttgctgc    58
```

<210> SEQ ID NO 231
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 231

```
ggaacgaggt gtcctgggaa cactcccggg tctgtaactt cggacaaatc acgctcgctt    60
tcccg                                                                65
```

<210> SEQ ID NO 232
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 232

```
aaacgagaga gtagccagac tctccgcgca tggagccgac ggcacccacc agcacaccg    59
```

<210> SEQ ID NO 233
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 233

```
tactcacgcg cgcactgcag gcctttgcgc acgacgcccc agatgaagtc    50
```

<210> SEQ ID NO 234

```
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 234
tgaccggaca gagcagagcg gggactgcaa ttcccagaag accccacggt aggggcgg      58

<210> SEQ ID NO 235
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 235
agacaatccc ggaggggaa aggcgagcag ctggcagaga gcccagtgcc ggcc            54

<210> SEQ ID NO 236
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 236
ggccgaagag tcgggagccg gagccgggag agcgaaagga gagggaccct ggc            53

<210> SEQ ID NO 237
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 237
ccaggctccg ctcgtagaag tgcgcaggcg tcaccgcgca tccaggagcc ac             52

<210> SEQ ID NO 238
<211> LENGTH: 56
<212> TYPE: DNA
<213> ORGANISM: Artificial Sequence
<220> FEATURE:
<223> OTHER INFORMATION: probe/primer/pcr

<400> SEQUENCE: 238
ctctgatgac gctccaaggg aagaggaagt ggggatcggc gagcgggtgg gtgcgc         56

<210> SEQ ID NO 239
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 239
tgaagggtaa tccgaggagg gctggtcact actttctggg tctggttttg cgttgagaat    60
gcccc                                                                 65

<210> SEQ ID NO 240
<211> LENGTH: 57
<212> TYPE: DNA
<213> ORGANISM: Artificial Sequence
<220> FEATURE:
<223> OTHER INFORMATION: probe/primer/pcr
```

<400> SEQUENCE: 240
cggtcctgca tgcaatgcaa gcctgagctc tcccgccata aggctgcagc ggtgtgg                57

<210> SEQ ID NO 241
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 241
cctggaggag gaggagtcag gccgggtagg agggctaagg aggttcccgg gaaggcaggg            60
ccc                                                                         63

<210> SEQ ID NO 242
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 242
gctgctgaca tgacttcttt gccactcggt gtcaaagtgg aggactccgc cttcggcaag           60
ccggc                                                                        65

<210> SEQ ID NO 243
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 243
gagcggcgca gggttggaga gggaagcgct cgtgcccacc ttgctcgcag                       50

<210> SEQ ID NO 244
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 244
ccgatgaccg cggggaggag gatggagatg ctctgtgccg gcagggtccc                       50

<210> SEQ ID NO 245
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 245
gccgccctac agacgttcgc acacctgggt gccagcgccc cagaggtccc                       50

<210> SEQ ID NO 246
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 246

-continued gggccgcaat caggtggagt cgagaggccg gaggaggggc aggaggaagg ggtg         54

<210> SEQ ID NO 247
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 247
cggcgggacc atgaagaagt tctctcggat gcccaagtcg agggcggca gcgg          54

<210> SEQ ID NO 248
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 248
gtgggcgcac gtgaccgaca tgtggctgta ttggtgcagc ccgccagggt gt           52

<210> SEQ ID NO 249
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 249
gaaagagccg gaaacacctg gtctctcaag caggtacagc ccgcttctcc ccagcacccc   60
ggtg                                                                64

<210> SEQ ID NO 250
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 250
gcagccgcag ctgaggtcac cccgctgagg tggtgggag gggaatggtt              50

<210> SEQ ID NO 251
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 251
gggcggccag cggtgactcc agatgagccg gccgtccgcg ttcgcgccgc              50

<210> SEQ ID NO 252
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 252
gggcaccacg aatgccggac gtgaagggga ggacggaggc gcgtagacgc              50

<210> SEQ ID NO 253
<211> LENGTH: 51

```
<212> TYPE: DNA
<213> ORGANISM: Artificial Sequence
<220> FEATURE:
<223> OTHER INFORMATION: probe/primer/pcr

<400> SEQUENCE: 253
gaggccgcca tcgcccctcc cccaacccgg agtgtgcccg taattaccgc c          51

<210> SEQ ID NO 254
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 254
cgcggggaac gatgcaacct gttggtgacg cttggcaact gcaggggcgc            50

<210> SEQ ID NO 255
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 255
cttgagacct caagccgcgc aggcgcccag ggcaggcagg tagcggccac            50

<210> SEQ ID NO 256
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 256
cacaccgtcc tcgcccggag cgcagaggcc gacgccctac gagtggatgc            50

<210> SEQ ID NO 257
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 257
cccttgcaca cgagctgacg gcgtgaacgg gggtgtcggg gttggtgcaa            50

<210> SEQ ID NO 258
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 258
gcaaagtgat acctggccgt cccaccctct ggtcccagaa ggagctctcg ctggagccag   60
gca                                                                63

<210> SEQ ID NO 259
<211> LENGTH: 56
<212> TYPE: DNA
<213> ORGANISM: Artificial Sequence
<220> FEATURE:
<223> OTHER INFORMATION: probe/primer/pcr
```

<400> SEQUENCE: 259
ggttggggga ctgcccgggg cttagatggc tccgagcccg tttgagcgtg gtctcg    56

<210> SEQ ID NO 260
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 260
cgttgaaagc gaagaaggag cggcagtcca gcagcaggca ttgcgccgct cgctc    55

<210> SEQ ID NO 261
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 261
gagtcctcaa caacgacagc ggggactgcg ggaccagggt aaagcggcga cggcg    55

<210> SEQ ID NO 262
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 262
gctcctgaga aagccctgcc cgctccgctc acggccgtgc cctggccaac tt    52

<210> SEQ ID NO 263
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 263
gatgctgctg ccggagctga ggtcttgcct ggagatccga acgagacacc acgtcaaccg    60
g    61

<210> SEQ ID NO 264
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 264
tggtggcagg agagcgatga gacgggaaag tgtgggcaa agcttacagt cattggtcca    60
ga    62

<210> SEQ ID NO 265
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 265
ccactcgcag tctgcgtgtg ggggaaacga gtgcccggcg tatgaaacgc ctaacttcgc    60

-continued gaaa 64

<210> SEQ ID NO 266
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 266
caggcggctc ccgcagtcta agggacctgg cgcgagtccg ggaagcggag g    51

<210> SEQ ID NO 267
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 267
ctgcacgcgg tgcgaagggg ccagcaggga aggagcagag gatgggggt    50

<210> SEQ ID NO 268
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 268
cggggccaca ggaccctggg gcttgagtca cacaagaatg tctctgggag acccgagaga    60
ctca    64

<210> SEQ ID NO 269
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 269
cttagaggag gaggagcagc ggcagcggca gcaggaggcg acagctgcca gccg    54

<210> SEQ ID NO 270
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 270
ctcataccag ataggcgcga acgcctctgg cagcggcgtc caggggtcc ggc    53

<210> SEQ ID NO 271
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 271
gggtgctggc acatccgagg cgttctcccg actctggacc gacgtgatgg gtatcctgg    59

<210> SEQ ID NO 272

```
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 272
catgataagc cagggacctc gcggcgcagg cggagggagg gagagcgtcg c       51

<210> SEQ ID NO 273
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 273 cccccccactc aacagcgtgt ctccgagccc gctgatgcta ctgcacccgc cg      52

<210> SEQ ID NO 274
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 274
tcccacctgc tgcccgagga agacttccgg gagaaacgct gtctccgagc ccccg    55

<210> SEQ ID NO 275
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 275
ccaggtgaag ccgaagggga agcggatggg gttgctgaac gcggagtcgg cg      52

<210> SEQ ID NO 276
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 276
cagtggccct gcgcgacgtt cggcgctacc agaactccga gctgctgatc agcaagc  57

<210> SEQ ID NO 277
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 277
aaggattacc tcgccctgaa cgaggacctg cgctcctgga ccgcagcgga cactgcgg 58

<210> SEQ ID NO 278
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 278
```

```
gcaggctcgt ggcggtcggt cagcggggcg ttctcccacc tgtagcgact caggttactg    60
aaaa                                                                 64

<210> SEQ ID NO 279
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 279
gagggaagtg ccctcctgca gcacgcgagg ttccgggacc ggctggcctg               50

<210> SEQ ID NO 280
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 280
gaagcgcgac ctcgggcggt tggaggggct accgggtctt accagtccgt ggcg          54

<210> SEQ ID NO 281
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 281
cccaacccga gcaagacctg cgctgaaacg gattggctgc cctccgcccg               50

<210> SEQ ID NO 282
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 282
agccgctctc ccgattgccc gccgacatga gctgcaacgg aggctcccac c             51

<210> SEQ ID NO 283
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 283
accacacggc caagggcacc tgaccctgtc aaaaccccaa atccagctgg gcgcg          55

<210> SEQ ID NO 284
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 284
ccgaggcagc cggatcacga agtcaggagt tcgagaccag cctgaccaac atggtgaaac    60
cccgt                                                                65
```

<210> SEQ ID NO 285
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 285
ccggcgtctc cgcgtggggc gcaccgtccg acccccccct cccggtgtgc          50

<210> SEQ ID NO 286
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 286
ggcgcagatg gcgctcgctg cgagatggat gctccagggc gggtaatcac tcctg    55

<210> SEQ ID NO 287
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 287
ccaggcctcc tggaaacggt gccggtgctg cagagcccgc gaggtgtctg          50

<210> SEQ ID NO 288
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 288
ggcgagaggt gagaagggaa gagggctccc ggctctctcg gggcgggaat cagtgggc  58

<210> SEQ ID NO 289
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 289
gcctgcctcg cctctgcccg agctgatgag cgagtcgacc aaaaaagagt tcgcggcg  58

<210> SEQ ID NO 290
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 290
cattgcggga ccctatttat cccgacacct ccctgacgt gggctcggaa cgctcccttg   60
gcag                                                              64

<210> SEQ ID NO 291
<211> LENGTH: 50
<212> TYPE: DNA
<213> ORGANISM: Artificial Sequence

```
<220> FEATURE:
<223> OTHER INFORMATION: probe/primer/pcr

<400> SEQUENCE: 291
cgaaggccgg agccacagcg ctcggtgtag atgccgcacg gctggccctc          50

<210> SEQ ID NO 292
<211> LENGTH: 56
<212> TYPE: DNA
<213> ORGANISM: Artificial Sequence
<220> FEATURE:
<223> OTHER INFORMATION: probe/primer/pcr

<400> SEQUENCE: 292
gggctggatg agtccggaag tggagattgg ctgcttagtg acgcgcggcg tcccgg    56

<210> SEQ ID NO 293
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 293
cgccagtgcg attctccctc ccggttccag tcgccgcgga cgatgcttcc tc        52

<210> SEQ ID NO 294
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 294
cgtccgagaa agcgcctggc gggaggaggt gcgcggcttt ctgctccagg          50

<210> SEQ ID NO 295
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 295
tccggctgcg ccacgctatc gagtcttccc tccctccttc tctgccccct ccgctcc    57

<210> SEQ ID NO 296
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 296
cagcctcagt ttccccattg gtaaagcatt gacggtggtt gcggacggct tctgcggaca  60
gagcc                                                             65

<210> SEQ ID NO 297
<211> LENGTH: 61
<212> TYPE: DNA
<213> ORGANISM: Artificial Sequence
<220> FEATURE:
<223> OTHER INFORMATION: probe/primer/pcr

<400> SEQUENCE: 297
```

```
cctgagacag gccgaaccca actcttcaca gggccgaatt ctttgcccgc agcccagcac    60
c                                                                   61

<210> SEQ ID NO 298
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 298 cagaggggggg tgccggggtc gcggactgcc accaggttga ggaaaggagg gg          52

<210> SEQ ID NO 299
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 299
cgacatcctg cggacctact cgggcgcctt cgtctgcctg gagattgtaa gtggggccgc    60

<210> SEQ ID NO 300
<211> LENGTH: 54
<212> TYPE: DNA
<213> ORGANISM: Artificial Sequence
<220> FEATURE:
<223> OTHER INFORMATION: probe/primer/pcr

<400> SEQUENCE: 300
accgcctcct ccccgctgtc tgggtcgcag gccttagcga cgggctgttc tccg          54

<210> SEQ ID NO 301
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 301
ctcgggactc cagggctgtc cctcccgcag gctgtccttc cacctccacc cca           53

<210> SEQ ID NO 302
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 302
cggccgctcc tcgtaggcca ggctggaggc aagctccttc tcctcaaagc tgcgctgc      58

<210> SEQ ID NO 303
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 303
catctcttcc cccgactccg acgactggtg cgtcttgccc ggacatgccc gg            52

<210> SEQ ID NO 304
<211> LENGTH: 61
```

```
<212> TYPE: DNA
<213> ORGANISM: Artificial Sequence
<220> FEATURE:
<223> OTHER INFORMATION: probe/primer/pcr

<400> SEQUENCE: 304
cccaagaccc taaagttcgt cgtcgtcatc gtcgcggtcc tgctgccagt gagtcccggc    60
c                                                                    61

<210> SEQ ID NO 305
<211> LENGTH: 52
<212> TYPE: DNA
<213> ORGANISM: Artificial Sequence
<220> FEATURE:
<223> OTHER INFORMATION: probe/primer/pcr

<400> SEQUENCE: 305
cccactcttc ccctgactcc gacggcgggt tcgtcctgcc agacatgcc cg             52

<210> SEQ ID NO 306
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 306
gtccccctct ctctctgccc cctcccggtg ccaggcgcgc ttttccccag g             51

<210> SEQ ID NO 307
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 307
cagcctgctg aggggaagag ggggtctccg ctcttcctca gtgcactctc tgactgaagc    60
ccggc                                                                65

<210> SEQ ID NO 308
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 308
actgactccg gaggctgcag ggctggagtg cgcggggctc ctacggccga g             51

<210> SEQ ID NO 309
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 309
ggccaggctc gggcaggggc cgtgctcagg tgcggcagac ggacgggccg               50

<210> SEQ ID NO 310
<211> LENGTH: 54
<212> TYPE: DNA
<213> ORGANISM: Artificial Sequence
<220> FEATURE:
```

<223> OTHER INFORMATION: probe/primer/pcr

<400> SEQUENCE: 310
ccgggcttct gggacgctca gccgtgcgct acccggtgca gctgctttct cacc                54

<210> SEQ ID NO 311
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 311
tttaggtaga cgtggaggcg actcagatcg cctcgcggtt cccgggatgg cgcggtcg          58

<210> SEQ ID NO 312
<211> LENGTH: 53
<212> TYPE: DNA
<213> ORGANISM: Artificial Sequence
<220> FEATURE:
<223> OTHER INFORMATION: probe/primer/pcr

<400> SEQUENCE: 312
tgaccaggac cgcaggcaag caccgcggcg acggttccag ccaggaaaat gag               53

<210> SEQ ID NO 313
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 313
gggccggacc cggcctctgg ctcgctcctg ctctttctca aacatggcgc g                 51

<210> SEQ ID NO 314
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 314
gccgcgctcc tcgcaccgcc ttctccgcag gtctttattc atcatctcat ctccctcttc        60
ccc                                                                      63

<210> SEQ ID NO 315
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 315
gagctgcgaa ctggtcggcg gcgcaaggcg cggactccgg tgagttgtgt                   50

<210> SEQ ID NO 316
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 316
gcccgcgttc ctctccctcc cgcctaccgc cactttcccg ccctgtgtgc                   50

<210> SEQ ID NO 317
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 317
acgcgtcgcg gagtcctcac tgccccgcct cgctctggca gagtggggag        50

<210> SEQ ID NO 318
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 318
gcgagcagcg gcctccagcg ctggtggctc cctttatagg agcgctggag acacggg        57

<210> SEQ ID NO 319
<211> LENGTH: 55
<212> TYPE: DNA
<213> ORGANISM: Artificial Sequence
<220> FEATURE:
<223> OTHER INFORMATION: probe/primer/pcr

<400> SEQUENCE: 319
ggggaaggcg gagggcgagg ggaagagtca ctgagctgcg gggcataggg ggtcc        55

<210> SEQ ID NO 320
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 320
ctctgctcgc gtgctgctct gaagttgttc cccgatgcgc cgtaggaagc tgggattctc        60
cca        63

<210> SEQ ID NO 321
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 321
agggaggtcg ttttcttcag ctccccaggt ggtctgtgct gggtgtgctg acggtccttt        60
tggga        65

<210> SEQ ID NO 322
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 322
gcccctggcc ctgactgctg gtgcgaggca gtgcacgact cagctggccg        50

<210> SEQ ID NO 323

```
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 323
ggccgggtaa cggagaggga gtcgccagga atgtggctct ggggactgcc tcgctcg      57

<210> SEQ ID NO 324
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 324
ggccgggact ttctggtaag gagaggaggt tacggggaac gacgcgctgc tttcatgccc   60

<210> SEQ ID NO 325
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 325
cagtctgggg accggggagg cggggagagg gaaggggaaa gcgcggacgc               50

<210> SEQ ID NO 326
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 326
gtctatcaaa agtcttttcg tttcccccctc cccctttccc caccgcccac caaaatgagc  60
cgcg                                                                 64

<210> SEQ ID NO 327
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 327
atgccgccat cgcggttcat gccgttctcg tggttcacac cgccctcagg g             51

<210> SEQ ID NO 328
<211> LENGTH: 51
<212> TYPE: DNA
<213> ORGANISM: Artificial Sequence
<220> FEATURE:
<223> OTHER INFORMATION: probe/primer/pcr

<400> SEQUENCE: 328
tcccggtctt cggatccgag ccggtcctcg ggaaagagcc tgccaccgcg t             51

<210> SEQ ID NO 329
<211> LENGTH: 64
<212> TYPE: DNA
<213> ORGANISM: Artificial Sequence
<220> FEATURE:
<223> OTHER INFORMATION: probe/primer/pcr
```

<400> SEQUENCE: 329
tgagaggctc cggtaaagcc gtccggcaat gttccacctg gaaagttcca gggcagggga    60
aggg                                                                64

<210> SEQ ID NO 330
<211> LENGTH: 63
<212> TYPE: DNA
<213> ORGANISM: Artificial Sequence
<220> FEATURE:
<223> OTHER INFORMATION: probe/primer/pcr

<400> SEQUENCE: 330
cccagggaga gggagaggag gcgggtggga gaggaggagg gtgtatctcc tttcgtcggc    60
ccg                                                                 63

<210> SEQ ID NO 331
<211> LENGTH: 50
<212> TYPE: DNA
<213> ORGANISM: Artificial Sequence
<220> FEATURE:
<223> OTHER INFORMATION: probe/primer/pcr

<400> SEQUENCE: 331
cccgtcttct ctcccgcagc tgcctcagtc ggctactctc agccaacccc               50

<210> SEQ ID NO 332
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 332 gaccccctt tggcccccta ccctgcagca agggtagcgt gacgtaatgc aacctcagca    60
tgtca                                                               65

<210> SEQ ID NO 333
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 333
ccccgaagcc cttgctttgt tctgtgagcg cctcgtgtca gccaggcgca gtgagctcac    60

<210> SEQ ID NO 334
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 334
cgcgcggcct tccccctgcg aggatcgcca ttggcccggg ttggctttgg aaagcgg       57

<210> SEQ ID NO 335
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 335
ccacccagtt caacgttcca cgaaccccca gaaccagccc tcatcaacag gcagcaagaa    60
gggcc    65

<210> SEQ ID NO 336
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 336
aagcagctgt gtaatccgct ggatgcggac cagggcgctc cccattcccg tcgggag    57

<210> SEQ ID NO 337
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 337
ccacgcaccc cctctcagtg gcgtcggaac tgcaaagcac ctgtgagctt gcggaagtca    60
gt    62

<210> SEQ ID NO 338
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 338
ccacgcaccc cctctcagtg gcgtcggaac tgcaaagcac ctgtgagctt gcggaagtca    60
gt    62

<210> SEQ ID NO 339
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 339
ccctccaccg gaagtgaaac cgaaacggag ctgagcgcct gactgaggcc gaaccccc    58

<210> SEQ ID NO 340
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 340
ttgtcccttt ttcgtttgct catccttttt ggcgctaact cttaggcagc cagcccagca    60
gcccg    65

<210> SEQ ID NO 341
<211> LENGTH: 59
<212> TYPE: DNA
<213> ORGANISM: Artificial Sequence
<220> FEATURE:
<223> OTHER INFORMATION: probe/primer/pcr

<400> SEQUENCE: 341
ttctcaggcc tatgccggag cctcgagggc tggagagcgg aagacaggc agtgctcgg    59

<210> SEQ ID NO 342
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 342
cagcgtttcc tgtggcctct gggacctctt ggccagggac aaggacccgt gacttccttg    60
cttgc    65

<210> SEQ ID NO 343
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 343
aggcaggccc gcaagccgtg tgagccgtcg cagccgtggc atcgttgagg agtgctgttt    60

<210> SEQ ID NO 344
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 344
gactctgggt atgttctcga aagttgttac aaccccaacc cagggttgac ctcaaacaca    60
ggagg    65

<210> SEQ ID NO 345
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 345
ctctggctct cctgctccat cgcgctcctc cgcgcccttg ccacctccaa cgcccgt    57

<210> SEQ ID NO 346
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 346
cgggagcgcg gctgttcctg gtagggccgt gtcaggtgac ggatgtagct aggggcg    58

<210> SEQ ID NO 347
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 347
ccccaagccg cagaaggacg acgggagggt aatgaagctg agcccaggtc tcctaggaag    60
gaga    64

<210> SEQ ID NO 348
<211> LENGTH: 60
<212> TYPE: DNA
<213> ORGANISM: Artificial Sequence
<220> FEATURE:
<223> OTHER INFORMATION: probe/primer/pcr

<400> SEQUENCE: 348
gggctcttcc gccagcaccg gaggaagaaa gaggagggc tggctggtca ccagagggtg    60

<210> SEQ ID NO 349
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 349
ttctcttcca tcccatcctc ccttctggtc ctcctttcca cagtgggagt ccgtgctcct    60
gctcc    65

<210> SEQ ID NO 350
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 350
ccgcctctgt gcctccgcca acccgacaac gcttgctccc accccgatcc ccgcacc    57

<210> SEQ ID NO 351
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 351
ccgcgccacg tgagggcggc aagagggcac tggccctgcg gcgaggcccc agcgagg    57

<210> SEQ ID NO 352
<211> LENGTH: 58
<212> TYPE: DNA
<213> ORGANISM: Artificial Sequence
<220> FEATURE:
<223> OTHER INFORMATION: probe/primer/pcr

<400> SEQUENCE: 352
cactgctgat aggtgcaggc aggacagtcc ctccaccgcg gctcggggcg tcctgatt    58

<210> SEQ ID NO 353
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 353
cgggagcctc gcggacgtga cgccgcgggc ggaagtgacg ttttcccgcg gttggac    57

```
<210> SEQ ID NO 354
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 354
tgtcctcccg gtgtcccgct tctccgcgcc ccagccgccg gctgccagct tttcggg      57

<210> SEQ ID NO 355
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 355
ggtgtcgcga caggtcctat tgcgggtgtc tgcggtggga agggcggtgg tgactgg      57

<210> SEQ ID NO 356
<211> LENGTH: 62
<212> TYPE: DNA
<213> ORGANISM: Artificial Sequence
<220> FEATURE:
<223> OTHER INFORMATION: probe/primer/pcr

<400> SEQUENCE: 356
acatatgaca acgcctgcca tattgtccct gcggcaaaac ccaacacgaa aagcacacag   60
ca                                                                  62

<210> SEQ ID NO 357
<211> LENGTH: 64
<212> TYPE: DNA
<213> ORGANISM: Artificial Sequence
<220> FEATURE:
<223> OTHER INFORMATION: probe/primer/pcr

<400> SEQUENCE: 357
ggaaaccctc acccaggaga tacacaggag cactggcttt ggcagcagct cacaatgaga   60
aaga                                                                64

<210> SEQ ID NO 358
<211> LENGTH: 65
<212> TYPE: DNA
<213> ORGANISM: Artificial Sequence
<220> FEATURE:
<223> OTHER INFORMATION: probe/primer/pcr

<400> SEQUENCE: 358
ttaccattgg cttagggaaa ggagcttact gggaactggg agctaggtgg cctgaggaga   60
ctggg                                                               65

<210> SEQ ID NO 359
<211> LENGTH: 57
<212> TYPE: DNA
<213> ORGANISM: Artificial Sequence
<220> FEATURE:
<223> OTHER INFORMATION: probe/primer/pcr

<400> SEQUENCE: 359
aagaacaggc acgcgtgctg gcagaaaccc ccggtatgac cgtgaaaacg gcccgcc      57

<210> SEQ ID NO 360
```

```
<211> LENGTH: 115
<212> TYPE: DNA
<213> ORGANISM: Artificial Sequence
<220> FEATURE:
<223> OTHER INFORMATION: probe/primer/pcr

<400> SEQUENCE: 360
ccggggactc agggcgcccc ctctgcggcc gacgcccggg gtgcagcggc cgccggggct    60
ggggccggcg ggagtccgcg ggaccctcca gaagagcggc cggcgccgtg actca       115

<210> SEQ ID NO 361
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 361 tcacggggc ggggagacgc                                                 20

<210> SEQ ID NO 362
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 362
gcacagggtg gggcagggag ca                                             22

<210> SEQ ID NO 363
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 363
accgggcctt ccgcgcccct                                                20

<210> SEQ ID NO 364
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 364
tcccacctcc cccaacattc cagttcct                                       28

<210> SEQ ID NO 365
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 365
tcacagagcc aggcaagcat gggtga                                         26

<210> SEQ ID NO 366
<211> LENGTH: 23
<212> TYPE: DNA
<213> ORGANISM: Artificial Sequence
<220> FEATURE:
<223> OTHER INFORMATION: probe/primer/pcr
```

-continued

<400> SEQUENCE: 366
ggagcagcag gctcgctcgg gga					23

<210> SEQ ID NO 367
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 367
gcccaaagtg cggggccaac cc					22

<210> SEQ ID NO 368
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 368
cggaaagagg aaggcatttg ctgggcaat					29

<210> SEQ ID NO 369
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 369
ccagcggccc cgcgggattt					20

<210> SEQ ID NO 370
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 370
ccgacagcgc ccggcccaga					20

<210> SEQ ID NO 371
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 371
tgggccaatc cccgcggctg					20

<210> SEQ ID NO 372
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 372
gggcggctgc ggggagcgat					20

<210> SEQ ID NO 373

```
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 373
cgccaggacc gcgcacagca                                            20

<210> SEQ ID NO 374
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 374
gcgggcaaga gagcgcggga g                                          21

<210> SEQ ID NO 375
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 375
agcgcgcagc caggggcgac                                            20

<210> SEQ ID NO 376
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 376
cgtgcgctca cccagccgca g                                          21

<210> SEQ ID NO 377
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 377
tgagggcccg gggtggggct                                            20

<210> SEQ ID NO 378
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 378
atatgcgccc ggcgcggtgg                                            20

<210> SEQ ID NO 379
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 379
```
ccgcagggga aggccgggga 20

<210> SEQ ID NO 380
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 380
tcctgaggcg gggccgtccg 20

<210> SEQ ID NO 381
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 381
ggaggccggg gacgccgaga 20

<210> SEQ ID NO 382
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 382
gccgccggct ccccgtatg 20

<210> SEQ ID NO 383
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 383
gcaggagcga cgcgcgccaa 20

<210> SEQ ID NO 384
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 384
cgggggaaac gcaggcgtcg g 21

<210> SEQ ID NO 385
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 385
cccccacccc tggacccgca g 21

<210> SEQ ID NO 386
<211> LENGTH: 20
<212> TYPE: DNA

<213> ORGANISM: Artificial Sequence
<220> FEATURE:
<223> OTHER INFORMATION: probe/primer/pcr

<400> SEQUENCE: 386
cgcccggctt tccggcgcac                              20

<210> SEQ ID NO 387
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 387
ccgctgggcc gccccttgct                              20

<210> SEQ ID NO 388
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 388
cgcttctcca tagctcgcca cacacacac                    29

<210> SEQ ID NO 389
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 389
tccgcgcacg cgcaagtcca                              20

<210> SEQ ID NO 390
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 390
cgtctcaact caccgccgcc accg                         24

<210> SEQ ID NO 391
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 391
gacaaatgcg ctgctcggag agactgcc                     28

<210> SEQ ID NO 392
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 392
tgcgcctgcg cagtgcagct tagtg                        25

<210> SEQ ID NO 393
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 393
gaagtcaagg gctttcaacc tcccctgcc                                    29

<210> SEQ ID NO 394
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 394
tggatcccgc acaggggctg ca                                           22

<210> SEQ ID NO 395
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 395
gccgcctgtg gttttccgcg cat                                          23

<210> SEQ ID NO 396
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 396
gcgcgctctc ccgcgcctct                                              20

<210> SEQ ID NO 397
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 397
ttccggccca gccccaaccc                                              20

<210> SEQ ID NO 398
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 398
tccgggtcag gcgcacaggg c                                            21

<210> SEQ ID NO 399
<211> LENGTH: 21
<212> TYPE: DNA
<213> ORGANISM: Artificial Sequence
<220> FEATURE:

<223> OTHER INFORMATION: probe/primer/pcr

<400> SEQUENCE: 399
gggggcggtg cctgcgccat a    21

<210> SEQ ID NO 400
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 400
ggcgcgggcc ctcaggttct cc    22

<210> SEQ ID NO 401
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 401
gcgtccgcgg ctcctcagcg    20

<210> SEQ ID NO 402
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 402
gggaggcgcc cagcgagcca    20

<210> SEQ ID NO 403
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 403
gcgcgcaggg ggccttatac aaagtcg    27

<210> SEQ ID NO 404
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 404
cccccacccc ctttctttct gggttttg    28

<210> SEQ ID NO 405
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 405
cgcgcgttcc ctcccgtccg    20

```
<210> SEQ ID NO 406
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 406
gccggcggag gcagccgttc                                               20

<210> SEQ ID NO 407
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 407
tgcctggtgc ccgagcgag c                                              21

<210> SEQ ID NO 408
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 408
cggcggcggc gctacctgga                                               20

<210> SEQ ID NO 409
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 409
gtggtggcca gcggggagcg                                               20

<210> SEQ ID NO 410
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 410
ggcggcactg aactcgcggc aa                                            22

<210> SEQ ID NO 411
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 411
cctcggcgat ccccggcctg a                                             21

<210> SEQ ID NO 412
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 412
acgcagggag cgcgcggagg                                              20

<210> SEQ ID NO 413
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 413
tgaaatactc ccccacagtt ttcatgtg                                     28

<210> SEQ ID NO 414
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 414
tccgggcgca cggggagctg                                              20

<210> SEQ ID NO 415
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 415
ggcggcggcg tccagccaga                                              20

<210> SEQ ID NO 416
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 416
agggtcgccg aggccgtgcg                                              20

<210> SEQ ID NO 417
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 417
ccgcgcctga tgcacgtggg                                              20

<210> SEQ ID NO 418
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 418
gccgggagcg ggcggaggaa                                              20

<210> SEQ ID NO 419
<211> LENGTH: 20
```

```
<212> TYPE: DNA
<213> ORGANISM: Artificial Sequence
<220> FEATURE:
<223> OTHER INFORMATION: probe/primer/pcr

<400> SEQUENCE: 419
aggggcgcac cgggctggct                                                    20

<210> SEQ ID NO 420
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 420
tgccacggga ggaggcggga a                                                  21

<210> SEQ ID NO 421
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 421
cgggcatcgg cgcgggatga                                                    20

<210> SEQ ID NO 422
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 422
acaccgccgg cgcccaccac                                                    20

<210> SEQ ID NO 423
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 423
cccccaacag cgcgcagcga                                                    20

<210> SEQ ID NO 424
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 424
gccccgctgg ggacctggga                                                    20

<210> SEQ ID NO 425
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 425
``` tcccgggggga cccactcgag gc    22

<210> SEQ ID NO 426
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 426
gcccgcggag gggcacacca    20

<210> SEQ ID NO 427
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 427
ggcccacgtg ctcgcgccaa    20

<210> SEQ ID NO 428
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 428
cggcggagcg gcgaggagga    20

<210> SEQ ID NO 429
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 429
gcctcgccgg ttcccgggtg    20

<210> SEQ ID NO 430
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 430
gcaggcgcgc cgatggcgtt    20

<210> SEQ ID NO 431
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 431
cctcccggct tctgcatcga gggc    24

<210> SEQ ID NO 432
<211> LENGTH: 20
<212> TYPE: DNA
<213> ORGANISM: Artificial Sequence

```
<220> FEATURE:
<223> OTHER INFORMATION: probe/primer/pcr

<400> SEQUENCE: 432
gcggtccgcg agtgggagcg                                          20

<210> SEQ ID NO 433
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 433
agcagcgccg cctcccaccc                                          20

<210> SEQ ID NO 434
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 434
ccgaccgtgc tggcggcgac                                          20

<210> SEQ ID NO 435
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 435
tcccgggctc cgctcgccaa                                          20

<210> SEQ ID NO 436
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 436
gcatggggtg ctcatcttcc cggagc                                   26

<210> SEQ ID NO 437
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 437
cccgagagcc ggagcgggga                                          20

<210> SEQ ID NO 438
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 438
gccgctgcag ggcgtctggg                                          20
```

```
<210> SEQ ID NO 439
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 439
gcgctgcccc aagctggctt cc                                              22

<210> SEQ ID NO 440
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 440
tcaggatgcc agcgtgacgg aagcaa                                          26

<210> SEQ ID NO 441
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 441
gggcggtgcc atcgcgtcca                                                 20

<210> SEQ ID NO 442
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 442
ggtgggtcgc cgccgggaga                                                 20

<210> SEQ ID NO 443
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 443
aggcggaggg ccacgcaggg                                                 20

<210> SEQ ID NO 444
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 444
ggtccggggg cgccgctgat                                                 20

<210> SEQ ID NO 445
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 445
gcggcctgcg gctcggttcc                                               20

<210> SEQ ID NO 446
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 446
cgggaaccgt ggcggcccct                                               20

<210> SEQ ID NO 447
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 447
gcggggaagg cggggaaggc                                               20

<210> SEQ ID NO 448
<211> LENGTH: 18
<212> TYPE: DNA
<213> ORGANISM: Artificial Sequence
<220> FEATURE:
<223> OTHER INFORMATION: probe/primer/pcr

<400> SEQUENCE: 448
gcctcccggt ttcaggcc                                                 18

<210> SEQ ID NO 449
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 449
cagcccgcgc accgaccagc                                               20

<210> SEQ ID NO 450
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 450
cccccagcca caccagacgt ggg                                           23

<210> SEQ ID NO 451
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 451
tgggcttcct gccccatggt tccct                                         25

<210> SEQ ID NO 452
```

```
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 452
tccgcgctgg gccgcagctt t                                              21

<210> SEQ ID NO 453
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 453
gcatggcccg gtggcctgca                                                20

<210> SEQ ID NO 454
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 454
tgggcagggg aggggagtgc ttga                                           24

<210> SEQ ID NO 455
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 455
tccccggcgc cttcctcctc c                                              21

<210> SEQ ID NO 456
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 456
tccaccgcgc ttcccggcta tgc                                            23

<210> SEQ ID NO 457
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 457
cccgcatctg accgcaggac ccc                                            23

<210> SEQ ID NO 458
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 458
```
tgcggacacg tgcttttccc gcat    24

<210> SEQ ID NO 459
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 459
ggagctggaa gagtttgtga gggcggtcc    29

<210> SEQ ID NO 460
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 460
cggccgccaa cgacgccaga    20

<210> SEQ ID NO 461
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 461
agcgcccggt cagcccgcag    20

<210> SEQ ID NO 462
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 462
tcccgccagg cccagcccct    20

<210> SEQ ID NO 463
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 463
ccgattcttc ccagcagatg gccccaa    27

<210> SEQ ID NO 464
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 464
acgcacaccg cccccaagcg    20

<210> SEQ ID NO 465
<211> LENGTH: 20
<212> TYPE: DNA

```
<213> ORGANISM: Artificial Sequence
<220> FEATURE:
<223> OTHER INFORMATION: probe/primer/pcr

<400> SEQUENCE: 465
taggccccga ggccggagcg                                            20

<210> SEQ ID NO 466
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 466
ggggttcgcg cgagcgcttt g                                          21

<210> SEQ ID NO 467
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 467
gccagtctcc cgccccctga gca                                        23

<210> SEQ ID NO 468
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 468
tgaggaggca gcggaccggg ga                                         22

<210> SEQ ID NO 469
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 469
gccggctcca cggacccacg                                            20

<210> SEQ ID NO 470
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 470
gccgccaccg ccaccatgcc                                            20

<210> SEQ ID NO 471
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 471
ttgagtaagg atgataccga gagggaaga                                  29
```

<210> SEQ ID NO 472
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 472
tgggccaggc acgtggctc a                                              21

<210> SEQ ID NO 473
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 473
cccggcgaag tgggcggctc                                               20

<210> SEQ ID NO 474
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 474
ggcggcctta ccctgccgcg ag                                            22

<210> SEQ ID NO 475
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 475
ggtggggccg gcgagggtca                                               20

<210> SEQ ID NO 476
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 476
tcggcgcgga ccggctcctc ta                                            22

<210> SEQ ID NO 477
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 477
ggcccatgcg gccccgtcac                                               20

<210> SEQ ID NO 478
<211> LENGTH: 22
<212> TYPE: DNA
<213> ORGANISM: Artificial Sequence
<220> FEATURE:

<223> OTHER INFORMATION: probe/primer/pcr

<400> SEQUENCE: 478
tgggattgcc aggggctgac cg                                    22

<210> SEQ ID NO 479
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 479
cgccggagca cgcggctact ca                                    22

<210> SEQ ID NO 480
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 480
ccctcggcgc cggcccgtta                                       20

<210> SEQ ID NO 481
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 481
gcacagcggc ggcgagtggg                                       20

<210> SEQ ID NO 482
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 482
tcacctcggg cggggcggac                                       20

<210> SEQ ID NO 483
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 483
gagacggggc cgggcgcaga                                       20

<210> SEQ ID NO 484
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 484
cgcattcggg ccgcaagctc c                                     21

```
<210> SEQ ID NO 485
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 485
ggcccgaaag ggccggagcg                                             20

<210> SEQ ID NO 486
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 486
acggcggccg ggtgaccgac                                             20

<210> SEQ ID NO 487
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 487
tccaccggcg gccgctcacc                                             20

<210> SEQ ID NO 488
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 488
gcggtcaggg accccttcc cc                                           22

<210> SEQ ID NO 489
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 489
cggccgaagc tgccgcccct                                             20

<210> SEQ ID NO 490
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 490
ggcggccttg tgccgctggg                                             20

<210> SEQ ID NO 491
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 491
tcgcgggagg agcggcgagg                                          20

<210> SEQ ID NO 492
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 492
tgcccaccag aagcccatca ccacc                                    25

<210> SEQ ID NO 493
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 493
tgggccatgt gccccacccc                                          20

<210> SEQ ID NO 494
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 494
cccgccagcc cagggcgaga                                          20

<210> SEQ ID NO 495
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 495 gcccectgtc cctttcccgg gact                                     24

<210> SEQ ID NO 496
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 496
ggtgggggtc cgcacccagc aat                                      23

<210> SEQ ID NO 497
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 497
ggggcccccg ggttgcgtga                                          20

<210> SEQ ID NO 498
<211> LENGTH: 24
```

```
<212> TYPE: DNA
<213> ORGANISM: Artificial Sequence
<220> FEATURE:
<223> OTHER INFORMATION: probe/primer/pcr

<400> SEQUENCE: 498
tgcctgcaca gacgacagca cccc                                              24

<210> SEQ ID NO 499
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 499
aggccgcgcc gggctcaggt                                                   20

<210> SEQ ID NO 500
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 500
cggggtagtc gcgcaggtgt cgg                                               23

<210> SEQ ID NO 501
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 501
tgcaggcgga gaatagcagc ctccctc                                           27

<210> SEQ ID NO 502
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 502
ccggaaatgc tgctgcaaga ggca                                              24

<210> SEQ ID NO 503
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 503
gcgtcggatc cctgagaact tcgaagcca                                         29

<210> SEQ ID NO 504
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 504
```

-continued cccggctccg cgggttccgt                    20

<210> SEQ ID NO 505
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 505
gcgtcgccgg ggctggacgt t                  21

<210> SEQ ID NO 506
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 506
ggggcctgcc gcctcgtcca                    20

<210> SEQ ID NO 507
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 507
cgcacaccgc tggcggacac c                  21

<210> SEQ ID NO 508
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 508
cgcaaaccat cttccccgac gcctt              25

<210> SEQ ID NO 509
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 509
gggccctccg ccgcctccaa                    20

<210> SEQ ID NO 510
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 510
ccaccaccgt ggcaaagcgt ccc                23

<210> SEQ ID NO 511
<211> LENGTH: 24
<212> TYPE: DNA
<213> ORGANISM: Artificial Sequence

```
<220> FEATURE:
<223> OTHER INFORMATION: probe/primer/pcr

<400> SEQUENCE: 511
tcacagcccc ttcctgcccg aaca                                    24

<210> SEQ ID NO 512
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 512
tgcttgatgc tcaccactgt tcttgctgc                               29

<210> SEQ ID NO 513
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 513
ggccaggccc ggtggctcac a                                       21

<210> SEQ ID NO 514
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 514
tgcgggacgg gtggcgggaa                                         20

<210> SEQ ID NO 515
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 515
ggcttggccc cgccacccag                                         20

<210> SEQ ID NO 516
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 516
ggcggggaag gcgaccgcag                                         20

<210> SEQ ID NO 517
<211> LENGTH: 19
<212> TYPE: DNA
<213> ORGANISM: Artificial Sequence
<220> FEATURE:
<223> OTHER INFORMATION: probe/primer/pcr

<400> SEQUENCE: 517
ggcgcccaac caccacgcc                                          19
```

```
<210> SEQ ID NO 518
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 518
gaaaagcccc ggccggcctc c                                              21

<210> SEQ ID NO 519
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 519
ccgcaggtgc gggggagcgt                                                20

<210> SEQ ID NO 520
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 520
ccccgcccac agcgcggagt t                                              21

<210> SEQ ID NO 521
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 521
agcaggggcc cggggcgat                                                 20

<210> SEQ ID NO 522
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 522
ccatgaccgc ggtggcttgt ggg                                            23

<210> SEQ ID NO 523
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 523
ggcaggtgct cagcgggcag acg                                            23

<210> SEQ ID NO 524
<211> LENGTH: 20
<212> TYPE: DNA
<213> ORGANISM: Artificial Sequence
<220> FEATURE:
<223> OTHER INFORMATION: probe/primer/pcr
```

<400> SEQUENCE: 524
gggtgcgccc tgcgctggct                                            20

<210> SEQ ID NO 525
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 525
gaatttggtc ctcctgcgcc tgcca                                      25

<210> SEQ ID NO 526
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 526
tggcttccgc ggcgccaatc                                            20

<210> SEQ ID NO 527
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 527
ggccaggaga ggggccgagc ct                                         22

<210> SEQ ID NO 528
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 528
cgagcgccgg ccccccttct                                            20

<210> SEQ ID NO 529
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 529
cggttgcgag ggcacccttt ggc                                        23

<210> SEQ ID NO 530
<211> LENGTH: 18
<212> TYPE: DNA
<213> ORGANISM: Artificial Sequence
<220> FEATURE:
<223> OTHER INFORMATION: probe/primer/pcr

<400> SEQUENCE: 530
tacccggacg cggtggcg                                              18

<210> SEQ ID NO 531

```
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 531
gcgccgccga gcctcagcca                                              20

<210> SEQ ID NO 532
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 532
tgcagcctca acctcctggg g                                            21

<210> SEQ ID NO 533
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 533
ccttgccgac ccagcctcga tccc                                         24

<210> SEQ ID NO 534
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 534
ggcggcgttc ggtggtgtcc c                                            21

<210> SEQ ID NO 535
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 535
cccggactcc cccgcgcaga                                              20

<210> SEQ ID NO 536
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 536 cggcccectg caagttccgc                                              20

<210> SEQ ID NO 537
<211> LENGTH: 19
<212> TYPE: DNA
<213> ORGANISM: Artificial Sequence
<220> FEATURE:
<223> OTHER INFORMATION: probe/primer/pcr

<400> SEQUENCE: 537
```
tgcccagggg agccctcca          19

<210> SEQ ID NO 538
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 538
gccggctgca ggccctcact ggt          23

<210> SEQ ID NO 539
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 539
tgtcacacct gccgatgaaa ctcctgcg          28

<210> SEQ ID NO 540
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 540
cccctgcgca ccctaccag gca          23

<210> SEQ ID NO 541
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 541
tcctggggga gcgcggtggg          20

<210> SEQ ID NO 542
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 542
agtggggccg ggcgagtgcg          20

<210> SEQ ID NO 543
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 543
gcgtccaggc tgtgcgctcc cc          22

<210> SEQ ID NO 544
<211> LENGTH: 20
<212> TYPE: DNA

```
<213> ORGANISM: Artificial Sequence
<220> FEATURE:
<223> OTHER INFORMATION: probe/primer/pcr

<400> SEQUENCE: 544
ggcgcggcgg tgcagcctct                                            20

<210> SEQ ID NO 545
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 545
gaggcggcgg cggtggcagt                                            20

<210> SEQ ID NO 546
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 546
cgcgcgaccc gccgattgtg                                            20

<210> SEQ ID NO 547
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 547
ccgcggacgc cgctctgcac                                            20

<210> SEQ ID NO 548
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 548
tgaacccggg aggcggaggt tgc                                        23

<210> SEQ ID NO 549
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 549
tctcggcggc gcggggagtc                                            20

<210> SEQ ID NO 550
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 550
aggcggccac gggagggggga                                           20
```

<210> SEQ ID NO 551
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 551
ggacccgagc ggggcggaga                                            20

<210> SEQ ID NO 552
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 552
aagcacctgg ggcggggcgg ag                                         22

<210> SEQ ID NO 553
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 553
gccgctcggg ggacgtggga                                            20

<210> SEQ ID NO 554
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 554
caccgccagc gtgccagccc                                            20

<210> SEQ ID NO 555
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 555
tattcttggc cgggtgcggt                                            20

<210> SEQ ID NO 556
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 556
ccgcttcccg cgagcgagcc                                            20

<210> SEQ ID NO 557
<211> LENGTH: 20
<212> TYPE: DNA
<213> ORGANISM: Artificial Sequence
<220> FEATURE:

```
<223> OTHER INFORMATION: probe/primer/pcr

<400> SEQUENCE: 557
cagccggcgc tccgcacctg                                               20

<210> SEQ ID NO 558
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 558
gcggagcgcg cttggcctca                                               20

<210> SEQ ID NO 559
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 559
ggcctcgagc ccacccagac ttggc                                         25

<210> SEQ ID NO 560
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 560
tgccgcgccg taagggccac c                                             21

<210> SEQ ID NO 561
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 561
acggcggtgg cggtgggtcg                                               20

<210> SEQ ID NO 562
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 562
aacctgccca gttactgccc cactccg                                       27

<210> SEQ ID NO 563
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 563
tccagcgccc gagccgtcca                                               20
```

```
<210> SEQ ID NO 564
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 564
gctgctgctg cccgcgtccg                                               20

<210> SEQ ID NO 565
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 565
cactgcttag gccacacgat cccccaa                                       27

<210> SEQ ID NO 566
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 566
ggccggacgc gcctcccaag                                               20

<210> SEQ ID NO 567
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 567
tcggccaggg tgccgagggc                                               20

<210> SEQ ID NO 568
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 568
tccgcccgcc ccacagccag                                               20

<210> SEQ ID NO 569
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 569
cgcgccccag cccacccact                                               20

<210> SEQ ID NO 570
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 570
ccgtgctggg cgcaggggaa                                              20

<210> SEQ ID NO 571
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 571
tgcgcacgcg cacagcctcc                                              20

<210> SEQ ID NO 572
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 572
cggtgagtgc ggcccgggga                                              20

<210> SEQ ID NO 573
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 573
tggccgagag ggagccccac acc                                          23

<210> SEQ ID NO 574
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 574
cccagcgccg caacgcccag                                              20

<210> SEQ ID NO 575
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 575
gccacaagcg ggcgggacgg                                              20

<210> SEQ ID NO 576
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 576
tcctctggac aacggggagc gggaa                                        25

<210> SEQ ID NO 577
<211> LENGTH: 20
```

```
<212> TYPE: DNA
<213> ORGANISM: Artificial Sequence
<220> FEATURE:
<223> OTHER INFORMATION: probe/primer/pcr

<400> SEQUENCE: 577
cgcgggttcc cggcgtctcc                                              20

<210> SEQ ID NO 578
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 578
gcgccgcccg tcctgcttgc                                              20

<210> SEQ ID NO 579
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 579
acgcgcggcc ctcctgcacc                                              20

<210> SEQ ID NO 580
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 580
gggcggggca agccctcacc tg                                           22

<210> SEQ ID NO 581
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 581
gggagcgccc cctggcggtt                                              20

<210> SEQ ID NO 582
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 582
gcgaatggtt cgcgccggcc t                                            21

<210> SEQ ID NO 583
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 583
```
tttccgccgg ctgggccctc                                              20

<210> SEQ ID NO 584
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 584
tctccgggtc ccccgcgtgc                                              20

<210> SEQ ID NO 585
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 585
gcagcccggg tagggttcac cgaaa                                        25

<210> SEQ ID NO 586
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 586
gggcggagag aggtcctgcc cagc                                         24

<210> SEQ ID NO 587
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 587
ccctcacccc agccgcgacc ctt                                          23

<210> SEQ ID NO 588
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 588
gcgatgacgg gatccgagag aaaggca                                      27

<210> SEQ ID NO 589
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 589
tccgcaggcc gcgggaaagg                                              20

<210> SEQ ID NO 590
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 590
ggccccagtc cacctctggg agcg                                              24

<210> SEQ ID NO 591
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 591
gcttggccgc ccccgggatg                                                   20

<210> SEQ ID NO 592
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 592
ccctccatgc gcaatcccaa gggc                                              24

<210> SEQ ID NO 593
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 593
gcggcgactg cgctgcccct                                                   20

<210> SEQ ID NO 594
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 594
tgggcttgcc tccccgcccc t                                                 21

<210> SEQ ID NO 595
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 595
ggcggcccaa ggagggcgaa                                                   20

<210> SEQ ID NO 596
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 596
gctgcgcggc tggcgatcca                                                   20

```
<210> SEQ ID NO 597
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 597
tcaccgcctc cggacccctc cc                                              22

<210> SEQ ID NO 598
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 598
cccttccagc cacccgccc tg                                               22

<210> SEQ ID NO 599
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 599
gcgggacacc gggaggacag cg                                              22

<210> SEQ ID NO 600
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 600
ccctgggttc ccggcttctc agcca                                           25

<210> SEQ ID NO 601
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 601
tggcggtgat gggcggagga gg                                              22

<210> SEQ ID NO 602
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 602
ccagcccgcc cggagcccat                                                 20

<210> SEQ ID NO 603
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 603
tgcccgcggg ggaatcgcag                                                   20

<210> SEQ ID NO 604
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 604
tgccgcgagc ccgtctgctc c                                                 21

<210> SEQ ID NO 605
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 605
tgcggccccc tcccggctga                                                   20

<210> SEQ ID NO 606
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 606
gcagcagggc gcggcttccc                                                   20

<210> SEQ ID NO 607
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 607
gccgcagcac gctcggacgg                                                   20

<210> SEQ ID NO 608
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 608
tgcggagtgc gggtcgggaa gc                                                22

<210> SEQ ID NO 609
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 609
ggcgcggggg caggtgagca                                                   20

<210> SEQ ID NO 610
```

```
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 610
ggcgcggggg caggtgagca t                                              21

<210> SEQ ID NO 611
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 611
cagtgacggg cggtgggcct g                                              21

<210> SEQ ID NO 612
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 612
cggcgaccct ttggccgctg g                                              21

<210> SEQ ID NO 613
<211> LENGTH: 19
<212> TYPE: DNA
<213> ORGANISM: Artificial Sequence
<220> FEATURE:
<223> OTHER INFORMATION: probe/primer/pcr

<400> SEQUENCE: 613
ccgcggcagc ccgggtgaa                                                 19

<210> SEQ ID NO 614
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 614
gggcgagcga gcgggaccga                                                20

<210> SEQ ID NO 615
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 615
tggggcagtg ccggtgtgct g                                              21

<210> SEQ ID NO 616
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 616
```
tcgctggcat tcgggccccc t                                    21

<210> SEQ ID NO 617
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 617
ggagccgtga tggagccggg agg                                  23

<210> SEQ ID NO 618
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 618
tgccagggtg tcttggctct ggcct                                25

<210> SEQ ID NO 619
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 619
ccggctccgg cggggaagga                                      20

<210> SEQ ID NO 620
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 620
ggccagggtg ccgtcgcgct t                                    21

<210> SEQ ID NO 621
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 621
tcggctcggt cctgaggaga aggactca                             28

<210> SEQ ID NO 622
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 622
gcgcggggaa cctgcggctg                                      20

<210> SEQ ID NO 623
<211> LENGTH: 21
<212> TYPE: DNA

```
<213> ORGANISM: Artificial Sequence
<220> FEATURE:
<223> OTHER INFORMATION: probe/primer/pcr

<400> SEQUENCE: 623
gccgccgctg ctttgggtgg g                                          21

<210> SEQ ID NO 624
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 624
cacctgagcc cgcgggggaa cc                                         22

<210> SEQ ID NO 625
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 625
gaacgccggc ctcaccggca                                            20

<210> SEQ ID NO 626
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 626
cccgtggtcc cagcgctcct gct                                        23

<210> SEQ ID NO 627
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 627
gtgcgacccg gcgcccaagc                                            20

<210> SEQ ID NO 628
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 628
tggctctgcg ctgcctttgg tggc                                       24

<210> SEQ ID NO 629
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 629
cgcgcgggcg gctcctttgt                                            20
```

<210> SEQ ID NO 630
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 630
tggcccgttg gcgaggttag agcg                                          24

<210> SEQ ID NO 631
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 631
gacccggcat ccgggcaggc                                               20

<210> SEQ ID NO 632
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 632
gcccggactg taatcacgtc cactggga                                      28

<210> SEQ ID NO 633
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 633
ccgccgccaa cgcgcaggtc                                               20

<210> SEQ ID NO 634
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 634
cgctgccagc tgccgctccg                                               20

<210> SEQ ID NO 635
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 635
agcgcccacc tgcgcctcgc                                               20

<210> SEQ ID NO 636
<211> LENGTH: 20
<212> TYPE: DNA
<213> ORGANISM: Artificial Sequence
<220> FEATURE:

-continued

<223> OTHER INFORMATION: probe/primer/pcr

<400> SEQUENCE: 636
gcgggccagg gcggcatgaa                                          20

<210> SEQ ID NO 637
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 637
ggctgcgacc tggggtccga cg                                       22

<210> SEQ ID NO 638
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 638
ggttaggagg gcggggcgcg tg                                       22

<210> SEQ ID NO 639
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 639
cagcgcacca acgcaggcga gg                                       22

<210> SEQ ID NO 640
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 640
tcggctggcc ccgcccactc                                          20

<210> SEQ ID NO 641
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 641
cggggttgcc gtcgcagcca                                          20

<210> SEQ ID NO 642
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 642
tccgcactcc cgcccggttc c                                        21

```
<210> SEQ ID NO 643
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 643
ggaccccctg ggcagcaccc tg                                              22

<210> SEQ ID NO 644
<211> LENGTH: 18
<212> TYPE: DNA
<213> ORGANISM: Artificial Sequence
<220> FEATURE:
<223> OTHER INFORMATION: probe/primer/pcr

<400> SEQUENCE: 644
cgaggcagcc ggatcacg                                                   18

<210> SEQ ID NO 645
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 645
ggcgcgtgcg ggcgttgtcc                                                 20

<210> SEQ ID NO 646
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 646
ccaggatgcg gcagcgccca c                                               21

<210> SEQ ID NO 647
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 647
cgatgcggcc cgcggaggag                                                 20

<210> SEQ ID NO 648
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 648
cgttctgcgc gcgcccgact c                                               21

<210> SEQ ID NO 649
<211> LENGTH: 23
<212> TYPE: DNA
<213> ORGANISM: Artificial Sequence
<220> FEATURE:
<223> OTHER INFORMATION: probe/primer/pcr
```

```
<400> SEQUENCE: 649
ccccgccgtg ggcgtagtaa ccg                                    23

<210> SEQ ID NO 650
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 650
aacccgcccg ggcagctcca                                        20

<210> SEQ ID NO 651
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 651
gcagcggtcg cgcctcgtcg                                        20

<210> SEQ ID NO 652
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 652
cgcaatcgcg ctgtctctga aagggg                                 26

<210> SEQ ID NO 653
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 653
ggagcgcccg ccgttgatgc c                                      21

<210> SEQ ID NO 654
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 654
ccatggcccg ctgcgccctc                                        20

<210> SEQ ID NO 655
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 655
tgggggcggg gtgcaggggt                                        20

<210> SEQ ID NO 656
<211> LENGTH: 20
```

```
<212> TYPE: DNA
<213> ORGANISM: Artificial Sequence
<220> FEATURE:
<223> OTHER INFORMATION: probe/primer/pcr

<400> SEQUENCE: 656
ccgaccctgc gcccggcagt                                          20

<210> SEQ ID NO 657
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 657
cggcttcaag tccacggccc tgtgatg                                  27

<210> SEQ ID NO 658
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 658
accccacctg cccgcgctgc                                          20

<210> SEQ ID NO 659
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 659
ggcgcgcgga gacgcagcag                                          20

<210> SEQ ID NO 660
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 660
cgtgagccgg cgctcctgat gc                                       22

<210> SEQ ID NO 661
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 661
ctgccgcggg ggtgccaagg                                          20

<210> SEQ ID NO 662
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 662
```
cctgctgcgc gcgctggctc                                                        20

<210> SEQ ID NO 663
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 663
cctggcggcc caggtcgctc ct                                                     22

<210> SEQ ID NO 664
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 664
gagcgccccg gccgcctgat                                                        20

<210> SEQ ID NO 665
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 665
cgccgcacgg gacagccagg                                                        20

<210> SEQ ID NO 666
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 666
gcccggacat gccccgccac                                                        20

<210> SEQ ID NO 667
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 667
cgggggccgc cgcctgactt                                                        20

<210> SEQ ID NO 668
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 668
ccagtggcgg ccctcggcct                                                        20

<210> SEQ ID NO 669
<211> LENGTH: 21
<212> TYPE: DNA
<213> ORGANISM: Artificial Sequence

```
<220> FEATURE:
<223> OTHER INFORMATION: probe/primer/pcr

<400> SEQUENCE: 669
cgcccggcgc ggataacggt c                                              21

<210> SEQ ID NO 670
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 670
tgctccgggt ggggagggag gc                                             22

<210> SEQ ID NO 671
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 671
tgcctgggcg cagaacgggg tc                                             22

<210> SEQ ID NO 672
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 672
gggtcctaat ccccaggctg cgctga                                         26

<210> SEQ ID NO 673
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 673
tccgcgtccc cggctgctcc                                                20

<210> SEQ ID NO 674
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 674
gggcagggct gacgttggga gcg                                            23

<210> SEQ ID NO 675
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 675
gccgtgggcg caggggctgt                                                20
```

```
<210> SEQ ID NO 676
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 676
cctgcgcacg cgggaagggc                                                    20

<210> SEQ ID NO 677
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 677
cgcggacgca gccgagctca a                                                  21

<210> SEQ ID NO 678
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 678
cgacccatgg cggggcaggc                                                    20

<210> SEQ ID NO 679
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 679
tccgctcccc gccctggct                                                     20

<210> SEQ ID NO 680
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 680
tgtgccgcgc ggttgggagg                                                    20

<210> SEQ ID NO 681
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 681
tcactcacgc tctcagcccg ggga                                               24

<210> SEQ ID NO 682
<211> LENGTH: 23
<212> TYPE: DNA
<213> ORGANISM: Artificial Sequence
<220> FEATURE:
<223> OTHER INFORMATION: probe/primer/pcr
```

```
<400> SEQUENCE: 682
cggcaagcgg gcttcgggaa gaa                                        23

<210> SEQ ID NO 683
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 683
ccccgcgggc cgggtgagaa                                            20

<210> SEQ ID NO 684
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 684
cggcggcggc tggagagcga                                            20

<210> SEQ ID NO 685
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 685
cgggccccgg gactcggctt                                            20

<210> SEQ ID NO 686
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 686
gacggaatgt ggggtgcggg cct                                        23

<210> SEQ ID NO 687
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 687
tgcggctgct gccgaggctc c                                          21

<210> SEQ ID NO 688
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 688
accgctgcgc gagggagggg                                            20

<210> SEQ ID NO 689
```

```
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 689
gggggtgcgg cgtctggtca gc                                            22

<210> SEQ ID NO 690
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 690
ggccggggga aatgcggcct                                               20

<210> SEQ ID NO 691
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 691
tgcctggtag gactgacggc tgcctttg                                      28

<210> SEQ ID NO 692
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 692
agcgcgggcg cctcgatctc c                                             21

<210> SEQ ID NO 693
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 693
tcccggctgg tcggcgctcc t                                             21

<210> SEQ ID NO 694
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 694
ccggggctgg gacggcgctt                                               20

<210> SEQ ID NO 695
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 695
```

```
gggcggggtg gggctggagc                                              20

<210> SEQ ID NO 696
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 696
gtgcggttgg gcggggccct                                              20

<210> SEQ ID NO 697
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 697
ggcggtgcct ccggggctca                                              20

<210> SEQ ID NO 698
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 698
ggcggtgcct ccggggctca                                              20

<210> SEQ ID NO 699
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 699
cgggagcccg cccccgagag                                              20

<210> SEQ ID NO 700
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 700
tcctgccatc cgcgcctttg ca                                           22

<210> SEQ ID NO 701
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 701
aggcacaggg gcagctccgg cac                                          23

<210> SEQ ID NO 702
<211> LENGTH: 23
<212> TYPE: DNA
```

```
<213> ORGANISM: Artificial Sequence
<220> FEATURE:
<223> OTHER INFORMATION: probe/primer/pcr

<400> SEQUENCE: 702
cgacccctcc gaccgtgctt ccg                                             23

<210> SEQ ID NO 703
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 703
cccgcagggt ggctgcgtcc                                                 20

<210> SEQ ID NO 704
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 704
gcgtctgccg gcccctcccc                                                 20

<210> SEQ ID NO 705
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 705
taggccgccg ggcagccacc                                                 20

<210> SEQ ID NO 706
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 706
ggggagcggg gacgcgagca                                                 20

<210> SEQ ID NO 707
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 707
gccggctggc tccccactct gc                                              22

<210> SEQ ID NO 708
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 708
tcgctcacgg cgtcccttg cc                                               22
```

<210> SEQ ID NO 709
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 709
tccccgctgc cctggcgctc                                               20

<210> SEQ ID NO 710
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 710
ggccagaggc aggcccgcag c                                             21

<210> SEQ ID NO 711
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 711
tgcccgggtc atcggacggg ag                                            22

<210> SEQ ID NO 712
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 712
cccagtgcgc acggcgaggc                                               20

<210> SEQ ID NO 713
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 713
agcgtcccag cccgcgcacc                                               20

<210> SEQ ID NO 714
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 714
tgctcccccg ggtcggagcc                                               20

<210> SEQ ID NO 715
<211> LENGTH: 20
<212> TYPE: DNA
<213> ORGANISM: Artificial Sequence
<220> FEATURE:

<223> OTHER INFORMATION: probe/primer/pcr

<400> SEQUENCE: 715
cgctcgcatt ggggcgcgtc                                         20

<210> SEQ ID NO 716
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 716
tgcggcaagc ccgccatgat g                                       21

<210> SEQ ID NO 717
<211> LENGTH: 31
<212> TYPE: DNA
<213> ORGANISM: Artificial Sequence
<220> FEATURE:
<223> OTHER INFORMATION: probe/primer/pcr

<400> SEQUENCE: 717
tcttgagcct caggagtgaa aaggcccctt g                            31

<210> SEQ ID NO 718
<211> LENGTH: 32
<212> TYPE: DNA
<213> ORGANISM: Artificial Sequence
<220> FEATURE:
<223> OTHER INFORMATION: probe/primer/pcr

<400> SEQUENCE: 718
ggaccatgag tgtttccatg cttggcatca ga                           32

<210> SEQ ID NO 719
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 719
tcagccactg cttcgcaggc tgacg                                   25

<210> SEQ ID NO 720
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 720
cggccagctg cgcggcgact                                         20

<210> SEQ ID NO 721
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 721
tcggagaagc gcgagggtc ca                                       22

-continued

```
<210> SEQ ID NO 722
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 722
gccgggtggg ggctgccttg                                              20

<210> SEQ ID NO 723
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 723
tcctcgcccg gcgcgattgg                                              20

<210> SEQ ID NO 724
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 724
ggccgtgcag ttggtcccct ggc                                          23

<210> SEQ ID NO 725
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 725
gcgagcctgc tgctcctctg gcacc                                        25

<210> SEQ ID NO 726
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 726
gccagagctg tgcaggctcg gcattt                                       26

<210> SEQ ID NO 727
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 727
tgcccagcaa atgccttcct ctttccg                                      27

<210> SEQ ID NO 728
<211> LENGTH: 24
<212> TYPE: DNA
<213> ORGANISM: Artificial Sequence
<220> FEATURE:
<223> OTHER INFORMATION: probe/primer/pcr
```

```
<400> SEQUENCE: 728
tggcctgacc accaatgcag ggga                                              24

<210> SEQ ID NO 729
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 729
tccacctggg cttctgggca ggga                                              24

<210> SEQ ID NO 730
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 730
agctggcctg cgccccgctg                                                   20

<210> SEQ ID NO 731
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 731
agccgcggca gcgccagtcc                                                   20

<210> SEQ ID NO 732
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 732
ggggccgggc cgctcagtct ct                                                22

<210> SEQ ID NO 733
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 733
gcagtgagcg tcaggagcac gtccagg                                           27

<210> SEQ ID NO 734
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 734
cccgatcccc cggcgcgaat                                                   20

<210> SEQ ID NO 735
<211> LENGTH: 20
```

```
<212> TYPE: DNA
<213> ORGANISM: Artificial Sequence
<220> FEATURE:
<223> OTHER INFORMATION: probe/primer/pcr

<400> SEQUENCE: 735
ggcgtgaccg tggcgcggaa                                               20

<210> SEQ ID NO 736
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 736
agcggcccgc agagctccac cc                                            22

<210> SEQ ID NO 737
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 737
ggcaggcggg cgcagggaag                                               20

<210> SEQ ID NO 738
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 738
tctgccccgg gttcacgcca t                                             21

<210> SEQ ID NO 739
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 739
cgggcgggcc ctggcgagta                                               20

<210> SEQ ID NO 740
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 740
gcaagcccgc cacccagggg ac                                            22

<210> SEQ ID NO 741
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 741
```

```
ggcccaggcg gatggggttg g                                              21

<210> SEQ ID NO 742
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 742
tccgagaggc gtgtggtagc gggaga                                         26

<210> SEQ ID NO 743
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 743
aggcggccgc gggcgttagc                                                20

<210> SEQ ID NO 744
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 744
aaggcagcgc gggccaccga                                                20

<210> SEQ ID NO 745
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 745
ggcatcctgc ccgccgcctg                                                20

<210> SEQ ID NO 746
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 746
tggggcgggg tctcgccgtc                                                20

<210> SEQ ID NO 747
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 747
tcgggctcgc gcacctcccc                                                20

<210> SEQ ID NO 748
<211> LENGTH: 21
<212> TYPE: DNA
<213> ORGANISM: Artificial Sequence
```

```
<220> FEATURE:
<223> OTHER INFORMATION: probe/primer/pcr

<400> SEQUENCE: 748
ccaggtgcgc gcttcgctcc c                                              21

<210> SEQ ID NO 749
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 749
acctgcgcca ccgccccacc                                                20

<210> SEQ ID NO 750
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 750
gccgagcaga gggggcacct gg                                             22

<210> SEQ ID NO 751
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 751
tcgcgccgct ctgcgttggg                                                20

<210> SEQ ID NO 752
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 752
ccgccggggc agaaggcgag                                                20

<210> SEQ ID NO 753
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 753
tccactggac agggtggga gcctctg                                         27

<210> SEQ ID NO 754
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 754
gcccaccggc gctgcgctct                                                20
```

```
<210> SEQ ID NO 755
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 755
gcggtgccag ccccgctgtg                                              20

<210> SEQ ID NO 756
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 756
gacccgcctg cgtcctccag gg                                           22

<210> SEQ ID NO 757
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 757
cccatcacag ccgcccaacc agc                                          23

<210> SEQ ID NO 758
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 758
gagcggggcg gagccgagga                                              20

<210> SEQ ID NO 759
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 759
tgcaattgtg cagtggctgc gtttgtttc                                    29

<210> SEQ ID NO 760
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 760
cccgaccgga tgctccttga ctttgcc                                      27

<210> SEQ ID NO 761
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 761
gcgagcgcgc gcaccgattg                                                     20

<210> SEQ ID NO 762
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 762
cactccgccg gccgctcctc a                                                   21

<210> SEQ ID NO 763
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 763 tcggggtcc cggccgaatg                                                      20

<210> SEQ ID NO 764
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 764
gctctcccag ctgcacgcca acttcttg                                            28

<210> SEQ ID NO 765
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 765
ggaggagcct ggcgctggcg agt                                                 23

<210> SEQ ID NO 766
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 766
tggctctgga ccgcagccgg gta                                                 23

<210> SEQ ID NO 767
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 767
acggcggcgt cccgggtcaa                                                     20

<210> SEQ ID NO 768
```

```
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 768
tggccaagcg ctgccactcg ga                                              22

<210> SEQ ID NO 769
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 769
cgcaggccgc tgcggtggag                                                 20

<210> SEQ ID NO 770
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 770
gcgcctgcgc catgtccacc a                                               21

<210> SEQ ID NO 771
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 771
tggtgcctcc cgcaaccctt ggc                                             23

<210> SEQ ID NO 772
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 772
gcccggctcc aggcggggaa                                                 20

<210> SEQ ID NO 773
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 773
gcaatgctgg ctgacctgga cc                                              22

<210> SEQ ID NO 774
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 774
```
cgcccgcccg tcgggatgag                                                    20

<210> SEQ ID NO 775
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 775 tgccccacc atccccacc a                                                    21

<210> SEQ ID NO 776
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 776
ggcgcgagcg gcgggaactg                                                    20

<210> SEQ ID NO 777
<211> LENGTH: 19
<212> TYPE: DNA
<213> ORGANISM: Artificial Sequence
<220> FEATURE:
<223> OTHER INFORMATION: probe/primer/pcr

<400> SEQUENCE: 777
ggcgccgctc gcgcatggt                                                     19

<210> SEQ ID NO 778
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 778
cccgctctgc cccgtcgcac                                                    20

<210> SEQ ID NO 779
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 779
gtagcgcggg cgagcggga                                                     20

<210> SEQ ID NO 780
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 780
agcgccgagc agggcgcgaa                                                    20

<210> SEQ ID NO 781
<211> LENGTH: 20
<212> TYPE: DNA

<213> ORGANISM: Artificial Sequence
<220> FEATURE:
<223> OTHER INFORMATION: probe/primer/pcr

<400> SEQUENCE: 781
ggcggcggcc acgcaggttc                                                    20

<210> SEQ ID NO 782
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 782
ccctcccgca cgctgggttg c                                                  21

<210> SEQ ID NO 783
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 783
tcacggccgc atccgccaca                                                    20

<210> SEQ ID NO 784
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 784
cggcgccggc cgctcttctg                                                    20

<210> SEQ ID NO 785
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 785
ccggcagaga atgggagcgg gagg                                               24

<210> SEQ ID NO 786
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 786
tcggccgggg cgccaggtct                                                    20

<210> SEQ ID NO 787
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 787
tggggctgcg ggcgatgcct                                                    20

```
<210> SEQ ID NO 788
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 788
ggctgcgggg accggggtgt                                              20

<210> SEQ ID NO 789
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 789
cggcccaagc cgcgcctcac                                              20

<210> SEQ ID NO 790
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 790
ccgcgcccgg aaccgctgct                                              20

<210> SEQ ID NO 791
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 791
tcggccggga gcgtgggagc                                              20

<210> SEQ ID NO 792
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 792
tgcagacatt ggcgcgttcc tcca                                         24

<210> SEQ ID NO 793
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 793
ggacccacgc gccgagccca t                                            21

<210> SEQ ID NO 794
<211> LENGTH: 28
<212> TYPE: DNA
<213> ORGANISM: Artificial Sequence
<220> FEATURE:
```

-continued

<223> OTHER INFORMATION: probe/primer/pcr

<400> SEQUENCE: 794
ggagggggcg agtgagggat taggtccg					28

<210> SEQ ID NO 795
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 795 tccccctcacg ccgatgccac g					21

<210> SEQ ID NO 796
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 796
ccatgcccgc cccagctcct ca					22

<210> SEQ ID NO 797
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 797
ccgccgtgat gttctgttcg ccacc					25

<210> SEQ ID NO 798
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 798
cgtggctgcc cctgcactcg tcg					23

<210> SEQ ID NO 799
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 799
tctggccagt ccgtgaaggc ctctga					26

<210> SEQ ID NO 800
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 800
ccggggtgca agggccacgc					20

-continued

```
<210> SEQ ID NO 801
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 801
cgccgcgctt cctcccgacg                                                 20

<210> SEQ ID NO 802
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 802
agcgacccgg ggcgtgaggc                                                 20

<210> SEQ ID NO 803
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 803
tgcggaaacc tatcaccgct tcctttcca                                       29

<210> SEQ ID NO 804
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 804
ggcagggcgg ggcagggttg                                                 20

<210> SEQ ID NO 805
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 805
gggtctccag actgatgggc cggtga                                          26

<210> SEQ ID NO 806
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 806
cgctgaagcc gctgctgtcg ctga                                            24

<210> SEQ ID NO 807
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 807
tcccacgctc ccgccgagcc                                               20

<210> SEQ ID NO 808
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 808
aaatatgccg gacgcggtgg                                               20

<210> SEQ ID NO 809
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 809
cgcctttccg cggcgggagc                                               20

<210> SEQ ID NO 810
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 810
cccagcccag gccgcaggca                                               20

<210> SEQ ID NO 811
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 811
ccccgcaggg gacctcataa cccaa                                         25

<210> SEQ ID NO 812
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 812
gagttggctc ggcgtccctg gca                                           23

<210> SEQ ID NO 813
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 813
tccctccgcc tggtgggtcc cc                                            22

<210> SEQ ID NO 814
<211> LENGTH: 26
```

```
<212> TYPE: DNA
<213> ORGANISM: Artificial Sequence
<220> FEATURE:
<223> OTHER INFORMATION: probe/primer/pcr

<400> SEQUENCE: 814
tgacccctgg cacatcagga aagggc                                          26

<210> SEQ ID NO 815
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 815
tgccccgcaa gaacggccca g                                               21

<210> SEQ ID NO 816
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 816
ggcctcggag tgcgacgcga gc                                              22

<210> SEQ ID NO 817
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 817
gcgccaaccc agacccgcgc tt                                              22

<210> SEQ ID NO 818
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 818
tgcaagcgcg gaggctgcga                                                 20

<210> SEQ ID NO 819
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 819
agccgggcca cgggcagaca                                                 20

<210> SEQ ID NO 820
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 820
```

```
cccgggcggc cacaaagggc                                          20

<210> SEQ ID NO 821
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 821
ccccatccca ggtgaccgcc ctg                                      23

<210> SEQ ID NO 822
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 822
tgactctggg ggaagcacgc gacg                                     24

<210> SEQ ID NO 823
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 823
ggtgcggccg aagccgtcgc                                          20

<210> SEQ ID NO 824
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 824
tgcccctcgg gccctcgctg                                          20

<210> SEQ ID NO 825
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 825
ggccacgggg accggggaca                                          20

<210> SEQ ID NO 826
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 826
gggcgccgca gggcgacaac                                          20

<210> SEQ ID NO 827
<211> LENGTH: 24
<212> TYPE: DNA
<213> ORGANISM: Artificial Sequence
```

```
<220> FEATURE:
<223> OTHER INFORMATION: probe/primer/pcr

<400> SEQUENCE: 827
gcagcgcgct ttgggaagga aggc                                          24

<210> SEQ ID NO 828
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 828
gggttccacc cgcgcccacg                                               20

<210> SEQ ID NO 829
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 829
tcgcggccca gaccccgac                                                20

<210> SEQ ID NO 830
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 830
cgagacccgg tgcgcctggg ag                                            22

<210> SEQ ID NO 831
<211> LENGTH: 18
<212> TYPE: DNA
<213> ORGANISM: Artificial Sequence
<220> FEATURE:
<223> OTHER INFORMATION: probe/primer/pcr

<400> SEQUENCE: 831
aggtgcccgc caccatgc                                                 18

<210> SEQ ID NO 832
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 832
cgcccaggct ggagtgcagt ggc                                           23

<210> SEQ ID NO 833
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 833
gccggcgagg tctccgcggt ct                                            22
```

```
<210> SEQ ID NO 834
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 834
cgcagggcca ccggctcgga                                              20

<210> SEQ ID NO 835
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 835
gccccggagc atgcgcgaga                                              20

<210> SEQ ID NO 836
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 836
cccctgggga ccoctgccat cctt                                         24

<210> SEQ ID NO 837
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 837
ttaccccgcg ccgcgccacc                                              20

<210> SEQ ID NO 838
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 838
gcgggccgag cccaccaacc                                              20

<210> SEQ ID NO 839
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 839
gcgcggtggc cgcttggagg                                              20

<210> SEQ ID NO 840
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 840
cccgccagcg gcctgtgcct                                              20

<210> SEQ ID NO 841
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 841
cgcgcatgcc aagcccgctg                                              20

<210> SEQ ID NO 842
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 842
ggcgcaggag cagttggggt cca                                          23

<210> SEQ ID NO 843
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 843
tggggtaggc ggaacgccaa ggg                                          23

<210> SEQ ID NO 844
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 844
cccgcttcac gcccccaccg                                              20

<210> SEQ ID NO 845
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 845
gcagcccggg tgggcaaggc                                              20

<210> SEQ ID NO 846
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 846
tgcagttgcc cttgccctgc gac                                          23

<210> SEQ ID NO 847
```

```
<210> SEQ ID NO 847
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 847
tggccgggcg cctccatcgt                                        20

<210> SEQ ID NO 848
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 848
gcctgcgatg ggctcggtgg g                                      21

<210> SEQ ID NO 849
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 849
ccgcggttcg catggcgctc                                        20

<210> SEQ ID NO 850
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 850
tgggccatct cgagccgctg cc                                     22

<210> SEQ ID NO 851
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 851
tgggggagtg cgggtcggag c                                      21

<210> SEQ ID NO 852
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 852
ctgccgcgcc cccagcacct                                        20

<210> SEQ ID NO 853
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 853
```
ggctgctggc ggggccgtct                                        20

<210> SEQ ID NO 854
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 854
gggcgcggcg acttgggggt                                        20

<210> SEQ ID NO 855
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 855
aaactgcgac tgcgcggcgt gag                                    23

<210> SEQ ID NO 856
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 856
tgctggggcc gtggggtgc                                         20

<210> SEQ ID NO 857
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 857
tccgcgctgc ccgggtcctt                                        20

<210> SEQ ID NO 858
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 858
gtggcggccc ccgcggatct                                        20

<210> SEQ ID NO 859
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 859
ggggaggcgc caccgccgtt                                        20

<210> SEQ ID NO 860
<211> LENGTH: 20
<212> TYPE: DNA

```
<213> ORGANISM: Artificial Sequence
<220> FEATURE:
<223> OTHER INFORMATION: probe/primer/pcr

<400> SEQUENCE: 860
ggagcgggag ggcgctggga                                              20

<210> SEQ ID NO 861
<211> LENGTH: 32
<212> TYPE: DNA
<213> ORGANISM: Artificial Sequence
<220> FEATURE:
<223> OTHER INFORMATION: probe/primer/pcr

<400> SEQUENCE: 861
tgaaggctgt cagtcgtgga agtgagaagt gc                                32

<210> SEQ ID NO 862
<211> LENGTH: 33
<212> TYPE: DNA
<213> ORGANISM: Artificial Sequence
<220> FEATURE:
<223> OTHER INFORMATION: probe/primer/pcr

<400> SEQUENCE: 862
ggagaaaatc caattgaagg ctgtcagtcg tgg                               33

<210> SEQ ID NO 863
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 863
ggggacaacc ggggcggatc cc                                           22

<210> SEQ ID NO 864
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 864
cccgggagga gaggcgaaca gcg                                          23

<210> SEQ ID NO 865
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 865
agtgcgcggg tgccgggtgg                                              20

<210> SEQ ID NO 866
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 866
tggcatcccc tacccgggcc cta                                          23
```

<210> SEQ ID NO 867
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 867
gaggctggtt ccttgtcgtc ggttggg                                        27

<210> SEQ ID NO 868
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 868
gcggggtcag gccggggtca                                                20

<210> SEQ ID NO 869
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 869
ggcagcggct ggagcggtgt ca                                             22

<210> SEQ ID NO 870
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 870
gcccgggcac acgccccatc                                                20

<210> SEQ ID NO 871
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 871
gcaccgccac gcccactgcc                                                20

<210> SEQ ID NO 872
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 872
tgtcatgctt ctttctcccc actgactca                                      29

<210> SEQ ID NO 873
<211> LENGTH: 22
<212> TYPE: DNA
<213> ORGANISM: Artificial Sequence
<220> FEATURE:

<223> OTHER INFORMATION: probe/primer/pcr

<400> SEQUENCE: 873
gcccaggctg gggtgcaatg gc                                          22

<210> SEQ ID NO 874
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 874
cgcctcgggg gccacggcat                                             20

<210> SEQ ID NO 875
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 875
cgtgggtcct ggcccgggga                                             20

<210> SEQ ID NO 876
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 876
tccccgggcg gccattaggc a                                           21

<210> SEQ ID NO 877
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 877
ggcgggggtg ggagtgatcc c                                           21

<210> SEQ ID NO 878
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 878
cgtcagtccc ggctgcgagt cca                                         23

<210> SEQ ID NO 879
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 879
ccggggtccg cgccatgctg                                             20

```
<210> SEQ ID NO 880
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 880
catggcgggg cccgagcgac                                         20

<210> SEQ ID NO 881
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 881
ccgcctcctt gccccgacac cc                                      22

<210> SEQ ID NO 882
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 882
tcggacacgc cttcgcctca gcc                                     23

<210> SEQ ID NO 883
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 883
cgagctgggc gcaggcgcaa                                         20

<210> SEQ ID NO 884
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 884
gcggggttgt gtgtggcgga gg                                      22

<210> SEQ ID NO 885
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 885
accgcgcccg gcctgcaaag                                         20

<210> SEQ ID NO 886
<211> LENGTH: 21
<212> TYPE: DNA
<213> ORGANISM: Artificial Sequence
<220> FEATURE:
<223> OTHER INFORMATION: probe/primer/pcr
```

```
<400> SEQUENCE: 886
gcggggccag agaggccgga a                                          21

<210> SEQ ID NO 887
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 887
gccccaaggg aagatgcagg gaggaa                                     26

<210> SEQ ID NO 888
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 888
gccccaaggg aagatgcagg gaggaa                                     26

<210> SEQ ID NO 889
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 889
gcccgcacgt gcaccaccca                                            20

<210> SEQ ID NO 890
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 890
gggtgacgaa gtggtgtctt taccgagga                                  29

<210> SEQ ID NO 891
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 891
ccgccgtgcg cctgtgggaa                                            20

<210> SEQ ID NO 892
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 892
ggctgctgcg ggaggatcac                                            20

<210> SEQ ID NO 893
<211> LENGTH: 29
```

```
<212> TYPE: DNA
<213> ORGANISM: Artificial Sequence
<220> FEATURE:
<223> OTHER INFORMATION: probe/primer/pcr

<400> SEQUENCE: 893
tgggcatcca gaaaaatggt ggtgatggc                                   29

<210> SEQ ID NO 894
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 894
gccgcgccgg gccctatgag                                             20

<210> SEQ ID NO 895
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 895
ccgccatgcg ggcagggacc                                             20

<210> SEQ ID NO 896
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 896
tgttacaggc tggacacggt ggctc                                       25

<210> SEQ ID NO 897
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 897
cggaacttgc aggggggccga                                            20

<210> SEQ ID NO 898
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 898
tgcaaaatcc tcccttccc gcaccc                                       26

<210> SEQ ID NO 899
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 899
```
gcgctggagc cacgcgacga                                                     20

<210> SEQ ID NO 900
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 900
ggggtccgct cccgcgttcg                                                     20

<210> SEQ ID NO 901
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 901
cgccccgggc tgagagctgg gt                                                  22

<210> SEQ ID NO 902
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 902
ggcccttcgg gggccgggtt                                                     20

<210> SEQ ID NO 903
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 903
tggccacaaa ggggccggaa tgg                                                 23

<210> SEQ ID NO 904
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 904
accccagcgc gtgggcggag                                                     20

<210> SEQ ID NO 905
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 905
gggctgcggg gcgccttgac                                                     20

<210> SEQ ID NO 906
<211> LENGTH: 20
<212> TYPE: DNA
<213> ORGANISM: Artificial Sequence

```
<220> FEATURE:
<223> OTHER INFORMATION: probe/primer/pcr

<400> SEQUENCE: 906
gcaccgcggc tggagcggac                                                 20

<210> SEQ ID NO 907
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 907
aggcgatccc aaggctgttg gaggc                                           25

<210> SEQ ID NO 908
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 908
tccacccgcc ttggcctccc a                                               21

<210> SEQ ID NO 909
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 909
cggcgggaag gcggggcaag                                                 20

<210> SEQ ID NO 910
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 910
ggagccgcgg cgtgagtgcg                                                 20

<210> SEQ ID NO 911
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 911
ggccggcacc ccacgccaag                                                 20

<210> SEQ ID NO 912
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 912
gcggggcgga gcgcacacct                                                 20
```

```
<210> SEQ ID NO 913
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 913
gcggccagca gcgcgtcctc                                           20

<210> SEQ ID NO 914
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 914
ccgacagccg gcaaggccca a                                         21

<210> SEQ ID NO 915
<211> LENGTH: 30
<212> TYPE: DNA
<213> ORGANISM: Artificial Sequence
<220> FEATURE:
<223> OTHER INFORMATION: probe/primer/pcr

<400> SEQUENCE: 915
ttgtttttgt ttgtttgttt tgaaagggag                                30

<210> SEQ ID NO 916
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 916
ccccggtttc cccgcgcctc                                           20

<210> SEQ ID NO 917
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 917
ggctggacgc gccctccgac a                                         21

<210> SEQ ID NO 918
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 918
tcccacgcgc ccgcccctac                                           20

<210> SEQ ID NO 919
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 919
cggccacgcc ttccgcggtg                                              20

<210> SEQ ID NO 920
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 920
ggctccgctg gggcgcaggt                                              20

<210> SEQ ID NO 921
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 921
gccgccccgt gtcgtgcgtc                                              20

<210> SEQ ID NO 922
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 922
ggcgtcagtt ggagtgtggg gtcgg                                        25

<210> SEQ ID NO 923
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 923
ccgagcgggg tgggccggat                                              20

<210> SEQ ID NO 924
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 924
catcgcgcgg gacccaaccc a                                            21

<210> SEQ ID NO 925
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 925
cagtgggtgg atctcacctg ccttcgg                                      27

<210> SEQ ID NO 926
```

```
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 926
gaggccgcgg ggctccgaca                                        20

<210> SEQ ID NO 927
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 927
gagcctgccc tataaaatcc ggggctcg                               28

<210> SEQ ID NO 928
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 928
tcccggcggg tggtgcctga                                        20

<210> SEQ ID NO 929
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 929
tctgagcgcc cgccgcctgc                                        20

<210> SEQ ID NO 930
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 930
ggctgccggc gcgggaccta                                        20

<210> SEQ ID NO 931
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 931
tccggggcat tccctccgcg at                                     22

<210> SEQ ID NO 932
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 932
```
tggcggcggc ccctgctcgt                                               20

<210> SEQ ID NO 933
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 933
cggcgcgcga ctgggaggga                                               20

<210> SEQ ID NO 934
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 934
ggcgccagcg caaccagagc g                                             21

<210> SEQ ID NO 935
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 935
cgaaggtggc gcggcctgga                                               20

<210> SEQ ID NO 936
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 936
cccagcgggc ttcgcgggag                                               20

<210> SEQ ID NO 937
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 937
cccgcttgcc ccgcccccta                                               20

<210> SEQ ID NO 938
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 938
cccacacctc cacctgctgg tgcct                                         25

<210> SEQ ID NO 939
<211> LENGTH: 20
<212> TYPE: DNA

```
<213> ORGANISM: Artificial Sequence
<220> FEATURE:
<223> OTHER INFORMATION: probe/primer/pcr

<400> SEQUENCE: 939
atgcagcccc gccggcaacg                                              20

<210> SEQ ID NO 940
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 940
ccggatgccc ggtgtgcctg g                                            21

<210> SEQ ID NO 941
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 941
gcgagcaggg acgcagctct ggtg                                         24

<210> SEQ ID NO 942
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 942
cgcgctcggc ccgctcagtg                                              20

<210> SEQ ID NO 943
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 943
tggtgccggc agggagggga                                              20

<210> SEQ ID NO 944
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 944
gggcggtggc gatggctggc                                              20

<210> SEQ ID NO 945
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 945
ggctgttggt cttttttccca gccccgaa                                    28
```

<210> SEQ ID NO 946
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 946
ccgggccggc agcgcagatg t                                              21

<210> SEQ ID NO 947
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 947
cggagggcga tggggccctg                                                20

<210> SEQ ID NO 948
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 948
ggggccgggc tgcgaagctg                                                20

<210> SEQ ID NO 949
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 949
tgcctgggca ccccacggac g                                              21

<210> SEQ ID NO 950
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 950
gccctacgtc cgggcagcac gc                                             22

<210> SEQ ID NO 951
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 951
ctgtgcgcgt ccccgccgtg                                                20

<210> SEQ ID NO 952
<211> LENGTH: 20
<212> TYPE: DNA
<213> ORGANISM: Artificial Sequence
<220> FEATURE:

<223> OTHER INFORMATION: probe/primer/pcr

<400> SEQUENCE: 952
tgcagcggcg cctcggaccc                                           20

<210> SEQ ID NO 953
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 953
ccgctgggcg cgctgggaag                                           20

<210> SEQ ID NO 954
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 954
ggcgcatgct ctgcgcgtat tggc                                      24

<210> SEQ ID NO 955
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 955
gggtgggcgg gccgttctga gg                                        22

<210> SEQ ID NO 956
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 956
gggctgccgg gttggcgcag                                           20

<210> SEQ ID NO 957
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 957
ggcgcgtgcg gaaaagctgc g                                         21

<210> SEQ ID NO 958
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 958
tccaggccgc cctcgggtca                                           20

```
<210> SEQ ID NO 959
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 959
ggggaggggg cgcagccaga                                              20

<210> SEQ ID NO 960
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 960
ggcagcgtgg tcttccactt cccct                                        26

<210> SEQ ID NO 961
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 961
gggatcgagg gatcgaggca gggga                                        25

<210> SEQ ID NO 962
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 962
cggccatgag cgcctccacg c                                            21

<210> SEQ ID NO 963
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 963
cccggtgtgc ggcagcgacg                                              20

<210> SEQ ID NO 964
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 964
ttggggcggc cggaagccag                                              20

<210> SEQ ID NO 965
<211> LENGTH: 20
<212> TYPE: DNA
<213> ORGANISM: Artificial Sequence
<220> FEATURE:
<223> OTHER INFORMATION: probe/primer/pcr
```

```
<400> SEQUENCE: 965
cgcagcggcg gcgtctcggt                                                   20

<210> SEQ ID NO 966
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 966
ccgcgacctc cccaagccac cc                                                22

<210> SEQ ID NO 967
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 967
ggcggccgac cgcgaacacc                                                   20

<210> SEQ ID NO 968
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 968
ccccatttcc gagtccggca gca                                               23

<210> SEQ ID NO 969
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 969
cccagcctgg cctctcctct caggca                                            26

<210> SEQ ID NO 970
<211> LENGTH: 29
<212> TYPE: DNA
<213> ORGANISM: Artificial Sequence
<220> FEATURE:
<223> OTHER INFORMATION: probe/primer/pcr

<400> SEQUENCE: 970
cggctctttc ctcctcaaga gatgcggtg                                         29

<210> SEQ ID NO 971
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 971
cgccgccgtc cctggtgcag                                                   20

<210> SEQ ID NO 972
<211> LENGTH: 20
```

```
<212> TYPE: DNA
<213> ORGANISM: Artificial Sequence
<220> FEATURE:
<223> OTHER INFORMATION: probe/primer/pcr

<400> SEQUENCE: 972
tggggacccc tcgccgcctg                                               20

<210> SEQ ID NO 973
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 973
gcgcccagcc cgccccaaga                                               20

<210> SEQ ID NO 974
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 974
caggggacgc gggcgtgcag                                               20

<210> SEQ ID NO 975
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 975
ccgggcgggg cccaactgct                                               20

<210> SEQ ID NO 976
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 976
cccgagcagg gccggagcag a                                             21

<210> SEQ ID NO 977
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 977
cccctccaca ttcccgcggt cct                                           23

<210> SEQ ID NO 978
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 978
```

| | |
|---|---|
| tcctttgtgg cctgggcagg atgcag | 26 |

<210> SEQ ID NO 979
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 979

| | |
|---|---|
| gcagcgcgcg gtttggggct | 20 |

<210> SEQ ID NO 980
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 980

| | |
|---|---|
| gaggcctgcg ggcgctgctg | 20 |

<210> SEQ ID NO 981
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 981

| | |
|---|---|
| tcacggttgc tgggccgtcg c | 21 |

<210> SEQ ID NO 982
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 982

| | |
|---|---|
| cggggtgggc ctcgcggaga | 20 |

<210> SEQ ID NO 983
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 983

| | |
|---|---|
| gcctgcgctc ctggcgccct | 20 |

<210> SEQ ID NO 984
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 984

| | |
|---|---|
| cgccttcgga gagcagagtc aacacgga | 28 |

<210> SEQ ID NO 985
<211> LENGTH: 28
<212> TYPE: DNA
<213> ORGANISM: Artificial Sequence

```
<220> FEATURE:
<223> OTHER INFORMATION: probe/primer/pcr

<400> SEQUENCE: 985
tgcccctaaa tgagaaaggg cccttgag                                      28

<210> SEQ ID NO 986
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 986
gccacgcccc gggaccggaa                                               20

<210> SEQ ID NO 987
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 987
tcccgcccag gggcctccca                                               20

<210> SEQ ID NO 988
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 988
ccccgcgccc ggccaaagaa                                               20

<210> SEQ ID NO 989
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 989
ggaccgccgc acagcccaa                                                20

<210> SEQ ID NO 990
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 990
gggcagcggt ggccgtgcat                                               20

<210> SEQ ID NO 991
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 991
ttcctgcgcc gccccctccc                                               20
```

```
<210> SEQ ID NO 992
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 992
ggcgtctccc tgtccccgcc tg                                              22

<210> SEQ ID NO 993
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 993
gccggcctcg cgcaccgtgt                                                 20

<210> SEQ ID NO 994
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 994
cccgggacgt gcgcgcttgg                                                 20

<210> SEQ ID NO 995
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 995
tgtcccccga gccgccctgc                                                 20

<210> SEQ ID NO 996
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 996
tcgctctcgt gcagcggcgt ca                                              22

<210> SEQ ID NO 997
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 997
cccgcgcgct gcagcatctc c                                               21

<210> SEQ ID NO 998
<211> LENGTH: 20
<212> TYPE: DNA
<213> ORGANISM: Artificial Sequence
<220> FEATURE:
<223> OTHER INFORMATION: probe/primer/pcr
```

<400> SEQUENCE: 998
ccccagctgc cgccatcgca                                             20

<210> SEQ ID NO 999
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 999
gcccgggccc gcctcaagga                                             20

<210> SEQ ID NO 1000
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 1000
tgccggcgag gccttttctc gg                                          22

<210> SEQ ID NO 1001
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1001
ggcgggtggg gagcgcgaac                                             20

<210> SEQ ID NO 1002
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1002
cccgccgccg ctggtcacct                                             20

<210> SEQ ID NO 1003
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1003
ccggctgcct cggcctccca                                             20

<210> SEQ ID NO 1004
<211> LENGTH: 18
<212> TYPE: DNA
<213> ORGANISM: Artificial Sequence
<220> FEATURE:
<223> OTHER INFORMATION: probe/primer/pcr

<400> SEQUENCE: 1004
ggtgtgcacc accacgcc                                               18

<210> SEQ ID NO 1005

<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1005
ggcgcgtccc ggcggcttct                                               20

<210> SEQ ID NO 1006
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1006
agtccctgcg ccccgccctg                                               20

<210> SEQ ID NO 1007
<211> LENGTH: 24
<212> TYPE: DNA
<213> ORGANISM: Artificial Sequence
<220> FEATURE:
<223> OTHER INFORMATION: probe/primer/pcr

<400> SEQUENCE: 1007
tgcccccaaa ctttccgcct gcac                                          24

<210> SEQ ID NO 1008
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1008
cttgcggcca cccggcgagc                                               20

<210> SEQ ID NO 1009
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 1009
tcgcgcggaa actctggctc gg                                            22

<210> SEQ ID NO 1010
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 1010
gctgcggccc agaggggtg a                                              21

<210> SEQ ID NO 1011
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1011
cggcgggctt gggtcccgtg                                              20

<210> SEQ ID NO 1012
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1012
tcccccgccg caccagcacc                                              20

<210> SEQ ID NO 1013
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1013
gcgcggtgcg gggacctgct                                              20

<210> SEQ ID NO 1014
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1014
gccggacgct cgccccgcat                                              20

<210> SEQ ID NO 1015
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 1015
gagtgctctg cagccccgac atggg                                        25

<210> SEQ ID NO 1016
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 1016
ccgcgcagac gtcggagccc aa                                           22

<210> SEQ ID NO 1017
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1017
tggccgaggc gcgtggcgag                                              20

<210> SEQ ID NO 1018
<211> LENGTH: 20
<212> TYPE: DNA

```
<213> ORGANISM: Artificial Sequence
<220> FEATURE:
<223> OTHER INFORMATION: probe/primer/pcr

<400> SEQUENCE: 1018
ggccgcgctg ccccagggat                                          20

<210> SEQ ID NO 1019
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1019 ccggggggcgg acgcagagga                                          20

<210> SEQ ID NO 1020
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 1020
gggggcggag cctgggaatg gg                                       22

<210> SEQ ID NO 1021
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1021
gggcgggccc tgtgggtgga                                          20

<210> SEQ ID NO 1022
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 1022
ccgctccccc atctccacgg acg                                      23

<210> SEQ ID NO 1023
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1023
gacccaggga ggcgcgggga                                          20

<210> SEQ ID NO 1024
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1024
tgcccggccg caggtgacca                                          20
```

<210> SEQ ID NO 1025
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1025
gcgccgggag tgggcaggga                                                 20

<210> SEQ ID NO 1026
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1026
acccaggccg gcgcgggaag                                                 20

<210> SEQ ID NO 1027
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1027
ttcccgccgc ccggtcctca                                                 20

<210> SEQ ID NO 1028
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1028
cgcgccggtg acggacgtgg                                                 20

<210> SEQ ID NO 1029
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 1029
aaccctccca gccaaaacgg gctca                                           25

<210> SEQ ID NO 1030
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1030
cgggcgaggc cgccctttgg                                                 20

<210> SEQ ID NO 1031
<211> LENGTH: 20
<212> TYPE: DNA
<213> ORGANISM: Artificial Sequence
<220> FEATURE:

<223> OTHER INFORMATION: probe/primer/pcr

<400> SEQUENCE: 1031
ggccgcggac gcccaggaaa                                              20

<210> SEQ ID NO 1032
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 1032
ccgtttggaa cgtggcccaa gaggc                                        25

<210> SEQ ID NO 1033
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1033
cccgcctccg ctccccgctt                                              20

<210> SEQ ID NO 1034
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 1034
ggtggcggcg gcagaggagg a                                            21

<210> SEQ ID NO 1035
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1035
cgcggggagc agaggcggtg                                              20

<210> SEQ ID NO 1036
<211> LENGTH: 19
<212> TYPE: DNA
<213> ORGANISM: Artificial Sequence
<220> FEATURE:
<223> OTHER INFORMATION: probe/primer/pcr

<400> SEQUENCE: 1036
gggcgcccgc gctgagggt                                               19

<210> SEQ ID NO 1037
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1037
gggcctggcc tcccggcgat                                              20

```
<210> SEQ ID NO 1038
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1038
cacccggcgt ccgcaccagc                                               20

<210> SEQ ID NO 1039
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1039
cggcgctggt ttggcggcct                                               20

<210> SEQ ID NO 1040
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 1040
ccaggagccc cggaggccac g                                             21

<210> SEQ ID NO 1041
<211> LENGTH: 26
<212> TYPE: DNA
<213> ORGANISM: Artificial Sequence
<220> FEATURE:
<223> OTHER INFORMATION: probe/primer/pcr

<400> SEQUENCE: 1041
gcgatctcct gcccaggtgt gtgctc                                        26

<210> SEQ ID NO 1042
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1042
actgcccggg ctcgccgcac                                               20

<210> SEQ ID NO 1043
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1043
tgcggcaacg gtggcacccc                                               20

<210> SEQ ID NO 1044
<211> LENGTH: 24
<212> TYPE: DNA
<213> ORGANISM: Artificial Sequence
<220> FEATURE:
<223> OTHER INFORMATION: probe/primer/pcr
```

```
<400> SEQUENCE: 1044
ggagcgaagc tggcggaacc cacc                                    24

<210> SEQ ID NO 1045
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1045
ggcggccgac ggggctttgc                                         20

<210> SEQ ID NO 1046
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1046
ggccgcgggt gcctcggtct                                         20

<210> SEQ ID NO 1047
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 1047
gcgctccagc catggcgcgt t                                       21

<210> SEQ ID NO 1048
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1048
gccggacggg cgtggggaga                                         20

<210> SEQ ID NO 1049
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1049
tcccccgcga ctgcccctcc                                         20

<210> SEQ ID NO 1050
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1050
gggtggcagc gggtgcggaa                                         20

<210> SEQ ID NO 1051
<211> LENGTH: 20
```

-continued

```
<212> TYPE: DNA
<213> ORGANISM: Artificial Sequence
<220> FEATURE:
<223> OTHER INFORMATION: probe/primer/pcr

<400> SEQUENCE: 1051
gctcgcccgc tcgcagccaa                                              20

<210> SEQ ID NO 1052
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 1052
cgaggttccg cagcccgagc ca                                           22

<210> SEQ ID NO 1053
<211> LENGTH: 21
<212> TYPE: DNA
<213> ORGANISM: Artificial Sequence
<220> FEATURE:
<223> OTHER INFORMATION: probe/primer/pcr

<400> SEQUENCE: 1053
gcgcggggga ccgaaaccgt g                                            21

<210> SEQ ID NO 1054
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1054
gccgagcccg gcccaaagcc                                              20

<210> SEQ ID NO 1055
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 1055
tgccaacgtt cacccggctg gc                                           22

<210> SEQ ID NO 1056
<211> LENGTH: 28
<212> TYPE: DNA
<213> ORGANISM: Artificial Sequence
<220> FEATURE:
<223> OTHER INFORMATION: probe/primer/pcr

<400> SEQUENCE: 1056
gacagtgcga gggaaaacca ccttcccc                                     28

<210> SEQ ID NO 1057
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1057
```
gggtcgggcc gggctggagc                                                        20

<210> SEQ ID NO 1058
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1058
gggtcgggcc gggctggagc                                                        20

<210> SEQ ID NO 1059
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1059
gcggggccga ggggctgagc                                                        20

<210> SEQ ID NO 1060
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1060
gcccggccac ctcggggagc                                                        20

<210> SEQ ID NO 1061
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 1061
actgtctgcc aagccagccc caggg                                                  25

<210> SEQ ID NO 1062
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1062
ggatggtggc gccgggctgc                                                        20

<210> SEQ ID NO 1063
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 1063
tccaggaggg ccaggtcaca gctgc                                                  25

<210> SEQ ID NO 1064
<211> LENGTH: 21
<212> TYPE: DNA
<213> ORGANISM: Artificial Sequence

```
<220> FEATURE:
<223> OTHER INFORMATION: probe/primer/pcr

<400> SEQUENCE: 1064
cggctggctc gcttggctgg c                                        21

<210> SEQ ID NO 1065
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1065
tccggcgctg ttgggcagcc                                          20

<210> SEQ ID NO 1066
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1066
cctgcgcacg cgggaagggc                                          20

<210> SEQ ID NO 1067
<211> LENGTH: 27
<212> TYPE: DNA
<213> ORGANISM: Artificial Sequence
<220> FEATURE:
<223> OTHER INFORMATION: probe/primer/pcr

<400> SEQUENCE: 1067
tcttcccttc tttcccacgc tgctccg                                  27

<210> SEQ ID NO 1068
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1068
cagcgccccc gcctccagca                                          20

<210> SEQ ID NO 1069
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1069
gctgcgcggc tggcgatcca                                          20

<210> SEQ ID NO 1070
<211> LENGTH: 22
<212> TYPE: DNA
<213> ORGANISM: Artificial Sequence
<220> FEATURE:
<223> OTHER INFORMATION: probe/primer/pcr

<400> SEQUENCE: 1070
gccgacgacc ggagggccca ct                                       22
```

<210> SEQ ID NO 1071
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1071
tgcccaggct ggcccctcgg                                          20

<210> SEQ ID NO 1072
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1072
cgcggccctc cccagccctc                                          20

<210> SEQ ID NO 1073
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1073
ccccgcccgg caactgagcg                                          20

<210> SEQ ID NO 1074
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1074
aagagcccgc gcgccgagcc                                          20

<210> SEQ ID NO 1075
<211> LENGTH: 23
<212> TYPE: DNA
<213> ORGANISM: Artificial Sequence
<220> FEATURE:
<223> OTHER INFORMATION: probe/primer/pcr

<400> SEQUENCE: 1075
tgcccactgc ggttaccccg cat                                      23

<210> SEQ ID NO 1076
<211> LENGTH: 25
<212> TYPE: DNA
<213> ORGANISM: Artificial Sequence
<220> FEATURE:
<223> OTHER INFORMATION: probe/primer/pcr

<400> SEQUENCE: 1076
gcatggtggt ggacatgtgc ggtca                                    25

<210> SEQ ID NO 1077
<211> LENGTH: 33
<212> TYPE: DNA
<213> ORGANISM: Artificial Sequence
<220> FEATURE:
<223> OTHER INFORMATION: probe/primer/pcr

```
<400> SEQUENCE: 1077
catagaagag gaaggcaaag gctgtgacag gca                                      33

<210> SEQ ID NO 1078
<211> LENGTH: 32
<212> TYPE: DNA
<213> ORGANISM: Artificial Sequence
<220> FEATURE:
<223> OTHER INFORMATION: probe/primer/pcr

<400> SEQUENCE: 1078
tcatcctaga cttgcagtca agatgcctgc cc                                       32

<210> SEQ ID NO 1079
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1079
agccagcggt gccggtgccc                                                     20

<210> SEQ ID NO 1080
<211> LENGTH: 20
<212> TYPE: DNA
<213> ORGANISM: Artificial Sequence
<220> FEATURE:
<223> OTHER INFORMATION: probe/primer/pcr

<400> SEQUENCE: 1080
gccccgctcc gccccagtgc                                                     20

<210> SEQ ID NO 1081
<211> LENGTH: 219
<212> TYPE: DNA
<213> ORGANISM: Artificial Sequence
<220> FEATURE:
<223> OTHER INFORMATION: probe/primer/pcr

<400> SEQUENCE: 1081
cacgggggcg gggagacgcg gggtgcactt ctcgccccga gggcctccgg cgaagcaacc         60
cggcagccgc ggcgcccgag ggcctggcgc tggtctgggg ctgcgccggg ggcgcctggc        120
tctggggtgc ggccggtcag gaatcccat cctggagcgc aggcggagag ccagtggctg        180
ggggcgggaa ggcttcttgg acccctcgcg cttctccga                               219

<210> SEQ ID NO 1082
<211> LENGTH: 243
<212> TYPE: DNA
<213> ORGANISM: Artificial Sequence
<220> FEATURE:
<223> OTHER INFORMATION: probe/primer/pcr

<400> SEQUENCE: 1082
cacagggtgg ggcagggagc atcaggggggc aggcagccac acccccgaca catcaagaca        60
cctgagtggc aggttcaagc cggaggcgct gtatttccac acaggaagaa ggccaaaaaa       120
ggtgacactg cccccctccca gtggctccat gctcctcagc tatggctgtc cgggccgcct      180
cactcaaagc cttgccctcc gctgctgcca ggctccttgc atgcaaggca gcccccaccc      240
ggc                                                                     243
```

```
<210> SEQ ID NO 1083
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1083
accgggcctt ccgcgcccct cgccccacgc cgcgggtgcg gtcctccctc cagcagaggg      60
ttccgggcgc cggcgcggcc cgcacggggc cgggagccct tcctgccggc cgggtgcgcg     120
cggcgccgcc gacagctgtt tgccatcggc gccgctcccg cccgcgtccc ggtgcgcgcc     180
ccgcccccgc caacaaccgc cgctctgatt ggcccggcgc ttgtctcttc tctccccgca     240
gccaatcgcg ccggg                                                      255

<210> SEQ ID NO 1084
<211> LENGTH: 231
<212> TYPE: DNA
<213> ORGANISM: Artificial Sequence
<220> FEATURE:
<223> OTHER INFORMATION: probe/primer/pcr

<400> SEQUENCE: 1084
cccacctccc ccaacattcc agttccttct tttccttcta ctcttcagcg gcctcagcct      60
gcgcacccca ggagcgtgga tgactacggc caccccgggc gcgcaccct ttcccaccac      120 cccagcatct ctgcagccca ggacacccgc ctcccccaca cccgcatcc ggtgtgtctc      180 cgcctggccc ggccggcgcg gcaggcgggc cagggacca actgcacggc c               231

<210> SEQ ID NO 1085
<211> LENGTH: 174
<212> TYPE: DNA
<213> ORGANISM: Artificial Sequence
<220> FEATURE:
<223> OTHER INFORMATION: probe/primer/pcr

<400> SEQUENCE: 1085
cacagagcca ggcaagcatg ggtgagagct cagaccatcc ttgttggact aaaaggaagg      60
ggcagactgc ccatgggggg cagccgagag ggtcaggccc ccataggtcc tcagcctgct     120
tcaacctcaa aggggatggg gggctgagtg gtgccagagg agcagcaggc tcgc            174

<210> SEQ ID NO 1086
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1086
ggagcagcag gctcgctcgg ggagagtagg gccttaggat agaagggaaa tgaactaaac      60
aaccagcttc ctcccaaacc agtttcaggc cagggctggg aatttcacaa aaaagcagaa     120
ggcgctctgt gaacatttcc tgccccgccc cagccccctt cctggcagca ttaccacact     180
gctcacctgt gaagcaatct tccggagaca gggccaaagg gccaagtgcc ccagtcagga     240
gctgcctata aatgc                                                      255

<210> SEQ ID NO 1087
<211> LENGTH: 255
<212> TYPE: DNA
<213> ORGANISM: Artificial Sequence
```

<220> FEATURE:
<223> OTHER INFORMATION: probe/primer/pcr

<400> SEQUENCE: 1087

```
gcccaaagtg cggggccaac ccagacagtc ccacttacca ggtcttctga aagacagctg    60
acaagagaca tgcagggctg agaggcagct cctttttata gcggttaggc ttggccagct   120
gcccacagct tcaggccatc agagacagct tctccctgcc agagttgcta cagtctctgg   180
tttctcaacc aggtgaatgt ggcaatcact gtgcagaatg aaaatttttgg gtggggaggt   240 aggagaagcg gaaag                                                    255
```

<210> SEQ ID NO 1088
<211> LENGTH: 167
<212> TYPE: DNA
<213> ORGANISM: Artificial Sequence
<220> FEATURE:
<223> OTHER INFORMATION: probe/primer/pcr

<400> SEQUENCE: 1088

```
ggaaagagga aggcatttgc tgggcaatag tgcccagaag gaaaaagcag gtagggggggc    60 tcttttttctg ggctgctggc atccactttgc ttgatccagc cagattccca ctcccatgcc   120
ctctccacta ttgcgattgc taatcccctg cattggtggt caggcca                 167
```

<210> SEQ ID NO 1089
<211> LENGTH: 236
<212> TYPE: DNA
<213> ORGANISM: Artificial Sequence
<220> FEATURE:
<223> OTHER INFORMATION: probe/primer/pcr

<400> SEQUENCE: 1089

```
cagcggcccc gcgggatttt gcccagctgc ttcgtgccct ctggtggcta aggcgtgtca    60
ttgcagtgcc ggcctcctgt catcctccct ttcttgtccg ccagaccctc tggcgccctg   120
cttacgactc aaacaggaga cagtgctgat tcatttccaa gcggccttcc tacacccaca   180
cctgcttcac atagatgagg tttccccggac agtccctgcc cagaagccca ggtgga      236
```

<210> SEQ ID NO 1090
<211> LENGTH: 210
<212> TYPE: DNA
<213> ORGANISM: Artificial Sequence
<220> FEATURE:
<223> OTHER INFORMATION: probe/primer/pcr

<400> SEQUENCE: 1090

```
ccgacagcgc ccggcccaga tccccacgcc tgccaggagc aagccgagag ccagccggcc    60
ggcgcactcc gactccgagc agtctctgtc cttcgaccccg agcccgcgc ctttccgggg   120 acccctgccc cgcgggcagc gctgccaacc tgccggccat ggagacccccg tcccagcggc   180 gcgccacccg cagcggggcg caggccagct                                    210
```

<210> SEQ ID NO 1091
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1091

```
gggccaatcc ccgcggctgg gcagagcgac ccgagggcgg cgccctgcag accacgtggc    60
```

```
ccgggaggcg ccgaggccag gtaggtggtg agttacttgg ctcggagcgg gcgaggggac    120
gcgtgggcgg agcggggctg gccagcctcg gcccccatga cccgctgtcc tgtgcccttt    180
cccagcgatg ggcgtgcagc cccccaactt ctcctgggtg cttccgggcc ggctggcggg    240
actggcgctg ccgcg                                                     255
```

<210> SEQ ID NO 1092
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1092

```
ggcggctgcg gggagcgatt ttccagcccg gtttgtgctc tgtgtgtttg tctgcctctg     60
gagggctggg tcctccttat tcacaggtga gtcacaccct gaaacacagg ctctcttcct    120
gtcaggactg agtcaggtag aagagtcgat aaaaccacct gatcaaggaa aaggaaggca    180
cagcggagcg cagagtgaga accaccaacc gaggcgccgg gcagcgaccc ctgcagcgga    240
gacagagact gagcg                                                     255
```

<210> SEQ ID NO 1093
<211> LENGTH: 155
<212> TYPE: DNA
<213> ORGANISM: Artificial Sequence
<220> FEATURE:
<223> OTHER INFORMATION: probe/primer/pcr

<400> SEQUENCE: 1093

```
gccaggaccg cgcacagcag cagggcgcgg gcgagcatcg cagcggcggg cagggcgcgg     60 cgcggggta ggctttgctg tctgagggcg tctggctgtg gagctgaagg aggcgctgct    120
gaggagttcc tggacgtgct cctgacgctc actgc                               155
```

<210> SEQ ID NO 1094
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1094

```
cgggcaagag agcgcgggag gaggaggagg agaaaaagga ggaggaggag gaggaggagg     60 cggcccccgca tccctaatga gggaatgaat ggagaggccc cctcggctgg cgcccgccca    120
cccggcggcg gccgccaagt gcctctgggc gctgcgtgcc gcgcccgctg ctccgcgcgc    180
agccggctcg ggccgctcct cctgactgag gcgcggcggc ggcggtggct gtgaccgcgc    240
ggaccgagcc gagac                                                     255
```

<210> SEQ ID NO 1095
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1095

```
gcgcgcagcc aggggcgacg cttccgctcc gagccgcggc ccggggccac gcgctaaggg     60
cccgaacttg gcagctgacc gtcccggaca ggggaggccct tcagcctcga cgcggcctgc   120
gtcctccgga gggccctgct ccgcccggga agcgtccgcc tcccgcccgc ccgcccgcag    180
```

```
atgtcgctgc ccctctggct gtcccggcct gaccgccgcg cgccgccctg ctgctcacct    240
acttccgcgc cacgg                                                     255

<210> SEQ ID NO 1096
<211> LENGTH: 215
<212> TYPE: DNA
<213> ORGANISM: Artificial Sequence
<220> FEATURE:
<223> OTHER INFORMATION: probe/primer/pcr

<400> SEQUENCE: 1096
gtgcgctcac ccagccgcag gcgcctgagc ggccagagcc gccaccgaac acgccgcacc    60
ggccaccgcc gttccctgat agattgctga tgcctggccg cgggaacgcc cacggaaccc    120
gcgtccacgg ggcggggccg gcggcgcgcg cgccccctgc cggccggggg gcggagtttc    180
ccgggcgcct gccgggtgga gctctgcggg ccgct                               215

<210> SEQ ID NO 1097
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1097
gagggcccgg ggtggggctg cgccctgagg gccctgccct gccctccgca cgcctctggc    60
cacggtccct tccccggctg tgggtctgcg gcccctgcgt gcgcagcgct cctggcctct    120
gcggccagcg cggggcgga gagaggagag tgcccggcag gcggcggctg ggccggcccg    180
gaactgggtc gtggaaggat cgcggggagc ggccctcagg ccttcggcct cactgcgtcc    240
ccacttccct gcgcc                                                     255

<210> SEQ ID NO 1098
<211> LENGTH: 217
<212> TYPE: DNA
<213> ORGANISM: Artificial Sequence
<220> FEATURE:
<223> OTHER INFORMATION: probe/primer/pcr

<400> SEQUENCE: 1098
tatgcgcccg gcgcggtggc tcacgcctgt aatcccagca ctttgggagg ccgaggcggg    60
cggatcacga ggtcaggaga tcgagaccat cctgactaac acggtgaaac cccgtctcta    120
ctaaaaatac aaaaattagc cgggcgcggt ggcgggtgcc tgtagtccca gctacttggg    180
aggctgaggc aggagaatgg cgtgaacccg ggcaga                              217

<210> SEQ ID NO 1099
<211> LENGTH: 244
<212> TYPE: DNA
<213> ORGANISM: Artificial Sequence
<220> FEATURE:
<223> OTHER INFORMATION: probe/primer/pcr

<400> SEQUENCE: 1099
cgcaggggaa ggccggggag ggaggtgtga agcggcggct ggtgcttggg tctacgggaa    60
tacgcataac agcggccgtc agggcgccgg gcaggcggag acgcgcggc ttcccccggg    120 ggcgccggc gcggcgcct cctcggccgc cgctgccgcg agaagcggga aagcagaagc      180
ggcggggccc gggcctcagg gcgcagggg cggcgcccgg ccactactcg ccagggcccg    240
```

```
cccg                                                                244
```

<210> SEQ ID NO 1100
<211> LENGTH: 249
<212> TYPE: DNA
<213> ORGANISM: Artificial Sequence
<220> FEATURE:
<223> OTHER INFORMATION: probe/primer/pcr

<400> SEQUENCE: 1100

```
cctgaggcgg ggccgtccgg caccctgtga tggggcgtgg cccctgggga ggctcccacc      60
agccctcaga ttcctcaggg ccgcagaggt gtggagctgg ttgggccggt tcttcaccct     120
cctcccctgg tgcttgcctg tgcccagca gggtgacagt gatgtagtag cgggtcctcc     180
tggaagaggg acgcgtgtgt agggtctggg caggctctgg caaggcagtc cctggggtgg     240
cgggcttgc                                                            249
```

<210> SEQ ID NO 1101
<211> LENGTH: 187
<212> TYPE: DNA
<213> ORGANISM: Artificial Sequence
<220> FEATURE:
<223> OTHER INFORMATION: probe/primer/pcr

<400> SEQUENCE: 1101

```
gaggccgggg acgccgagag ccgggtcttc tacctgaaga tgaagggtga ctactaccgc      60
tacctggccg aggtggccac cggtgacgac aagaagcgca tcattgactc agcccggtca     120
gcctaccagg aggccatgga catcagcaag aaggagatgc cgcccaccaa ccccatccgc     180
ctgggcc                                                              187
```

<210> SEQ ID NO 1102
<211> LENGTH: 239
<212> TYPE: DNA
<213> ORGANISM: Artificial Sequence
<220> FEATURE:
<223> OTHER INFORMATION: probe/primer/pcr

<400> SEQUENCE: 1102

```
ccgccggctc ccccgtatga ggagctgcca tagctttcga atccacctgt tttgaacaac      60
aggattagtg cctgtgccac gtcccacgcc tccgagaaac ccgcaggctc ccggaggctt     120
cgccccttca aacactgccc gagtctccct aaccttcctc gccgccttcc tgcgggtgac     180
ccccaaacgc cccagctccg ctcccgccct tcctctcccg ctaccacacg cctctcgga     239
```

<210> SEQ ID NO 1103
<211> LENGTH: 187
<212> TYPE: DNA
<213> ORGANISM: Artificial Sequence
<220> FEATURE:
<223> OTHER INFORMATION: probe/primer/pcr

<400> SEQUENCE: 1103

```
caggagcgac gcgcgccaaa aggcggcggg aaggaggcgg ggcagagcgc gcccgggacc      60
ccgacttgga cgcggccagc tgagaggcg gagcgccggg aggagacctt ggccccgccg     120
cgactcggtg gcccgcgctg ccttcccgcg cgccgggcta aaaaggcgct aacgcccgcg     180
gccgcct                                                              187
```

<210> SEQ ID NO 1104
<211> LENGTH: 255

```
<212> TYPE: DNA
<213> ORGANISM: Artificial Sequence
<220> FEATURE:
<223> OTHER INFORMATION: probe/primer/pcr

<400> SEQUENCE: 1104
cgggggaaac gcaggcgtcg ggcacagagt cggcaccggc gtccccagct ctgccgaaga      60
tcgcggtcgg gtctggcccg cgggaggggc cctggcgccg gacctgcttc ggccctgcgt     120
gggcggcctc gccgggctct gcaggagcga cgcgcgccaa aaggcggcgg gaaggaggcg     180
gggcagagcg cgcccgggac cccgacttgg acgcggccag ctggagaggc ggagcgccgg     240
gaggagacct tggcc                                                     255

<210> SEQ ID NO 1105
<211> LENGTH: 221
<212> TYPE: DNA
<213> ORGANISM: Artificial Sequence
<220> FEATURE:
<223> OTHER INFORMATION: probe/primer/pcr

<400> SEQUENCE: 1105 cccccccaccc tggacccgca ggctcaggag tccacgcggg gagaggggat ggagaactct      60
cctcgcttcg tcctctctcc cggggaatcc ctaaccccgc actgcgttac ctgtcgcttt     120
ggggaggccg ctgccgggat ccggcccga acagcccggg ggggcagggg cggggggtcgt     180 cgagggggatg gggggcagaga gcaggcggcg ggcaggatgc c                       221

<210> SEQ ID NO 1106
<211> LENGTH: 174
<212> TYPE: DNA
<213> ORGANISM: Artificial Sequence
<220> FEATURE:
<223> OTHER INFORMATION: probe/primer/pcr

<400> SEQUENCE: 1106
gcccggcttt ccggcgcact ccaggggggcg tggctcgggt ccacccgggc tgcgagccgg      60
cagcacaggc caataggcaa ttagcgcgcg ccaggctgcc ttccccgcgc cggacccggg     120
acgtctgaac ggaagttcga cccatcggcg acccgacggg gagaccccgc ccca          174

<210> SEQ ID NO 1107
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1107
cgctgggccg ccccttgctc ttagccagag gtagcccctc accccgcgac ttaccccaca      60
ccccgctctc cagaaccccc atatgggcgc tcaccgcccg cccgcacagc tcgaacaggg     120
cggggggagc gttggggccc gaggccgagc tcttcgctgg cgccgcctcc gggacgtgg      180 cctccatggt cgttgccgcc gctacctcac agaaccagca actccgggcg cgccaggcct     240
cgggcgccgc catct                                                     255

<210> SEQ ID NO 1108
<211> LENGTH: 253
<212> TYPE: DNA
<213> ORGANISM: Artificial Sequence
<220> FEATURE:
<223> OTHER INFORMATION: probe/primer/pcr
```

```
<400> SEQUENCE: 1108
gcttctccat agctcgccac acacacacac acacgccacg caccgtataa aagcctaaat    60
gacacaccac tgcagcgttc aaacgctggg aagaagactc ccttgtggca ccggaaaccc   120
acgaggttgg aagtgggagg ggaagagggc cagatacttc acctgaaaat ccgccaggat   180
catctcccgg tccatgttgg acgccatggc ggccgccgag ttccgcggct ccgggagcga   240
agcgcgcacc tgg                                                      253

<210> SEQ ID NO 1109
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1109
ccgcgcacgc gcaagtccag gccgccgcgg ccctggaata gagactcgcc cttgatgtcc    60
ctctcgaagt agtaggcggc atcgccgata tccacgtcac cggcggcctt ctgagacgtg   120
ttctgccgca gctcgatctg gatggtgggc tgctcgtagt gcacggccgc cacgaacttg   180
gggtgcagcc gatagcgctc gcggaagagc cgcctcagct cggcgtccag gtctgagtgg   240
ttgaaggcgc cggcg                                                    255

<210> SEQ ID NO 1110
<211> LENGTH: 233
<212> TYPE: DNA
<213> ORGANISM: Artificial Sequence
<220> FEATURE:
<223> OTHER INFORMATION: probe/primer/pcr

<400> SEQUENCE: 1110
gtctcaactc accgccgcca ccgccgcgca gccccgcggc cgctgctcca tagccctccg    60
acgggcgccc aggggcttcc cggctccgtg ctctctgccc gtcgtggttc cgccttcagc   120
cccgcgcccg cagggcccgc cccgcgccgt cgagaagggc ccgcctggcg ggcgggggga   180
ggcggggccg cccgagccca accgagtccg accaggtgcc cctctgctc ggc           233

<210> SEQ ID NO 1111
<211> LENGTH: 203
<212> TYPE: DNA
<213> ORGANISM: Artificial Sequence
<220> FEATURE:
<223> OTHER INFORMATION: probe/primer/pcr

<400> SEQUENCE: 1111
acaaatgcgc tgctcggaga gactgccgcg gcaaccaact ggacacccca agagctcact    60
cctccgcggt tttatattcc gacttgcgca caggagcggg gtgcgggggc gcagggagtg   120
tgggtaacag gcatagattc cgcttgcgca atacgtggta agaaaccagc tgtgaggggc   180
tggcccaacg cagagcggcg cga                                           203

<210> SEQ ID NO 1112
<211> LENGTH: 181
<212> TYPE: DNA
<213> ORGANISM: Artificial Sequence
<220> FEATURE:
<223> OTHER INFORMATION: probe/primer/pcr

<400> SEQUENCE: 1112
gcgcctgcgc agtgcagctt agtgcgtcgg cgcgcagttc tcccgcccgt ttcagcggcg    60
```

-continued

```
cagcttctgt agttgggcta ctggaggggt cgctcagaaa cctcatactt ctcgggtcag    120
ggaaggtttg ggaggatgct gaggcctgag atctcatcaa cctcgccttc tgccccggcg    180
g                                                                    181

<210> SEQ ID NO 1113
<211> LENGTH: 172
<212> TYPE: DNA
<213> ORGANISM: Artificial Sequence
<220> FEATURE:
<223> OTHER INFORMATION: probe/primer/pcr

<400> SEQUENCE: 1113
aagtcaaggg ctttcaacct ccctgcccc attcatacag tggaaggtct aacccaggct     60
tgtcagccta agaacacggg atctcttcac tgtggttcat gtgtagagtg gagtttccat    120
gctgagagag acaagcaaag aagaccagag gctcccaccc ctgtccagtg ga           172

<210> SEQ ID NO 1114
<211> LENGTH: 254
<212> TYPE: DNA
<213> ORGANISM: Artificial Sequence
<220> FEATURE:
<223> OTHER INFORMATION: probe/primer/pcr

<400> SEQUENCE: 1114
tggatcccgc acaggggctg caggtggagc tacctgccag tccctgccg tgcgctcgca     60 ttcctcagcc cttgggtggt ccatgggact gggcgccatg gagcagggg tggtgcttgt    120 cggggaggct ggggccgcac aggagcccat ggagtgggtg ggaggctcag gcatggcggg    180
ctgcaggtcc ggagccctgc cctgcgggaa cgcagctaag gctcggtgag aaatagagcg    240
cagcgccggt gggc                                                     254

<210> SEQ ID NO 1115
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1115
ccgcctgtgg ttttccgcgc attgtgaggg atgaggggtg gaggtggtat tagacgcagc     60
cgaatcctcc ctcagagtcc gccaggtggg cgtctcaggg gtgggagtgg ccgcgtcgtg    120
aagcggagag aggatttctc tcctggtcct ggagaaggcc cccggcggcc ggcggcatcc    180
ctcgctggcg agtcccggga gcgaggtggt ctctgcaggg gaggaagttc ccgggcggcg    240
cggcctgcgt cacag                                                    255

<210> SEQ ID NO 1116
<211> LENGTH: 231
<212> TYPE: DNA
<213> ORGANISM: Artificial Sequence
<220> FEATURE:
<223> OTHER INFORMATION: probe/primer/pcr

<400> SEQUENCE: 1116
cgcgctctcc cgcgcctctg cccgccccg gcgcccgccc ccgccgctcc tcccgactcc     60 ccgccccgg cccgggtcac ttgccgtcgc ggtgggcggc ccccggcgag tccacacccc    120
tgccccgcct cctccggta ggaaactccg ggaccctgca aggatgact caccccagtg     180
```

```
attcaaccgc gccaccgagc gcggagctgc cctggaggac gcaggcgggt c          231
```

<210> SEQ ID NO 1117
<211> LENGTH: 246
<212> TYPE: DNA
<213> ORGANISM: Artificial Sequence
<220> FEATURE:
<223> OTHER INFORMATION: probe/primer/pcr

<400> SEQUENCE: 1117

```
tccggcccag ccccaacccc gacctaagta accggctatc ggccacccat tggctgaagt    60
ccctgagcac ctgttgggag gaaggctgct gcgtgcagcc ggaaagtcct gcgtccctcc   120
gctcttaccg cggcaggaac cacagcctcc ccgaacctca gggtttgtat ggatttcgcc   180
caggggaaag cgctccaacg cgcggtgcaa acggaagcca ctggctggtt gggcggctgt   240
gatggg                                                             246
```

<210> SEQ ID NO 1118
<211> LENGTH: 237
<212> TYPE: DNA
<213> ORGANISM: Artificial Sequence
<220> FEATURE:
<223> OTHER INFORMATION: probe/primer/pcr

<400> SEQUENCE: 1118

```
ccgggtcagg cgcacagggc agcggcgctg ccggaggacc agggccggcg tgccggcgtc    60
cagcgaggat gcgcagactg cctcaggccc ggcgccgccg cacagggcat cgccgacccc   120
ggtcgggcgg gaacaccccg cccctccccgg gctccgcccc agctccgccc ccgcgcgccc  180
cggccccgcc ccgcgcgct ctcttgcttt tctcaggtcc tcggctccgc cccgctc      237
```

<210> SEQ ID NO 1119
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1119

```
ggggcggtgc ctgcgccata tatgggagcg gccgcccctc gccgcgcccc tcgccgccgc    60
cgccgccgcg ctcgccgact gactgcctga cggcgccgcg agccggcccg agccccgcga   120
gccccgcgag ccccgccgcc gccgagcgcc accgagcgcc gccgccgccc cccgccacgc   180
accgcggctc ctcgcgtcca gccgcggcca aggaagttac tactcgccca aataaatctt   240
gaaaagaaac aaacg                                                   255
```

<210> SEQ ID NO 1120
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1120

```
gcgcgggccc tcaggttctc cctatcgaag cggtctatgg agatagttgg atactcggcc    60
atctgccccct cgaaagaact catagcgccg ccgatcccag agtccgggac cccaaaaccg   120
cagctgaagc caaggccagc cctgaccgcg ccgccacttc cgggaagccg cgcgctgcct   180
cgccattggg cggccgaacg cagccacgtc caatcagagg agtccggaga ccggggcaa    240
agtcaaggag catcc                                                   255
```

<210> SEQ ID NO 1121
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1121

```
cgtccgcggc tcctcagcgt ccccctttac ggtctgggcg gactgcgggg gctggggagg      60
ttctggggac cgggagagtg gccaccttct tcctcctcgc gaagagcagg ccgggcctac     120
ccgtccgccc gctctgccgt ccgctggccg gccgactgct gcccgatcac tcctgaggcc     180
gccgttgggc gacagggcgg tgcgggagga ggactgcgca ggcgcagtgg gccaggcggc     240
ccggcgacca atcgg                                                     255
```

<210> SEQ ID NO 1122
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1122

```
ggaggcgccc agcgagccag agtggtggct ggtcccgcgc ggtgagtggg attggggcac      60
ttggggcgct cggggcctgc gtcggatact cgggtccgct cgggagcgcg ctggccgcaa     120
cgagggcggc gcgggcccgg gcgatggcgt ggcttgcgtc tcccgcctcc gggcagggcc     180
tggccgccgg gcggggggcgg gagggccacg cgggcccagg gtggggccgc ggcctgcgcg     240
gcgggcgggc cgggt                                                     255
```

<210> SEQ ID NO 1123
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1123

```
cgcgcagggg gccttataca aagtcggaga agtagctggg tcgctggccg gccagggact      60
caagccgcct caggtgagcg ctccttggcg ctacttccgg tctcaggtga ggccgccgga     120
agcgggcact tggccctaag acccgctaca gtgcgtcctc gctgacaggc tcaatcacca     180
cggcgaggcc aaggcgcggg gccgcggccc gcccgagaag cctgagctgg gccccgacac     240
cccctgcccg acatt                                                     255
```

<210> SEQ ID NO 1124
<211> LENGTH: 168
<212> TYPE: DNA
<213> ORGANISM: Artificial Sequence
<220> FEATURE:
<223> OTHER INFORMATION: probe/primer/pcr

<400> SEQUENCE: 1124

```
ccccaccccc tttctttctg ggttttgatg tggatgtctt tctatttgtt caggaaattg      60
tgacgtgtgt tctgggcagg gtttgaggtt ttggaacatt ttctaaaagg gacagagagc     120
accctgctac atttcctaat caagaagttg gcgtgcagct gggagagc                 168
```

<210> SEQ ID NO 1125

<211> LENGTH: 224
<212> TYPE: DNA
<213> ORGANISM: Artificial Sequence
<220> FEATURE:
<223> OTHER INFORMATION: probe/primer/pcr

<400> SEQUENCE: 1125

```
gcgcgttccc tcccgtccgc ccccaagccc cgcgggcctc gcccaccctg cccgccgccc    60
ctccgccggc ggccgccctc tgcggcgccc ctttccggtc agtggagggg cgggaggagg   120
ggcgggggtg cgcggggcgg ggggagaagt cctggagcgg gtttggggttg cagtttcctt  180
gtgccgggga tcctgtcccc tactcgccag cgccaggctc ctcc                    224
```

<210> SEQ ID NO 1126
<211> LENGTH: 154
<212> TYPE: DNA
<213> ORGANISM: Artificial Sequence
<220> FEATURE:
<223> OTHER INFORMATION: probe/primer/pcr

<400> SEQUENCE: 1126

```
ccggcggagg cagccgttcg gaggattatt cgtcttctcc ccattccgct gccgccgctg    60
ccaggcctct ggctgctgag gagaagcagg cccagtcgct gcaaccatcc agcagccgcc   120
gcagcagcca ttacccggct gcggtccaga gcca                               154
```

<210> SEQ ID NO 1127
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1127

```
gcctggtgcc ccgagcgagc cgggagtagc tgcggcggtg cccgcccccct ctctccgccc    60
ctccagcgga gctggtctcc ggccgggcac cgtcgcgggc ccccctggcc cggccacctg   120
ggaccgtgct ggggagtctg ccacttccct ctctcccctg gcccgcaaag ttttggcgga   180
gccatcgctg gggctgagcg cgccccccggg gggagatcgg ggagcgcccg atgccgggcg   240
gccggagcca ttgac                                                    255
```

<210> SEQ ID NO 1128
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1128

```
ggcggcggcg ctacctggag gcgcggtggc gggcaggtgc ccgaactgca cggcgatgca    60
gaggtcgttg tccaggggga acttgtggca gtgcagcatc tcaggccagg gaagccgta   120
ggcctccatg agcggcgcgc agccggcgcg cacggcctcg cacagcgagc ggcacgggta   180
gatgggccgg tcgagacaga cgggcgcaaa gagcgagcac aggaagacct gcgtatccga   240
gtggcagcgc ttggc                                                    255
```

<210> SEQ ID NO 1129
<211> LENGTH: 255
<212> TYPE: DNA
<213> ORGANISM: Artificial Sequence
<220> FEATURE:
<223> OTHER INFORMATION: probe/primer/pcr

```
<400> SEQUENCE: 1129
tggtggccag cggggagcgc ccgggcgcca tcggcgcgtc ctgctccacc agggcgaccc      60
tgggcgctga gaagcgggaa tcttccttgg ggaccagggc gacgcctcct gctgccgccc     120
ccggcgggac agccgcggct cctcctccag ccgccgcgcc acccagagcc cgaggtttgc     180
ccttcagaag cggacccgca gactcctcgg actcagagcc atcctcctcc tcaacctcca     240
ccgcagcggc ctgcg                                                      255

<210> SEQ ID NO 1130
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1130
gcggcactga actcgcggca atttgtcccg cctctttcgc ttcacggcag ccaatcgctt      60
ccgccagaga aagaaaggcg ccgaaatgaa acccgcctcc gttcgccttc ggaactgtcg     120
tcacttccgt cctcagactt ggaggggcgg ggatgaggag ggcggggagg acgacgaggg     180
cgaagagggt gggtgagagc cccggagccc gagccgaagg gcgagccgca aacgctaagt     240
cgctggccat tggtg                                                      255

<210> SEQ ID NO 1131
<211> LENGTH: 206
<212> TYPE: DNA
<213> ORGANISM: Artificial Sequence
<220> FEATURE:
<223> OTHER INFORMATION: probe/primer/pcr

<400> SEQUENCE: 1131
ctcggcgatc cccggcctga acgggtagga ggggttgggg gattccgcca tcccttgttt      60
tgaggcggga acgcaaccct cgaccgccca ctgcgctccc acccacaccc agagtaataa     120
gctgtgattg caggctgggt cctcaccgtc tgctcgccag tcttctcctt tgaggactca     180
gaagccaagg gttgcgggag gcacca                                          206

<210> SEQ ID NO 1132
<211> LENGTH: 242
<212> TYPE: DNA
<213> ORGANISM: Artificial Sequence
<220> FEATURE:
<223> OTHER INFORMATION: probe/primer/pcr

<400> SEQUENCE: 1132
cgcagggagc gcgcggaggc ccgcagggtg cccgcctggc cgcagaggcc gcgacgcccc      60
ctccgccacc ctcgggccgc cgaaagaacg ggcagccggg aaatcccgtg tccccactcg     120
tggcagagga cgctgtgggg cgggcgggct gcgggctccc ggcgccttcc cgcagaggcg     180
gcgacagcgg ccgccccccc cgcggggccg ggccggggaa ctttcccgc ctggagccgg     240 gc                                                                    242

<210> SEQ ID NO 1133
<211> LENGTH: 255
<212> TYPE: DNA
<213> ORGANISM: Artificial Sequence
<220> FEATURE:
<223> OTHER INFORMATION: probe/primer/pcr
```

<400> SEQUENCE: 1133

```
gaaatactcc cccacagttt tcatgtgatc aggaattcag cataggctat aagacggagt      60
gctccatgtc aatagagaat atttccacag gtgtgctagg cacttgtggt agatgttgca     120
gggaagtcag gactggggac agcttggtcc ctacttcaag gttacagtct aggagctgag     180
agtggcaaag tgacctgatt ctacagggta aaagcoccag agataaatga cataggtcca     240
ggtcagccag cattg                                                      255
```

<210> SEQ ID NO 1134
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1134

```
ccgggcgcac ggggagctgg gcggacggcg gcccccgcct cctccgggga cgcggcacga      60
gacgcgggga cgcgcggacg ccacgctcag cggccgcccc cggcctccgc gccgccttcc     120
tcccgggagc agccccgacg cgcgcgggcc cggaccgccg gggttgtcat ggcagcagct     180
ccatccctga ccgccacttt ctcccggtgc cgcctcggag cgagcgggct ggcgggcggc     240
gcggactgcg cgctc                                                      255
```

<210> SEQ ID NO 1135
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1135

```
gcggcggcgt ccagccagag ccctgtggaa gcggcggcga cacttgggct gggcagtgtc      60
tctgatgcct cccagcgcca gcgactgctc ttattcccgc cgctgtgggt cgggaaagtt     120
ccgccagtgc acagcaacca atgggcggag gggtcctttg cccctggggtt gcgtcaccct    180
catgcttcca gaacctggag gatccagcag gaccgtccca cttgtatttg cattgaggtc     240
attgatggaa atggt                                                      255
```

<210> SEQ ID NO 1136
<211> LENGTH: 230
<212> TYPE: DNA
<213> ORGANISM: Artificial Sequence
<220> FEATURE:
<223> OTHER INFORMATION: probe/primer/pcr

<400> SEQUENCE: 1136

```
gggtcgccga ggccgtgcgc ttatagccgg gatgacgccg cagttgggcc ggatcagctg      60
acccgcgtgt ttgcacccgg accggtcacg tgggcgcggc cggcgtgcgc ggggcggggc     120
ggagcggggc ctggcctggg cggggcaacc tcggcgcacg cgcacagcgc ccgggcgggg     180
ggcggggtgg tggtgcgcct gccgcgccta cagttcccgc cgctcgcgcc                230
```

<210> SEQ ID NO 1137
<211> LENGTH: 219
<212> TYPE: DNA
<213> ORGANISM: Artificial Sequence
<220> FEATURE:
<223> OTHER INFORMATION: probe/primer/pcr

<400> SEQUENCE: 1137

```
cgcgcctgat gcacgtgggc gcgctcctga aacccgaaga gcactcgcac ttccccgcgg      60
cggtgcaccc ggccccgggc gcacgtgagg acgagcatgt gcgcgcgccc agcgggcacc     120
accaggcggg ccgctgccta ctgtgggcct gcaaggcgtg caagcgcaag accaccaacg     180
ccgaccgccg caaggccgcc accatgcgcg agcggcgcc                            219
```

<210> SEQ ID NO 1138
<211> LENGTH: 234
<212> TYPE: DNA
<213> ORGANISM: Artificial Sequence
<220> FEATURE:
<223> OTHER INFORMATION: probe/primer/pcr

<400> SEQUENCE: 1138

```
ccgggagcgg gcggaggaag ggccgggcgt ccggcgcaag cccgcgccgc cccagccccg      60
gccccggccc ggcccgcaca cgccgcttac ctggaagccg gcgacgctgc cgcccacctc    120
cctgctgcgt gtcgcaaacc gaacagcggg cgttggccct cctgccggac actcctctgc    180
cagcgccgct ctggccgagt cgcgggggcc gaatgtgcga cggggcagag cggg          234
```

<210> SEQ ID NO 1139
<211> LENGTH: 244
<212> TYPE: DNA
<213> ORGANISM: Artificial Sequence
<220> FEATURE:
<223> OTHER INFORMATION: probe/primer/pcr

<400> SEQUENCE: 1139

```
ggggcgcacc gggctggctc ctctgtccgg cccgggagcc cgaggcgcta cggggtgcgc      60
gggacagcga gcgggcgggt gcgcccgggc gcggcggcgg cagcgtcggg gaccggagc     120 tccaggctgc gccttgcgcc cgggtcagac attatttagc tcttcggttg agcttcgatt    180
ggtcaaacgg cgccgccccc ccccccccgc ccccgccc cgctccccg ctcgcccgcg       240 ctac                                                                  244
```

<210> SEQ ID NO 1140
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1140

```
gccacgggag gaggcgggaa cccagcgagg ccccgagggg ctgggggac cggccggccg      60 gacaaagcgg ggccgggccg ggccggggcg gggccgtgcg gggctcaccg gagatcagag    120
gcccggacag cttcttgatc gccgcgccgt tggcgctggc ggccgcggtg ccggccgcgg    180
gacgtcccga aatccccgag tgcagctggt cagcgagagg ctcctggccg cgctgcccct   240
ggttcgcgcc ctgct                                                     255
```

<210> SEQ ID NO 1141
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1141

```
cgggcatcgg cgcgggatga gaaaccaacc tgatacttat cgtgtgccga gttccctcct      60
```

```
tgtatcctga ctaagcacag cgaataaccc tgtccttgtt ctaaccccag gtcttgaaga    120
aatactgtcc cagctgagcc ccgcgtttac aagatgaaga ggcgcccag atgcgctgaa     180 agaaaggcca agctcgtgc ctccttccac tgcctgcggt agaacctggt cccgcatagc     240
ttggactcgg ataag                                                    255
```

<210> SEQ ID NO 1142
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1142

```
acaccgccgg cgcccaccac caccagctta tattccgtca tcgctcctca ggggcctgcg    60
gcccggggtc ctcctacagg gtctcctgcc ccacctgcca aggagggccc tgctcagcca    120
ggcccaggcc cagccccagg ccccacaggg cagctgctgg cagggccatc tgaagggcaa    180
acccacagcg gtccctgggc cccaacgcca ggcagcaagg actgcagcgt gcctacctgt    240
gcagctgcaa cccag                                                    255
```

<210> SEQ ID NO 1143
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1143

```
ccccaacagc gcgcagcgaa ctccactgcc gctgcctccg ccccagagac acgttgcagg    60
ccagagcggc cggggcgcgg ggcatcacgg gacggcctca cctggcctct tggaggactc    120
ccgaagcccg aggccgccaa ccgaaggagg ccccgccccc ggaggcaccg cctcgcctct    180
ttccgccagc gcccgcagga cccggatgag agcgcacgct tcggggtctc cgggaagtcg    240
cggcgccttc ggatg                                                    255
```

<210> SEQ ID NO 1144
<211> LENGTH: 165
<212> TYPE: DNA
<213> ORGANISM: Artificial Sequence
<220> FEATURE:
<223> OTHER INFORMATION: probe/primer/pcr

<400> SEQUENCE: 1144

```
ccccgctggg gacctgggaa agagggaaag gcttccccgg ccagctgcgc ggcgactccg    60
gggactccag ggcgcccctc tgcggccgac gcccggggtg cagcggccgc cggggctggg    120
gccggcggga gtccgcggga ccctccagaa gagcggccgg cgccg                   165
```

<210> SEQ ID NO 1145
<211> LENGTH: 247
<212> TYPE: DNA
<213> ORGANISM: Artificial Sequence
<220> FEATURE:
<223> OTHER INFORMATION: probe/primer/pcr

<400> SEQUENCE: 1145

```
cccgggggac ccactcgagg cggacggggc cccctgcacc cctcttccct ggcggggaga    60
aaggctgcag cggggcgatt tgcatttcta tgaaaaccgg actacagggg caactccgcc    120
gcagggcagg cgcggcgcct cagggatggc ttttgggctc tgccctcgc tgctcccggc    180
```

```
gtttggcgcc cgcgccccct cccctgcgc ccgccccgc cccctcccg ctcccattct    240 ctgccgg                                                           247
```

<210> SEQ ID NO 1146
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1146

```
cccgcggagg ggcacaccag gcgggtgttg gggaggacgc agagggctgg ggctggagcc    60
caggcggggc aggggcggg gcggagctgg gtccgaggcc ggcggggcg cctccatccc    120 acgccctcct cccccgcgcg cccgcccgct ctcgggtgac tccgcaacct gtcgctcagg    180
ttcctcctct cccggccccg ccccggcccg gccccgccga gcgtcccacc cgcccgcggg    240
agacctggcg ccccg                                                     255
```

<210> SEQ ID NO 1147
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1147

```
gcccacgtgc tcgcgccaac ccctacgccc cagcgcgcct tctccaccca cgcacgggcc    60
tcggacgcat ttccagcccc ggcgttggtt gtggatgctg acatccacc gcctccaggc    120 agtttcgccg tcacaccgtc gccatctgta gccaaagcaa aacatatcct aactgagact    180
ttgcagctct tgtggccact ctgggctcac cgggaacatg agtggaagag cccgagtgaa    240
ggccagaggc atcgc                                                     255
```

<210> SEQ ID NO 1148
<211> LENGTH: 254
<212> TYPE: DNA
<213> ORGANISM: Artificial Sequence
<220> FEATURE:
<223> OTHER INFORMATION: probe/primer/pcr

<400> SEQUENCE: 1148

```
ggcggagcgg cgaggaggag gagcaggagc gcgcagccag cgggtccacg catctcagca    60
cttccagacc aactccggca ccttccacac ccctgccccgg gctgggggct ccagagagcgg    120 ccgcgaagcg actccgatcc tccctctgag ccttgctcag ctctgccccg cgcctcccgg    180
gctccggtcc gcgcggcggg gtccctgctc ctgcgccccg ggcgcgcttc ccggacaccc    240
cggtccccgc agcc                                                      254
```

<210> SEQ ID NO 1149
<211> LENGTH: 201
<212> TYPE: DNA
<213> ORGANISM: Artificial Sequence
<220> FEATURE:
<223> OTHER INFORMATION: probe/primer/pcr

<400> SEQUENCE: 1149

```
cctcgcggt tccgggtgg cgcgcgttcg ctgcctcctc agctccagga tgatcggcca    60
gaagacgctc tactcctttt tctcccccag ccccgccagg aagcgacacg ccccagccc    120
```

```
cgagccggcc gtccagggga ccggcgtggc tggggtgcct gaggaaagcg gagatgcggc      180
ggtgaggcgc ggcttgggcc g                                                201
```

<210> SEQ ID NO 1150
<211> LENGTH: 130
<212> TYPE: DNA
<213> ORGANISM: Artificial Sequence
<220> FEATURE:
<223> OTHER INFORMATION: probe/primer/pcr

<400> SEQUENCE: 1150

```
caggcgcgcc gatggcgttt ctgaggtgac gccgcccaca ccgggcttct ccggggcgg       60 aggaaacacc tatgaacccct ccggcagcct tccttgccgg gcgccaggta agcagcggtt    120
ccgggcgcgg                                                            130
```

<210> SEQ ID NO 1151
<211> LENGTH: 203
<212> TYPE: DNA
<213> ORGANISM: Artificial Sequence
<220> FEATURE:
<223> OTHER INFORMATION: probe/primer/pcr

<400> SEQUENCE: 1151

```
ctcccggctt ctgcatcgag ggccttccag ggccagccct tgggggctcc cagatggggc      60
gtccacgtga cccactgccc ccacgcccgc gcgcgggccc cagcagcccc agagctgcgc    120
caacttcgtt cactccgcgc tcaccttacg ggggtccccg cgtgaccgca tggggtagcc    180
cctgctccca cgctcccggc cga                                            203
```

<210> SEQ ID NO 1152
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1152

```
cggtccgcga gtgggagcgg ctgcttgtgg gcagggtgga cgcggggcca cgtcttggcc      60
ggcgttttgc ggggtcttcc tgttctgaac gcgcgtaact tttgcctcag tatctcactt    120
cttggaatcc ggcggcgttc acgtgtgtgc tccagagaag ggcgccagag ggtattccct    180
gaaagtgaaa ggtcggcgaa agaggagtaa agacggcgag acgcgtccac gcagggggag    240
tctgtgcggt ttgga                                                     255
```

<210> SEQ ID NO 1153
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1153

```
gcagcgccgc ctcccacccc gggcttgtgc tgaatgggtt ctgattgtgc acggggtgca      60
cactgggcat ttcttggaag gggcacactg acgcgcgcac acacgccccc gacgcgcacg    120
cgccccgcgc gcactcacac tcaccccgc gcacactcac ccccgcgcac actcacgctg    180
ccgccgcgct gaggtgcagc gcacggggct tcacctgcaa cgtgtcgatt ggacggatgg    240
gctcggcgcg tgggt                                                     255
```

```
<210> SEQ ID NO 1154
<211> LENGTH: 203
<212> TYPE: DNA
<213> ORGANISM: Artificial Sequence
<220> FEATURE:
<223> OTHER INFORMATION: probe/primer/pcr

<400> SEQUENCE: 1154
cgaccgtgct ggcggcgact tcaccgcagt cggctcccag ggagaaagcc tggcgagtga    60
ggcgcgaaac cggaggggtc ggcgaggatg cgggcgaagg accgagcgtg gaggcctcat   120
gcctccgggg aaaggaaggg gtggtggtgt ttgcgcaggg ggagcgaggg ggagccggac   180
ctaatccctc actcgccccc tcc                                           203

<210> SEQ ID NO 1155
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1155
cccgggctcc gctcgccaac ctgttactgc tgcagaacgc caggaagctc agcctgatcc    60
cacagattag ggtaaaatat cccgggggc cgaagtggaa accggagttg cgtcattgct    120
cccacccgat atcaccttgg cagcgaccgc ggctgaccac gttcccggcc tgtcgcgaat   180
ctcacccaag ggagctgagt ctcagcttcc ctggtccctg gtcccgagtt ccgccttccc   240
cccccgcccc gtggc                                                    255

<210> SEQ ID NO 1156
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1156
catggggtgc tcatcttccc ggagctgagg agctggggcg ggcatgggt gctcatcttc     60 ctggagctga ggagctggga cgggcatggg gtgctcatcc tcctggagct gaggatctgg   120
ggcgggtgtg ggatgctcat cctcctggag ctgaggagct ggggcgggca tggggtgctc   180
atcttcccgg agctgaggag ctgggcggg catggggtgc tcatcttccc agagctgagg   240
agctggggcg ggcat                                                    255

<210> SEQ ID NO 1157
<211> LENGTH: 202
<212> TYPE: DNA
<213> ORGANISM: Artificial Sequence
<220> FEATURE:
<223> OTHER INFORMATION: probe/primer/pcr

<400> SEQUENCE: 1157
ccgagagccg gagcggggag ggcccgccaa gtcagcattc cagccggtga ttgcaatgga    60
caccgaactg ctgcgacaac agagacgcta caactcaccg cgggtcctgc tgagcgacag   120
cacccccttg gagcccccgc ccttgtatct catggaggat tacgtgggca gccccgtggt   180
ggcgaacaga acatcacggc gg                                            202

<210> SEQ ID NO 1158
<211> LENGTH: 169
<212> TYPE: DNA
```

```
<213> ORGANISM: Artificial Sequence
<220> FEATURE:
<223> OTHER INFORMATION: probe/primer/pcr

<400> SEQUENCE: 1158
ccgctgcagg gcgtctgggc ttctgggggc agagaagact cacgcagtga gcagtccgca    60
agcccgctgg cggcagcggc ggtgctccgt ccagggcgag aagctgcagc gctcgggccg   120
gggtccctcc tgtcgcagca gctcctcgac gagtgcaggg gcagccacg              169

<210> SEQ ID NO 1159
<211> LENGTH: 213
<212> TYPE: DNA
<213> ORGANISM: Artificial Sequence
<220> FEATURE:
<223> OTHER INFORMATION: probe/primer/pcr

<400> SEQUENCE: 1159
gcgctgcccc aagctggctt ccgctgcctg ctctgggctg ggctgggctg ggctgggctg    60
gtaggacctg ctcccagggc gggaggggac acacccacct cagcagatct cagcccatcc   120
ctcccagctc agtgcactca cccaaccccca cacgggccaa ggagagagtg aagaggaagc  180
attgccctca gaggccttca cggactggcc aga                               213

<210> SEQ ID NO 1160
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1160
caggatgcca gcgtgacgga agcaagtaac caccaaggca tcaccactgg cgctaaactt    60
ctcacttccg gagtgctgca agcgcagaaa atatacgtca tgtgcggagg cggagcttcc   120
gccctgcgcg tcgtattaga cggaaaccga gcgggcccat tttcatggg tttgcggacc   180 caccagcgaa ggcgggaggt gtcgcaggga catcttctgg ctgtttccgt cgcctgcgtg   240
gcccttgcac cccgg                                                    255

<210> SEQ ID NO 1161
<211> LENGTH: 248
<212> TYPE: DNA
<213> ORGANISM: Artificial Sequence
<220> FEATURE:
<223> OTHER INFORMATION: probe/primer/pcr

<400> SEQUENCE: 1161
ggcggtgcca tcgcgtccac ttccccggcc gccccattcc agctccggag ctcggccgca    60
gaaacgcccg ctccagaagg cggccccgc ccccggccc aaggacgtgt gttggtccag    120
ccccccggtt ccccgagacc cacgcggcc ggcaaccgct ctgggtctcg cggtccctcc   180
ccgcgccagg ttcctggccg ggcagtccgg ggccggcggg ctcacctgcg tcggaggaa   240 gcgcggcg                                                            248

<210> SEQ ID NO 1162
<211> LENGTH: 189
<212> TYPE: DNA
<213> ORGANISM: Artificial Sequence
<220> FEATURE:
<223> OTHER INFORMATION: probe/primer/pcr

<400> SEQUENCE: 1162
```

```
gtgggtcgcc gccgggagaa gcgtgagggg acagatttgt gaccggcgcg gttttttgtca    60 gcttactccg gccaaaaaag aactgcacct ctggagcggg ttagtggtgg tggtagtggg   120
ttgggacgag cgcgtcttcc gcagtcccag tccagcgtgg cggggagcg cctcacgccc    180 cgggtcgct                                                           189
```

<210> SEQ ID NO 1163
<211> LENGTH: 239
<212> TYPE: DNA
<213> ORGANISM: Artificial Sequence
<220> FEATURE:
<223> OTHER INFORMATION: probe/primer/pcr

<400> SEQUENCE: 1163

```
ggcggagggc cacgcagggg agacagaggg cctccacagg ggccaggggg aagtgtggga    60
actgagtctc ccccagacga ggcttcactt ggacacgtgt atgtggtcac cggggggaaac  120 tgagcagttc tgacttccct tggaaggcgt ggaattagga gagaaatccc ttagtgggca   180
cacgagtgag tgccccttgg agtccatctg tggaaaggaa gcggtgatag gtttccgca    239
```

<210> SEQ ID NO 1164
<211> LENGTH: 205
<212> TYPE: DNA
<213> ORGANISM: Artificial Sequence
<220> FEATURE:
<223> OTHER INFORMATION: probe/primer/pcr

<400> SEQUENCE: 1164

```
gtccgggggc gccgctgatt ggccgattca acagacgcgg gtgggcagct cagccgcatc    60
gctaagcccg gccgcctccc aggctggaat ccctcgacac ttggtccttc ccgccccgcc   120
cttccgtgcc ctgcccttcc ctgcccttcc ccgccctgcc ccgcccggcc cggcccggcc   180
ctgcccaacc ctgccccgcc ctgcc                                         205
```

<210> SEQ ID NO 1165
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1165

```
cggcctgcgg ctcggttccc gcctcttccc cacccccagc ccgcgctgc cctctcggtc     60 cccctgcgcg accccaggct cggccctgc ccggcctgcc ggggtggccc ggggtgggg    120 tgggagccct ttgtctgcgt gggtcgcctc gcgtctctct ctcccacccc acctctgaga   180
tttcttgcca gcacctggag cccgaaacca gaagagttgt cagcccaaca agaatatagg   240
atcaccggcc catca                                                    255
```

<210> SEQ ID NO 1166
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1166

```
gggaaccgtg gcggccctc ctggccctgg gaggtggtcc cgctgccccc ctgacttccg     60
tgcactgagc ccctggccct gccgcagcc ccggccctgg actcggcggc cgcggaggac   120
```

```
ctgtcggacg cgctgtgcga gtttgacgcg gtgctggccg acttcgcgtc gcccttccac    180
gagcgccact tccactacga ggagcacctg gagcgcatga agcggcgcag cagcgccagt    240
gtcagcgaca gcagc                                                     255
```

<210> SEQ ID NO 1167
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1167

```
cggggaaggc ggggaaggcg gggaaggcgg ggaaggcggg gaaggcgggg aaggcgggga    60
tggtgagacg gtgaggcggg gcggggcctg gggcgcgggc ggggcgggga ggggtggggc    120
ggggcccggg ggcgctggac cgcggtgctg cgggacggat cccggcggc tgcgcgggag    180 gctgcgagcc tgggctccca gggagttcga ctggcagagg cgggtgcagg gaacccgcgg    240
ctcggcggga gcgtg                                                     255
```

<210> SEQ ID NO 1168
<211> LENGTH: 218
<212> TYPE: DNA
<213> ORGANISM: Artificial Sequence
<220> FEATURE:
<223> OTHER INFORMATION: probe/primer/pcr

<400> SEQUENCE: 1168

```
cctcccggtt tcaggccatt ctcctgcctc agcctcccaa gtagctggga ctacaggcgc    60
ctgccaccac tcccggctaa ttttttgtat tttagtaga cgggggtt tcaccgtgtt       120 agccaggatg gtctcgatct gcttacctcg tgatccgccc gcctcggcct cccaaagtgc    180
tgggattaca ggcgtgagcc accgcgtccg gcatattt                            218
```

<210> SEQ ID NO 1169
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1169

```
agcccgcgca ccgaccagcg ccccagttcc ccacagacgc cggcgggccc gggagcctcg    60
cggacgtgac gccgcgggcg gaagtgacgt tttcccgcgg ttggacgcgg cgctcagttg    120
ccgggcgggg gagggcgcgt ccggtttttc tcagggacg ttgaaattat ttttgtaacg    180
ggagtcggga gaggacgggg cgtgccccga cgtgcgcgcg cgtcgtcctc cccggcgctc    240
ctccacagct cgctg                                                     255
```

<210> SEQ ID NO 1170
<211> LENGTH: 221
<212> TYPE: DNA
<213> ORGANISM: Artificial Sequence
<220> FEATURE:
<223> OTHER INFORMATION: probe/primer/pcr

<400> SEQUENCE: 1170

```
ccccagccac accagacgtg ggagcttagg atgagagcgg cctccgagca gatgatcacc    60
ctggaacgac gccaaacgcg accccctacca gaggactcgc gcatgcgcag cgcagcctgg   120
gccggcggcc tgggcaggat gtagtcgcga gcagcgcacc gggcccacgc cagcggaatt    180
```

```
gcgcatgcgc agggccgcct ctgcctgcgg cctgggctgg g          221
```

<210> SEQ ID NO 1171
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1171

```
tgggcttcct gccccatggt tccctctgtt cccaaagggt ttctgcagtt tcacggagct    60
tttcacattc cactcggttt ttttttttt  gagactcgct ctgtcgccca ggctggaatg   120
cagtggcgcg atctcggctc actgcaagct ccgcctcccg ggttcacgcc attctgcttc   180
agcctcccaa gtagctggga ttataggcgc cgccaccac  gcccggctaa tggctaattt   240
tttgtatttt ttttt                                                    255
```

<210> SEQ ID NO 1172
<211> LENGTH: 153
<212> TYPE: DNA
<213> ORGANISM: Artificial Sequence
<220> FEATURE:
<223> OTHER INFORMATION: probe/primer/pcr

<400> SEQUENCE: 1172

```
ccgcgctggg ccgcagcttt ccggagcgca gaggaagctg gccagcctgc agatagcact    60
gggaaagaca ccgcggaact cccgcgagcg gagacccgcc aaggcccctc cagggacctg   120
tcttcctaac tgccagggac gccgagccaa ctc                                153
```

<210> SEQ ID NO 1173
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1173

```
gcatggcccg gtggcctgca ctccagtgag gtggctgaac tctgaccagc caagagaaaa    60
ccccctctc  cgcccaaaac agctccccac tccccagcc  tgcccccacc ctccccacat   120
tccagtcttt cactgtcgcc ccaggcaact tggctgccca agaccaagcc ccaccaagaa   180
gctggagggc caggcaagtc caggatgggc aagcagggaa gcacgagagg gagaaacaga   240
ggtgaggaag gaagg                                                    255
```

<210> SEQ ID NO 1174
<211> LENGTH: 239
<212> TYPE: DNA
<213> ORGANISM: Artificial Sequence
<220> FEATURE:
<223> OTHER INFORMATION: probe/primer/pcr

<400> SEQUENCE: 1174

```
gggcagggga ggggagtgct tgagtattgg ggctacactc accacaagag cagcaaacaa    60
agcactgggt gtggtagagg ctgtccaggg cctggcaggc attgctctgc ccatagatgc   120
ctttgttgca cttgatacag gtgcctgaga agagaaaagt gtcacactct actcccccag   180
gtcaaaacca gggattccca agctttcctg actgcccttt cctgatgtgc cagggg tca   239
```

<210> SEQ ID NO 1175

```
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1175
ccccggcgcc ttcctcctcc ggactccgct gcatgcctcg cttgcggtgg tccgatcggc      60
tttctccggg agctttcctc tccccgccac gccccgtct  ccccggccgt ccccgcgcct     120
ctcggcctcc ctttcattag ccccacatct gtctttccca tgggagggag cgcgcgcctt    180
ccgcccagcg gggcccttag cagagcctct ccaatcctcg gcgcctcccc tacacagggt    240
tcgctgggcc gttct                                                      255

<210> SEQ ID NO 1176
<211> LENGTH: 202
<212> TYPE: DNA
<213> ORGANISM: Artificial Sequence
<220> FEATURE:
<223> OTHER INFORMATION: probe/primer/pcr

<400> SEQUENCE: 1176
ccaccgcgct tcccggctat gcgaaagtga aaacgagggg cgcccaaggc cctgcttctt    60 ccccttcct cttcccttg cccagccgcg acttcttcct cactgatctc ccggggggcgg     120 agacgctgag ttccccggag acgagttagt caccaagaag aggcggtgac agagagcgcg    180
gctcgcgtcg cactccgagg cc                                              202

<210> SEQ ID NO 1177
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1177
ccgcatctga ccgcaggacc ccagcgctac caagtgcctg ttcttggacc cccagccgag    60 caggggaag catccccagc tcccgcaccc aagtccctgg cgccgctgcc gggccgccct     120
ccctgatgcc cagcgcgcag cctgccggcg ccgcgccttc tggacggctc tcgccgcacc    180
tcctgagctc agcccgcggc cccgcagtgg ggcggcctca cttactggcg gggaagcgcg    240
ggtctgggtt ggcgc                                                      255

<210> SEQ ID NO 1178
<211> LENGTH: 233
<212> TYPE: DNA
<213> ORGANISM: Artificial Sequence
<220> FEATURE:
<223> OTHER INFORMATION: probe/primer/pcr

<400> SEQUENCE: 1178
gcggacacgt gcttttcccg cattaggggg ggtctcccgg cgcgcgcccc gccgccacct    60
gttgaggaaa gcgagcgcac ctcctgcagc tcaggctccg ggcgccagcc ctgccccgca    120 gcccagagc ccgtcgcagc tcgggtggtc cctcccggc ccagcgctcg ccgcctgctc      180
ttcgccctgc aagtttcaag aggcagttat ttctcgcagc ctccgcgctt gca            233

<210> SEQ ID NO 1179
<211> LENGTH: 226
<212> TYPE: DNA
<213> ORGANISM: Artificial Sequence
```

<220> FEATURE:
<223> OTHER INFORMATION: probe/primer/pcr

<400> SEQUENCE: 1179

| | |
|---|---|
| gagctggaag agtttgtgag ggcggtcccg ggagcggatt gggtctggga gttcccagag | 60 |
| gcggctataa gaaccgggaa ctgggcgcgg ggagctgagt tgctggtagt gcccgtggtg | 120 |
| cttggttcga ggtggccgtt agttgactcc gcggagttca tctccctggt tttcccgtcc | 180 |
| taacgtcgct cgcctttcag tcaggatgtc tgcccgtggc ccggct | 226 |

<210> SEQ ID NO 1180
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1180

| | |
|---|---|
| ggccgccaac gacgccagag ccggaaatga cgacaacggt gagggttctc gggcggggcc | 60 |
| tgggacaggc agctccgggg tccgcggttt cacatcggaa acaaaacagc ggctggtctg | 120 |
| gaaggaacct gagctacgag ccgcggcggc agcggggcgg cggggaagcg tatgtgcgtg | 180 |
| atggggagtc cgggcaagcc aggaaggcac cgcggacatg ggcggccgcg ggcagggccc | 240 |
| ggcccttttgt ggccg | 255 |

<210> SEQ ID NO 1181
<211> LENGTH: 183
<212> TYPE: DNA
<213> ORGANISM: Artificial Sequence
<220> FEATURE:
<223> OTHER INFORMATION: probe/primer/pcr

<400> SEQUENCE: 1181

| | |
|---|---|
| gcgcccggtc agcccgcagc gcccggccag cccgcagcgc cggagcccgc agtgcgtgcg | 60 |
| aggggctctc ggcaggtcca gacgcctcgc cgagcccagc ccgcagctcc ccgggccgcg | 120 |
| ccgcgcccgc ccacagggcc cacagccctg cttcggctct cagggcggtc acctgggatg | 180 |
| ggg | 183 |

<210> SEQ ID NO 1182
<211> LENGTH: 195
<212> TYPE: DNA
<213> ORGANISM: Artificial Sequence
<220> FEATURE:
<223> OTHER INFORMATION: probe/primer/pcr

<400> SEQUENCE: 1182

| | |
|---|---|
| cccgccaggc ccagcccctc cctggccagc ccgtccttg tccccaaact gggcccgccc | 60 |
| ggccgccagg ccgccgggcc tccggggccc tcgcgcatcc ggctccgaaa gctgcgcgca | 120 |
| gccatcatca gggcccttct ggtgttagaa gagaccccgg catcatcttt tcgtcgcgtg | 180 |
| cttcccccag agtca | 195 |

<210> SEQ ID NO 1183
<211> LENGTH: 171
<212> TYPE: DNA
<213> ORGANISM: Artificial Sequence
<220> FEATURE:
<223> OTHER INFORMATION: probe/primer/pcr

<400> SEQUENCE: 1183
cgattcttcc cagcagatgg ccccaaagtt cagttcctga attgcctcgc ggagccgcgg    60
gctgcaacgt gaggcggccg ctgccagtcg actcaaccac cggagtggcc cctgcagttg   120
gatagcaacg agaatcctcc aggggtgcag ggcgacggct tcggccgcac c            171

<210> SEQ ID NO 1184
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1184
cgcacaccgc ccccaagcgg ccggccgagg gagcgccgcg gcagcgggag aggcgtctct    60
gtgggccccc tggcagccgc ggcaggaaag ggcccgaagg cagcgaaggc gaacgcggcg   120
caccaacctg ccggccccgc cgacgccgcg ctcacctccc tccggggcgg gcgtggggcc   180
agctcaggac aggcgctcgg gggacgcgtg tcctcacccc acggggacgg tggaggagag   240
tcagcgaggg cccga                                                    255

<210> SEQ ID NO 1185
<211> LENGTH: 169
<212> TYPE: DNA
<213> ORGANISM: Artificial Sequence
<220> FEATURE:
<223> OTHER INFORMATION: probe/primer/pcr

<400> SEQUENCE: 1185
aggccccgag gccggagcgg cggaggggggc ggcccctccc acagggtctt cccacccaca    60
gggcacccag gcgcagcgga gccaggaggg ggcttacccg cgggcaggga cggagcacgc   120
cggggccctg gaggggcgac gctcgctcgt gtccccggtc cccgtggcc               169

<210> SEQ ID NO 1186
<211> LENGTH: 249
<212> TYPE: DNA
<213> ORGANISM: Artificial Sequence
<220> FEATURE:
<223> OTHER INFORMATION: probe/primer/pcr

<400> SEQUENCE: 1186
gggttcgcgc gagcgctttg tgctcatgga ccagccgcac aactttgaa ggctcgccgg     60 cccatgtggg gtctttctgg cggcgcgccg cctgcagccc cctaaagcg cggggctgg    120 agttgttgag cagccccgcc gctgtggtcc atgtagccgc tggccgcgcg cggactgcgg   180
ctcggcgtgc gcgtgttccc ggccgtcccg cctcggcgag ctccctcatg ttgtcgccct   240
gcggcgccc                                                           249

<210> SEQ ID NO 1187
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1187
ccagtctccc gcccccctgag catgcacgca ctttggttgc agtgcaatgc tctgacttcc    60
aaatgggaga gacaagtggc ggaaaatagg gtcttctccc acctcccacc ccccatccc   120 gactctttttg cccttctttt ggtccaagag attttgaaac cgtgcagaac gagggagagg   180
ggcaggctgc agccgggcag ataacaaaac acccccaaa gtgggcctcg catcggccct   240

```
cgcattcctg tagag                                                    255

<210> SEQ ID NO 1188
<211> LENGTH: 233
<212> TYPE: DNA
<213> ORGANISM: Artificial Sequence
<220> FEATURE:
<223> OTHER INFORMATION: probe/primer/pcr

<400> SEQUENCE: 1188
gaggaggcag cggaccgggg acaccctggg ggaacttccc gagctccgcg acctcgaagc     60
ctggcccttc cttctccctg gtcctacatg cctccctccc ccactgtccg ggtcctggc    120 ctcgacgccg aggggtgtcc ctctcctctc ctggtcaggg aacgcagcaa ctgaggcggc   180
gcggcccaga tgagacggga agcgcctgcg ggccgtgggc gcgggtggaa ccc          233

<210> SEQ ID NO 1189
<211> LENGTH: 232
<212> TYPE: DNA
<213> ORGANISM: Artificial Sequence
<220> FEATURE:
<223> OTHER INFORMATION: probe/primer/pcr

<400> SEQUENCE: 1189
ccggctccac ggacccacgg aagggcaagg gggcggcctc ggggcggcgg gacagttgtc    60
ggagggcgcc ctccaggccc aagccgcctt ctccggcccc cgccatggcc ggggcggca   120 gtcagagctg gagctccggg gaatcagacg ggcagccaaa ggagcagacg cccgagaagc   180
ccaggtgagc ggctgggccg cgccggacgg gcgtcggggg tctgggccgc ga           232

<210> SEQ ID NO 1190
<211> LENGTH: 247
<212> TYPE: DNA
<213> ORGANISM: Artificial Sequence
<220> FEATURE:
<223> OTHER INFORMATION: probe/primer/pcr

<400> SEQUENCE: 1190
ccgccaccgc caccatgccc aacttcgccg gcacctggaa gatgcgcagc agcgagaatt    60
tcgacgagct gctcaaggca ctgggtaagc tggtgcagag ggcgcgcccc gacggggaga   120
tgcggcccgg aggtgccctg gtcccggaag tgccccggtc ctgggggggg tggaagttgg   180
ggagcccagg caggagggag tccccggggc aatagatcgc cttgtctccc aggcgcaccg   240
ggtctcg                                                             247

<210> SEQ ID NO 1191
<211> LENGTH: 203
<212> TYPE: DNA
<213> ORGANISM: Artificial Sequence
<220> FEATURE:
<223> OTHER INFORMATION: probe/primer/pcr

<400> SEQUENCE: 1191
tgagtaagga tgataccgag agggaagaaa aaataccct ctttgggcca ggcacggtgg     60
ctcacccctg taatcccagc actttgggag gctgaggcga gcggatcacg agatcagaag   120
atcgagacca tcctggctaa cacagtgaaa ccccatctct accaaaaata caaaaaatta   180
gccaggcatg gtggcgggca cct                                           203

<210> SEQ ID NO 1192
```

```
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1192
tgggccaggc acggtggctc acccctgtaa tcccagcact ttgggaggct gaggcgagcg    60
gatcacgaga tcagaagatc gagaccatcc tggctaacac agtgaaaccc catctctacc   120
aaaaatacaa aaaattagcc aggcatggtg gcgggcacct gtagtcccag ctacttggga   180
ggctgaggca ggagaatcct ttgaacccag gaggcggagc ttgcagtgag ctgagattgt   240
gccactgcac tccag                                                    255

<210> SEQ ID NO 1193
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1193
ccggcgaagt gggcggctcc ccaagcgccc aggctgcgca gcacgatggc cgccccgcc    60
gcgcaccgcg tgtgcccgca cgcccgcccc ctgcgccccg gggacgcctc tccgcccctc   120
cccctgcccc tccgcccacc gcgcggtcgc cccacgcgc gggcgctgct tcgccgcccg   180
ggaggccgcc tcccgccccg ggaccggata acgccctaaa tcagcgcagc tgaggcgagg   240
ccgtggcccc cgcag                                                    255

<210> SEQ ID NO 1194
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1194
gcggccttac cctgccgcga gcgcctgtga cagcggcgcc gctgtgctcg cgaccccggc    60
tccgggcctc tgccgacctc aggggcagga aagagtcgcc cggcgggatg ggcggggagg   120
ctgggtgcgc ggcggccgtg ggtgccgagg gccgcgtgaa gagcctgggt ctggtgttcg   180
aggacgagcg caagggctgc tattccagcg gcgagacagt ggccgggcac gtgctgctgg   240
aggcgtccga gccgg                                                    255

<210> SEQ ID NO 1195
<211> LENGTH: 217
<212> TYPE: DNA
<213> ORGANISM: Artificial Sequence
<220> FEATURE:
<223> OTHER INFORMATION: probe/primer/pcr

<400> SEQUENCE: 1195
gtggggccgg cgagggtcag gggcatcgcg gccgcgaccc cattctgcag cccccgaggc    60
tcgcccgact cctggctgcc ctggactccc ctccctcctc cctcccgcct cctcgcccag   120
ggcccggctc acctggcggc ggggcgcggg acgccgcggg cgggacggcg gggggctccg   180
gggcgctccg gggcggctct cgcgcatgct ccggggc                             217

<210> SEQ ID NO 1196
<211> LENGTH: 250
```

```
<212> TYPE: DNA
<213> ORGANISM: Artificial Sequence
<220> FEATURE:
<223> OTHER INFORMATION: probe/primer/pcr

<400> SEQUENCE: 1196
cggcgcggac cggctcctct accactttct ccagctgcac tgccacccag cctgcctggt    60
gctggtgctc aacacgcagc cggccgagga ggtgcggccg cgctggcgcg ggagtgaggg   120
gactccgaga gtgttgaggg cctcctgagc ggatgcgagg cctctgacag ggatggaggg   180
gctctgaggg ggattcaggc ccctgacact acgcgatgac acagagaagg atggcagggg   240
tccccagggg                                                           250

<210> SEQ ID NO 1197
<211> LENGTH: 215
<212> TYPE: DNA
<213> ORGANISM: Artificial Sequence
<220> FEATURE:
<223> OTHER INFORMATION: probe/primer/pcr

<400> SEQUENCE: 1197
gcccatgcgg ccccgtcacg tgatgcaagg atcgccggcc tttccgccag agggcggcac    60
agaactacaa ctcccagcaa gctcccaagg cggccctccg cgcaatgccg ctaccggaag   120
tgcgggtcgc gcttccggcg gcgtcccggg gccagggggg tgcgccttc tccgcgtcgg    180 ggcggcccgg agcgcggtgg cgcggcgcgg ggtaa                               215

<210> SEQ ID NO 1198
<211> LENGTH: 184
<212> TYPE: DNA
<213> ORGANISM: Artificial Sequence
<220> FEATURE:
<223> OTHER INFORMATION: probe/primer/pcr

<400> SEQUENCE: 1198
gggattgcca ggggctgacc ggagtgttgc tgggaaggag cctcagctcc gctccaggtc    60
ctccaccagg taggactggg actcccttag ggcctggagg agcaagtcct tgcaggtcca   120
gttccaggct ggtgtgaaac tgaagagctt ccgcatcttg cttgggttgg tgggctcggc   180
ccgc                                                                184

<210> SEQ ID NO 1199
<211> LENGTH: 234
<212> TYPE: DNA
<213> ORGANISM: Artificial Sequence
<220> FEATURE:
<223> OTHER INFORMATION: probe/primer/pcr

<400> SEQUENCE: 1199
gccggagcac gcggctactc aggccgaacc ccgacccgga cccggcacgc ggcctcggcg    60
agggcgggcg ggagtgtcct cctccgggac agccggactc ccgccgactt ctgggcggcg   120
gggagggctc caggcccggc tctcccgggc ccccgcacgc gatgcgcggc ccctgcagct   180
gctccgtgcc ccgagacgcg cccgaggcct cggacctcca agcggccacc gcgc         234

<210> SEQ ID NO 1200
<211> LENGTH: 255
<212> TYPE: DNA
<213> ORGANISM: Artificial Sequence
<220> FEATURE:
<223> OTHER INFORMATION: probe/primer/pcr
```

<400> SEQUENCE: 1200

```
cctcggcgcc ggcccgttag ttgcccgggc ccgagccggc cgggcccgcg ggttgccgag      60
cccgctgacg tcagcccggg tttcccccccc ccaccggggc ttccccatcc cccgaggctt    120
cccgggaggg ctgcgagtcc ggggagcgtg cggggtcgcc accatcggga cccccagagg    180
agagaggact tggggcggga gccgcgcggg acgctgtccc cctcccgccc cccacccat     240 ttacagattg ggaga                                                      255
```

<210> SEQ ID NO 1201
<211> LENGTH: 205
<212> TYPE: DNA
<213> ORGANISM: Artificial Sequence
<220> FEATURE:
<223> OTHER INFORMATION: probe/primer/pcr

<400> SEQUENCE: 1201

```
cacagcggcg gcgagtgggt cgtgcacgcg gatgcggggt gggagtgggg gcgcacgcgc      60
gggcgtgggc gagcgggccc cggcagtgca cacacacgcg aggggcgggc gacagatgca    120
gtgcgtgcgc cggagcccaa gcgcacaaac ggaaagagcg ggcgcggtgc gcaggggcgg    180
gcgcccagcg ggcttggcat gcgcg                                           205
```

<210> SEQ ID NO 1202
<211> LENGTH: 220
<212> TYPE: DNA
<213> ORGANISM: Artificial Sequence
<220> FEATURE:
<223> OTHER INFORMATION: probe/primer/pcr

<400> SEQUENCE: 1202

```
cacctcgggc ggggcggact cggctgggcg gactcagcgg ggcgggcgca ggcgcagggc      60
gggtcctttg cgtccggccc tctttcccct gaccataaaa gcagccgctg gctgctgggc    120
cctaccaagc cttccacgtg cgccttatag cctctcaact tcttgcttgg gatctccaac    180
ctcaccgcgg ctcgaaatgg accccaactg ctcctgcgcc                           220
```

<210> SEQ ID NO 1203
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1203

```
agacggggcc gggcgcagac gccccgcccc gcccttgcac ccagcccgct gagtccgcac      60
cgcccgcggt cccggcctgg gctgtgcgca ggagatgggc caagtgcaag gtcccttgag    120
cgcagctggg cgcacaccgc aggacggccc ctttcgcacc ggctcgcgag ggaggcgctg    180
tgccccccgt gtgcggcttc tctcacccctg ccaggccttc ccagcttccc tgaggttgcc    240
tgctacaccc gcccc                                                      255
```

<210> SEQ ID NO 1204
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1204

```
gcattcgggc cgcaagctcc gcgccccagc cctgcgcccc ttcctctccc gtcgtcaccg      60
```

```
cttcccttct tccaagaaag ttcgggtcct gaggagcgga gcggcctgga agcctcgcgc    120
gctccggacc ccccagtgat gggagtgggg ggtgggtggt gaggggcgag cgcggctttc    180 ctgcccctc cagcgcagac cgaggcgggg gcgtctggcc gcggagtccg cggggtgggc     240
tcgcgcgggc ggtgg                                                    255
```

```
<210> SEQ ID NO 1205
<211> LENGTH: 171
<212> TYPE: DNA
<213> ORGANISM: Artificial Sequence
<220> FEATURE:
<223> OTHER INFORMATION: probe/primer/pcr

<400> SEQUENCE: 1205
gcccgaaagg gccggagcgt gtcccccgcc agggcgcagg ccccagcccc ccgcacccct    60
attgtccagc cagctggagc tccggccaga tcccgggctg ccgcctctgc tgccttccct   120
gagcgggagc ggagcgcaga gaaaagttca agccttgccc accgggctg c             171
```

```
<210> SEQ ID NO 1206
<211> LENGTH: 212
<212> TYPE: DNA
<213> ORGANISM: Artificial Sequence
<220> FEATURE:
<223> OTHER INFORMATION: probe/primer/pcr

<400> SEQUENCE: 1206
cggcggccgg gtgaccgacc actgcttacc aggaggggag actggcaggg ggggctcaag    60
gaacatctgg tgggtgtccc cttcacaaga ctcggcctgc agagttcgtg caggagttc    120 gcacatagga gagcaccggt ccgggagtgc caggctcgtg cccggccggg gagaggagtg   180
ggagactaag tcgcagggca agggcaactg ca                                 212
```

```
<210> SEQ ID NO 1207
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1207
ccaccggcgg ccgctcacct cctgctcctt ctcctggtcc gggcgggccg gcctgggctc    60
ccactccaga gggcagccgg tccttcgccg gtgcccaggc cgcagggctg atgccccgc   120 tcagctgagg gaaggggaag tggaggggag aagtgccggg ctggggccag gcggccaggg   180
cgccgcacgg ctctcacccg gccggtgtgt gtccccgcag gagagtgtgc tgggcagacg   240
atgctggaca cgatg                                                    255
```

```
<210> SEQ ID NO 1208
<211> LENGTH: 239
<212> TYPE: DNA
<213> ORGANISM: Artificial Sequence
<220> FEATURE:
<223> OTHER INFORMATION: probe/primer/pcr

<400> SEQUENCE: 1208
cggtcaggga cccccttccc ccttcaagct gactccctcc cacaaggctc ttcagatctc    60
gttgtatttt gggattgatg ggggaaaaat ccaaatttgt ttgtttgctt ccctttttc   120 ggtggtgggg aaaggtggca ggcttttggg gacaaccatg gaggggtcct ccgtctcggc   180
```
ctcttcgcat atccccctcc gtgatcctgc cttcccccc caccgagccc atcgcaggc 239

<210> SEQ ID NO 1209
<211> LENGTH: 240
<212> TYPE: DNA
<213> ORGANISM: Artificial Sequence
<220> FEATURE:
<223> OTHER INFORMATION: probe/primer/pcr

<400> SEQUENCE: 1209
ggccgaagct gccgcccctc ctcccaaccg gcgggtcaga tctcgctccc tttcggacaa     60
cttacctcgg agaggagtca aggggagagg ggaggggagg gggggagggg gcaagagaga    120
gaggggggag aagagggatc ttctcgctta tttcattgtt cccccatctt cagggagcgg    180
gggcagcggc tcctcaaggc ggcgggcgcc ggcgtcttca gagcgccatg cgaaccgcgg    240

<210> SEQ ID NO 1210
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1210
gcggccttgt gccgctgggg gctcctcctc gccctcttgc ccccggagc cgcgagcacc     60
caaggtgggt ctggtgtggg gaggggacgg agcagcggcg ggaccctgcc ctgtggatgc    120
cccgccgagg tcccgcggcc ggcggggcca gaggggcccg gacgagctct cctatcccga    180
agttgtggac agtcgagacg ctcagggcag ccgggccctg gggccctcgg gcgggagggg    240
gcagttacac ggcag                                                    255

<210> SEQ ID NO 1211
<211> LENGTH: 241
<212> TYPE: DNA
<213> ORGANISM: Artificial Sequence
<220> FEATURE:
<223> OTHER INFORMATION: probe/primer/pcr

<400> SEQUENCE: 1211
cgcgggagga gcggcgaggc cctcacctgg cgccttttat gcccgcggcc ggtggagggg     60
ggaagggagg aatggtgtca ggggcggata tctgagccct gaggaatttg caggctcctg    120
agagcaaata tgggctctct ccccattggt caattccctc cctcccaga gaccagaggc     180
ccctgccctc cagaggtgcc ccgccccggt ccgcgcagaa gctccgaccc gcactccccc    240
a                                                                   241

<210> SEQ ID NO 1212
<211> LENGTH: 223
<212> TYPE: DNA
<213> ORGANISM: Artificial Sequence
<220> FEATURE:
<223> OTHER INFORMATION: probe/primer/pcr

<400> SEQUENCE: 1212
gcccaccaga agcccatcac caccagcaaa gccaccacca aagccaccac ccaagccagc     60
accaaggcca ccaccatatc ctcccccaaa gccactacca aagctgctgc tgctgctgct    120
gaagccaccg ccatagccgc ccccagccc gcaggctccc ccagaggaga agcgggagga    180
tgagacagac aggccgcccc cgtaggtgct ggggcgcgg cag                      223

```
<210> SEQ ID NO 1213
<211> LENGTH: 165
<212> TYPE: DNA
<213> ORGANISM: Artificial Sequence
<220> FEATURE:
<223> OTHER INFORMATION: probe/primer/pcr

<400> SEQUENCE: 1213
gggccatgtg ccccacccca cagccccacc ctgccctgcc caccacccca agcccggccc      60
tgggtcccag ggtcccgcca ggcccgctgg gtggaatgtg gtcatgtttc agactgccga     120
tggcttccac ttcccagaca ggcccagacg gccccgccag cagcc                     165

<210> SEQ ID NO 1214
<211> LENGTH: 177
<212> TYPE: DNA
<213> ORGANISM: Artificial Sequence
<220> FEATURE:
<223> OTHER INFORMATION: probe/primer/pcr

<400> SEQUENCE: 1214
ccgccagccc agggcgagag tcagggacgc ggcgtcgggc gagctgcgcg ggccccgggg      60
gaggcgcgac cccggaggca cctgtccgga tccctccccg ccttgctcag atctctggtt     120
cgcggagctc cgaggcgcgc tcggcccgaa ccgcgcgacc cccaagtcgc cgcgccc        177

<210> SEQ ID NO 1215
<211> LENGTH: 151
<212> TYPE: DNA
<213> ORGANISM: Artificial Sequence
<220> FEATURE:
<223> OTHER INFORMATION: probe/primer/pcr

<400> SEQUENCE: 1215 gcccctgtc cctttcccgg gactctacta cctttaccca gagcagaggg tgaaggcctc       60
ctgagcgcag ggccccagtt atctgagaaa ccccacagcc tgtccccgt ccaggaagtc     120 tcagcgagct cacgccgcgc agtcgcagtt t                                    151

<210> SEQ ID NO 1216
<211> LENGTH: 209
<212> TYPE: DNA
<213> ORGANISM: Artificial Sequence
<220> FEATURE:
<223> OTHER INFORMATION: probe/primer/pcr

<400> SEQUENCE: 1216 gtggggtcc gcacccagca ataacccggg tcttcccgct ccggctcctg ccccagtaag       60
cgttggaccg ggagacgcag tgctcagcat cggtcagcag ggggcgcaag gaccccgccc    120
cgccgagtcc gcgccaaagt ttctcatcct ccacccgccc acgctccgca ccccctccgc    180
ggctgcccag caccccacg gccccagca                                        209

<210> SEQ ID NO 1217
<211> LENGTH: 220
<212> TYPE: DNA
<213> ORGANISM: Artificial Sequence
<220> FEATURE:
<223> OTHER INFORMATION: probe/primer/pcr

<400> SEQUENCE: 1217
gggcccccgg gttgcgtgag gacacctcct ctgaggggcg ccgcttgccc ctctccggat      60
cgcccggggc cccggctggc cagaggatgg acgaggagga ggatggagcg ggcgccgagg    120
```

```
agtcgggaca gccccggagc ttcatgcggc tcaacgacct gtcggggggcc ggggggccggc    180 cggggccggg gtcagcagaa aaggacccgg gcagcgcgga                            220
```

<210> SEQ ID NO 1218
<211> LENGTH: 212
<212> TYPE: DNA
<213> ORGANISM: Artificial Sequence
<220> FEATURE:
<223> OTHER INFORMATION: probe/primer/pcr
<400> SEQUENCE: 1218

```
gcctgcacag acgacagcac ccccggcggg ggagagcggc cccagcggag actcggcagg      60
gctcaggttt cctggaccgg atgactgacc tgagcccggg gccgggcgg cgctggccgg       120 gcacaggatg cgcggcccgg agagcgcatc ccggccatcc gcccgcgctc ggccccgcag      180
cgcagctgct gcagatccgc gggggccgcc ac                                    212
```

<210> SEQ ID NO 1219
<211> LENGTH: 244
<212> TYPE: DNA
<213> ORGANISM: Artificial Sequence
<220> FEATURE:
<223> OTHER INFORMATION: probe/primer/pcr
<400> SEQUENCE: 1219

```
ggccgcgccg ggctcaggtt ccaccccccgg gagcgcgggg cggagccagg ccggcgccga     60
ggctcagtgc cctccccgct ccgcggcgcc ggctgcgaag ttgagcgaaa agtttgaggc      120
cggagggagc gaggccgggg agtccgctcc agcggggcgc tccagtccct cagacgtggg     180
ctgagcttgg gacgagctgc gttccgcccc aggccactgt agggaacggc ggtggcgcct    240
cccc                                                                   244
```

<210> SEQ ID NO 1220
<211> LENGTH: 253
<212> TYPE: DNA
<213> ORGANISM: Artificial Sequence
<220> FEATURE:
<223> OTHER INFORMATION: probe/primer/pcr
<400> SEQUENCE: 1220

```
ggggtagtcg cgcaggtgtc gggcgcggag ccgcttggcc tcctccacga agggccgctt     60
ctcgtcctcg tccagcagct tccactgcgc gcccaggcgc ttggagatct cggagttgtg    120
catcttgggg ttctgctgcg ccatctggcg gcgctgagcg gagctccaca ccatgaacgc    180
gttcatcggc cgcttcacct tctccagggg cagcgtcccg ggggccgcgg ggctcccagc    240
gccctcccgc tcc                                                         253
```

<210> SEQ ID NO 1221
<211> LENGTH: 255
<212> TYPE: DNA
<213> ORGANISM: Artificial Sequence
<220> FEATURE:
<223> OTHER INFORMATION: probe/primer/pcr
<400> SEQUENCE: 1221

```
tgcaggcgga gaatagcagc ctccctctgc caagtaagag gaaccggcct aaaggacatt     60
ttctctctct ctcctcccct ctcatcgggt gaatagtgag ctgctccggc aaaaagaaac    120
cggaaatgct gctgcaagag gcagaaatgt aaatgtggag ccaaacaata acagggctgc    180
cgggcctctc agattgcgac ggtcctcctc ggcctggcgg gcaaacccct ggtttagcac    240
```

```
ttctcacttc cacga                                              255

<210> SEQ ID NO 1222
<211> LENGTH: 163
<212> TYPE: DNA
<213> ORGANISM: Artificial Sequence
<220> FEATURE:
<223> OTHER INFORMATION: probe/primer/pcr

<400> SEQUENCE: 1222
ccggaaatgc tgctgcaaga ggcagaaatg taaatgtgga gccaaacaat aacagggctg    60
ccgggcctct cagattgcga cggtcctcct cggcctggcg ggcaaacccc tggtttagca   120
cttctcactt ccacgactga cagccttcaa ttggattttc tcc                     163

<210> SEQ ID NO 1223
<211> LENGTH: 233
<212> TYPE: DNA
<213> ORGANISM: Artificial Sequence
<220> FEATURE:
<223> OTHER INFORMATION: probe/primer/pcr

<400> SEQUENCE: 1223
gcgtcggatc cctgagaact tcgaagccat cctggctgag gctaatctcc gctgtgcttc    60
ctctgcagta tgaagacttt ggagactcaa ccgttagctc cggactgctg tccttcagac   120
caggacccag ctccagccca tccttctccc cacgcttccc cgatgaataa aaatgcggac   180
tctgaactga tgccaccgcc tcccgaaagg ggggatccgc cccggttgtc ccc          233

<210> SEQ ID NO 1224
<211> LENGTH: 172
<212> TYPE: DNA
<213> ORGANISM: Artificial Sequence
<220> FEATURE:
<223> OTHER INFORMATION: probe/primer/pcr

<400> SEQUENCE: 1224
ccggctccgc gggttccgtg ggtcgcccgc gaaatctgat ccgggatgcg gcggcccaat    60
cggaaggtgg accgaaatcc cgcgacagca agaggcccgt agcgacccgc ggtgctaagg   120
aacacagtgc tttcaaaaga attggcgtcc gctgttcgcc tctcctcccg gg           172

<210> SEQ ID NO 1225
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1225
cgtcgccggg gctggacgtt cgcagcggcg cttcggaagg gggccccgcg ggagcagccg    60
cccgcgtctc cagcagcttc cccttgccag gcgccgcgcg cgcccggtat ccccgggtgt   120
ccacctgtgc gtgggggct gtttcccgtc tgtccagccg cgcccacttc tcaggcccaa   180
aggccagcag gaagggtccc ggaggtggct gggggcgtcc acctgagaag ctccgctctc   240
gctcagacac cccac                                              255

<210> SEQ ID NO 1226
<211> LENGTH: 255
<212> TYPE: DNA
<213> ORGANISM: Artificial Sequence
<220> FEATURE:
```

<223> OTHER INFORMATION: probe/primer/pcr

<400> SEQUENCE: 1226

| gggcctgccg cctcgtccac cgtccgtcgt gaggccggca gcggacacgt gctcatccca | 60 |
| cggggaggcc ccgcgcagcg cggaggacgc gcctgagaga gaaaaggggt tcgggagaag | 120 |
| cccgaggacc cggcccgtga ctgggcgcgc cctatgcaaa tgagcgggcg ggccctcgt | 180 |
| gttgctgaac gagggcgggt tcgcgatgta aataagccca gaggtggggt ctttggagag | 240 |
| cacttagggc ccggg | 255 |

<210> SEQ ID NO 1227
<211> LENGTH: 173
<212> TYPE: DNA
<213> ORGANISM: Artificial Sequence
<220> FEATURE:
<223> OTHER INFORMATION: probe/primer/pcr

<400> SEQUENCE: 1227

| gcacaccgct ggcggacacc ccagtaacaa gtgagagcgc tccacccgc agtccccccc | 60 |
| gcctctcctc cctgggtccc ctcggctctc ggaagaaaaa ccaacagcat ctccagctct | 120 |
| cgcgcggaat tgtctcttca actttaccca accgacgaca aggaaccagc ctc | 173 |

<210> SEQ ID NO 1228
<211> LENGTH: 216
<212> TYPE: DNA
<213> ORGANISM: Artificial Sequence
<220> FEATURE:
<223> OTHER INFORMATION: probe/primer/pcr

<400> SEQUENCE: 1228

| gcaaaccatc ttccccgacg ccttccacat aagatgccct cctgcgggcc ctcacctttt | 60 |
| gacactgcct cccaccgcac tggggtcaac tctcacccaa gggttccgcc accttccacc | 120 |
| accaaaccag cctgtccctg ccacatgccc ccgggcccc agcgctcatc ctctgcccag | 180 |
| gcccgctctt gaccctgac cccggcctga ccccgc | 216 |

<210> SEQ ID NO 1229
<211> LENGTH: 236
<212> TYPE: DNA
<213> ORGANISM: Artificial Sequence
<220> FEATURE:
<223> OTHER INFORMATION: probe/primer/pcr

<400> SEQUENCE: 1229

| ggccctccgc cgcctccaac cgcgcaccag gagctgggca cggcggcagc ggcggcagcg | 60 |
| gcggcgtcgc gctcggccat ggtcaccagc atggcctcga tcctggacgg cggcgactac | 120 |
| cggcccgagc tctccatccc gctgcaccac gccatgagca tgtcctgcga ctcgtctccg | 180 |
| cctggcatgg gcatgagcaa cacctacacc acgctgacac cgctccagcc gctgcc | 236 |

<210> SEQ ID NO 1230
<211> LENGTH: 247
<212> TYPE: DNA
<213> ORGANISM: Artificial Sequence
<220> FEATURE:
<223> OTHER INFORMATION: probe/primer/pcr

<400> SEQUENCE: 1230

| caccaccgtg gcaaagcgtc cccgcgcggt gaagggcgtc aggtgcagct ggctggacat | 60 |
| ctcggcgaag tcgcggcggt agcggcggga gaagtcgtcg ccggcctggc ggagggtcag | 120 |

```
gtggaccaca ggtggcaccg ggctgagcgc aggccccgcg gcggcgccgg gggcagccgg    180
ggtctgcagc ggcgaggtcc tggcgaccgg gtcccgggat gcggctggat ggggcgtgtg    240
cccgggc                                                              247
```

<210> SEQ ID NO 1231
<211> LENGTH: 185
<212> TYPE: DNA
<213> ORGANISM: Artificial Sequence
<220> FEATURE:
<223> OTHER INFORMATION: probe/primer/pcr

<400> SEQUENCE: 1231

```
cacagcccct tcctgcccga acatgttgga ggccttttgg aagctgtgca gacaacagta     60
acttcagcct gaatcatttc tttcaattgt ggacaagctg ccaagaggct tgagtaggag    120
aggagtgccg ccgaggcggg gcggggcggg gcgtggagct gggctggcag tgggcgtggc    180
ggtgc                                                                185
```

<210> SEQ ID NO 1232
<211> LENGTH: 242
<212> TYPE: DNA
<213> ORGANISM: Artificial Sequence
<220> FEATURE:
<223> OTHER INFORMATION: probe/primer/pcr

<400> SEQUENCE: 1232

```
gcttgatgct caccactgtt cttgctgctc aagggaaacc aagtatatat ttgtggatag     60
atcctaactc agatgatact gtcagaatat ataagattcc tataccacat cctgaactct    120
gaaagttgca gttctacgta gaagttcact gagggttgta agagtcagaa tggactccat    180
ggaagttatg gggtgtgaat caaacctcac aggtgagtca gtggggagaa agaagcatga    240
ca                                                                   242
```

<210> SEQ ID NO 1233
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1233

```
ggccaggccc ggtggctcac acctgtaatc ccagcacttt gggaggccga ggtgggcgga     60
ttgcctgagg tcaggagttt gagaccagcc tggccaacat ggtgaaaccc cgtctctact    120
aaaaatacca aaaattagcc agtcgtagtg gtgggcacct gtaatcccag ctattcagga    180
ggctgaggca ggaggatcac ttgaacccaa gaggcgggag ttgcagtgag cagagatcac    240
gccattgcac cccag                                                     255
```

<210> SEQ ID NO 1234
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1234

```
gcgggacggg tggcgggaag gagggaggcg cggctgggga gagcgctcgg gagctgccgg     60
gcgctgcgga ccccgtttag tcctaacctc aatcctgcga gggaggggac gcatcgtcct    120
```

```
cctcgcctta cagacgccga aacggagggt cccattaggg acgtgactgg cgcgggcaac    180
acacacagca gcgacagccg ggaggtaagc cgcgtcccag cggctccgcg gccgggctcg    240
cagtcgcccc agtga                                                     255
```

<210> SEQ ID NO 1235
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1235

```
gcttggcccc gccacccaga ccctcccccc gggggcgccc agcttggcct ctgggtcccg    60
gcgcacgcgg accccaagtc ggggaggccg ggctgaccgc ggccgcctcc ccggctccgg    120
gtaggaggtg ggcagagaag gtgggctgag gggaggagaa actgggctgc gggggtccgg    180
gagggtggat tccgagaaac tatgtgccca gctgaccctg cccgccccgc cgcggccctg    240
cagtccccgg gccag                                                     255
```

<210> SEQ ID NO 1236
<211> LENGTH: 211
<212> TYPE: DNA
<213> ORGANISM: Artificial Sequence
<220> FEATURE:
<223> OTHER INFORMATION: probe/primer/pcr

<400> SEQUENCE: 1236

```
gcggggaagg cgaccgcagc ccacctaccg ctggacgcgg gttggggacc ccgccgcccg    60
gccagctttg ttcgggggcc cgcggcccct cccgggcccc cgcaccgcct cgggtgaccc    120
gcggtgtccc agcgcgttga cgcagcctgt gatccctcgc gaggcgagga gaaggtcggg    180
ggcttggctc tgcctaatgg ccgcccgggg a                                   211
```

<210> SEQ ID NO 1237
<211> LENGTH: 221
<212> TYPE: DNA
<213> ORGANISM: Artificial Sequence
<220> FEATURE:
<223> OTHER INFORMATION: probe/primer/pcr

<400> SEQUENCE: 1237

```
gcgcccaacc accacgcccg cctaattttt gtattttag tagagacggg ttttcaccat     60
tttggccagg ctggtctcga accccgacct caggtgatct gcccaaaagt gctgggatta    120
caggcgtcag ccaccgcgcc cggccgggac cctctcttct aactcggagc tgggtgtggg    180
gacctccagt cctaaaacaa gggatcactc ccaccccgc c                         221
```

<210> SEQ ID NO 1238
<211> LENGTH: 179
<212> TYPE: DNA
<213> ORGANISM: Artificial Sequence
<220> FEATURE:
<223> OTHER INFORMATION: probe/primer/pcr

<400> SEQUENCE: 1238

```
aaaagccccg gccggcctcc ccagggtccc cgaggacgaa gttgaccctg accgggccgt    60
ctcccagttc tgaggcccgg gtcccactgg aactcgcgtc tgagccgccg tcccggaccc    120
ccggtgcccg ccggtccgca gaccctgcac cgggcttgga ctcgcagccg ggactgacg    179
```

```
<210> SEQ ID NO 1239
<211> LENGTH: 184
<212> TYPE: DNA
<213> ORGANISM: Artificial Sequence
<220> FEATURE:
<223> OTHER INFORMATION: probe/primer/pcr

<400> SEQUENCE: 1239
cgcaggtgcg ggggagcgtg cggccgggtc catgcgcctg cgggcggcgg ggggagacgc    60
gttgccttcg gccgggacca ctgcacctgc ccgcgtgggt aatgcgcccg ccgcagactc   120
cgcgcacgac tccgcctggg agcgcgttgg gggccgttgg agtccagcat ggcgcggacc   180
ccgg                                                                184

<210> SEQ ID NO 1240
<211> LENGTH: 241
<212> TYPE: DNA
<213> ORGANISM: Artificial Sequence
<220> FEATURE:
<223> OTHER INFORMATION: probe/primer/pcr

<400> SEQUENCE: 1240
cccgcccaca gcgcggagtt tagtctgcgc gtgcctcgct cgagaacgcg ctcgtgcgca    60
tgcccacaaa ggccaaggag ggagtgcgca ggtcacgtgc gccggtggtc agcgcgcgca   120
ttgcctgccc cggaagtggt cggcgcgcgg cgcggcgcgc ctgggcgcta agatggcggc   180
ggcgtgagtt gcatgttgtg tgaggatccc ggggccgccg cgtcgctcgg gccccgccat   240
g                                                                  241

<210> SEQ ID NO 1241
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1241 gcagggccc gggggcgatg ccacccggtg ccgactgagg ccaccgcacc atggcccgct     60
cgctgacctg gcgctgctgc ccctggtgcc tgacggagga tgagaaggcc gccgcccggg   120
tggaccagga gatcaacagg atcctcttgg agcagaagaa gcaggaccgc ggggagctga   180
agctgctgct tttgggtgag tccagggtcg gtgggcggtg ggtggtgggc agtgggcggt   240
ggccagccgg caggg                                                   255

<210> SEQ ID NO 1242
<211> LENGTH: 171
<212> TYPE: DNA
<213> ORGANISM: Artificial Sequence
<220> FEATURE:
<223> OTHER INFORMATION: probe/primer/pcr

<400> SEQUENCE: 1242
catgaccgcg gtggcttgtg ggaaaagtgg ctcggaaccc caaatcccgg ttagattgca    60
ggcaccgccg gacgctggct cccggaggtt ttagtttttcc ctctaccagg agtgtgaaga  120
cacagagact tattgcgctg gcgaagatgg ctgaggcgaa ggcgtgtccg a            171

<210> SEQ ID NO 1243
<211> LENGTH: 166
<212> TYPE: DNA
<213> ORGANISM: Artificial Sequence
<220> FEATURE:
```

<223> OTHER INFORMATION: probe/primer/pcr

<400> SEQUENCE: 1243

| | |
|---|---|
| gcaggtgctc agcgggcaga cgccccgccc cgccccgcca ggttctgttg ggggcgaggc | 60 |
| ccgcgcaagc cccgcctctt ccccggcacc aggggcgggc ccaggtgcgc ccagggccgg | 120 |
| ggagcggccg cgcaggtgcc tgccctttgc gcctgcgccc agctcg | 166 |

<210> SEQ ID NO 1244
<211> LENGTH: 187
<212> TYPE: DNA
<213> ORGANISM: Artificial Sequence
<220> FEATURE:
<223> OTHER INFORMATION: probe/primer/pcr

<400> SEQUENCE: 1244

| | |
|---|---|
| ggtgcgccct gcgctggcta aagtgcgcaa gcgcgcgagg ctcgggcctt tcaaaccccg | 60 |
| gcgcgccggc gccggcgtcg acactgcgca agcccagtcg cgcctctcca gagcgggaag | 120 |
| agcgctgcgt tccttagcaa cgagcgtttc ctccagcccc gcctccctcc gccacacaca | 180 |
| accccgc | 187 |

<210> SEQ ID NO 1245
<211> LENGTH: 222
<212> TYPE: DNA
<213> ORGANISM: Artificial Sequence
<220> FEATURE:
<223> OTHER INFORMATION: probe/primer/pcr

<400> SEQUENCE: 1245

| | |
|---|---|
| aatttggtcc tcctgcgcct gccaagattg tctgagtatt gatcgaaccc aggagttcga | 60 |
| gatcagcttg agcaagatag cgagaacccc cgcccctcca cctcgtctca aaaaaaaaaa | 120 |
| aaaatcgtct cagtagcgaa tagtctaacg gagaatgaca gggaaattgg tgatcctttc | 180 |
| tgggcccaag agttagaaat ggctttgcag gccgggcgcg gt | 222 |

<210> SEQ ID NO 1246
<211> LENGTH: 200
<212> TYPE: DNA
<213> ORGANISM: Artificial Sequence
<220> FEATURE:
<223> OTHER INFORMATION: probe/primer/pcr

<400> SEQUENCE: 1246

| | |
|---|---|
| ggcttccgcg gcgccaatct ccacccgcag tctccgcctc ccgcacctgt ggtccgggcc | 60 |
| tcacggtttc agcgccgcga ggcctcacct gctggtcttg gagcctcaag ggaaagactg | 120 |
| cagagggatc gaggcggccc actgccagca cggccagcgt ggcccagggc tcgcagcact | 180 |
| tccggcctct ctggccccgc | 200 |

<210> SEQ ID NO 1247
<211> LENGTH: 202
<212> TYPE: DNA
<213> ORGANISM: Artificial Sequence
<220> FEATURE:
<223> OTHER INFORMATION: probe/primer/pcr

<400> SEQUENCE: 1247

| | |
|---|---|
| gccaggagag gggccgagcc tgcacaggag cttcctcggt tttccgagcg ccggcccccc | 60 |
| ttctctgcct gggaggaggt ggttagagtc ccctgggtgt gtgccccgca gagggagctc | 120 |
| tggcctcagt gcccagtgtg cagaccaatg agagcccag agagaaagac ggtcatttcc | 180 |

-continued tccctgcatc ttcccttggg gc                                           202

<210> SEQ ID NO 1248
<211> LENGTH: 158
<212> TYPE: DNA
<213> ORGANISM: Artificial Sequence
<220> FEATURE:
<223> OTHER INFORMATION: probe/primer/pcr

<400> SEQUENCE: 1248
cgagcgccgg ccccccttct ctgcctggga ggaggtggtt agagtcccct gggtgtgtgc    60
cccgcagagg gagctctggc ctcagtgccc agtgtgcaga ccaatgagag ccccagagag   120
aaagacggtc atttcctccc tgcatcttcc cttggggc                          158

<210> SEQ ID NO 1249
<211> LENGTH: 203
<212> TYPE: DNA
<213> ORGANISM: Artificial Sequence
<220> FEATURE:
<223> OTHER INFORMATION: probe/primer/pcr

<400> SEQUENCE: 1249
ggttgcgagg gcacccttttg gcccgggggc gcgcaggaga gggcaggggc caggggtttc    60
ctgggcgagg gcgcggggac gagcaggaaa aggccgggggt gggggtggaa ttcctcggcg   120 ggcaggggggc gcatgcgccg ggcaccgtgg ggcgggacgt ggcccgggag gagctggggg   180
gactgggtgg tgcacgtgcg ggc                                          203

<210> SEQ ID NO 1250
<211> LENGTH: 168
<212> TYPE: DNA
<213> ORGANISM: Artificial Sequence
<220> FEATURE:
<223> OTHER INFORMATION: probe/primer/pcr

<400> SEQUENCE: 1250
acccggacgc ggtggcgcgc gcctgtaatc ccagctactc gggagcctga ggcaggagaa    60
tcgcttgaat ccgggaggcg gaggttgcag taagccgaga tcgcgccact gcaccccagc   120
ctgggcgaca gagcaagact cctcggtaaa gacaccactt cgtcaccc                168

<210> SEQ ID NO 1251
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1251
cgccgccgag cctcagccac gcctctgtgc agcggggaag actcctctcg cgccttctca    60
gtcagtcacg gatgatgctg acccagcgct ccggggcttt ctaccaagta atcagtccag   120
acaaatgcca aaacgaccgc cacaaggagg acaacggaag tcccgccgcg accgcgcgtg   180
cgcttacgga aacaccacct ttcggaggcc tcattggctg aaggtcgccg tcgcccaacg   240
caggccattc tgggt                                                   255

<210> SEQ ID NO 1252
<211> LENGTH: 179
<212> TYPE: DNA
<213> ORGANISM: Artificial Sequence
<220> FEATURE:

<223> OTHER INFORMATION: probe/primer/pcr

<400> SEQUENCE: 1252

| gcagcctcaa cctcctgggg tcaagtgatc atcctggctc aaccacccaa gtagccggga | 60 |
| ctacgggtgg ccgccaccat gcccggataa ttttttttatt tttgtggaga tgggggtccc | 120 |
| acgatgttgc ccagtccagt cttgaactcc tgggctcaag tgatcctccc gcagcagcc | 179 |

<210> SEQ ID NO 1253
<211> LENGTH: 150
<212> TYPE: DNA
<213> ORGANISM: Artificial Sequence
<220> FEATURE:
<223> OTHER INFORMATION: probe/primer/pcr

<400> SEQUENCE: 1253

| cttgccgacc cagcctcgat ccctgcggc gtccaggtcc caatgcccca acgcaggcca | 60 |
| cccccggctc ctctgtggac tcacgaagac aaggtccggc cgctcgggcc gcgagagtcg | 120 |
| cgccatcacc accattttc tggatgccca | 150 |

<210> SEQ ID NO 1254
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1254

| gcggcgttcg gtggtgtccc ggtgcagcca cgcgagagta gaagggtgga aaggggaggt | 60 |
| gcccagtgaa atggagcctg tcccgtgcac tttcgggcat ttcgagcatc ttgtgggctc | 120 |
| tcccaagtcg cggcccctcc tctgagagcc acagtcaggt ctgtcctcag gggtcgaggc | 180 |
| ggctgcgctg gggcctcggc ccgggaggag gcgggggggca cggccttttcc attttccctg | 240 |
| ctcccctctg cagaa | 255 |

<210> SEQ ID NO 1255
<211> LENGTH: 151
<212> TYPE: DNA
<213> ORGANISM: Artificial Sequence
<220> FEATURE:
<223> OTHER INFORMATION: probe/primer/pcr

<400> SEQUENCE: 1255

| ccggactccc ccgcgcagac caccgtgcca ggacagcccg ctcgggagtc gggcctggaa | 60 |
| gcaggcggac agcgtcacct ccccgcagcc gccggctggg accgcggcc agcctttacc | 120 |
| caggctcgcc cggtccctgc ccgcatggcg g | 151 |

<210> SEQ ID NO 1256
<211> LENGTH: 237
<212> TYPE: DNA
<213> ORGANISM: Artificial Sequence
<220> FEATURE:
<223> OTHER INFORMATION: probe/primer/pcr

<400> SEQUENCE: 1256

| ggcccctgc aagttccgcc tcccgggttc acaccattct cctgcctcag cctccccagc | 60 |
| agctgggact acaggcacct gccgccacgc ccggctaatt ttttgtatttt ttagtagaga | 120 |
| cagggttca ccatgttagc caggatggtc tcgatctcct gaccttgtga tctgcccgcc | 180 |
| tcggcctccc aaagtgttgg gattacaggc gtgagccacc gtgtccagcc tgtaaca | 237 |

<210> SEQ ID NO 1257
<211> LENGTH: 194
<212> TYPE: DNA
<213> ORGANISM: Artificial Sequence
<220> FEATURE:
<223> OTHER INFORMATION: probe/primer/pcr

<400> SEQUENCE: 1257

```
gcccagggga gccctccatt tgtagaatga atgagagtcc aggttatgaa cagtgcctgg      60
agtgtaggaa caccctcctt tgcctctttg acaggtctgc atcataacac tttttttttt     120
tttttgagac agagtctcac tctgtcgccc aggctggagt gcagtggcac gatctcggcc     180
ccctgcaagt tccg                                                       194
```

<210> SEQ ID NO 1258
<211> LENGTH: 207
<212> TYPE: DNA
<213> ORGANISM: Artificial Sequence
<220> FEATURE:
<223> OTHER INFORMATION: probe/primer/pcr

<400> SEQUENCE: 1258

```
ccggctgcag gccctcactg gttgggtccg cccgcgaggg tgccctgggc ccggtgtctc      60
tcctccttct gaagtttgtt cccatccacc cggcatcacc gaccggtttt atcccgctga    120
ggccctggga gatgggtctg gcgaggctcg taggccgcgg attggctggc tgggtgcagg    180
ggggtgcggg aaggggagga ttttgca                                        207
```

<210> SEQ ID NO 1259
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1259

```
gtcacacctg ccgatgaaac tcctgcgtaa gaagatcgag aagcggaacc tcaaattgcg      60
gcagcggaac ctaaagtttc agggtgagat gcgttgactc gcggtggctc agaagaccca    120
cgcgcgagcc ctggcgcgtt cgggcggccg ggggcccagc tgctctgtgt gacggaggca    180
gcttcccctg cagcgtgtgt gattggggag agtgaaaagg cagcttccac tcgggacccg    240
cgctgctgcc cactc                                                     255
```

<210> SEQ ID NO 1260
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1260

```
ccctgcgcac ccctaccagg caggctcgct gcctttcctc cctcttgtct ctccagagcc      60
ggatcttcaa ggggagcctc cgtgcccccg gctgctcagt ccctccggtg tgcaggaccc    120
cggaagtcct ccccgcacag ctctcgcttc tctttgcagc ctgtttctgc gccggaccag    180
tcgaggactc tggacagtag aggccccggg acgaccgagc tgatggcgtc ttcgaccccca   240
tcttcgtccg caacc                                                     255
```

<210> SEQ ID NO 1261

```
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1261
cctgggggag cgcggtgggg gtaagataag ggatggggc tccgagggct gggaactgca     60
ggaaggaaag aagcggcggg gccgcccggg tcaaggggcc acgtggggga gggcgggcag    120
gcgggaccgg gaggtcaata actgcagcgt ccgagctgag cccaggggag cgggcgagga    180
gaaagaagcc tcagagcgcc cgggaagcct cgcgcgcctg ggaggcttcc atctcccggg    240
acccagctct cagcc                                                    255

<210> SEQ ID NO 1262
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1262
gtggggccgg gcgagtgcgc ggcatcccag gccggcccga acgctccgcc cgcggtgggc     60
cgacttcccc tcctcttccc tctctccttc ctttagcccg ctggcgccgg acacgctgcg    120
cctcatctct tggggcgttc ttccccgttg gccaaccgtc gcatcccgtg caactttggg    180
gtagtggccg tttagtgttg aatgttcccc accgagagcg catggcttgg gaagcgaggc    240
gcgaacccgg ccccc                                                    255

<210> SEQ ID NO 1263
<211> LENGTH: 234
<212> TYPE: DNA
<213> ORGANISM: Artificial Sequence
<220> FEATURE:
<223> OTHER INFORMATION: probe/primer/pcr

<400> SEQUENCE: 1263
cgtccaggct gtgcgctccc cgttctcccc tcctccccac ttctccccac gccttgctcg     60
tctcccgccc tcctccgaca accgctcccc tcaccctcca ccctaccccc cgcccctcct    120
ccttcctccc cggcatgcgc catatggtct tcccggtcca gccaagagcc tggaaccacg    180
tgacctgccc atttgtatgc cgcggagcgc tccattccgg ccccctttgtg gcca         234

<210> SEQ ID NO 1264
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1264
gcgcggcggt gcagcctctc ccgagcgcgc tgggtcgcct ctgctcggtc tggggtctgc     60
caggcgcgat ccccccggtg cagccgagcc cctccgcaga ctctgcgcag gaaagcgaaa    120
ctacccggca ggagaaaagg cagcgctggc gcccggcccc cttccgcccc caccaatcac    180
cgggcggctc cgcgctcagc caattagacg cggctgttcc gtgggcgcca ccgcctccct    240
ctgcgggccg ctgct                                                    255

<210> SEQ ID NO 1265
<211> LENGTH: 255
```

```
<212> TYPE: DNA
<213> ORGANISM: Artificial Sequence
<220> FEATURE:
<223> OTHER INFORMATION: probe/primer/pcr

<400> SEQUENCE: 1265
aggcggcggc ggtggcagtg gcacccggcg gggaagcagc agccaaaccc gcgcatgatc     60
tcgagagttt cagcaacatc cagggactgg gctcagcccc ggagcgagag ggtcgtccgc    120
tgagaagctg cgccggagac gcgggaagct gctgccataa ggaggagct ctgggaagcc    180 ggaggacagg aggagacggg agtccagggg cagacgagtg gagcccgagg aggcagggtg    240
gagggagagt caagg                                                     255

<210> SEQ ID NO 1266
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1266
gcgcgacccg ccgattgtgt cgagtcagca gcggcagcgg ggacgcgcga agccatggct     60
cccgcccgcg ctcgggaggg cgccgggggt cctgcgcctc cgggaggttt gtggccgagc    120
gcggcgcggc cccgagcggc cccgcagcgc ccggctcccc gccgctcgct ctccaggcgc    180
cgacccgcct gcgtcgccac cctctcgccg ctccctgccg ccaccttcct cccgcccggg    240
tgccgggcgt ccgct                                                     255

<210> SEQ ID NO 1267
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1267
cgcggacgcc gctctgcacc tgttgccgcc gtcactcatc ccgccaggcg ggcggggccg     60
cgcgggtggc ttggtcagga cctgccattc agcccagtcg ggctccggtg ctcgccccgg    120
acggcgcccc aagcgggtcc cggccccgct gagcacctcc agcagtggca cagcctctgg    180
aggggtccgg gacgaagcca cccgcgcggt aggggcgac ttagcggttt cagcctccaa    240
cagccttggg atcgc                                                     255

<210> SEQ ID NO 1268
<211> LENGTH: 197
<212> TYPE: DNA
<213> ORGANISM: Artificial Sequence
<220> FEATURE:
<223> OTHER INFORMATION: probe/primer/pcr

<400> SEQUENCE: 1268
tgaacccggg aggcggaggt tgctgtgagc cgagatggca ccattgcact ccagcctggg     60
caacaagagc gaaactccgt cccccgaaca aaaaattcaa atgggaaaga gaggcagatg    120
gcagagaaca gggaggggc tgggcaccgt ggctcatgcc tgtaatccca gcactttggg    180
aggccaaggc gggtgga                                                   197

<210> SEQ ID NO 1269
<211> LENGTH: 224
<212> TYPE: DNA
```

<213> ORGANISM: Artificial Sequence
<220> FEATURE:
<223> OTHER INFORMATION: probe/primer/pcr

<400> SEQUENCE: 1269

```
ctcggcggcg cggggagtcg gaggacgcag ccaagcggcg gcggcgagga gggtcacagc    60
cggaaagagg cagcggtggc gcctgcagac gccgcgcagc ccgggcagcc ccacagcgca   120
agctggctgc cgcggcggcg ggggctttat cggcggcgcc gcgcgggccc ccgccccttc   180
ctgccgcccc cgccccggc ccgccttgcc ccgccttccc gccg                    224
```

<210> SEQ ID NO 1270
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1270

```
aggcggccac gggaggggga ggggctggca acggcgccgt gggggcgggg ctcgctttgt    60
gcaaggtccg cgctgattgg gccgtgggcg cgcgggtccc ggcctgcgtc gtgggactgg   120
cgttttttggc gccggctgtg aggggagcgc ggggtggtg gaatcgggcg gtctccggtt   180
cgccaatgtg gctgggtccg taggcttggg cagccttgga gttcctcaga gaccccgcgc   240
tcggtcccgg cacgc                                                   255
```

<210> SEQ ID NO 1271
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1271

```
gacccgagcg gggcggagag tggcaggagg aggcgaatct ccgcgctccg gcgaacttta    60
tcgggttgaa gtttctgctg tcgcctcccc tttgcgtgcg gagctgggct ttgcgtgcgc   120
cgcttctgga aagtcggctc cagtcatatc cctgggcgct gcctgcgcc gctcctcccg   180
cgcttctcac ggcacctgac acgcggaggc ggcggccgag ggtggggtgc cggccaccac   240
caccccttggc gtggg                                                  255
```

<210> SEQ ID NO 1272
<211> LENGTH: 218
<212> TYPE: DNA
<213> ORGANISM: Artificial Sequence
<220> FEATURE:
<223> OTHER INFORMATION: probe/primer/pcr

<400> SEQUENCE: 1272

```
agcacctggg gcggggcgga gcggggcgcg cgggcccaca cctgtggaga gggccgcgcc    60
ccaactgcag cgccggggct gggggagggg agcctactca ctcccccaac tcccgggcgg   120
tgactcatca acgagcacca gcggccagag gtgagcagtc ccgggaaggg gccgagaggc   180
ggggccgcca ggtcgggcag gtgtgcgctc cgccccgc                          218
```

<210> SEQ ID NO 1273
<211> LENGTH: 253
<212> TYPE: DNA
<213> ORGANISM: Artificial Sequence
<220> FEATURE:
<223> OTHER INFORMATION: probe/primer/pcr

<400> SEQUENCE: 1273
ccgctcgggg gacgtgggag gggaggcggg aaacagctta gtgggtgtgg ggtcgcgcat        60
tttcttcaac caggaggtga ggaggtttcg acatggcggt gcagccgaag gagacgctgc       120
agttggagag cgcggccgag gtcggcttcg tgcgcttctt tcagggcatg ccggagaagc       180
cgaccaccac agtgcgcctt ttcgaccggg gcgacttcta tacggcgcac ggcgaggacg       240
cgctgctggc cgc                                                         253

<210> SEQ ID NO 1274
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1274
accgccagcg tgccagcccc gcccctaccc accagtgtgc cagccccgcc cttccccacg        60
tcgccgcgcg cccgggggcg gggcctggcg cgcaccgccc gcgcacggcg aggcgcctgt       120
tgattggcca ctggggcccg ggttcctccg gcggagcgcg cctcccccca gatttcccgc       180
cagcaggagc cgcgcggtag atgcggtgct tttaggagct ccgtccgaca gaacggttgg       240
gccttgccgg ctgtc                                                       255

<210> SEQ ID NO 1275
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1275
attcttggcc gggtgcggtg gctcacgcct gtaatcccag cactttggga ggctgaggtg        60
ggtggatcac ctgaggtcaa gagttcgaga ccagcctggc caacatggtg aaaccccgtc       120
tctactaaaa atacaaaaat tagccgggcg tggtggtggg cacctgtaat cccagctact       180
cagaaggttg aggcaggaga atcgcttgaa cccgggagaa ggaggttgca gtgagccgag       240
atcgcgccat tgcac                                                       255

<210> SEQ ID NO 1276
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1276
cgcttcccgc gagcgagccg cccagagcgc tctgctggcg gcagaggcgg cggcgaggct        60
ggcgcgcttg ccgccgtctg ctcgcccgc ggaggcgacc tggcagacg ctgctgggaa        120 ctttgaaaaa ctttcctgga gccaggcttg ccgcagattc gagggaagc ctcggccgcg        180 tcccaccccc tcccaaatcc gagtctgcgg agcctgggag ggctcccagc ttcctatcca       240
aaccgcgccg gggca                                                       255

<210> SEQ ID NO 1277
<211> LENGTH: 255
<212> TYPE: DNA
<213> ORGANISM: Artificial Sequence
<220> FEATURE:

<223> OTHER INFORMATION: probe/primer/pcr

<400> SEQUENCE: 1277

| agccggcgct | ccgcacctgc | ccctcagcgc | ctgccgtccg | ccccaccgcc | gcggcgcccc | 60 |
| gcactcctgg | gcgggccagg | ggagcgggct | gggcgggcga | tcgggcacgc | gggatccctg | 120 |
| gtcgagcccc | ctttcctccc | gggtccacag | cgagtcccct | gaggaaggag | ggacctggga | 180 |
| ggaaaccacc | ctctggggcg | gctccggcct | ccagcccccg | ccccgtctca | tcgcgccggg | 240 |
| cgcccggtgc | gcctg | | | | | 255 |

<210> SEQ ID NO 1278
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1278

| cggagcgcgc | ttggcctcac | aggacagtgg | gtgtggctgg | ggtgacgggg | cagggtgggg | 60 |
| aagactggcc | taacaccagc | gccctctgcc | ccatggctgg | ccagggaccc | gcgagtccct | 120 |
| ggacacgcac | tggccaacgc | cagaccccat | ctcatcgggt | ggggaagtcg | cggggacact | 180 |
| gtcagggcgc | cgaagtccgg | acccggctca | gaggcggtgg | caggtgaatt | gctgcggcgc | 240 |
| cgggtagggg | cgggc | | | | | 255 |

<210> SEQ ID NO 1279
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1279

| ggcctcgagc | ccacccagac | ttggccaagc | agccctcggc | cagaccaagc | acactccctc | 60 |
| ggaggcctgg | cagggcccct | gctttaccct | gcccccacg | ccccgcccg | accgaccct | 120 |
| cccaggcagc | ccctcagcgt | ctgccgcccg | cccttgggcc | tttccggcca | gcccctcctc | 180 |
| ccgcccacgc | ccagaacagc | ccatgctctt | ggaggagagc | aggtgggctt | gaccgggact | 240 |
| ggcccctcac | cgcgg | | | | | 255 |

<210> SEQ ID NO 1280
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1280

| gccgcgccgt | aagggccacc | cccagaggcc | gaggaggtgg | ggctggcctg | gctttctggc | 60 |
| caggtggggc | ttgtccaacc | ccacaaacat | cagggctcac | cctggatgtg | aagagaagg | 120 |
| agcgaccccc | aaaacgaagc | ggctggatct | gaccttccaa | ggcctgttgg | cgacgcaggg | 180 |
| ccccaggag | gcagagcgcg | cgcctggccc | gggcgatggg | cctcccgtcc | ccccagggct | 240 |
| gcctccccgc | cggtg | | | | | 255 |

<210> SEQ ID NO 1281
<211> LENGTH: 236
<212> TYPE: DNA
<213> ORGANISM: Artificial Sequence
<220> FEATURE:
<223> OTHER INFORMATION: probe/primer/pcr

<400> SEQUENCE: 1281

```
cggcggtggc ggtgggtcgg cgaccggcgg gccgaagact ggaagcccgg gccgctgagg      60
ctccgcagcc ccctccgcgc cgccccggcc cgccccgcc gcgccgcccc ttccctcccc     120
gcgcccgccc cttcttcccc gcagggtcag cgctggggct ccggccgtag agccacgtga     180
ccctggcagg ccctgctcgc ggggcttggc gacaaggacg cacgacacgg ggcggc         236
```

<210> SEQ ID NO 1282
<211> LENGTH: 194
<212> TYPE: DNA
<213> ORGANISM: Artificial Sequence
<220> FEATURE:
<223> OTHER INFORMATION: probe/primer/pcr

<400> SEQUENCE: 1282

```
acctgcccag ttactgcccc actccgcgga ataagctctt acccaccgct cctcttcttc      60
aattcatttc tgttatggaa ctgtcgcggc actacaaagt ctctatgtag ttataaataa     120
acgttatctg gaagagcagc cgacaacaac tttcaagatc tccaattccc cgaccccaca     180
ctccaactga cgcc                                                       194
```

<210> SEQ ID NO 1283
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1283

```
ccagcgcccg agccgtccag gcggccagca ggagcagtgc caaaccgggc agcatcgcga      60
ccctgcgcgg ggcaccgagt gcgctgctgt gcgagtggga tccgccgcgt ccttgctctg     120
cccgcgccgc caccgccgcc gtctcccggg gccccgcgc acgctcctcc gcgtgctctc      180
gcctaccgct gccgaggaaa ctgacggagc ccgagcgcgg cggcggggct cagagccagg     240
cgagtcagct gatcc                                                      255
```

<210> SEQ ID NO 1284
<211> LENGTH: 233
<212> TYPE: DNA
<213> ORGANISM: Artificial Sequence
<220> FEATURE:
<223> OTHER INFORMATION: probe/primer/pcr

<400> SEQUENCE: 1284

```
ctgctgctgc ccgcgtccga ggctcgcggg cggcgggccc gggtgagtgc acacccggcg      60
cgctgccggg ctcccggatg tgtcaccttg tcccgctgca gccgagatgc cggggagcg     120
gggccttcca cacccctcc gtgggtgtgt ggtgagtgtg ggtgtgtgcg cgtctcctcg     180
cgtccctcgc tgaggtgcct actgtgtctg catgggttgg gtcccgcgcg atg            233
```

<210> SEQ ID NO 1285
<211> LENGTH: 182
<212> TYPE: DNA
<213> ORGANISM: Artificial Sequence
<220> FEATURE:
<223> OTHER INFORMATION: probe/primer/pcr

<400> SEQUENCE: 1285
```

```
actgcttagg ccacacgatc ccccaagcct gggctgccag acgtcgccat cattgttcca    60
tgcagatcat gcccatcctg tgcagaaggt cactatagga acacatggca cagggaagaa   120
aacgcccata gaaattcaca tggtgcttgt ctaaaccgaa ggcaggtgag atccacccac   180
tg                                                                  182
```

<210> SEQ ID NO 1286
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1286

```
gccggacgcg cctcccaagg gcgcgggtcc gaggcgcaag gcgagctgga gaccccgaaa    60
accagggcca ctcggggagt gtcaggaagc acgactgggc gccttaggac gtccgggcag   120
acgcggcccc cgaggagccc cagaggagcc ccagaggagc cgcctgaccc ggccccgacg   180
tgcgcgatcg agcccgggct cgccaaagcc cccgcgcccc tccggcccgg acaggccgag   240
tggacattgt cggag                                                    255
```

<210> SEQ ID NO 1287
<211> LENGTH: 152
<212> TYPE: DNA
<213> ORGANISM: Artificial Sequence
<220> FEATURE:
<223> OTHER INFORMATION: probe/primer/pcr

<400> SEQUENCE: 1287

```
cggccagggt gccgagggcc agcatggaca ccaggaccag ggcgcagatc accttgttct    60
ccatggtggc cattgcctcc tctctgctcc aaaggcgacc ccgagtcagg gatgagaggc   120 cgccccgagcc ccggatttta tagggcaggc tc                                152
```

<210> SEQ ID NO 1288
<211> LENGTH: 243
<212> TYPE: DNA
<213> ORGANISM: Artificial Sequence
<220> FEATURE:
<223> OTHER INFORMATION: probe/primer/pcr

<400> SEQUENCE: 1288

```
ccgcccgccc cacagccagc ggctccgcgc ccctgcagc cacgatgccc gcggcccggc    60
cgcccgccgc gggactccgc gggatctcgc tgttcctcgc tctgctcctg gggagcccgg   120
cggcagcgct ggagcgaggt aagcgccccg aggggcgggg cgggcagggg gcaaagttgc   180
cgggagagcg gggcagccag gggtcggggc tgaccagggc gactcaggca ccacccgccg   240
gga                                                                 243
```

<210> SEQ ID NO 1289
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1289

```
gcgccccagc ccacccactc gcgtgcccac ggcggcatta ttccctataa ggatctgaac    60
gatccggggg cggcccgcc ccgttacccc ttgcccccgg ccccgccccc ttttggagg   120 gccgatgagg taatgcggct ctgccattgg tctgaggggg cgggccccaa cagcccgagg   180
```

```
cggggtcccc gggggcccag cgctatatca ctcggccgcc caggcagcgg cgcagagcgg    240
gcagcaggca ggcgg                                                     255
```

<210> SEQ ID NO 1290
<211> LENGTH: 244
<212> TYPE: DNA
<213> ORGANISM: Artificial Sequence
<220> FEATURE:
<223> OTHER INFORMATION: probe/primer/pcr

<400> SEQUENCE: 1290

```
cgtgctgggc gcaggggaaa cagcgacgca cgggacaaaa caagcttgca gaacagcagg    60
gggcagagag gctgtaaaca agccaacggg ctgcacttgt agcggttctg ttgccaatgc   120
cattcagacc ccagtccggg attccgcgct cggggtgcga gaggccgctc ccggggaggg   180
gcgggacccg ggcggggcgg gaggggcggg gcgcccgggc ctattaggtc ccgcgccggc   240
agcc                                                                244
```

<210> SEQ ID NO 1291
<211> LENGTH: 179
<212> TYPE: DNA
<213> ORGANISM: Artificial Sequence
<220> FEATURE:
<223> OTHER INFORMATION: probe/primer/pcr

<400> SEQUENCE: 1291

```
gcgcacgcgc acagcctccg gccggctatt tccgcgagcg cgttccatcc tctaccgagc    60
gcgcgcgaag actacggagg tcgactcggg agcgcgcacg cagctccgcc ccgcgtccga   120
cccgcggatc ccgcggcgtc cggcccgggt ggtctggatc gcggagggaa tgccccgga    179
```

<210> SEQ ID NO 1292
<211> LENGTH: 226
<212> TYPE: DNA
<213> ORGANISM: Artificial Sequence
<220> FEATURE:
<223> OTHER INFORMATION: probe/primer/pcr

<400> SEQUENCE: 1292

```
ggtgagtgcg gcccggggag gggaggggac cagggcgacc ggagccccca gcgatcccgc    60
ctggagcggc cgccaagctc cctcgggcac ccgggttcag cgggtcccga tccgagggcg   120
tgcgagctga gcctcctgga ccgggtccgc cgcggacctc ggcctgtcac ctgaaggtgc   180
cgcgtggtct ctgaggacgt ctgtcgacga gcaggggccg ccgcca                 226
```

<210> SEQ ID NO 1293
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1293

```
ggccgagagg gagccccaca cctcggtctc cccagaccgg ccctggccgg gggcatcccc    60
ctaaacttcg gatccctcct cggaaatggg accctctctg gccgcctcc cagcggtggt   120 ggcgaggagc aaacgacacc aggtagcctg ccgcggggca gagagtggac gcgggaaagc   180
cggtggctcc cgccgtgggc cctactgtgc gcgggcggcg gccgagcccg ggccgctccc   240
tcccagtcgc gcgcc                                                    255
```

<210> SEQ ID NO 1294
<211> LENGTH: 243
<212> TYPE: DNA
<213> ORGANISM: Artificial Sequence
<220> FEATURE:
<223> OTHER INFORMATION: probe/primer/pcr

<400> SEQUENCE: 1294

```
ccagcgccgc aacgcccagg gtgtggggcg gagtaagatg tgaaacctct tcagctcacg    60
gcaccgggct gcaaccgagg tctgaatgtt gcgaaagcgc cccagacgcc gccgctgctt   120
tccggccgcc ccctcggcta cagccgccat ttccacgctc caccaatcaa atccattctc   180
gaggaagacg caccgccccc acacgccccg accaatcgct cgcgctctgg ttgcgctggc   240
gcc                                                                 243
```

<210> SEQ ID NO 1295
<211> LENGTH: 250
<212> TYPE: DNA
<213> ORGANISM: Artificial Sequence
<220> FEATURE:
<223> OTHER INFORMATION: probe/primer/pcr

<400> SEQUENCE: 1295

```
ccacaagcgg gcgggacggc tggagactgc cgggacagcg gctgccggtg ctacgcgggt    60
ggtgggcggc ccgaaaatga gcgccctccg gggacagggg gctctgcggg gcggcgacag   120
ctggattccc agcgcgcaca aagcctgcgg gaggatccat tgtagcggtc gctcctcccc   180
gcttagcgag ggcgggcgca ggggcggggg atgtcgaagg gtcaggtttg tccaggccgc   240
gccaccttcg                                                          250
```

<210> SEQ ID NO 1296
<211> LENGTH: 249
<212> TYPE: DNA
<213> ORGANISM: Artificial Sequence
<220> FEATURE:
<223> OTHER INFORMATION: probe/primer/pcr

<400> SEQUENCE: 1296

```
cctctggaca acggggagcg ggaaaaaagc tacgcaggag cttggatcgg gcgaagctcg    60
cgggaaaccg ctctgggtgc gcaggacaaa gacgcgggga cagcggggag ggccggccgc   120
agcctgccgg gctgccccca cggcgcggaa cgcgcgcagc aacctccacc aggcctccgc   180
gtctggactc ccgccctgcc tctgggcctc ctccgcccac cggcggcgtc tcccgcgaag   240
cccgctggg                                                           249
```

<210> SEQ ID NO 1297
<211> LENGTH: 178
<212> TYPE: DNA
<213> ORGANISM: Artificial Sequence
<220> FEATURE:
<223> OTHER INFORMATION: probe/primer/pcr

<400> SEQUENCE: 1297

```
gcgggttccc ggcgtctcca aagctaccgc tgccggaaga gcgcggcgcc cgacggagcc    60
gtgtggaggc caaaactcct cccggaagcc gctactggcc ccgcttgcca ggcccagcgt   120
cttttctgca taggacccgg gggaagccgg gaagccgtta gggggcgggg caagcggg     178
```

<210> SEQ ID NO 1298
<211> LENGTH: 255

```
<212> TYPE: DNA
<213> ORGANISM: Artificial Sequence
<220> FEATURE:
<223> OTHER INFORMATION: probe/primer/pcr

<400> SEQUENCE: 1298
cgccgcccgt cctgcttgct gctgggtccg gttgccgagg cggaaaagtc gcaagctcct    60
tcagtcagtc ttcttcctca gctccttccg actccggaag ctgctgtttg ggcccaggct   120
ccctgcatcc gagagccctg ggctgactgc ttctgaggcc ccgccccact actgcctgca   180
gcgggcttcc ttactccgcc tgctggttcc tactggagga gaggccagca tgcttgtcag   240
gcaccagcag gtgga                                                    255

<210> SEQ ID NO 1299
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1299
cgcgcggccc tcctgcacct cggccagcac tcgtagcgcg ctgggcgagc cggaccggaa    60
gttgaagaag tgaagcgccg cgcgcgccgc ctgctgcagg agcctgcgcg ggaccccagc   120
atcctgaggc tgcccagggt cgtcggggtc cccggacccc gcgggcgccg ccaccggggc   180
gagcaacagc agcagcgcga gcagcggggc ggtggggcgc gggcccctgg gcccggacca   240
gggagcaggc agccg                                                    255

<210> SEQ ID NO 1300
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1300
ggcggggcaa gccctcacct gcgccaatca gggtgcggag taggccccgc aggcgcctca    60
cccattgagg gggcgggctg acagagcaga ggaaggaagg gggtgagggg cctgtggtgg   120
ggatcctggg gctgtcgggc tgagtatgcc gtgtgggtgg agaggaagcc tcgggaaat   180 cgcccaggtg aagggagggc ttggtgtggg gacttgcact gggcagaggg gcagcttccc   240
tgagagcagc taagc                                                    255

<210> SEQ ID NO 1301
<211> LENGTH: 129
<212> TYPE: DNA
<213> ORGANISM: Artificial Sequence
<220> FEATURE:
<223> OTHER INFORMATION: probe/primer/pcr

<400> SEQUENCE: 1301
ggagcgcccc ctggcggttt cagggcggct caccgagagg gcgccgggag cgcccggttg    60
gggaacgcgc ggctggcggc gtggggacca cccggcagga ccaggcacca gagctgcgtc   120
cctgctcgc                                                           129

<210> SEQ ID NO 1302
<211> LENGTH: 255
<212> TYPE: DNA
<213> ORGANISM: Artificial Sequence
<220> FEATURE:
```

<223> OTHER INFORMATION: probe/primer/pcr

<400> SEQUENCE: 1302
cgaatggttc gcgccggcct atatttaccc gagatcttcc tcccggacgg caaggatgtg    60
aggcaggcga gccggacgcc gctcgcagca ccggagaggg cgcactgcaa aggcgggcag   120
cagaccgtgg agagcccggg agcggagctg gacaccgcct cggagggaag aaatgaggta   180
gcggcggttc ccggacccgg ccatgcccgt cccctgttct cggagcccag cgccgtctcg   240
gccaggccag cccgg                                                    255

<210> SEQ ID NO 1303
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1303
ttccgccggc tgggccctcc gtctaccccc agcggcgagg ggcggggccg gcgcgggcgc    60
agaggcgtca cgcactccat ggtaacgacg ctcggcccga agatggcggc cgaatggggc   120
ggaggagtgg gttactcggg ctcaggcccg gccggagcc ggtggcgctg gagcgggtct    180
gtgtgggtcc gaagcgtttt actcctgttg ggcgggctcc gggccagcgc cacatctact   240
cccgtctcct tgggc                                                    255

<210> SEQ ID NO 1304
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1304
ctccgggtcc cccgcgtgcc cggcccgccc cggcccgctt cccgggcgct gtcttactcc    60
gggcccgggg cgcctgctcc gcgccgcgtc tgcgaaccgg tgacctggtt tcccctccag   120
ccctcacggc tgtccgactt gcgcggcggt ggcggcggcg gccaagagca ggcaaacccg   180
gctccgccag gggcgcagcg aggaaatggc ctcctggcgc acaccccgcc gccgccgcca   240
gccatcgcca ccgcc                                                    255

<210> SEQ ID NO 1305
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1305
cagcccgggt agggttcacc gaaagttcac tcgcatatat taggcaattc aatctttcat    60
tctgtgtgac agaagtagta ggaagtgagc tgttcagagg caggagggtc tattctttgc   120 caaaggggg accagaattc ccccatgcga gctgtttgag gactgggatg ccgagaacgc    180
gagcgatccg agcagggttt gtctgggcac cgtcggggta ggatccggaa cgcattcgga   240 aggcttttg caagc                                                     255

<210> SEQ ID NO 1306
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1306

```
ggcggagaga ggtcctgccc agctgttggc gaggagtttc ctgtttcccc cgcagcgctg      60
agttgaagtt gagtgagtca ctcgcgcgca cggagcgacg acaccccgc gcgtgcaccc      120 gctcgggaca ggagccggac tcctgtgcag cttccctcgg ccgccggggg cctccccgcg    180
cctcgccggc ctccaggccc cctcctggct ggcgagcggg cgccacatct ggcccgcaca    240
tctgcgctgc cggcc                                                       255
```

<210> SEQ ID NO 1307
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1307

```
cctcacccca gccgcgaccc ttcaaggcca agaggcggca gagcccgagg cctgcacgag      60
cagctctctc ttcaggagtg aaggaggcca cgggcaagtc gccctgacgc agacgctcca    120
ccagggccgc gcgctcgccg tccgccacat accgctcgta gtattcgtgc tcagcctcgt    180
agtggcgcct gacgtcgcgt tcgcgggtag ctacgatgag cggcgacag accaggcaca     240 gggccccatc gccct                                                       255
```

<210> SEQ ID NO 1308
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1308

```
cgatgacggg atccgagaga aaggcaaggc ggaaggggtg aggccggaag ccgaagtgcc      60
gcagggagtt agcggcgtct cggttgccat ggagaccagg agctccaaaa cgcggaggtc    120
tttagcgtcc cggaccaacg agtgccaggg acaatgtgg gcgccaactt cgccaccagc     180
cgggtccagc agcccagcc agcccacctg gaagtcctcc ttgtattcct ccctcgccta     240
ctctgaggcc ttcca                                                       255
```

<210> SEQ ID NO 1309
<211> LENGTH: 240
<212> TYPE: DNA
<213> ORGANISM: Artificial Sequence
<220> FEATURE:
<223> OTHER INFORMATION: probe/primer/pcr

<400> SEQUENCE: 1309

```
ccgcaggccg cgggaaaggc gcgccgagtc ctgcagctgc tctcccggtt cgggaaacgc      60
gcggggcggg ggcgtcgggc ttgggacagg ggaggatacc agggccacct tccccaaccc    120
aggccgcggg ggcccggcct ccccgatgca gaccacagcg ccctcacggg ctgccctcag    180
gccgcgcagc gggcagccgc cagccgtcac cccggggagc gtccgtgggg tgcccaggca    240
```

<210> SEQ ID NO 1310
<211> LENGTH: 206
<212> TYPE: DNA
<213> ORGANISM: Artificial Sequence
<220> FEATURE:

<223> OTHER INFORMATION: probe/primer/pcr

<400> SEQUENCE: 1310

| | | |
|---|---|---|
| gccccagtcc acctctggga gcgcctgcgc cgctccgcgg agagtccgtg gatctcacag | 60 | |
| tgagcgagtt gggacccagg gaggggaaaa gagaggaccc cggcgagcca ttgctggggc | 120 | |
| ggcgggctgg agggttatct gggaagtcag ccccggcctc ggtcctctcc acgttgctgc | 180 | |
| ctacgcgtgc tgcccggacg tagggc | 206 | |

<210> SEQ ID NO 1311
<211> LENGTH: 206
<212> TYPE: DNA
<213> ORGANISM: Artificial Sequence
<220> FEATURE:
<223> OTHER INFORMATION: probe/primer/pcr

<400> SEQUENCE: 1311

| | | |
|---|---|---|
| cttggccgcc cccgggatgg ggcgagggt cccgagggc ttgggagggc ggcttgggag | 60 | |
| agagctccgg ctccggaacg aggtgtcctg ggaacactcc cgggtctgta acttcggaca | 120 | |
| aatcacgctc gctttcccgg cctcagtgtg ccgttctgta acttgggtct aaccccggct | 180 | |
| cgcacacacg gcggggacgc gcacag | 206 | |

<210> SEQ ID NO 1312
<211> LENGTH: 247
<212> TYPE: DNA
<213> ORGANISM: Artificial Sequence
<220> FEATURE:
<223> OTHER INFORMATION: probe/primer/pcr

<400> SEQUENCE: 1312

| | | |
|---|---|---|
| cctccatgcg caatcccaag ggcggagagg aatttcagca gctacgagca acagaaagga | 60 | |
| aacgagagag tagccagact ctccgcgcat ggagccgacg gcacccacca gcacaccgcc | 120 | |
| ggcgcccca gccactactg cacgtccgcc ccgccccgc ccgctccgc ccggcgcacc | 180 | |
| tgatgcccaa actggttgca cgggaagccg agcaccacca ggccccgggg tccgaggcgc | 240 | |
| cgctgca | 247 | |

<210> SEQ ID NO 1313
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1313

| | | |
|---|---|---|
| gcggcgactg cgctgccct tggctgcccc ttccgctctc gtaggcgcgc ggggccacta | 60 | |
| ctcacgcgcg cactgcaggc ctttgcgcac gacgcccag atgaagtcgc cacagaggtc | 120 | |
| gcaccacgtg tgcgtggcgg gccccgcggg ctggaagcgg tggccacggc cagggaccag | 180 | |
| ctgccgtgtg gggttgcacg cggtgccccg cgcgatgcgc agcgcgttgg cacgctccag | 240 | |
| ccgggtgcgg ccctt | 255 | |

<210> SEQ ID NO 1314
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1314

```
gggcttgcct ccccgccccat accttccagg atgttgacag ctgggaatga aaggcagagg      60
gagggagcgc ggggccggag cgccgcctgg gagtgtgccc actgggtggc cgcctgaggg     120
acccgggaac agagggcaaa aagtcctgtg accggacaga gcagagcggg gactgcaatt     180
cccagaagac cccacggtag gggcgggacc caagatggcc gcttgtctgg ggacaggagc     240
ggaggccaat acgcg                                                      255
```

```
<210> SEQ ID NO 1315
<211> LENGTH: 239
<212> TYPE: DNA
<213> ORGANISM: Artificial Sequence
<220> FEATURE:
<223> OTHER INFORMATION: probe/primer/pcr

<400> SEQUENCE: 1315
gcggcccaag gagggcgaac gcctaagact gcaaaggctc gggggagaac ggctctcgga      60
gaacgggctg gggaaggacg tggctctgaa gacggacagc cctgaggaac cgcggggcgc     120
ccagatggaa ctcgttagcg ccccgagtgc agacaatccc ggaggggaa aggcgagcag      180 ctggcagaga gcccagtgcc ggccaaccgc gcgagcgcct cagaacggcc cgcccaccc     239
```

```
<210> SEQ ID NO 1316
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1316
ctgcgcggct ggcgatccag gagcgagcac agcgcccggg cgagcgccgg ggggagcgag      60
caggggcgac gagaaacgag gcaggggagg gaagcagatg ccagcgggcc gaagagtcgg     120
gagccggagc cgggagagcg aaaggagagg ggacctggcg gggcacttag gagccaaccg     180
aggagcagga gcacggactc ccactgtgga aaggaggacc agaagggagg atgggatgga     240
agagaagaaa aagca                                                      255
```

```
<210> SEQ ID NO 1317
<211> LENGTH: 174
<212> TYPE: DNA
<213> ORGANISM: Artificial Sequence
<220> FEATURE:
<223> OTHER INFORMATION: probe/primer/pcr

<400> SEQUENCE: 1317
caccgcctcc ggaccccctcc ctcatcagaa agcccaggct ccgctcgtag aagtgcgcag     60
gcgtcaccgc gcatccagga gccacgtgtc aggagtcacg tgtcaggtgt cacgtgtcag    120
gcgtcacgtg gctggaggcc gttggagcgc ctgcgcagct tttccgcacg cgcc           174
```

```
<210> SEQ ID NO 1318
<211> LENGTH: 229
<212> TYPE: DNA
<213> ORGANISM: Artificial Sequence
<220> FEATURE:
<223> OTHER INFORMATION: probe/primer/pcr

<400> SEQUENCE: 1318
ccttccagcc accccgccct gggcgcctct ggcgcgctct gatgacgctc caagggaaga     60
ggaagtgggg atcggcgagc gggtgggtgc gcctcgggcc gcgggactcg cagccgccac    120
```

```
cgccgctgcc gcctctacgg ccgcgtcaga actgaagaga ggaaggggag gagccgagtc    180
gagcctaagc tgccgcccga tcttacccct gacccgaggg cggcctgga              229
```

<210> SEQ ID NO 1319
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1319

```
cgggacaccg ggaggacagc gcgggcgagg cgctgcaagc ccgcgcgcag ctccgggggg    60
ctccgacccg ggggagcaga atgagccgtt gctggggcac agccagagtt ttcttggcct   120
tttttatgca aatctggagg gtgggggag caagggagga gccaatgaag ggtaatccga   180
ggagggctgg tcactacttt ctgggtctgg ttttgcgttg agaatgcccc tcacgcgctt   240
gctggaaggg aattc                                                    255
```

<210> SEQ ID NO 1320
<211> LENGTH: 198
<212> TYPE: DNA
<213> ORGANISM: Artificial Sequence
<220> FEATURE:
<223> OTHER INFORMATION: probe/primer/pcr

<400> SEQUENCE: 1320

```
cctgggttcc cggcttctca gccactggag ctgccagtct caaattaccg gaggggaggg    60
agggcaggcc tggatctcag gatctcggtc ctgcatgcaa tgcaagcctg agctctcccg   120
ccataaggct gcagcggtgt gggctccttg tgcccagatc ctttgtattc ataggggggaa   180 gtggaagacc acgctgcc                                                 198
```

<210> SEQ ID NO 1321
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1321

```
ggcggtgatg ggcggaggag gaggaagagg aggaggagga agaggaggag ggggaaaacg    60
atgacaggag ctggggccgg ggggggaaat tgggggggacg cgggcggagg cgcggtgcgc   120
gccggcggtg gcgggcacga gccccgcgcc tggaggagga ggagtcaggc cgggtaggag   180
ggctaaggag gttcccggga aggcagggcc cccctcccc cccctcccc ccccccacac    240 acacacactc ccctg                                                    255
```

<210> SEQ ID NO 1322
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1322

```
cagcccgccc ggagcccatg cccggcggct ggccagtgct gcggcagaag gggggggcccg    60 gctctgcatg gccccggctg ctgacatgac ttctttgcca ctcggtgtca aagtggagga   120
ctccgccttc ggcaagccgg cgggggggagg cgcgggccag gccccagcg ccgccgcggc    180 cacggcagcc gccatgggcg cggacgagga gggggccaag cccaaagtgt ccccttcgct   240
```

-continued cctgcccttc agcgt    255

<210> SEQ ID NO 1323
<211> LENGTH: 242
<212> TYPE: DNA
<213> ORGANISM: Artificial Sequence
<220> FEATURE:
<223> OTHER INFORMATION: probe/primer/pcr

<400> SEQUENCE: 1323
gcccgcgggg gaatcgcagt gagcagcgcg gggcgaggcc gccgcggacg ccccgtcgga    60
tgtgcccttc gctgggccga gcggcgcagg gttggagagg gaagcgctcg tgcccacctt    120
gctcgcaggt gcccttgctg acctgggtga tggccttctc cccgcggctc tcggccctct    180
ggctggcggc gcgcagctgg cagccgctcg ggtaggtggt gccgtcgctg ccgcacaccg    240
gg    242

<210> SEQ ID NO 1324
<211> LENGTH: 186
<212> TYPE: DNA
<213> ORGANISM: Artificial Sequence
<220> FEATURE:
<223> OTHER INFORMATION: probe/primer/pcr

<400> SEQUENCE: 1324
gccgcgagcc cgtctgctcc cgccctgccc gtgcactctc cgcagccgcc ctccgccaag    60
ccccagcgcc cgctcccatc gccgatgacc gcggggagga ggatggagat gctctgtgcc    120
ggcagggtcc ctgcgctgct gctctgcctg ggtaagttct cccctctgg cttccggccg    180 ccccaa    186

<210> SEQ ID NO 1325
<211> LENGTH: 253
<212> TYPE: DNA
<213> ORGANISM: Artificial Sequence
<220> FEATURE:
<223> OTHER INFORMATION: probe/primer/pcr

<400> SEQUENCE: 1325 gcggcccct cccggctgag cctataaagc ggcaggtgcg cgccgcccta cagacgttcg    60
cacacctggg tgccagcgcc ccagaggtcc cgggacagcc cgaggcgccg cgcccgccgc    120
cccgagctcc ccaagccttc gagagcggcg cacactcccg gtctccactc gctcttccaa    180
cacccgctcg ttttggcggc agctcgtgtc ccagagaccg agttgcccca gagaccgaga    240
cgccgccgct gcg    253

<210> SEQ ID NO 1326
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1326
cagcagggcg cggcttccct ttcccggggc ctggggccgc aatcaggtgg agtcgagagg    60
ccggaggagg ggcaggagga aggggtgcgg tcgcgatccg gacccggagc cagcgcggag    120
cacctgcgcc cgcggctgac accttcgctc gcagtttgtt cgcagtttac tcgcacacca    180 gtttcccccca ccgcgctttg ggtaagttca gcctcccggc gcgtccccgc gagcctcgcc    240
cacagccgcc tgctg                                                    255

<210> SEQ ID NO 1327
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1327
ccgcagcacg ctcggacggg ccaggggcgg cgacccctcg cggacgcccg gctgcgcgcc     60
gggccgggga cttgcccttg cacgctccct gcgccctcca gctcgccggc gggaccatga    120
agaagttctc tcggatgccc aagtcggagg gcggcagcgg cggcggagcg gcgggtggcg    180
gggctggcgg ggccgggggcc ggggccggct gcggctccgg cggctcgtcc gtggggtcc    240 gggtgttcgc ggtcg                                                    255

<210> SEQ ID NO 1328
<211> LENGTH: 199
<212> TYPE: DNA
<213> ORGANISM: Artificial Sequence
<220> FEATURE:
<223> OTHER INFORMATION: probe/primer/pcr

<400> SEQUENCE: 1328
gcggagtgcg ggtcgggaag cggagagaga agcagctgtg taatccgctg gatgcggacc     60
agggcgctcc ccattcccgt cgggagcccg ccgattggct gggtgtgggc gcacgtgacc    120
gacatgtggc tgtattggtg cagcccgcca gggtgtcact ggagacagaa tggaggtgct    180
gccggactcg gaaatgggg                                                199

<210> SEQ ID NO 1329
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1329 gcgcggggggc aggtgagcat gcgaaggttg gaggccgcgc cccttgctga ggcgcagctg     60
gctgctcttt tcgggccggc atacgcgcgc agccgcagct gaggtcaccc cgctgaggtg    120
gtggggaggg gaatggttat tcttgaggca ccgcatctct tgaggaggaa agagccggaa    180
acacctggtc tctcaagcag gtacagcccg cttctcccca gcaccccggt gtgggcttcc    240
caaggtcctg cctga                                                    255

<210> SEQ ID NO 1330
<211> LENGTH: 178
<212> TYPE: DNA
<213> ORGANISM: Artificial Sequence
<220> FEATURE:
<223> OTHER INFORMATION: probe/primer/pcr

<400> SEQUENCE: 1330
ggcgcggggg caggtgagca tgcgaaggtt ggaggccgcg cccccttgctg aggcgcagct     60 ggctgctctt ttcgggccgg catacgcgcg cagccgcagc tgaggtcacc ccgctgaggt    120
ggtggggagg ggaatggtta ttcttgaggc accgcatctc ttgaggagga aagagccg     178

<210> SEQ ID NO 1331
<211> LENGTH: 152

```
<212> TYPE: DNA
<213> ORGANISM: Artificial Sequence
<220> FEATURE:
<223> OTHER INFORMATION: probe/primer/pcr

<400> SEQUENCE: 1331
agtgacgggc ggtgggcctg gggcggccag cggtgactcc agatgagccg gccgtccgcg     60
ttcgcgccgc ggcggtgcgg ttgtcgcgga tcagcaggat cggagtgcgg ggctgctggg    120
cggaggcgtt ggctgcacca gggacggcgg cg                                  152

<210> SEQ ID NO 1332
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1332 ggcgacccctt tggccgctgg cctgatccgg agacccaggg ctgcctccag gtccggacgc    60
ggggcgtcgg gctccgggca ccacgaatgc cggacgtgaa ggggaggacg gaggcgcgta   120
gacgcggctg gggacgaacc cgaggacgca ttgctccctg gacgggcacg cgggacctcc   180
cggagtgcct ccctgcaaca cttccccgcg acttgggctc cttgacacag gcccgtcatt   240
tctctttgca ggttc                                                    255

<210> SEQ ID NO 1333
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1333
cgcggcagcc cgggtgaatg gagcgaggcg gcaggtcatc cccgtgcagc gcccgggtat    60
ttgcataatt tatgctcgcg ggaggccgcc atcgcccctc ccccaacccg gagtgtgccc   120
gtaattaccg ccggccaatc ggcgcgtcg cgcggccccg ggagtcggct cgggctaagc    180
tggccagggc gtctccaggc agtgaaacag aggcggggtc ggcgggcgat tagcggccga   240
ggcacgctcc tcttg                                                    255

<210> SEQ ID NO 1334
<211> LENGTH: 250
<212> TYPE: DNA
<213> ORGANISM: Artificial Sequence
<220> FEATURE:
<223> OTHER INFORMATION: probe/primer/pcr

<400> SEQUENCE: 1334
ggcgagcgag cgggaccgag cggggagcgg gtggaggcgg cgccacggcg cgcacacact    60
cgcacacacg cgctcccact ccaccccccgg ccgctcccg cccgaggggc cgcgcggcgg   120
ccgcggggaa cgatgcaacc tgttggtgac gcttggcaac tgcaggggcg cccgcggtcc   180 ctgccccccac gccctccgcg cgggccccgc caccccggcc ccgacggcgc ctgcacgccc   240
gcgtcccctg                                                          250

<210> SEQ ID NO 1335
<211> LENGTH: 206
<212> TYPE: DNA
<213> ORGANISM: Artificial Sequence
<220> FEATURE:
```

<223> OTHER INFORMATION: probe/primer/pcr

<400> SEQUENCE: 1335

| ggggcagtgc cggtgtgctg ccctctgcct tgagacctca agccgcgcag gcgcccaggg | 60 |
| caggcaggta gcggccacag aagagccaaa agctcccggg ttggctggta aggacaccac | 120 |
| ctccagcttt agccctctgg ggccagccag ggtagccggg aagcagtggt ggcccgccct | 180 |
| ccagggagca gttgggcccc gcccgg | 206 |

<210> SEQ ID NO 1336
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1336

| cgctggcatt cgggccccct ccagactttta gcccggtgcc ggcgccccct gggcccggcc | 60 |
| cgggcctcct ggcgcagccc ctcggggggcc cgggcacacc gtcctcgccc ggagcgcaga | 120 |
| ggccgacgcc ctacgagtgg atgcggcgca gcgtggcggc cggaggcggc ggtggcagcg | 180 |
| gtaaggaccc ttccctcgcc ctgcgcctct ggacctgcag gtgctcgggc gcggcccagg | 240 |
| ccgccccctg tctga | 255 |

<210> SEQ ID NO 1337
<211> LENGTH: 213
<212> TYPE: DNA
<213> ORGANISM: Artificial Sequence
<220> FEATURE:
<223> OTHER INFORMATION: probe/primer/pcr

<400> SEQUENCE: 1337

| gagccgtgat ggagccggga ggagaggcgc atcctcagca gagcttccct cccttgcaca | 60 |
| cgagctgacg gcgtgaacgg gggtgtcggg gttggtgcaa ctatagaagg gaaaggctgg | 120 |
| gcggggtca cacatacctc agtggcaggc aggcaggcgg caggcagagc gcgctctccg | 180 |
| ggcagtctga aggaccgcgg gaatgtggag ggg | 213 |

<210> SEQ ID NO 1338
<211> LENGTH: 185
<212> TYPE: DNA
<213> ORGANISM: Artificial Sequence
<220> FEATURE:
<223> OTHER INFORMATION: probe/primer/pcr

<400> SEQUENCE: 1338

| gccagggtgt cttggctctg gcctgagtcg ggtatgtgaa agccttttgg ggcaggaagg | 60 |
| ggcaaagtga tacctggccg tcccaccctc tggtcccaga aggagctctc gctggagcca | 120 |
| ggcagcctcc agtcccccctc ctttcagcct tgtcattctc tgcatcctgc ccaggccaca | 180 |
| aagga | 185 |

<210> SEQ ID NO 1339
<211> LENGTH: 175
<212> TYPE: DNA
<213> ORGANISM: Artificial Sequence
<220> FEATURE:
<223> OTHER INFORMATION: probe/primer/pcr

<400> SEQUENCE: 1339

| cggctccggc ggggaaggag gcgggctgcg gctgcggctg gggctgaagc tggggctggg | 60 | gttgggggac tgcccggggc ttagatggct ccgagcccgt ttgagcgtgg tctcggactg    120 ctaactggac caacggcaac tgtctgatga gtgccagccc caaaccgcgc gctgc        175

<210> SEQ ID NO 1340
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1340
gccagggtgc cgtcgcgctt ggcgccgtcc agggcggcgc tgcgctcgtc cagcaacacc    60
acggcgtggt aggcgccggc cagcaggcgg ccgcggagct cggcgttggg cacgatgtgc    120
tccaggccca tggcgccctt ggccggcgc cgcacgatgg tgctgaagcg cacgttgaca     180
gagccggcga tgtggccggc gttgaaagcg aagaaggagc ggcagtccag cagcaggcat    240
tgcgccgctc gctcc                                                    255

<210> SEQ ID NO 1341
<211> LENGTH: 217
<212> TYPE: DNA
<213> ORGANISM: Artificial Sequence
<220> FEATURE:
<223> OTHER INFORMATION: probe/primer/pcr

<400> SEQUENCE: 1341
cggctcggtc ctgaggagaa ggactcagcc gcggctgcgg gacccgggca ccggaggcg     60 gtggcggcgg cggcggcggc agcagcggcg acagcagagg aggaagagga ggaagaagga    120
aagaaaaaga agaaccagga ggagtcctca acaacgacag cggggactgc gggaccaggg    180
taaagcggcg acggcggcga cggcccagca accgtga                            217

<210> SEQ ID NO 1342
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1342
cgcggggaac ctgcggctgc ccgggcaagg ccacgaggct tcttataccc ggtcctcgcc    60
cctccagcgc cggcctcgcc cgcgctcctg agaaagccct gcccgctccg ctcacggccg    120
tgccctggcc aacttcctgc tgcggccggc ggggcctggg aagcccgtgc ccccttccct    180
gcccgggcct cgaggacttc ctcttggcag gcgctggggc cctctgagag caggcaggcc    240
cggcctttgt ctccg                                                    255

<210> SEQ ID NO 1343
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1343
ccgccgctgc tttgggtggg gggctgacag ggctgcgcgc gtcgcgctct tggctggggc    60
tgcgcgggcc cggggcgctg cgggcggctc agcggcagct gccgcgctct gcgcctcctc    120
tgggcgcact gcctggggagc acgagactgg tttgtctgat gctgctgccg gagctgaggt    180

```
cttgcctgga gatccgaacg agacaccacg tcaaccggcg cggggagtcc cgtgaagaca    240
tgagggcgcc aggag                                                    255

<210> SEQ ID NO 1344
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1344
acctgagccc gcggggggaac cccccccca ccccgggga acccccccca ccccgccgc      60 cccccgcctg caagttgtta ccagtaaata aagggatcc tattttagca agccacacag    120
cattagaggg caaataatag tttggtggca ggagagcgat gagacgggaa agtgtgggc    180 aaagcttaca gtcattggtc cagattctaa ctggcctgtt agccaaaaag taaggttttc    240
tttacctccg tgttg                                                    255

<210> SEQ ID NO 1345
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1345
aacgccggcc tcaccggcag acgcgcgccc tcctcccaga tgcgcaggtg accccggcgg    60
gcggcgcggg aaagggaaga gctccgcgag gccgcgcggg ggggaagcgg gagaagccgc    120
tcttcctatt ccactcgcag tctgcgtgtg ggggaaacga gtgcccggcg tatgaaacgc    180
ctaacttcgc gaaataaaga gagacgtata aaagttcaag aattctgtcc agactcaagg    240 gcccttttctc attta                                                   255

<210> SEQ ID NO 1346
<211> LENGTH: 184
<212> TYPE: DNA
<213> ORGANISM: Artificial Sequence
<220> FEATURE:
<223> OTHER INFORMATION: probe/primer/pcr

<400> SEQUENCE: 1346
ccgtggtccc agcgctcctg ctatttgcat tccaaagcag acacctcatg cgctcaaccc    60
cgcccgcagg cggctcccgc agtctaaggg acctggcgcg agtccgggaa gcggagggcg    120
cagctgcgca gggaagggg ccggggcgg gaccagggcg cgcgttccgg tcccggggcg    180
tggc                                                                184

<210> SEQ ID NO 1347
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1347
tgcgacccgg cgcccaagca gcctgggacc ttgcgcggac ctgacccctt cagaccgcag    60
gcagtctggg aggaggtccg gccggggag gtgcaggatc ccgccgtgt ctctttgacg    120 acttggggac tgtcacggtt ctctcccggc gcccctgggt tcttttgtcc tgcacgcggt    180 gcgaagggc cagcagggaa ggagcagagg atgggggtg gggttgttgg agccccgcgg    240
```

```
aggtctggga ggccc                                               255

<210> SEQ ID NO 1348
<211> LENGTH: 166
<212> TYPE: DNA
<213> ORGANISM: Artificial Sequence
<220> FEATURE:
<223> OTHER INFORMATION: probe/primer/pcr

<400> SEQUENCE: 1348
ggctctgcgc tgcctttggt ggctcctccc tggtcctcta aatgtgacac caggcggatg    60
cggggccaca ggaccctggg gcttgagtca cacaagaatg tctctgggag acccgagaga   120
ctcacagtta tgaaacagga ccatggttct ttggccgggc gcgggg                  166

<210> SEQ ID NO 1349
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1349
gcgcgggcgg ctcctttgtg tccagccgcc gccaccggag ctcccggggc ctccgcgggg    60
agcgcgtccc ccgcatccgc ccgaccccg gggctggcac gtgctgcgcc cggtccgctg    120 aggggcgga ggccccgatc tccccgaccc cccttctctg cttagaggag gaggagcagc    180
ggcagcggca gcaggaggcg acagctgcca gccgaggagg cgcggcggag aggggactgc    240
ggtcagctgc gtcca                                                    255

<210> SEQ ID NO 1350
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1350
ggcccgttgg cgaggttaga gcgccaggtt gtaagaatcg ggtctgtgga cctcatacca    60
gataggcgcg aacgcctctg gcagcggcgt ccagggggtc cggcggcact cgcggtgggg   120
ctgcctgggt tgcgggtgac gatctgcggg gtcccgcacc cggccccgcg gagcccggac   180
ccgcacgtag gcggcgcggc aaaggcacac cctcctcgcg gccgcgaacc cagcgccgtc   240
ctcgcagcgc ggcaa                                                    255

<210> SEQ ID NO 1351
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1351
acccggcatc cgggcaggct gcgcgcgggt gcggggcgag ggcgccgcgg ggactgggac    60
gcacggcccg cgcgcgggac acggccatgg aggacgcggg agcagctggc ccggggccgg   120
agcctgagcc cgagcccgag ccggagcccg agcccgcgcc ggagccggaa ccggagccca   180
agccgggtgc tggcacatcc gaggcgttct cccgactctg gaccgacgtg atgggtatcc   240
tggtaagtta cctgg                                                    255
```

```
<210> SEQ ID NO 1352
<211> LENGTH: 156
<212> TYPE: DNA
<213> ORGANISM: Artificial Sequence
<220> FEATURE:
<223> OTHER INFORMATION: probe/primer/pcr

<400> SEQUENCE: 1352
cccggactgt aatcacgtcc actgggaact ggcgcagtag tggaggggac gcgatcaggc      60
ccgtggctgc gcccagagca tgataagcca gggacctcgc ggcgcaggcg agggaggga     120 gagcgtcgcg gacccaggcg gggacaggga gacgcc                              156

<210> SEQ ID NO 1353
<211> LENGTH: 238
<212> TYPE: DNA
<213> ORGANISM: Artificial Sequence
<220> FEATURE:
<223> OTHER INFORMATION: probe/primer/pcr

<400> SEQUENCE: 1353
cgccgccaac gcgcaggtct acggtcagac cggcctcccc tacggccccg ggtctgaggc      60
tgcggcgttc ggctccaacg gcctgggggg tttcccccca ctcaacagcg tgtctccgag     120
cccgctgatg ctactgcacc cgccgccgca gctgtcgcct ttcctgcagc cccacggcca     180
gcaggtgccc tactacctgg agaacgagcc cagcggctac acggtgcgcg aggccggc      238

<210> SEQ ID NO 1354
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1354
gctgccagct gccgctccgg ctcccacttc ccacctgctg cccgaggaag acttccggga      60
gaaacgctgt ctccgagccc ccgcgccgcc gcgctccctc cgctgcagca gcggccaccg     120
ggtgcgcccg gagccctggg acggcctaaa ccagtatctc gcgggccccg cgccgggctc     180
cgggaatggc cgcagcagcc ctggcgaccc gggcccctcg gagctcccct tcaggatcgt     240
gcaccaagcg cgcac                                                     255

<210> SEQ ID NO 1355
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1355
gcgcccacct gcgcctcgcg gggtccccga ggtcccgcca ccgagcgccc aaggcgggat      60
cccagcgcgt cctgcagccc gcccagcttc agggccggcc cggcgcgcgc aggtgcggca     120
ctcaccggcc aggtgaagcc gaaggggaag cggatggggt tgctgaacgc ggagtcggcg     180
cccccgccgt cgggcagact gaaggagtcg acgcccagca cggggtgac ggcgctgccg     240 taggtgcagg gcggc                                                     255

<210> SEQ ID NO 1356
<211> LENGTH: 149
<212> TYPE: DNA
<213> ORGANISM: Artificial Sequence
```

```
<220> FEATURE:
<223> OTHER INFORMATION: probe/primer/pcr

<400> SEQUENCE: 1356
cgggccaggg cggcatgaag aagtcccgcc gctacgtgcc cggcacagtg gccctgcgcg    60
acgttcggcg ctaccagaac tccgagctgc tgatcagcaa gctgccgctc ctgcgagagc   120
tcggcggtga cgccgctgca cgagagcga                                     149

<210> SEQ ID NO 1357
<211> LENGTH: 250
<212> TYPE: DNA
<213> ORGANISM: Artificial Sequence
<220> FEATURE:
<223> OTHER INFORMATION: probe/primer/pcr

<400> SEQUENCE: 1357
gctgcgacct ggggtccgac ggacgcctcc tccgcgggta tgaacagtat gcctacgatg    60
gcaaggatta cctcgccctg aacgaggacc tgcgctcctg gaccgcagcg gacactgcgg   120
ctcagatctc caagcgcaag tgtgaggcgg ccaatgtggc tgaacaaagg agagcctacc   180
tggagggcac gtgcgtggag tggctccaca gatacctgga gaacgggaag gagatgctgc   240
agcgcgcggg                                                          250

<210> SEQ ID NO 1358
<211> LENGTH: 155
<212> TYPE: DNA
<213> ORGANISM: Artificial Sequence
<220> FEATURE:
<223> OTHER INFORMATION: probe/primer/pcr

<400> SEQUENCE: 1358
gttaggaggg cggggcgcgt gcgcgcgcac ctcgctcacg cgccggcgcg ctccttttgc    60
aggctcgtgg cggtcggtca cggggcgtt ctcccacctg tagcgactca ggttactgaa   120
aaggcgggaa aacgctgcga tggcggcagc tgggg                              155

<210> SEQ ID NO 1359
<211> LENGTH: 207
<212> TYPE: DNA
<213> ORGANISM: Artificial Sequence
<220> FEATURE:
<223> OTHER INFORMATION: probe/primer/pcr

<400> SEQUENCE: 1359
agcgcaccaa cgcaggcgag ggactggggg aggagggaag tgccctcctg cagcacgcga    60
ggttccggga ccggctggcc tgctggaact cggccaggct cagctggctc ggcgctgggc   120
agccaggagc ctgggccccg gggagggcgg tccggggcgg cgcggtgggc cgagcgcggg   180
tcccgcctcc ttgaggcggg cccgggc                                       207

<210> SEQ ID NO 1360
<211> LENGTH: 173
<212> TYPE: DNA
<213> ORGANISM: Artificial Sequence
<220> FEATURE:
<223> OTHER INFORMATION: probe/primer/pcr

<400> SEQUENCE: 1360
cggctggccc cgcccactct ccgcggccgg aagtggcggc gccgagtgag gtaaatgcgt    60
gcccggaagc gcgacctcgg gcggttggag gggctaccgg gtcttaccag tccgtggcgg   120
```

| | |
|---|---|
| gagtcccgga ggaccctcga cgggggagtt gccgagaaaa ggcctcgccg gca | 173 |

<210> SEQ ID NO 1361
<211> LENGTH: 225
<212> TYPE: DNA
<213> ORGANISM: Artificial Sequence
<220> FEATURE:
<223> OTHER INFORMATION: probe/primer/pcr

<400> SEQUENCE: 1361

| | |
|---|---|
| ggggttgccg tcgcagccag ctgagtgttg cgccaggggg acaggtatgt tccaggcagt | 60 |
| ggcaagccca acccgagcaa gacctgcgct gaaacggatt ggctgccctc cgccggagt | 120 |
| ccgttctccc tgcagcggcc agtgcagagc tcagaggctc agaaactcgc tctcagcccc | 180 |
| ctggaggcgg agcccgggag ataaggttcg cgctccccac ccgcc | 225 |

<210> SEQ ID NO 1362
<211> LENGTH: 223
<212> TYPE: DNA
<213> ORGANISM: Artificial Sequence
<220> FEATURE:
<223> OTHER INFORMATION: probe/primer/pcr

<400> SEQUENCE: 1362

| | |
|---|---|
| ccgcactccc gcccggttcc ccggccgtcc gcctatcctt ggccccctcc gctttctccg | 60 |
| cgccggcccg cctcgcttat gcctcggcgc tgagccgctc tcccgattgc ccgccgacat | 120 |
| gagctgcaac ggaggctccc acccgcggat caacactctg gccgcatga tccgcgccga | 180 |
| gtctggcccg gacctgcgct acgaggtgac cagcggcggc ggg | 223 |

<210> SEQ ID NO 1363
<211> LENGTH: 150
<212> TYPE: DNA
<213> ORGANISM: Artificial Sequence
<220> FEATURE:
<223> OTHER INFORMATION: probe/primer/pcr

<400> SEQUENCE: 1363

| | |
|---|---|
| ggaccccctg ggcagcaccc tggccaccct tccatccaca acatccagac cacacggcca | 60 |
| agggcacctg accctgtcaa aaccccaaat ccagctgggc gcggtggctc atgcctgtaa | 120 |
| tcccagcatt tgggaggccg aggcagccgg | 150 |

<210> SEQ ID NO 1364
<211> LENGTH: 107
<212> TYPE: DNA
<213> ORGANISM: Artificial Sequence
<220> FEATURE:
<223> OTHER INFORMATION: probe/primer/pcr

<400> SEQUENCE: 1364

| | |
|---|---|
| gaggcagccg gatcacgaag tcaggagttc gagaccagcc tgaccaacat ggtgaaaccc | 60 |
| cgtctctact aaaatacaaa aattagccgg gcgtggtggt gcacacc | 107 |

<210> SEQ ID NO 1365
<211> LENGTH: 244
<212> TYPE: DNA
<213> ORGANISM: Artificial Sequence
<220> FEATURE:
<223> OTHER INFORMATION: probe/primer/pcr

<400> SEQUENCE: 1365

| | |
|---|---|
| gcgcgtgcgg gcgttgtccc ggcaaccagg gggcggggct gggcgtggca ccgccccgcg | 60 |

```
ctccgctgcc aggggcggga gggaggaatg gttgcttcac gccccggggg aagagacggg    120
aagctcggct ctgggttgcg ggccccggcg tctccgcgtg gggcgcaccg tccgacccc     180 ccctcccggt gtgcagcgcc ccgcaccgcc ccgcctcgcc tgggagaagc cgccgggacg    240
cgcc                                                                  244
```

<210> SEQ ID NO 1366
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1366

```
caggatgcgg cagcgcccac ccgcgcggcg tggaggggc cggggcggc gctcggcgca       60 gatggcgctc gctgcgagat ggatgctcca gggcgggtaa tcactcctgg ctcaacacag    120
catcccgggc ggagcggatg ccagatccca ccgctaagag cctgggctgg aaagcaatc    180 tttccaggca gccccagcc cggtgcgccg gccccgacaa gtcccagccc tcggaggcag    240
ggcggggcgc aggga                                                     255
```

<210> SEQ ID NO 1367
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1367

```
gatgcggccc gcggaggaga gagcaggagg acggacggga gggacctccg cggggagggc     60
gcgcggggga ggcggggagg gaggcgggag ggggagggga cggtgtggat ggccccgagg   120
tccaaaaaga aagcgcccaa cggctggacg cacaccccgc caggcctcct ggaaacggtg   180
ccggtgctgc agagcccgcg aggtgtctgg gagttgggcg agagctgcag acttggaggc   240
tcttatacct ccgtg                                                     255
```

<210> SEQ ID NO 1368
<211> LENGTH: 193
<212> TYPE: DNA
<213> ORGANISM: Artificial Sequence
<220> FEATURE:
<223> OTHER INFORMATION: probe/primer/pcr

<400> SEQUENCE: 1368

```
gttctgcgcg cgcccgactc cgctgcccgc ccgccaggc ctccgggagg tggggctgg       60 gaggcgtccc ccgctcccgc cccctcccca ccgttcaatg aaagatgaac tggcgagagg   120
tgagaaggga agagggctcc cggctctctc ggggcgggaa tcagtgggcc agagctcgcc   180
gggtggccgc aag                                                       193
```

<210> SEQ ID NO 1369
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1369

```
cccgccgtgg gcgtagtaac cgccaccgcc gccgccccc gcgccaccac caccgccgcc      60
```

```
tgcctcgcct ctgcccgagc tgatgagcga gtcgaccaaa aaagagttcg cggcggggct      120
ctccgagcat gacattgttg tgggataatt tggcgaaggg agcagatagc cctttctggc      180
tgacatttct tgtgcaaaac atgctgaata cgattagcaa tcccccgca ccgcggcggg       240 cgcccgcagc caatc                                                       255
```

<210> SEQ ID NO 1370
<211> LENGTH: 212
<212> TYPE: DNA
<213> ORGANISM: Artificial Sequence
<220> FEATURE:
<223> OTHER INFORMATION: probe/primer/pcr

<400> SEQUENCE: 1370

```
acccgcccgg gcagctccag tcccggactc cgcagctcgg agcgcagcca gccacggcca      60
ttgcgggacc ctatttatcc cgacacctcc cctgacgtgg gctcggaacg ctcccttggc     120
agctgcagcc gcggcgcggg ctcccccctcg gccgccccac ccccaggccc gtcggtgcag    180
aagcggtgac atcaccccct ctgggccgca gc                                    212
```

<210> SEQ ID NO 1371
<211> LENGTH: 221
<212> TYPE: DNA
<213> ORGANISM: Artificial Sequence
<220> FEATURE:
<223> OTHER INFORMATION: probe/primer/pcr

<400> SEQUENCE: 1371

```
cagcggtcgc gcctcgtcgg gcgacggctg gcagcgaagg ccggagccac agcgctcggt      60
gtagatgccg cacggctggc cctcgctcag tgcgcacgtc aggcagcagc cgcagcccgg     120
ctcgcgcacc agctccgcgc acacggcggg cggaggcgcg cactgggcca gtgcacgcgc    180
gtcgcacggc tcgcagcgca ccacgggacc caagcccgcc g                          221
```

<210> SEQ ID NO 1372
<211> LENGTH: 237
<212> TYPE: DNA
<213> ORGANISM: Artificial Sequence
<220> FEATURE:
<223> OTHER INFORMATION: probe/primer/pcr

<400> SEQUENCE: 1372

```
gcaatcgcgc tgtctctgaa aggggtggag aaggggctgg atgagtccgg aagtggagat      60
tggctgctta gtgacgcgcg gcgtcccgga agttgacaga tacagggcga gaggcagtgg    120
aggcgggact tggatagggg cggaacctga gactaccttt ctgcgatcac aggattcccg    180
gcggtgactt gaccccggaa gtggggtgtg aagctccggt gctggtgcgg cggggga        237
```

<210> SEQ ID NO 1373
<211> LENGTH: 230
<212> TYPE: DNA
<213> ORGANISM: Artificial Sequence
<220> FEATURE:
<223> OTHER INFORMATION: probe/primer/pcr

<400> SEQUENCE: 1373

```
gagcgcccgc cgttgatgcc ccagctgctc tggccgcgat gggcactgca ggggcttttcc     60 tgtgcgcggg gtctccagca tctccacgaa ggcagagttg ggggtctggc agcgcgttct   120
ggactttgcc cgccgccagt gcgattctcc ctccggttc cagtcgccgc ggacgatgct    180
tcctcccacc caccgcccgc gggctcagag agcaggtccc cgcaccgcgc                230
```

<210> SEQ ID NO 1374
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1374

| | |
|---|---|
| catggcccgc tgcgccctct ccgccggttg gggagagaag ctcctggagc ggccagatac | 60 |
| ctgttggctc ctgagcagca tcgcccagtg cagcctccgt caggaaaagc agcagaatcg | 120 |
| acagccccag ggggcgagcg gggtccatgt gcaggggggt cgggcggccc gctgggcaag | 180 |
| gcgtccgaga aagcgcctgg cgggaggagg tgcgcggctt tctgctccag gcggcccggg | 240 |
| tgcccgcttt atgcg | 255 |

<210> SEQ ID NO 1375
<211> LENGTH: 216
<212> TYPE: DNA
<213> ORGANISM: Artificial Sequence
<220> FEATURE:
<223> OTHER INFORMATION: probe/primer/pcr

<400> SEQUENCE: 1375

| | |
|---|---|
| gggggcgggg tgcaggggtg gaggggcggg gaggcgggct ccggctgcgc cacgctatcg | 60 |
| agtcttccct ccctccttct ctgccccctc cgctcccgct ggagccctcc accctacaag | 120 |
| tggcctacag ggcacaggtg aggcgggact ggacagctcc tgctttgatc gccggagatc | 180 |
| tgcaaattct gcccatgtcg gggctgcaga gcactc | 216 |

<210> SEQ ID NO 1376
<211> LENGTH: 179
<212> TYPE: DNA
<213> ORGANISM: Artificial Sequence
<220> FEATURE:
<223> OTHER INFORMATION: probe/primer/pcr

<400> SEQUENCE: 1376

| | |
|---|---|
| cgaccctgcg cccggcagtc cccgggggcc gtgcgcccgg cccaggctcg gaggtccagc | 60 |
| ccagcggcgg ctcaggctgc gcgcctggct cccagcctca gtttccccat tggtaaagca | 120 |
| ttgacggtgg ttgcggacgg cttctgcgga cagagccttg ggctccgacg tctgcgcgg | 179 |

<210> SEQ ID NO 1377
<211> LENGTH: 214
<212> TYPE: DNA
<213> ORGANISM: Artificial Sequence
<220> FEATURE:
<223> OTHER INFORMATION: probe/primer/pcr

<400> SEQUENCE: 1377

| | |
|---|---|
| ggcttcaagt ccacggccct gtgatgggat gtgggcaggg cctgagacag gccgaaccca | 60 |
| actcttcaca gggccgaatt cttttgcccgc agcccagcac cccgaaggag cttgcctcgg | 120 |
| cttcaaggcg cacctaatgg gcaccggatc gctgggggcgc tgaggatgcc gctccggggc | 180 |
| ctccacgagg cggcctcgcc acgcgcctcg gcca | 214 |

<210> SEQ ID NO 1378
<211> LENGTH: 255
<212> TYPE: DNA
<213> ORGANISM: Artificial Sequence
<220> FEATURE:

<223> OTHER INFORMATION: probe/primer/pcr

<400> SEQUENCE: 1378

| ccccacctgc ccgcgctgct tctacctgaa actggccaag ggcccgagcc cggaccggag | 60 |
| ccgtgacttc cctccgccgg ccacggggct gcccggatcc gccgggttat gtcgcttggc | 120 |
| tttgggctca ggggtcaccg tgggcagagg ggggtgccgg ggtcgcggac tgccaccagg | 180 |
| ttgaggaaag gaggggcctt ttggctgggg aaagagcgtg gtgggggacc cgcggccgat | 240 |
| ggaatccctg gggca | 255 |

<210> SEQ ID NO 1379
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1379

| gcgcgcggag acgcagcagc ggcagcggca gcatgtcggc cggcggagcg tcagtcccgc | 60 |
| cgcccccgaa cccgccgtg tccttcccgc cgccccgggg tcaccctgcc gccggcccc | 120 |
| gacatcctgc ggacctactc gggcgccttc gtctgcctgg agattgtaag tggggccgcc | 180 |
| ggagcgaggg tcgcgcgggg agcgaggaca ggcggcggca tccttgtccc ccgggctgtc | 240 |
| ttcctctgcg tccgc | 255 |

<210> SEQ ID NO 1380
<211> LENGTH: 242
<212> TYPE: DNA
<213> ORGANISM: Artificial Sequence
<220> FEATURE:
<223> OTHER INFORMATION: probe/primer/pcr

<400> SEQUENCE: 1380

| gtgagccggc gctcctgatg cggagaggtg cggccatgtc ctggctggga gcgaagcgcc | 60 |
| ctcgctcggg cagtcggagc gaactgtctc ccgcgcgctc cgccagccgg gccctcccgc | 120 |
| tgggcccacc ccccgagggg cggggccaga gcgggcggca ccgcctcctc cccgctgtct | 180 |
| gggtcgcagg ccttagcgac gggctgttct ccggccccgc cccattccca ggctccgccc | 240 |
| cc | 242 |

<210> SEQ ID NO 1381
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1381

| tgccgcgggg gtgccaaggg aagtgccagc tcagagggac catgtgggcg caggcaccca | 60 |
| ggcggcgccg ggaggcctct cgggactcca gggctgtccc tcccgcaggc tgtccttcca | 120 |
| cctccacccc aggccaacgc cctccgcca gcccagggtc ctgtgtcctc gagtccttcc | 180 |
| tgggcaccct ggtcccatcc ttagccctgc ccgagggggcc cagccctgct ccaaaagggc | 240 |
| tgtggctcca cccac | 255 |

<210> SEQ ID NO 1382
<211> LENGTH: 232
<212> TYPE: DNA
<213> ORGANISM: Artificial Sequence
<220> FEATURE:
<223> OTHER INFORMATION: probe/primer/pcr

<400> SEQUENCE: 1382

```
ctgctgcgcg cgctggctct tctgcgaggc ctgcttgagc ttgttgccgc ctttgggctc    60
cgggccctcc agctcgtccc tgcagcgccg cggccgctcc tcgtaggcca ggctggaggc   120
aagctccttc tcctcaaagc tgcgctgcag cttctggagg gcgccctccc tctccaacag   180
cttctgctcc agtcctgga tgctgcactc gtccgtggag atgggggagc gg            232
```

<210> SEQ ID NO 1383
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1383

```
ctggcggccc aggtcgctcc tgcccaaccc ggggacccat ctcttccccc gactccgacg    60
actggtgcgt cttgcccgga catgcccggc cgcaggcgac ccgggccacg caccccccgcc  120
gtgtccccct ctctcccctgc cctctccagg cgccaggcac gctcttcccc agccagggac  180
cgcggcgggg actcaccaac agcaggaccg cggcgacaac gagcacaagg gtcttgggga  240
cccggggccc aggcc                                                    255
```

<210> SEQ ID NO 1384
<211> LENGTH: 242
<212> TYPE: DNA
<213> ORGANISM: Artificial Sequence
<220> FEATURE:
<223> OTHER INFORMATION: probe/primer/pcr

<400> SEQUENCE: 1384

```
agcgccccgg ccgcctgatg gccgaggcag ggtgcgaccc aggacccagg acggcgtcgg    60
gaaccatacc atggcccgga tccccaagac cctaaagttc gtcgtcgtca tcgtcgcggt   120
cctgctgcca gtgagtcccg gccgcggtcc ctggctgggg aagagcgcac ctggcgccgg   180
gaggggcag ggagacgggg acacggcagg gatgcctggc cctggtcacc tgcggccggg   240
ca                                                                  242
```

<210> SEQ ID NO 1385
<211> LENGTH: 191
<212> TYPE: DNA
<213> ORGANISM: Artificial Sequence
<220> FEATURE:
<223> OTHER INFORMATION: probe/primer/pcr

<400> SEQUENCE: 1385

```
gccgcacggg acagccaggg ggagcgcgcg ctctgctccc tcgcggcccg gtcgctcctg    60
cccagcccgg gcaccccact cttcccctga ctccgacggc gggttcgtcc tgcccagaca   120
tgcccggccg caggcgaccc gggccaagca tccccaccgt gtccccctct ctccctgccc   180
actcccggcg c                                                        191
```

<210> SEQ ID NO 1386
<211> LENGTH: 203
<212> TYPE: DNA
<213> ORGANISM: Artificial Sequence
<220> FEATURE:
<223> OTHER INFORMATION: probe/primer/pcr -continued

```
<400> SEQUENCE: 1386
cccggacatg ccccgccaca agtgacccgg gccaggcacc cccgccgcgt cccctctct      60 ctctgccccc tcccggtgcc aggcgcgctt tccccaggc aggaccgcgg tggggactca    120
cctgcagcag gaccccgacg acgacaaact tgaaggtctt gtggacccgg agccgagggc   180
tggcttcccg cgccggcctg ggt                                            203

<210> SEQ ID NO 1387
<211> LENGTH: 251
<212> TYPE: DNA
<213> ORGANISM: Artificial Sequence
<220> FEATURE:
<223> OTHER INFORMATION: probe/primer/pcr

<400> SEQUENCE: 1387
cgggggccgc cgcctgactt cggacaccgg ccccgcaccc gccaggaggg gagggaaggg    60
gaggcgggga gagcgacggc gggggcgggg cgtggaccc cgcctccccc ggcacagcct    120
gctgagggga agaggggtc tccgctcttc ctcagtgcac tctctgactg aagcccggcg    180
cgtggggtgc agcgggagtg cgaggggact ggacaggtgg gaagatggga atgaggaccg   240
ggcggcggga a                                                         251

<210> SEQ ID NO 1388
<211> LENGTH: 252
<212> TYPE: DNA
<213> ORGANISM: Artificial Sequence
<220> FEATURE:
<223> OTHER INFORMATION: probe/primer/pcr

<400> SEQUENCE: 1388
cagtggcggc cctcggcctg cggtcggagg cggcgcgggc ggggaggcgg cgctgcgggc    60
tgggtgcgcc ccggctcccg gaggtgcggc gagcaggaag gcgcggggcg gcgggcgcgc   120
ggcactgact ccggaggctg cagggctgga gtgcgcgggg ctcctacggc cgagccctcg   180
gagccgcccc gcgcagccaa tcagctcccg gcggggcgag ccgcactcgt taccacgtcc   240
gtcaccggcg cg                                                        252

<210> SEQ ID NO 1389
<211> LENGTH: 166
<212> TYPE: DNA
<213> ORGANISM: Artificial Sequence
<220> FEATURE:
<223> OTHER INFORMATION: probe/primer/pcr

<400> SEQUENCE: 1389
gcccggcgcg gataacggtc cggcgggagg acacggcggt ccctacagca tcgcggcggg    60
ccaggctcgg gcaggggccg tgctcaggtg cggcagacgg acgggccggc gcctctgaag   120
tcacccggct cctttacgaa ctgagcccgt tttggctggg agggtt                  166

<210> SEQ ID NO 1390
<211> LENGTH: 219
<212> TYPE: DNA
<213> ORGANISM: Artificial Sequence
<220> FEATURE:
<223> OTHER INFORMATION: probe/primer/pcr

<400> SEQUENCE: 1390
gctccgggtg gggagggagg ctggcagctc accccggggg gcgaggggtc tgcgttagcc    60
gtagccacgg gagcccgggc ttctgggacg ctcagccgtg cgctacccgg tgcagctgct   120
```

```
ttctcaccag ctcgcgggtg ggtcctgccg cggctcggcg acccgcgccc ccttgcgagc      180
gacccagcgt gaaaccagcc caaagggcgg cctcgcccg                             219
```

<210> SEQ ID NO 1391
<211> LENGTH: 235
<212> TYPE: DNA
<213> ORGANISM: Artificial Sequence
<220> FEATURE:
<223> OTHER INFORMATION: probe/primer/pcr

<400> SEQUENCE: 1391

```
gcctgggcgc agaacggggt ccctcggcag gaccctcgcc gcgacagcct cagcagggga      60
tcgtcgagca aaagcccgca ggaatgctcc tttctgggc cccgccctcc cggccgacag       120
cttttaggta gacgtggagg cgactcagat cgcctcgcgg ttcccgggat ggcgcggtcg      180 ccccaacgc gaggctgcct ggggcacccg gctcttttcc tgggcgtccg cggcc            235
```

<210> SEQ ID NO 1392
<211> LENGTH: 215
<212> TYPE: DNA
<213> ORGANISM: Artificial Sequence
<220> FEATURE:
<223> OTHER INFORMATION: probe/primer/pcr

<400> SEQUENCE: 1392

```
ggtcctaatc cccaggctgc gctgacagga ttaggctccg ttcctcccca taatgttccc      60
aggacgagcc tcatggggac gaactacaaa tcccagcatg caccagtctt cgcccgcccg      120
gcgggagggc aacggctgac caggaccgca ggcaagcacc gcggcgacgg ttccagccag      180
gaaaatgaga gcctcttggg ccacgttcca aacgg                                 215
```

<210> SEQ ID NO 1393
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1393

```
ccgcgtcccc ggctgctcct cctcgtgctg gcggcggcgg cggcggcggc ggcggcgctg      60
ctcccggggg cgacgggtga gcggcggcgc ggcgggcggg cgactgcggg gcgcgcgggc      120
cggacccggc ctctggctcg ctcctgctct ttctcaaaca tggcgcgggg ccggggcgc       180 aggtggcggc gccggggccc gggccgggct ctcgtggcgc cgcgcggctc ggcggctgcc      240
gggcgaaccg caagc                                                       255
```

<210> SEQ ID NO 1394
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1394

```
ggcagggctg acgttgggag cgctatgagc tgccgggcag ggtcctcacc gggggcttcc      60
tctgcgggcc agggctgccg ggcgccaccg ggacgcgagc gcgcacgcct cggcccggcg      120
gccgcgctcc tcgcaccgcc ttctccgcag gtctttattc atcatctcat ctccctcttc      180
cccttctcct tctcctttgc ctccttctcc tttgcctcct tctcctcctc ttcctccccc      240
```

```
tcctccacca ccacc                                                    255

<210> SEQ ID NO 1395
<211> LENGTH: 248
<212> TYPE: DNA
<213> ORGANISM: Artificial Sequence
<220> FEATURE:
<223> OTHER INFORMATION: probe/primer/pcr

<400> SEQUENCE: 1395
ccgtgggcgc aggggctgtg gccggggcgg tgggcgggcg gtgccgccag gtgagactgg    60
ctgccgtggc gcggagctgc gaactggtcg gcggcgcaag gcgcggactc cggtgagttg   120
tgtggagcgc gcgcggccat gggcgcgggc cacgggcggg tgggagggtg gggggccaga   180
ggggcggggg agggtcactc ggcggctccc ggtgccgccg ccgcccgcca ccgcctctgc   240
tccccgcg                                                           248

<210> SEQ ID NO 1396
<211> LENGTH: 159
<212> TYPE: DNA
<213> ORGANISM: Artificial Sequence
<220> FEATURE:
<223> OTHER INFORMATION: probe/primer/pcr

<400> SEQUENCE: 1396
cctgcgcacg cgggaagggc tgccggaggc gcccgtaggg aggcgcgcgc gcgggcggct    60
cagggcccgc gttcctctcc ctcccgccta ccgccacttt cccgccctgt gtgcgccccc   120 accccccacca ccatcttccc accctcagcg cgggcgccc                         159

<210> SEQ ID NO 1397
<211> LENGTH: 199
<212> TYPE: DNA
<213> ORGANISM: Artificial Sequence
<220> FEATURE:
<223> OTHER INFORMATION: probe/primer/pcr

<400> SEQUENCE: 1397
gcggacgcag ccgagctcaa agccgctctg gccgcagggt gcggacgcgt cgcggagtcc    60
tcactgcccc gcctcgctct ggcagagtgg ggagccagcc ggcaaagaat tccgttttca   120
gctgggccaa ggggccggcg tctccccacc cccttaggct ccgcccctg tccgctgtga    180 tcgccgggag gccaggccc                                               199

<210> SEQ ID NO 1398
<211> LENGTH: 227
<212> TYPE: DNA
<213> ORGANISM: Artificial Sequence
<220> FEATURE:
<223> OTHER INFORMATION: probe/primer/pcr

<400> SEQUENCE: 1398
gacccatggc ggggcaggcg gcggcgctgt cgggcgggca ggggtggcgg gaggcggtgg    60
cgcagcgagc agcggcctcc agcgctggtg gctcccttta taggagcgct ggagacacgg   120
gccccgcccg ccctgcagcc ccgccctgca gtcccggagc gccgaggagt gcgcgccccc   180
tcgcccccgc cccacctcgg ctgggaggct ggtgcggacg ccgggtg                 227

<210> SEQ ID NO 1399
<211> LENGTH: 255
<212> TYPE: DNA
<213> ORGANISM: Artificial Sequence
```

```
<220> FEATURE:
<223> OTHER INFORMATION: probe/primer/pcr

<400> SEQUENCE: 1399
ccgctccccg cccctggctc cgcctggccc cactcccctc cgcgcgcctt ccctcttctc    60
ccccgctccc cgcggacgct cctctctttc ccagtgggcc aactttatgc tgaaatttct   120
tttctgccct tttttgggat gtttccccat tgggaggcgg agccgggctg cggcggggaa   180
ggcggagggc gagggaaga gtcactgagc tgcggggcat aggggggtccg gggcgaggtg   240 ccttctccca cccag                                                    255

<210> SEQ ID NO 1400
<211> LENGTH: 191
<212> TYPE: DNA
<213> ORGANISM: Artificial Sequence
<220> FEATURE:
<223> OTHER INFORMATION: probe/primer/pcr

<400> SEQUENCE: 1400
tgtgccgcgc ggttgggagg agggtcgtga gcgtgagcgt gggagcgctg ggggctctgc    60
tcgcgtgctg ctctgaagtt gttccccgat gcgccgtagg aagctgggat tctcccatcc   120
ggacgtggga cgcaggggag gggtaggttt caccgtccgg gctgatgact cgtggcctcc   180
ggggctcctg g                                                        191

<210> SEQ ID NO 1401
<211> LENGTH: 184
<212> TYPE: DNA
<213> ORGANISM: Artificial Sequence
<220> FEATURE:
<223> OTHER INFORMATION: probe/primer/pcr

<400> SEQUENCE: 1401
cactcacgct ctcagcccgg ggaatcccag cggggaggag ggagggaggt cgttttcttc    60
agctccccag gtggtctgtg ctgggtgtgc tgacggtcct tttgggaaaa caggtccacc   120
tttgccagcg taattcagaa agagatgtaa ttttctgaga gcacacacct gggcaggaga   180
tcgc                                                                184

<210> SEQ ID NO 1402
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1402
ggcaagcggg cttcgggaag aatgcagttg gtgaggaagc tcggcgaggc gtgcccgtgc    60
agctgcccct ggccctgact gctggtgcga ggcagtgcac gactcagctg gccggggcct   120
gctgtcccgc cggtgccacg cacctgcaga cgcccgggct gtgccatctc ctgggccggt   180
ccgggggctg gggcggggcg aaaaagaaaa agctctgatc tctgccttcg cctcgcgcag   240
ctgtgcggcg agccc                                                    255

<210> SEQ ID NO 1403
<211> LENGTH: 255
<212> TYPE: DNA
<213> ORGANISM: Artificial Sequence
<220> FEATURE:
<223> OTHER INFORMATION: probe/primer/pcr
```

<400> SEQUENCE: 1403

```
cccgcgggcc gggtgagaac aggtggcgcc ggcccgacca ggcgctttgt gtcggggcgc      60
gaggatctgg agcgaactgc tgcgcctcgg tgggccgctc ccttccctcc cttgctcccc     120
cgggcggccg cacgccgggt cggccgggta acggagaggg agtcgccagg aatgtggctc     180
tggggactgc ctcgctcggg aaggggaga gggtggccac ggtgttagga gaggcgcggg     240
agccgagagg tggcg                                                      255
```

<210> SEQ ID NO 1404
<211> LENGTH: 239
<212> TYPE: DNA
<213> ORGANISM: Artificial Sequence
<220> FEATURE:
<223> OTHER INFORMATION: probe/primer/pcr

<400> SEQUENCE: 1404

```
ggcggcggct ggagagcgag gaggagcggg tggccccgcg ctgcgcccgc cctcgcctca      60
cctggcgcag gtaggtgtgg ccgcgtcccc tacccggccg ggactttctg gtaaggagag     120
gaggttacgg ggaacgacgc gctgctttca tgccctttct tgttctacct tcatcggccg     180
aggtaaaagt gctgaaacca tgtgaataaa atacaggtgg gttccgccag cttcgctcc      239
```

<210> SEQ ID NO 1405
<211> LENGTH: 253
<212> TYPE: DNA
<213> ORGANISM: Artificial Sequence
<220> FEATURE:
<223> OTHER INFORMATION: probe/primer/pcr

<400> SEQUENCE: 1405

```
gggccccggg actcggcttg cacgagccag tctggggacc ggggaggcgg ggagagggaa      60
ggggaaagcg cggacgcggc ccaaacctcc agtagccgca gccgccgtcg ccgagtaggg     120
ccgggcagcc agccgggcct ggcgcagcat cagtgcccgc tgccgcttcc gctcgatact     180
cgcccgcacc gaggcaggca gctccgcggg ttgctctaaa gccgccgcct ccggcaaagc     240
cccgtcggcc gcc                                                        253
```

<210> SEQ ID NO 1406
<211> LENGTH: 209
<212> TYPE: DNA
<213> ORGANISM: Artificial Sequence
<220> FEATURE:
<223> OTHER INFORMATION: probe/primer/pcr

<400> SEQUENCE: 1406

```
acggaatgtg gggtgcgggc ctgaatatta taaacaaaac caaaaaacac tggctggaaa      60
ggaagtaagc ggattcttcg taaagtctat caaaagtctt ttcgtttccc cctccccctt     120
tccccaccgc ccaccaaaat gagccgcgtt tgagcacctc aggtctggaa agccggccag     180
gagtgggga gaccgaggca cccgcggcc                                        209
```

<210> SEQ ID NO 1407
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1407

```
gcggctgctg ccgaggctcc tggtttccac cgccgccctc ggggatcatg ccgccatcgc      60
```

```
ggttcatgcc gttctcgtgg ttcacaccgc cctcagggtt catattaccc atgaggcctg    120
gagctccttg gccaacatgg ccttctgcgc ttgatgctgc cccagctga ggtgtggggc    180 ttatttttac ctggtataca ctcaggcagt agaacacggt gtcgtggacg agcgaacgcg    240
ccatggctgg agcgc                                                     255

<210> SEQ ID NO 1408
<211> LENGTH: 200
<212> TYPE: DNA
<213> ORGANISM: Artificial Sequence
<220> FEATURE:
<223> OTHER INFORMATION: probe/primer/pcr

<400> SEQUENCE: 1408
ccgctgcgcg agggaggggg cccgaggcgc cccggcccg cctcctccc ggtcttcgga     60 tccgagccgg tcctcgggaa agagcctgcc accgcgtccc cgcagccacc ctctccgcgt   120
gcccggccct ctccagtggc gggggcacgt gggcgcgcgg ggtgcgtggc aagccgcccc   180
tctccccacg cccgtccggc                                               200

<210> SEQ ID NO 1409
<211> LENGTH: 230
<212> TYPE: DNA
<213> ORGANISM: Artificial Sequence
<220> FEATURE:
<223> OTHER INFORMATION: probe/primer/pcr

<400> SEQUENCE: 1409
ggggtgcggc gtctggtcag ccaggggtga attctcagga ctggtcggca gtcaaggtga    60
ggaccctgag tgtaaactga agagaccacc cccacctgta acaaagaggg ccccactaag   120
tcccgcttct gcatttggtc ctgagaggct ccggtaaagc cgtccggcaa tgttccacct   180
ggaaagttcc agggcagggg aagggtgggg ggaggggcag tcgcggggga               230

<210> SEQ ID NO 1410
<211> LENGTH: 246
<212> TYPE: DNA
<213> ORGANISM: Artificial Sequence
<220> FEATURE:
<223> OTHER INFORMATION: probe/primer/pcr

<400> SEQUENCE: 1410
gccgggggaa atgcggcctc taagctctcc gctgaggcgg cttggaagga atagtgactg    60
acgtggaggt gggggaggtg gctggcccgg gcgaggccca gggagaggga gaggaggcgg   120
gtgggagagg aggagggtgt atctcctttc gtcggcccgc cccttggctt ctgcactgat   180
ggtgggtgga tgagtaatgc atccaggaag cctggaggcc tgtggtttcc gcacccgctg   240
ccaccc                                                              246

<210> SEQ ID NO 1411
<211> LENGTH: 230
<212> TYPE: DNA
<213> ORGANISM: Artificial Sequence
<220> FEATURE:
<223> OTHER INFORMATION: probe/primer/pcr

<400> SEQUENCE: 1411
tgcctggtag gactgacggc tgcctttgtc ctcctcctct ccaccccgcc tcccccacc     60 ctgccttccc ccctcccccc gtcttctctc ccgcagctgc ctcagtcggc tactctcagc   120
```

| caaccccct caccacccct ctccccaccc gcccccccgc cccgtcggc ccagcgctgc | 180 |
| cagcccgagt tgcagagag gtaactccct ttggctgcga gcgggcgagc | 230 |

<210> SEQ ID NO 1412
<211> LENGTH: 184
<212> TYPE: DNA
<213> ORGANISM: Artificial Sequence
<220> FEATURE:
<223> OTHER INFORMATION: probe/primer/pcr

<400> SEQUENCE: 1412

| gcgcgggcgc ctcgatctcc cgcgcgcgcg cgtgcgcgag acccccttt ggcccctac | 60 |
| cctgcagcaa gggtagcgtg acgtaatgca acctcagcat gtcagcagca atataaagga | 120 |
| gaatgaggcg gcgcgcctcc cagacgcaga gtagattgtg attggctcgg gctgcggaac | 180 |
| ctcg | 184 |

<210> SEQ ID NO 1413
<211> LENGTH: 240
<212> TYPE: DNA
<213> ORGANISM: Artificial Sequence
<220> FEATURE:
<223> OTHER INFORMATION: probe/primer/pcr

<400> SEQUENCE: 1413

| cccggctggt cggcgctcct cgcaggcggt gtcccggtcc ggagcgatct gcgcgctcgg | 60 |
| ccccgcggcc gcgccctccc cgaagccctt gctttgttct gtgagcgcct cgtgtcagcc | 120 |
| aggcgcagtg agctcacggg ggcgtcccgg gtccgcatcc tcccaggagc tggggagccg | 180 |
| ctcgctgggc gcggacccgc tgcctgacgc tgcaaactac acggtttcgg tccccgcgc | 240 |

<210> SEQ ID NO 1414
<211> LENGTH: 129
<212> TYPE: DNA
<213> ORGANISM: Artificial Sequence
<220> FEATURE:
<223> OTHER INFORMATION: probe/primer/pcr

<400> SEQUENCE: 1414

| ccggggctgg gacggcgctt ccaggcggag aaagacctcc gcgggccgcg cgcggccttc | 60 |
| cccctgcgag gatcgccatt ggcccgggtt ggctttggaa agcggcggtg gctttgggcc | 120 |
| gggctcggc | 129 |

<210> SEQ ID NO 1415
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1415

| gggcggggtg gggctggagc tcctgtctct tggccagctg aatggaggcc cagtggcaac | 60 |
| acaggtcctg cctggggatc aggtctgctc tgcaccccac cttgctgcct ggagccgccc | 120 |
| acctgacaac ctctcatccc tgctctgcag atccggtccc atcccactg cccacccac | 180 |
| ccccccagca ctccacccag ttcaacgttc cacgaacccc cagaaccagc cctcatcaac | 240 |
| aggcagcaag aaggg | 255 |

<210> SEQ ID NO 1416
<211> LENGTH: 255

```
<212> TYPE: DNA
<213> ORGANISM: Artificial Sequence
<220> FEATURE:
<223> OTHER INFORMATION: probe/primer/pcr

<400> SEQUENCE: 1416
gtgcggttgg gcggggccct gtgcccact  gcggagtgcg ggtcgggaag cggagagaga      60
agcagctgtg taatccgctg gatgcggacc agggcgctcc ccattcccgt cgggagcccg     120
ccgattggct gggtgtgggc gcacgtgacc gacatgtggc tgtattggtg cagcccgcca     180
gggtgtcact ggagacagaa tggaggtgct gccggactcg gaaatggggt aggtgctgga     240
gccaccatgg ccagg                                                      255

<210> SEQ ID NO 1417
<211> LENGTH: 127
<212> TYPE: DNA
<213> ORGANISM: Artificial Sequence
<220> FEATURE:
<223> OTHER INFORMATION: probe/primer/pcr

<400> SEQUENCE: 1417
ggcggtgcct ccggggctca cctggctgca gccacgcacc ccctctcagt ggcgtcggaa      60
ctgcaaagca cctgtgagct tgcggaagtc agttcagact ccagcccgct ccagcccggc    120
ccgaccc                                                               127

<210> SEQ ID NO 1418
<211> LENGTH: 127
<212> TYPE: DNA
<213> ORGANISM: Artificial Sequence
<220> FEATURE:
<223> OTHER INFORMATION: probe/primer/pcr

<400> SEQUENCE: 1418
ggcggtgcct ccggggctca cctggctgca gccacgcacc ccctctcagt ggcgtcggaa      60
ctgcaaagca cctgtgagct tgcggaagtc agttcagact ccagcccgct ccagcccggc    120
ccgaccc                                                               127

<210> SEQ ID NO 1419
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1419
cgggagcccg ccccgagag  gtgggctgcg ggcgctcgag gcccagccgc cgccgccgcc      60
gccgccgccg ccgcctccgc cgccgccgcc gccgccgccg ccgccgcgct gccgcacgcc    120
ccctggcagc ggcgcctccg tcaccgccgc cgcccgcgct cgccgtcggc ccgccgcccg    180
ctcagaggcg gccctccacc ggaagtgaaa ccgaaacgga gctgagcgcc tgactgaggc    240 cgaaccccg  gcccg                                                      255

<210> SEQ ID NO 1420
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1420
```

```
tcctgccatc cgcgcctttg cacttttctt tttgagttga catttcttgg tgcttttgg      60 tttctcgctg ttgttgggtg cttttggtt tgttcttgtc ccttttcgt ttgctcatcc      120 tttttggcgc taactcttag gcagccagcc cagcagcccg aagcccgggc agccgcgctc    180
cgcggccccg gggcagcgcg gcgggaaccg cagccaagcc ccccgacacg gggcgcacgg    240
gggccgggca gcccg                                                     255
```

<210> SEQ ID NO 1421
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1421

```
aggcacaggg gcagctccgg cacggctttc tcaggcctat gccggagcct cgagggctgg    60
agagcgggaa gacaggcagt gctcggggag ttgcagcagg acgtcaccag gagggcgaag    120
cggccacggg agggggcccc cgggacattg cgcagcaagg aggctgcagg ggctcggcct    180
gcgggcgccg gtcccacgag gcactgcggc ccagggtctg gtgcggagag ggcccacagt    240
ggacttggtg acgct                                                     255
```

<210> SEQ ID NO 1422
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1422

```
cgacccctcc gaccgtgctt ccggtgaggg tcctgggccc ctttcccact ctctagagac    60
agagaaatag ggcttcgggc gcccagcgtt tcctgtggcc tctgggacct cttggccagg    120
gacaaggacc cgtgacttcc ttgcttgctg tgtggcccgg gagcagctca gacgctggct    180
ccttctgtcc ctctgcccgt ggacattagc tcaagtcact gatcagtcac aggggtggcc    240
tgtcaggtca ggcgg                                                     255
```

<210> SEQ ID NO 1423
<211> LENGTH: 213
<212> TYPE: DNA
<213> ORGANISM: Artificial Sequence
<220> FEATURE:
<223> OTHER INFORMATION: probe/primer/pcr

<400> SEQUENCE: 1423

```
cccgcagggt ggctgcgtcc ttccagggcc tggcctgagg gcaggggtgg tttgctcccc    60
cttcagcctc cggggctgg ggtcagtgcg gtgctaacac ggctctctct gtgctgtggg     120
acttccaggc aggcccgcaa gccgtgtgag ccgtcgcagc cgtggcatcg ttgaggagtg    180
ctgtttccgc agctgtgacc tggccctcct gga                                 213
```

<210> SEQ ID NO 1424
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1424

```
gcgtctgccg gcccctcccc ttgtccgtcc cctccgcgcc gctggcgcgc gccttctgaa    60
```

```
tgccaagcat tgccataaac tccggggaca aaagcctggg tcacaaaagc cccctctaga    120
agttcacacc ctgaggcttc cctggcaagg ctggggccg tttggccctt ccatgtggac    180
tgcaaaaaca gtgttggaat gcaggactct gggtatgttc tcgaaagttg ttacaacccc    240
aacccagggt tgacc                                                    255

<210> SEQ ID NO 1425
<211> LENGTH: 117
<212> TYPE: DNA
<213> ORGANISM: Artificial Sequence
<220> FEATURE:
<223> OTHER INFORMATION: probe/primer/pcr

<400> SEQUENCE: 1425
taggccgccg ggcagccacc gcgctcctct ggctctcctg ctccatcgcg ctcctccgcg    60
cccttgccac ctccaacgcc cgtgcccagc agcgcgcggc tgcccaacag cgccgga      117

<210> SEQ ID NO 1426
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1426
ggggagcggg gacgcgagca gcaccagaat ccgcgggagc gcggctgttc ctggtagggc    60
cgtgtcaggt gacggatgta gctagggggc gagctgcctg gagttgcgtt ccaggcgtcc    120
ggcccctggg ccgtcaccgc ggggcgcccg cgctgagggt gggaagatgg tggtgggggt    180 ggggcgcac acaggcggg aaagtggcgg taggcgggag ggagaggaac gcgggccctg    240
agccgcccgc gcgcg                                                    255

<210> SEQ ID NO 1427
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1427
gccggctggc tccccactct gccagagcga ggcggggcag tgaggactcc gcgacgcgtc    60
cgcaccctgc ggccagagcg gctttgagct cggctgcgtc cgcgctaggc gcttttccc    120 agaagcaatc caggcgcgcc cgctggttct tgagcgccag gaaaagcccg gagctaacga    180
ccggccgctc ggccactgca cggggcccca agccgcagaa ggacgacggg agggtaatga    240
agctgagccc aggtc                                                    255

<210> SEQ ID NO 1428
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1428
tcgctcacgg cgtccccttg cctggaaaga taccgcggtc cctccagagg atttgaggga    60
cagggtcgga gggggctctt ccgccagcac cggaggaaga aagaggaggg gctggctggt    120
caccagaggg tggggcggac cgcgtgcgct cggcggctgc ggagaggggg agagcaggca    180
```

```
gcgggcggcg gggagcagca tggagccggc ggcggggagc agcatggagc cttcggctga    240
ctggctggcc acggc                                                      255

<210> SEQ ID NO 1429
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1429
tccccgctgc cctggcgctc cccctttgat ttattagggc tgccgggttg gcgcagattg     60
cttttttctt tcttccatcc catcctccct tctggtcctc ctttccacag tgggagtccg    120
tgctcctgct cctcggttgg ctcctaagtg ccccgccagg tccctctcc tttcgctctc     180 ccggctccgg ctcccgactc ttcggcccgc tggcatctgc ttccctcccc tgcctcgttt    240
ctcgtcgccc ctgct                                                      255

<210> SEQ ID NO 1430
<211> LENGTH: 115
<212> TYPE: DNA
<213> ORGANISM: Artificial Sequence
<220> FEATURE:
<223> OTHER INFORMATION: probe/primer/pcr

<400> SEQUENCE: 1430
ggccagaggc aggcccgcag ctccctgccc cgcctctgtg cctccgccaa cccgacaacg     60
cttgctccca ccccgatccc cgcacccgcg cgaagtgggc cctccggtcg tcggc         115

<210> SEQ ID NO 1431
<211> LENGTH: 109
<212> TYPE: DNA
<213> ORGANISM: Artificial Sequence
<220> FEATURE:
<223> OTHER INFORMATION: probe/primer/pcr

<400> SEQUENCE: 1431
tgcccgggtc atcggacggg aggccgcgcc acgtgagggc ggcaagaggg cactggccct     60
gcggcgaggc cccagcgagg ggcgcttccc cgaggggcca gcctgggca               109

<210> SEQ ID NO 1432
<211> LENGTH: 170
<212> TYPE: DNA
<213> ORGANISM: Artificial Sequence
<220> FEATURE:
<223> OTHER INFORMATION: probe/primer/pcr

<400> SEQUENCE: 1432
cccagtgcgc acggcgaggc agtagcccgg ccccgcactg ctgataggtg caggcaggac     60
agtccctcca ccgcggctcg gggcgtcctg attggtgcgg agccacgtca gtcgcacccg    120
gagaagggtc tgggaggagg cggaggcgga gagggctggg gagggccgcg               170

<210> SEQ ID NO 1433
<211> LENGTH: 138
<212> TYPE: DNA
<213> ORGANISM: Artificial Sequence
<220> FEATURE:
<223> OTHER INFORMATION: probe/primer/pcr

<400> SEQUENCE: 1433
agcgtcccag cccgcgcacc gaccagcgcc ccagttcccc acagacgccg gcgggcccgg     60
```

-continued

```
gagcctcgcg gacgtgacgc cgcgggcgga agtgacgttt tcccgcggtt ggacgcggcg      120
ctcagttgcc gggcgggg                                                    138

<210> SEQ ID NO 1434
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1434
tgctcccccg ggtcggagcc ccccggagct gcgcgcgggc ttgcagcgcc tcgcccgcgc      60
tgtcctcccg gtgtcccgct tctccgcgcc ccagccgccg gctgccagct tttcggggcc     120
ccgagtcgca cccagcgaag agagcgggcc cgggacaagc tcgaactccg gccgcctcgc     180
ccttccccgg ctccgctccc tctgcccccct cggggtcgcg cgcccacgat gctgcagggc     240
cctggctcgc tgctg                                                      255

<210> SEQ ID NO 1435
<211> LENGTH: 124
<212> TYPE: DNA
<213> ORGANISM: Artificial Sequence
<220> FEATURE:
<223> OTHER INFORMATION: probe/primer/pcr

<400> SEQUENCE: 1435
cgctcgcatt ggggcgcgtc ccccatccgc ccccaactgt ggtgtcgcga caggtcctat      60
tgcgggtgtc tgcggtggga agggcggtgg tgactgggag catgcgggt aaccgcagtg     120 ggca                                                                  124

<210> SEQ ID NO 1436
<211> LENGTH: 196
<212> TYPE: DNA
<213> ORGANISM: Artificial Sequence
<220> FEATURE:
<223> OTHER INFORMATION: probe/primer/pcr

<400> SEQUENCE: 1436
tgcggcaagc ccgccatgat gtccacgtga caaaagccat gatatacata tgacaacgcc      60
tgccatattg tccctgcggc aaaacccaac acgaaaagca cacagcaaag acaaagaggc     120
ccgccatgtt ttacactgcg gcaagacctt cagccgccat cttttcctgt gtgaccgcac     180
atgtccacca ccatgc                                                    196

<210> SEQ ID NO 1437
<211> LENGTH: 128
<212> TYPE: DNA
<213> ORGANISM: Artificial Sequence
<220> FEATURE:
<223> OTHER INFORMATION: probe/primer/pcr

<400> SEQUENCE: 1437
tcttgagcct caggagtgaa aaggcccctt gggaaaccct cacccaggag atacacagga      60
gcactggctt tggcagcagc tcacaatgag aaagatgcct gtcacagcct ttgccttcct     120
cttctatg                                                              128

<210> SEQ ID NO 1438
<211> LENGTH: 255
<212> TYPE: DNA
```

```
<213> ORGANISM: Artificial Sequence
<220> FEATURE:
<223> OTHER INFORMATION: probe/primer/pcr

<400> SEQUENCE: 1438
ggaccatgag tgtttccatg cttggcatca gacatgtctt ctacccctat tcagtctgtc      60
atccactggt caagaatccc aaacattcta aaactgtgtc cacatctctt ctgggtaact     120
cttatgattg gagggcttcc tgaggtgtga agtctatcac agatccagtg actaacttct     180
agcttcatct tattctcact taggggagaa gagttgaggc ccaagcaaac ctcttcttac     240
cattggctta gggaa                                                     255

<210> SEQ ID NO 1439
<211> LENGTH: 255
<212> TYPE: DNA
<213> ORGANISM: Artificial Sequence
<220> FEATURE:
<223> OTHER INFORMATION: probe/primer/pcr

<400> SEQUENCE: 1439
tcagccactg cttcgcaggc tgacgttact gacgtggtgc cagcgacgga gggcgagaac      60
gccagcgcgg cgcagccgga cgtgaacgcg cagatcaccg cagcggttgc ggcagaaaac     120
agccgcatta tggggatcct caactgtgag gaggctcacg gacgcgaaga acaggcacgc     180
gtgctggcag aaaccccccgg tatgaccgtg aaaacggccc gccgcattct ggccgcagca     240
ccacagagtg cacag                                                     255

<210> SEQ ID NO 1440
<211> LENGTH: 155
<212> TYPE: DNA
<213> ORGANISM: Artificial Sequence
<220> FEATURE:
<223> OTHER INFORMATION: probe/primer/pcr

<400> SEQUENCE: 1440
cggccagctg cgcggcgact ccggggactc cagggcgccc ctctgcggcc gacgcccggg      60
gtgcagcggc cgccgggggct ggggccggcg ggagtccgcg ggaccctcca gaagagcggc     120
cggcgccgtg actcagcact ggggcggagc ggggc                                155
```